United States Patent
Tam et al.

(10) Patent No.: US 10,106,778 B2
(45) Date of Patent: Oct. 23, 2018

(54) SELECTIVE TARGETING OF CANCER STEM CELLS

(71) Applicant: Whitehead Institute for Biomedical Research, Cambridge, MA (US)

(72) Inventors: Wai Leong Tam, Singapore (SG); Robert A. Weinberg, Brookline, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 2 days.

(21) Appl. No.: 14/441,697

(22) PCT Filed: Nov. 8, 2013

(86) PCT No.: PCT/US2013/069121
§ 371 (c)(1),
(2) Date: May 8, 2015

(87) PCT Pub. No.: WO2014/074805
PCT Pub. Date: May 15, 2014

(65) Prior Publication Data
US 2016/0017292 A1    Jan. 21, 2016

Related U.S. Application Data

(60) Provisional application No. 61/724,249, filed on Nov. 8, 2012.

(51) Int. Cl.
| | | |
|---|---|---|
| *A61K 45/06* | (2006.01) | |
| *C12N 15/113* | (2010.01) | |
| *C12N 5/09* | (2010.01) | |
| *G01N 33/50* | (2006.01) | |
| *A61K 31/404* | (2006.01) | |
| *A61K 31/506* | (2006.01) | |
| *A61K 31/7105* | (2006.01) | |
| *A61K 31/713* | (2006.01) | |
| *A61K 31/337* | (2006.01) | |
| *A61K 31/403* | (2006.01) | |
| *A61K 31/4045* | (2006.01) | |
| *A61K 31/437* | (2006.01) | |
| *A61K 31/553* | (2006.01) | |
| *A61K 31/704* | (2006.01) | |
| *A61K 38/08* | (2006.01) | |
| *A61N 5/10* | (2006.01) | |

(52) U.S. Cl.
CPC .......... *C12N 5/0693* (2013.01); *A61K 31/337* (2013.01); *A61K 31/403* (2013.01); *A61K 31/404* (2013.01); *A61K 31/4045* (2013.01); *A61K 31/437* (2013.01); *A61K 31/506* (2013.01); *A61K 31/553* (2013.01); *A61K 31/704* (2013.01); *A61K 31/713* (2013.01); *A61K 31/7105* (2013.01); *A61K 38/08* (2013.01); *A61K 45/06* (2013.01); *A61N 5/10* (2013.01); *C12N 15/113* (2013.01); *G01N 33/5011* (2013.01); *C12N 2310/11* (2013.01); *C12N 2310/14* (2013.01); *C12N 2310/141* (2013.01); *C12N 2320/31* (2013.01); *C12N 2501/727* (2013.01)

(58) Field of Classification Search
None
See application file for complete search history.

(56) References Cited

U.S. PATENT DOCUMENTS

| | | | |
|---|---|---|---|
| 3,854,480 | A | 12/1974 | Zaffaroni |
| 4,452,775 | A | 6/1984 | Kent |
| 4,675,189 | A | 6/1987 | Kent et al. |
| 5,075,109 | A | 12/1991 | Tice et al. |
| 5,133,974 | A | 7/1992 | Paradissis et al. |
| 5,211,657 | A | 5/1993 | Yamada et al. |
| 5,223,409 | A | 6/1993 | Ladner et al. |
| 5,407,686 | A | 4/1995 | Patel et al. |
| 5,736,152 | A | 4/1998 | Dunn |
| 6,124,133 | A | 9/2000 | Taylor et al. |
| 2002/0042079 | A1 | 4/2002 | Simon et al. |
| 2004/0101936 | A1 | 5/2004 | Endo et al. |
| 2004/0110728 | A1* | 6/2004 | Macdonald ........... C07C 237/04 514/114 |
| 2005/0182006 | A1* | 8/2005 | McSwiggen ....... A61K 49/0008 514/44 A |
| 2005/0209310 | A1 | 9/2005 | Chaplin et al. |
| 2006/0040980 | A1 | 2/2006 | Lind et al. |

(Continued)

FOREIGN PATENT DOCUMENTS

| | | |
|---|---|---|
| WO | WO 93/018778 A1 | 9/1993 |
| WO | WO 94/029328 A1 | 12/1994 |

(Continued)

OTHER PUBLICATIONS

French et al. (Cancer Research (2003) 63:5962-5969).*

(Continued)

*Primary Examiner* — J. E. Angell

(74) *Attorney, Agent, or Firm* — Wolf, Greenfield & Sacks, P.C.

(57) ABSTRACT

Aspects of the invention relate to methods and related compositions for preferentially targeting cancer stem cells. In some embodiments, the methods utilize PKC-α/FRA1 pathway inhibitors to target carcinoma cells. Also provided are methods for identifying a candidate compound for selectively inhibiting growth of cancer stem cell, and methods for obtaining cells that have undergone an epithelial to mesenchymal transition.

21 Claims, 42 Drawing Sheets

Specification includes a Sequence Listing.

(56) References Cited

U.S. PATENT DOCUMENTS

| | | |
|---|---|---|
| 2006/0141549 A1 | 6/2006 | Mahajan et al. |
| 2007/0105133 A1 | 5/2007 | Clarke et al. |
| 2007/0172818 A1 | 7/2007 | Fisher et al. |
| 2008/0033189 A1 | 2/2008 | Naidu |
| 2008/0267957 A1 | 10/2008 | Arnold et al. |
| 2009/0054312 A1 | 2/2009 | Wolf et al. |
| 2009/0203713 A1 | 8/2009 | Beachy et al. |
| 2010/0069458 A1 | 3/2010 | Atadja et al. |
| 2010/0162416 A1 | 6/2010 | Krtolica et al. |
| 2011/0191868 A1 | 8/2011 | Gupta et al. |
| 2012/0159655 A1 | 6/2012 | Lorens et al. |
| 2014/0294729 A1 | 10/2014 | Gupta et al. |

FOREIGN PATENT DOCUMENTS

| | | |
|---|---|---|
| WO | WO 1995/024929 | 9/1995 |
| WO | WO 99/005156 A1 | 2/1999 |
| WO | WO 2003/035661 A1 | 5/2003 |
| WO | WO 2003/045932 A1 | 6/2003 |
| WO | WO 2003/048166 A1 | 6/2003 |
| WO | WO 2004/000859 A2 | 12/2003 |
| WO | WO 2005/056549 A1 | 6/2005 |
| WO | WO 2006/101925 A2 | 9/2006 |
| WO | WO 2007/005611 A2 | 1/2007 |
| WO | WO 2007/024971 A2 | 3/2007 |
| WO | WO 2007/035744 A1 | 3/2007 |
| WO | WO 2008/051493 A2 | 5/2008 |
| WO | WO 2008/122038 A1 | 10/2008 |
| WO | WO 2009/126310 | 10/2009 |
| WO | WO 2013/119923 A1 | 8/2013 |

OTHER PUBLICATIONS

Dean et al. (Cancer Research (1996) 56:3499-3507).*
Chan et al. (Curr Opin Urol. (2010) 20(5): 393-397).*
Geiger et al. (Anticancer Drug Res (1998) 13(1):35-45).*
Xin et al. (Cancer Res (2011) 71(21):6601-6610).*
Hedvat et al. (Cancer Cell Res (2009) 16(6):487-497).*
Von Pawel et al. (Bulletin Can (2004) 91(5):E70-76).*
Economopoulou et al. (Oncologist (2012) 17(11):1394-401).*
Al-Hajj et al., Prospective identification of tumorigenic breast cancer cells. Proc Natl Acad Sci U S A. Apr. 1, 2003;100(7):3983-8. Epub Mar. 10, 2003.
Allen et al., Synthesis of C-2 functionalised 1,6,8-trioxadispiro[4.1.5.3]pentadec-13-enes. J. Chem. Soc., Perkin Trans. 1998;1:2403-2412.
Baba et al., PKA-dependent regulation of the histone lysine demethylase complex PHF2-ARID5B. Nat Cell Biol. Jun. 2011;13(6):668-75. doi:10.1038/ncb2228. Epub May 1, 2011.
Bao et al., Glioma stem cells promote radioresistance by preferential activation of the DNA damage response. Nature. Dec. 7, 2006;444(7120):756-60. Epub Oct. 18, 2006.
Carbone et al., Multistep and multifactorial carcinogenesis: when does a contributing factor become a carcinogen? Semin Cancer Biol. Dec. 2004;14(6):399-405.
Carpenter et al., Motility induction in breast carcinoma by mammary epithelial laminin 332 (laminin 5). Mol Cancer Res. Apr. 2009;7(4):462-75. doi: 10.1158/1541-7786.MCR-08-0148. Epub Apr. 7, 2009.
Cheng et al., Phosphorylation and activation of cAMP-dependent protein kinase by phosphoinositide-dependent protein kinase. Proc Natl Acad Sci U S A. Aug. 18, 1998;95(17):9849-54.
Cifone et al., Correlation of patterns of anchorage-independent growth with in vivo behavior of cells from a murine fibrosarcoma. Proc Natl Acad Sci U S A. Feb. 1980;77(2):1039-43.
Dasgupta et al., Nicotine induces cell proliferation, invasion and epithelial-mesenchymal transition in a variety of human cancer cell lines. Int J Cancer. Jan. 1, 2009;124(1):36-45. doi: 10.1002/ijc.23894.

Dean et al., Tumour stem cells and drug resistance. Nat Rev Cancer. Apr. 2005;5(4):275-84.
Diehn et al., Cancer stem cells and radiotherapy: new insights into tumor radioresistance. J Natl Cancer Inst. Dec. 20, 2006;98(24):1755-7.
Docherty et al., TGF-beta1-induced EMT can occur independently of its proapoptotic effects and is aided by EGF receptor activation. Am J Physiol Renal Physiol. May 2006;290(5):F1202-12. Epub Dec. 20, 2005.
Dontu et al., In vitro propagation and transcriptional profiling of human mammary stem/progenitor cells. Genes Dev. May 15, 2003;17(10):1253-70.
Drinyaev et al., Antitumor effect of avermectins. Eur J Pharmacol. Oct. 6, 2004 6;501(1-3):19-23.
Elenbaas et al., Human breast cancer cells generated by oncogenic transformation of primary mammary epithelial cells. Genes Dev. Jan. 1, 2001;15(1):50-65.
Frisch et al., Disruption of epithelial cell-matrix interactions induces apoptosis. J Cell Biol. Feb. 1994;124(4):619-26.
Gregory et al., The miR-200 family and miR-205 regulate epithelial to mesenchymal transition by targeting ZEB1 and SIP1. Nat Cell Biol. May 2008;10(5):593-601. doi: 10.1038/ncb1722. Epub Mar. 30, 2008.
Gu et al., Measuring cell motility using quantum dot probes. Methods Mol Biol. 2007;374:125-31.
Gupta et al., Identification of selective inhibitors of cancer stem cells by high-throughput screening. Cell. Aug. 21, 2009;138(4):645-59. Epub Aug. 13, 2009.
Gura, Systems for identifying new drugs are often faulty. Science. Nov. 7, 1997;278(5340):1041-2.
Hahn et al., Creation of human tumour cells with defined genetic elements. Nature. Jul. 2, 1999;400(6743):464-8.
Hollier et al., The epithelial-to-mesenchymal transition and cancer stem cells: a coalition against cancer therapies. J Mammary Gland Biol Neoplasia. Mar. 2009;14(1):29-43. Epub Feb. 26, 2009.
Hurt et al., CD44+ CD24(-) prostate cells are early cancer progenitor/stem cells that provide a model for patients with poor prognosis. Br J Cancer. Feb. 26, 2008;98(4):756-65. Epub Feb. 12, 2008.
Jechlinger et al., Autocrine PDGFR signaling promotes mammary cancer metastasis. J Clin Invest. Jun. 2006;116(6):1561-70.
Jia et al., Activation of protein kinase A and exchange protein directly activated by cAMP promotes adipocyte differentiation of human mesenchymal stem cells. PLoS One. 2012;7(3):e34114. doi:10.1371/journal.pone.0034114. Epub Mar. 27, 2012.
Jiang et al., Role of Wnt/beta-catenin signaling pathway in epithelial-mesenchymal transition of human prostate cancer induced by hypoxia-inducible factor-1alpha. Int J Urol. Nov. 2007;14(11):1034-9.
Jinushi et al., Milk fat globule EGF-8 promotes melanoma progression through coordinated Akt and twist signaling in the tumor microenvironment. Cancer Res. Nov. 1, 2008;68(21):8889-98. doi: 10.1158/0008-5472.CAN-08-2147.
Kelland, Of mice and men: values and liabilities of the athymic nude mouse model in anticancer drug development. Eur J Cancer. Apr. 2004;40(6):827-36.
Kerbel, Human tumor xenografts as predictive preclinical models for anticancer drug activity in humans: better than commonly perceived-but they can be improved. Cancer Biol Ther. Jul.-Aug. 2003;2(4 Suppl 1):S134-9.
Kim et al., Occurrence of ionophore antibiotics in water and sediments of a mixed-landscape watershed. Water Res. Jul. 2006;40(13):2549-60.
Klein et al., Targeting the EGFR and the PKB pathway in cancer. Curr Opin Cell Biol. Apr. 2009;21(2):185-93. doi: 10.1016/j.ceb.2008.12.006. Epub Feb. 11, 2009.
Krawetz et al., Wnt6 induces the specification and epithelialization of F9 embryonal carcinoma cells to primitive endoderm. Cell Signal. Mar. 2008;20(3):506-17. Epub Nov. 7, 2007.
Kunz-Schughart et al., The use of 3-D cultures for high-throughput screening: the multicellular spheroid model. J Biomol Screen. Jun. 2004;9(4):273-85.
Lamouille et al., Molecular mechanisms of epithelial-mesenchymal transition. Nat Rev Mol Cell Biol. Mar. 2014;15(3):178-96. doi: 10.1038/nrm3758.

(56) References Cited

OTHER PUBLICATIONS

Lee et al., The epithelial-mesenchymal transition: new insights in signaling, development, and disease. J Cell Biol. Mar. 27, 2006;172(7):973-81.
Lester et al., uPAR induces epithelial-mesenchymal transition in hypoxic breast cancer cells. J Cell Biol. Jul. 30, 2007;178(3):425-36.
Li et al., Identification of pancreatic cancer stem cells. Cancer Res. Feb. 1, 2007;67(3):1030-7.
Lim et al., Epigenetic changes induced by reactive oxygen species in hepatocellular carcinoma: methylation of the E-cadherin promoter. Gastroenterology. Dec. 2008;135(6):2128-40, 2140.e1-8. doi: 10.1053/j.gastro.2008.07.027. Epub Jul. 31, 2008.
Littlewood et al., A modified oestrogen receptor ligand-binding domain as an improved switch for the regulation of heterologous proteins. Nucleic Acids Res. May 25, 1995;23(10):1686-90.
Liu et al., Activated androgen receptor downregulates E-cadherin gene expression and promotes tumor metastasis. Mol Cell Biol. Dec. 2008;28(23):7096-108. doi: 10.1128/MCB.00449-08. Epub Sep. 15, 2008.
Liu et al., Analysis of gene expression and chemoresistance of CD133+ cancer stem cells in glioblastoma. Mol Cancer. Dec. 2, 2006;5:67.
Liu et al., The prognostic role of a gene signature from tumorigenic breast-cancer cells. N Engl J Med. Jan. 18, 2007;356(3):217-26.
Lo et al., Epidermal growth factor receptor cooperates with signal transducer and activator of transcription 3 to induce epithelial-mesenchymal transition in cancer cells via up-regulation of TWIST gene expression. Cancer Res. Oct. 1, 2007;67(19):9066-76.
Mani et al., The epithelial-mesenchymal transition generates cells with properties of stem cells. Cell. May 16, 2008;133(4):704-15.
Manotham et al., Transdifferentiation of cultured tubular cells induced by hypoxia. Kidney Int. Mar. 2004;65(3):871-80.
Mitani et al., Salinomycin: a new monovalent cation ionophore. Biochem Biophys Res Commun. Oct. 27, 1975;66(4):1231-6.
Molina-Oritiz et al., Functional characterization of Snail2 mediated E-cadherin repression. Int Workshop Cancer Stem Cells. 2$^{nd}$ ed. Dec. 2, 2007;65.
Morel et al., Generation of breast cancer stem cells through epithelial-mesenchymal transition. PLoS One. Aug. 6, 2008;3(8):e2888.
Moustakas et al., Signaling networks guiding epithelial-mesenchymal transitions during embryogenesis and cancer progression. Cancer Sci. Oct. 2007;98(10):1512-20. Epub Jul. 23, 2007.
Mushinski et al., Inhibition of tumor cell motility by the interferon-inducible GTPase MxA. J Biol Chem. May 29, 2009;284(22):15206-14. doi: 10.1074/jbc.M806324200. Epub Mar. 18, 2009.
Nakamura et al., Polarized hydroxyapatite promotes spread and motility of osteoblastic cells. J Biomed Mater Res A. Feb. 2010;92(2):783-90. doi: 10.1002/jbm.a.32404.
O'Brien et al., A human colon cancer cell capable of initiating tumour growth in immunodeficient mice. Nature. Jan. 4, 2007;445(7123):106-10. Epub Nov. 19, 2006.
Onder et al., Loss of E-cadherin promotes metastasis via multiple downstream transcriptional pathways. Cancer Res. May 15, 2008;68(10):3645-54.
Pagliarini et al., A genetic screen in Drosophila for metastatic behavior. Science. Nov. 14, 2003;302(5648):1227-31. Epub Oct. 9, 2003.
Pérez-Caro et al., Killing time for cancer stem cells (CSC): discovery and development of selective CSC inhibitors. Curr Med Chem. 2006;13(15):1719-25.
Phillips et al., The response of CD24(-/low)/CD44+ breast cancer-initiating cells to radiation. J Natl Cancer Inst. Dec. 20, 2006;98(24):1777-85.
Qin et al., The mammalian Scribble polarity protein regulates epithelial cell adhesion and migration through E-cadherin. J Cell Biol. Dec. 19, 2005;171(6):1061-71. Epub Dec. 12, 2005.
Ricci-Vitiani et al., Identification and expansion of human colon-cancer-initiating cells. Nature. Jan. 4, 2007;445(7123):111-5. Epub Nov. 19, 2006.
Sakai et al., Inducible expression of p57KIP2 inhibits glioma cell motility and invasion. J Neuro-oncol. Jul. 2004;68(3):217-23.
Sato et al., Targeted disruption of TGF-beta1/Smad3 signaling protects against renal tubulointerstitial fibrosis induced by unilateral ureteral obstruction. J Clin Invest. Nov. 2003;112(10):1486-94.
Shipitsin et al., Molecular definition of breast tumor heterogeneity. Cancer Cell. Mar. 2007;11(3):259-73.
Singh et al., Identification of human brain tumour initiating cells. Nature. Nov. 18, 2004;432(7015):396-401.
Sledge et al., Phase III trial of doxorubicin, paclitaxel, and the combination of doxorubicin and paclitaxel as front-line chemotherapy for metastatic breast cancer: an intergroup trial (E1193). J Clin Oncol. Feb. 15, 2003;21(4):588-92.
Sobrado et al., New insight in the regulation of E-cadherin and EMT: the role of BHLH factors E2-A2 and E2-2B. Int Workshop Cancer Stem Cells. 2$^{nd}$ ed. Dec. 2, 2007;88.
Stewart et al., Lentivirus-delivered stable gene silencing by RNAi in primary cells. RNA. Apr. 2003;9(4):493-501.
Stingl et al., Purification and unique properties of mammary epithelial stem cells. Nature. Feb. 23, 2006;439(7079):993-7. Epub Jan. 4, 2006.
Szotek et al., Ovarian cancer side population defines cells with stem cell-like characteristics and Mullerian Inhibiting Substance responsiveness. Proc Natl Acad Sci U S A. Jul. 25, 2006;103(30):11154-9. Epub Jul. 18, 2006.
Tam et al., Protein kinase C α is a central signaling node and therapeutic target for breast cancer stem cells. Cancer Cell. Sep. 9, 2013;24(3):347-64. doi: 10.1016/j.ccr.2013.08.005.
Tang et al., C3a mediates epithelial-to-mesenchymal transition in proteinuric nephropathy. J Am Soc Nephrol. Mar. 2009;20(3):593-603. doi: 10.1681/ASN.2008040434. Epub Jan. 21, 2009.
Tang et al., Cancer stem cell: target for anti-cancer therapy. FASEB J. Dec. 2007;21(14):3777-85. Epub Jul. 11, 2007.
Templeton et al., Cancer stem cells: progress and challenges in lung cancer. Stem Cell Investigation. 2014;1:9.
Thiery, Epithelial-mesenchymal transitions in tumour progression. Nat Rev Cancer. Jun. 2002;2(6):442-54.
Wahab et al., A critical look at growth factors and epithelial-to-mesenchymal transition in the adult kidney. Interrelationships between growth factors that regulate EMT in the adult kidney. Nephron Exp Nephrol. 2006;104(4):e129-34. Epub Aug. 10, 2006.
Yang et al., Twist, a master regulator of morphogenesis, plays an essential role in tumor metastasis. Cell. Jun. 25, 2004;117(7):927-39.
Zavadil et al., TGF-beta and epithelial-to-mesenchymal transitions. Oncogene. Aug. 29, 2005;24(37):5764-74.
Zeng et al., Biliverdin reductase mediates hypoxia-induced EMT via PI3-kinase and Akt. J Am Soc Nephrol. Feb. 2008;19(2):380-7. doi: 10.1681/ASN.2006111194. Epub Jan. 9, 2008.
Carell et al., A Novel Procedure for the Synthesis of Libraries Containing Small Organic Molecules. Angew. Chem. Int. Ed. Engl. 1994;33: 2059-2061. doi:10.1002/anie.199420591.
Carell et al., A Solution-Phase Screening Procedure for the Isolation of Active Compounds from a Library of Molecules. Angew. Chem. Int. Ed. Engl. 1994;33: 2061-2064.
Carter et al., Antisense technology for cancer therapy: does it make sense? Br J Cancer. May 1993;67(5):869-76.
Cho et al., An unnatural biopolymer. Science. Sep. 3, 1993;261(5126):1303-5.
Choung et al., Chemical modification of siRNAs to improve serum stability without loss of efficacy. Biochem Biophys Res Commun. Apr. 14, 2006;342(3):919-27.
Cull et al., Screening for receptor ligands using large libraries of peptides linked to the C terminus of the lac repressor. Proc Natl Acad Sci U S A. Mar. 1, 1992;89(5):1865-9.
Cwirla et al., Peptides on phage: a vast library of peptides for identifying ligands. Proc Natl Acad Sci U S A. Aug. 1990;87(16):6378-82.
Czarnik, Encoding methods for combinatorial chemistry. Curr Opin Chem Biol. Jun. 1997;1(1):60-6.
De Paula et al., Hydrophobization and bioconjugation for enhanced siRNA delivery and targeting. RNA. Apr. 2007;13(4):431-56.

(56) References Cited

OTHER PUBLICATIONS

Devlin et al., Random peptide libraries: a source of specific protein binding molecules. Science. Jul. 27, 1990;249(4967):404-6.

Dewitt et al.,"Diversomers": an approach to nonpeptide, nonoligomeric chemical diversity. Proc Natl Acad Sci U S A. Aug. 1, 1993;90(15):6909-13.

Dosaka-Akita et al., Abnormal p53 expression in human lung cancer is associated with histologic subtypes and patient smoking history. Am J Clin Pathol. Nov. 1994;102(5):660-4.

Erb et al., Recursive deconvolution of combinatorial chemical libraries. Proc Natl Acad Sci U S A. Nov. 22, 1994;91(24):11422-6.

Felici et al., Selection of antibody ligands from a large library of oligopeptides expressed on a multivalent exposition vector. J Mol Biol. Nov. 20, 1991;222(2):301-10.

Feng et al., Neoplastic reversion accomplished by high efficiency adenoviral-mediated delivery of an anti-ras ribozyme. Cancer Res. May 15, 1995;55(10):2024-8.

Fernandes, Technological advances in high-throughput screening. Curr Opin Chem Biol. Oct. 1998;2(5):597-603.

Fodor et al., Multiplexed biochemical assays with biological chips. Nature. Aug. 5, 1993;364(6437):555-6.

French et al., Antitumor activity of sphingosine kinase inhibitors. J Pharmacol Exp Ther. Aug. 2006;318(2):596-603.

Gallop et al., Applications of combinatorial technologies to drug discovery. 1. Background and peptide combinatorial libraries. J Med Chem. Apr. 29, 1994;37(9):1233-51.

Herschlag et al., An RNA chaperone activity of non-specific RNA binding proteins in hammerhead ribozyme catalysis. EMBO J. Jun. 15, 1994;13(12):2913-24. Erratum in: EMBO J Aug. 15, 1994;13(16):3926.

Houghten et al., The use of synthetic peptide combinatorial libraries for the identification of bioactive peptides. Biotechniques. Sep. 1992;13(3):412-21.

Iwase et al., Synthesis and properties of modified siRNA having amide-linked oligoribonucleosides at their 3' overhang regions. Nucleic Acids Symp Ser (Oxf). 2006;(50):175-6.

Jankowsky et al., Oligonucleotide facilitators may inhibit or activate a hammerhead ribozyme. Nucleic Acids Res. Feb. 1, 1996;24(3):423-9.

Jones et al., Tagging ribozyme reaction sites to follow trans-splicing in mammalian cells. Nat Med. Jun. 1996;2(6):643-8.

Lam et al., A new type of synthetic peptide library for identifying ligand-binding activity. Nature. Nov. 7, 1991;354:82-84. doi:10.1038/354082a0.

Lam, Application of combinatorial library methods in cancer research and drug discovery. Anticancer Drug Des. Apr. 1997;12(3):145-67.

Lange et al., In vitro and in vivo effects of synthetic ribozymes targeted against BCR/ABL mRNA. Leukemia. Nov. 1993;7(11):1786-94.

Lewin et al., Ribozyme rescue of photoreceptor cells in a transgenic rat model of autosomal dominant retinitis pigmentosa. Nat Med. Aug. 1998;4(8):967-71. Erratum in: Nat Med Sep. 1998;4(9):1081.

Lim et al., FTY720 analogues as sphingosine kinase 1 inhibitors: enzyme inhibition kinetics, allosterism, proteasomal degradation, and actin rearrangement in MCF-7 breast cancer cells. J Biol Chem. May 27, 2011;286(21):18633-40. doi: 10.1074/jbc.M111.220756.

Neve et al., A collection of breast cancer cell lines for the study of functionally distinct cancer subtypes. Cancer Cell. Dec. 2006;10(6):515-27.

Ohkawa et al., Multiple site-specific cleavage of HIV RNA by transcribed ribozymes from shotgun-type trimming plasmid. Nucleic Acids Symp Ser. 1993;(29):121-2.

Pyne et al., Sphingosine kinase inhibitors and cancer: seeking the golden sword of Hercules. Cancer Res. Nov. 1, 2011;71(21):6576-82. doi:10.1158/0008-5472.CAN-11-2364.

Quattrone et al., Reversion of the invasive phenotype of transformed human fibroblasts by anti-messenger oligonucleotide inhibition of urokinase receptor gene expression. Cancer Res. Jan. 1, 1995;55(1):90-5.

Sawhney et al., Bioerodible hydrogels based on photopolymerized poly(ethylene glycol)-co-poly(.alpha.-hydroxy acid) diacrylate macromers. Macromolecules. 1993;26(4):581-587.

Scott et al., Searching for peptide ligands with an epitope library. Science. Jul. 27, 1990;249(4967):386-90.

Sullenger et al., Ribozyme-mediated repair of defective mRNA by targeted, trans-splicing. Nature. Oct. 13, 1994;371(6498):619-22.

Sundberg, High-throughput and ultra-high-throughput screening: solution- and cell-based approaches. Curr Opin Biotechnol. Feb. 2000;11(1):47-53.

Thomson et al., Kinase switching in mesenchymal-like non-small cell lung cancer lines contributes to EGFR inhibitor resistance through pathway redundancy. Clin Exp Metastasis. 2008;25(8):843-54. doi: 10.1007/s10585-008-9200-4.

Tonelli et al., FTY720 and (S)-FTY720 vinylphosphonate inhibit sphingosine kinase 1 and promote its proteasomal degradation in human pulmonary artery smooth muscle, breast cancer and androgen-independent prostate cancer cells. Cell Signal. Oct. 2010;22(10):1536-42. doi: 10.1016/j.cellsig.2010.05.022.

Valera et al., Expression of GLUT-2 antisense RNA in beta cells of transgenic mice leads to diabetes. J Biol Chem. Nov. 18, 1994;269(46):28543-6.

Xia et al., Gene silencing activity of siRNAs with a ribodifluorotoluyl nucleotide. ACS Chem Biol. Apr. 25, 2006;1(3):176-83.

Young et al., Integrating high-content screening and ligand-target prediction to identify mechanism of action. Nat Chem Biol. Jan. 2008;4(1):59-68.

Zuckermann et al. Discovery of nanomolar ligands for 7-transmembrane G-protein-coupled receptors from a diverse N-(substituted)glycine peptoid library. J Med Chem. Aug. 19, 1994;37(17):2678-85.

PCT/US2009/002254, Dec. 2, 2009, International Search Report and Written Opinion.

PCT/US2009/002254, Oct. 21, 2010, International Preliminary Report and Patentability.

EP 09729661.0, Oct. 7, 2011, Extended European Search Report.
EP 11158438.9, Oct. 7, 2011, Extended European Search Report.
PCT/US2013/069121, May 21, 2015, International Preliminary Report on Patentability.
PCT/US2013/069121, Mar. 13, 2014, International Search Report and Written Opinion.
PCT/US2015/028239, Jul. 15, 2015, International Search Report and Written Opinion.

\* cited by examiner

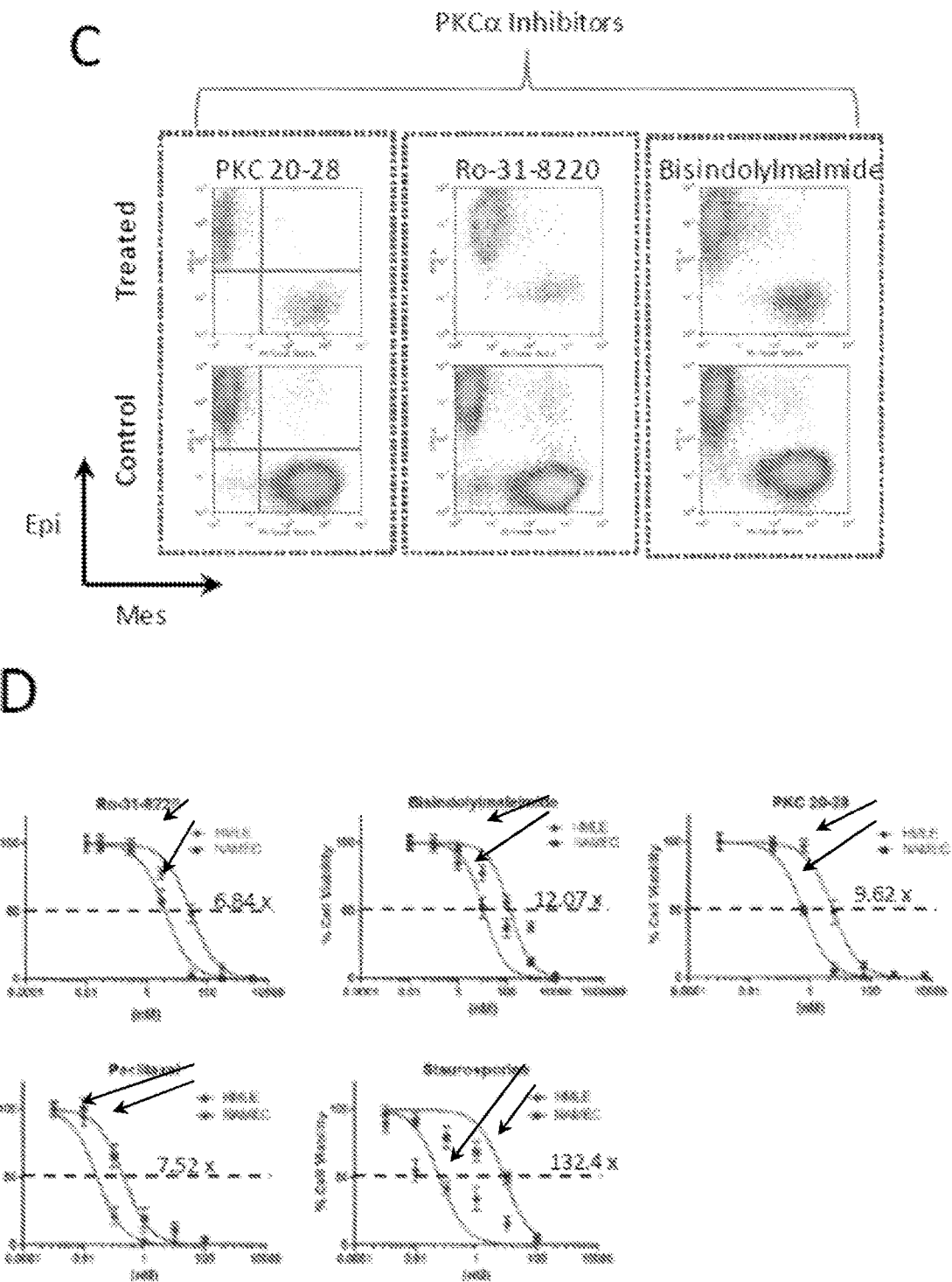
FIG. 2 – cont.

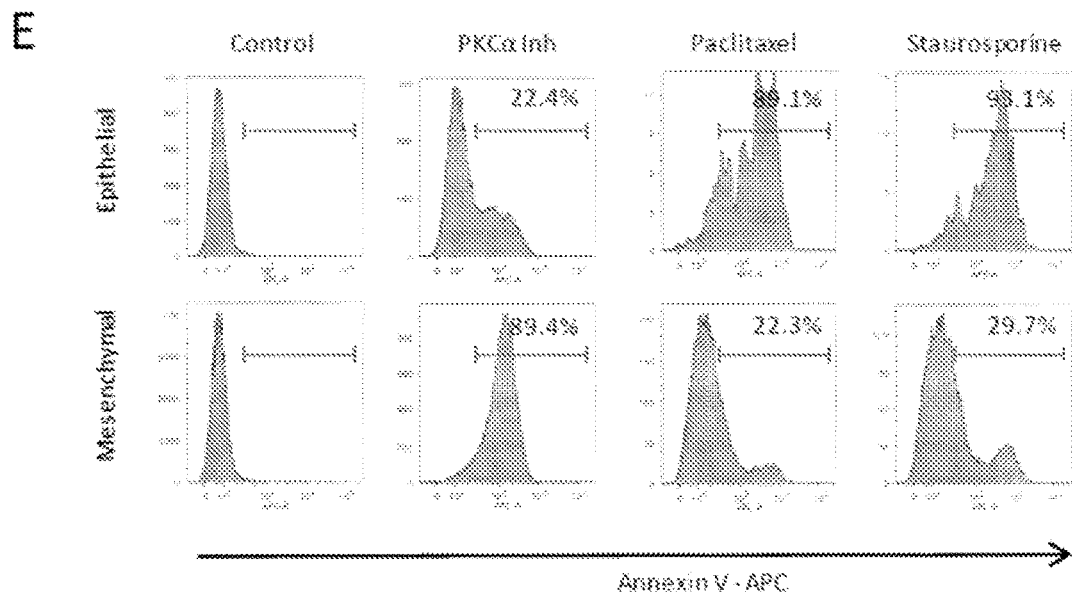
FIG. 2 – cont.

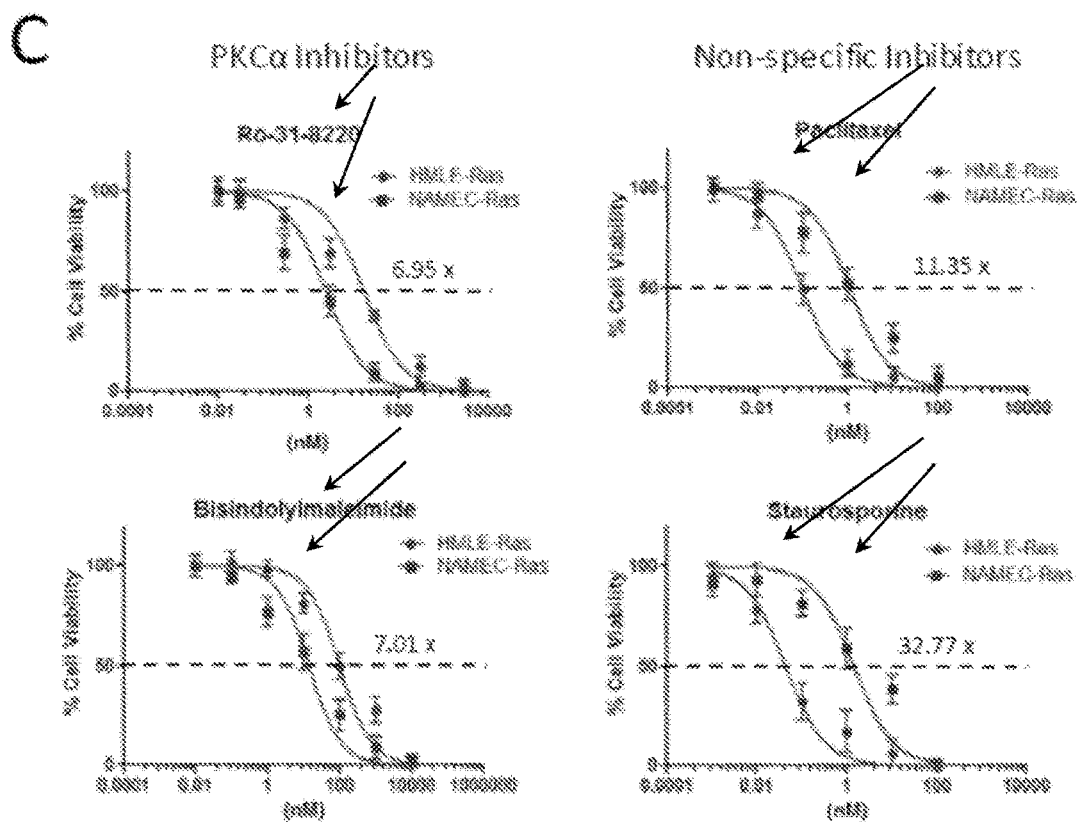
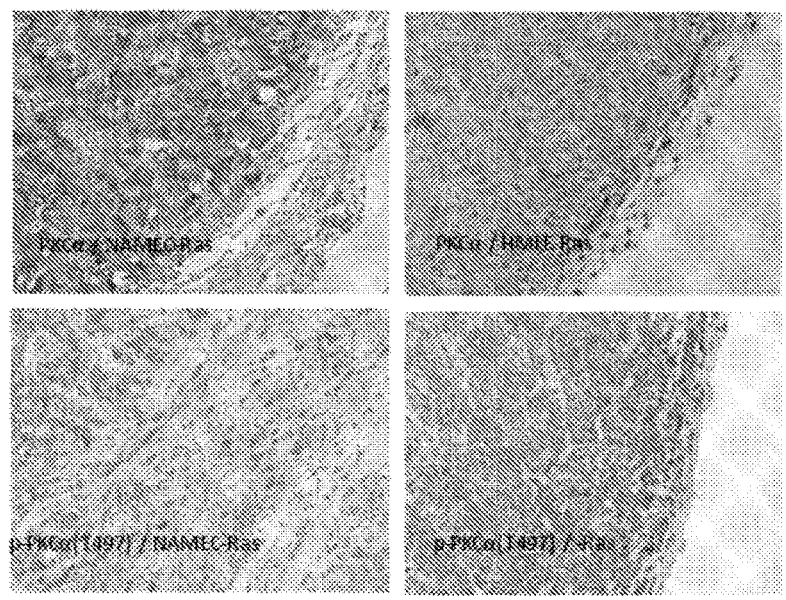
FIG. 3 – cont.

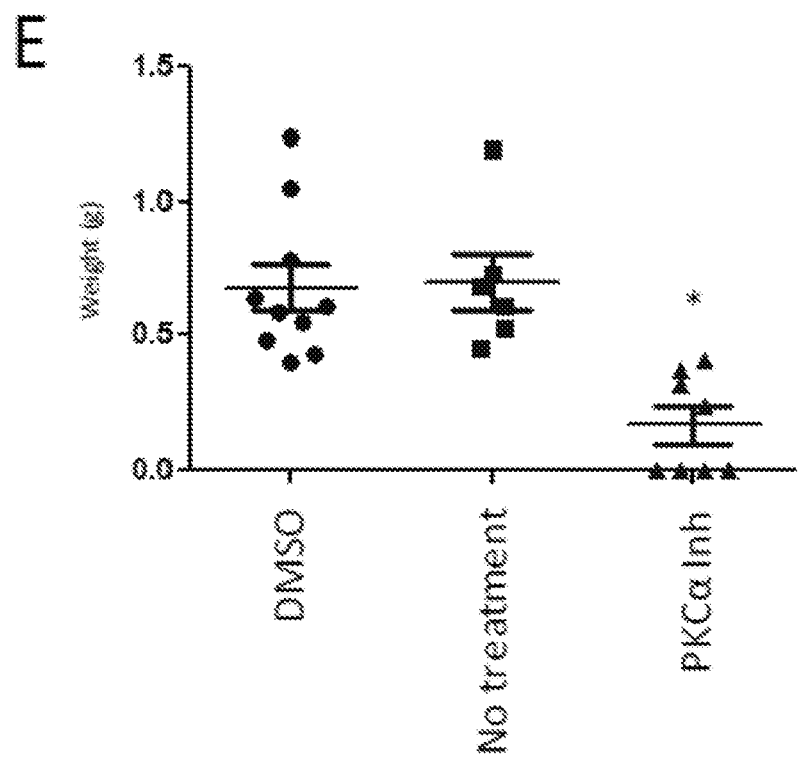
FIG. 3 – cont.

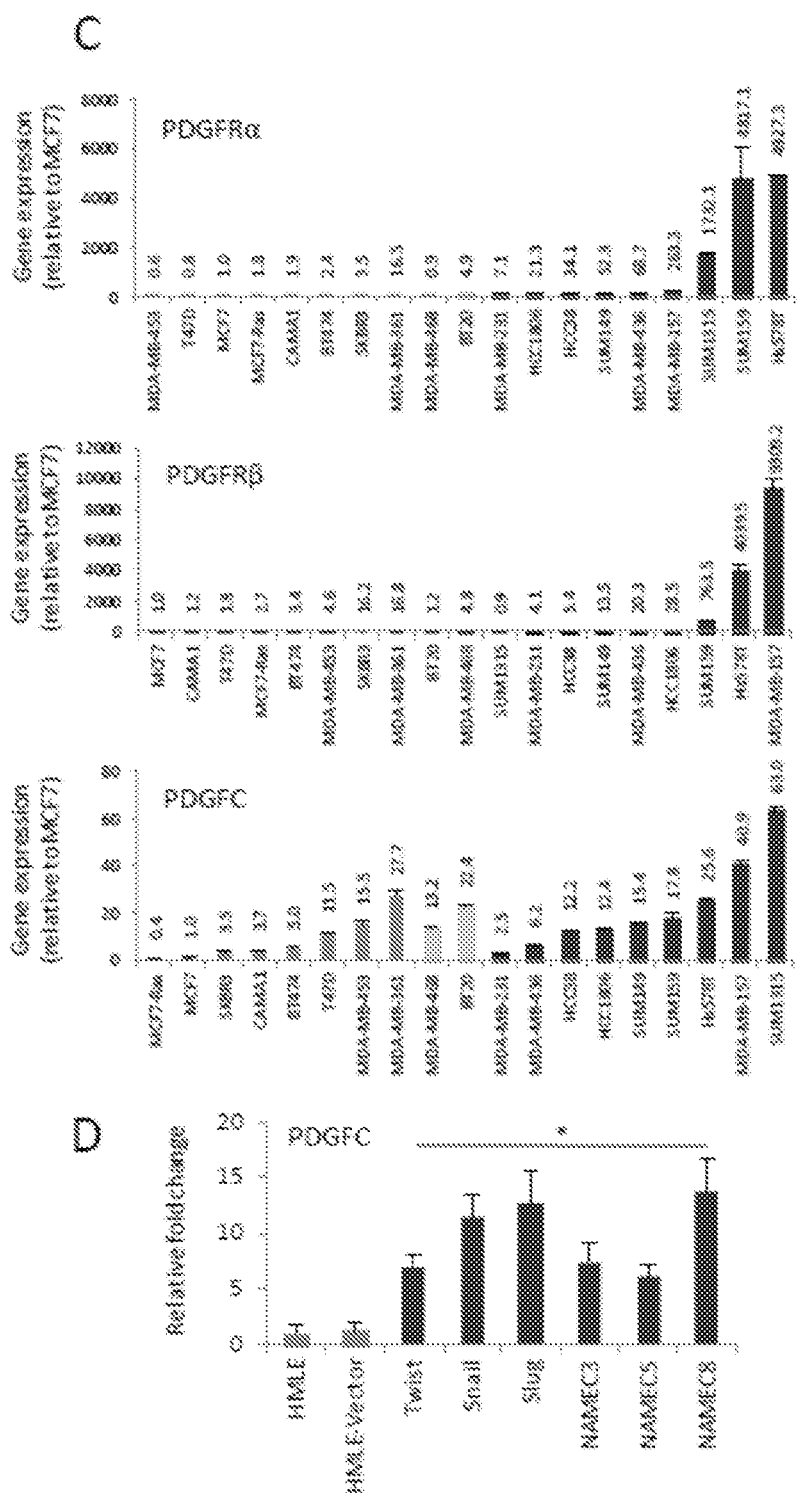
FIG. 4 – cont.

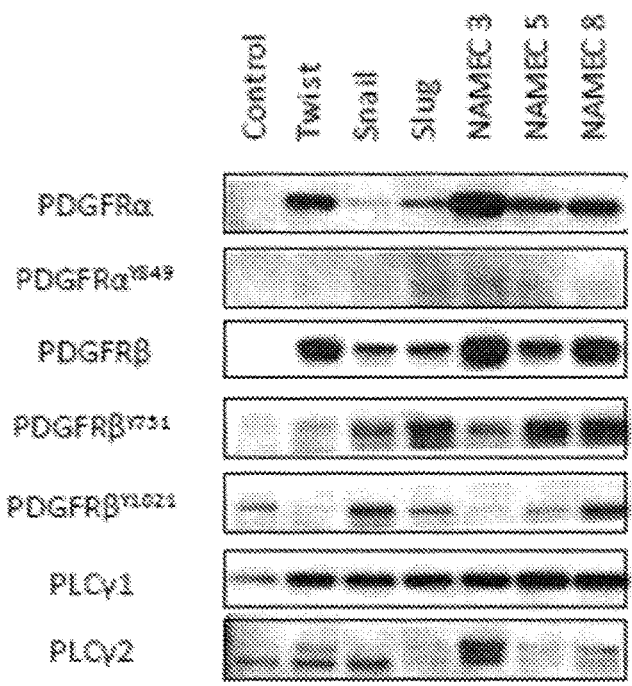
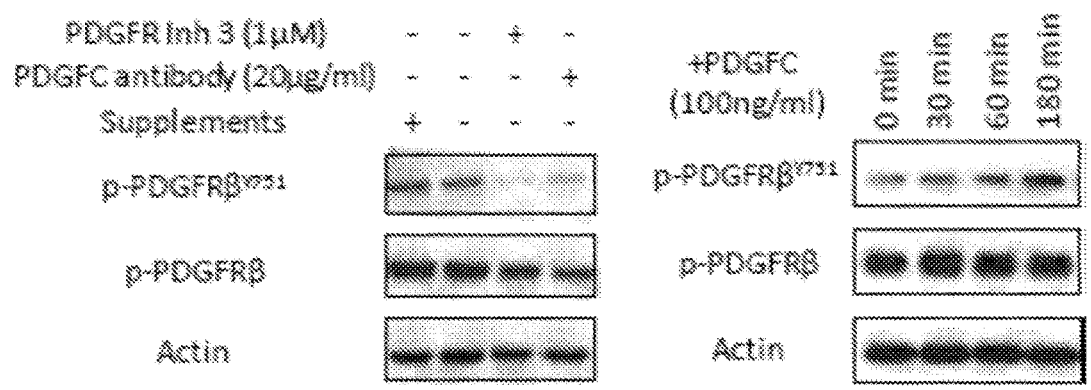
FIG. 4 – cont.

G
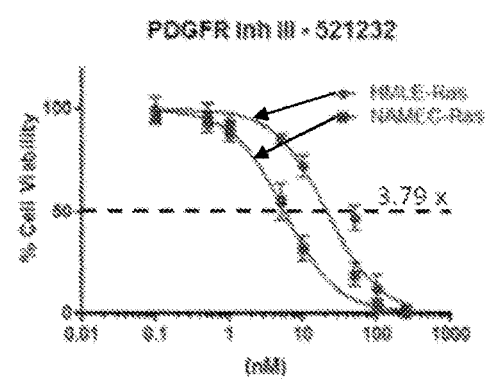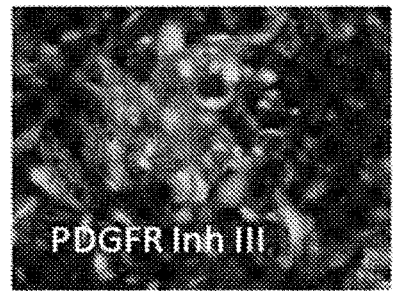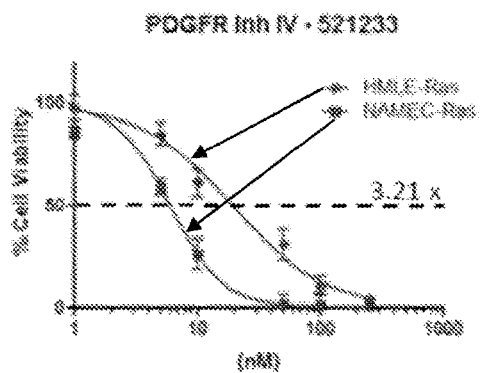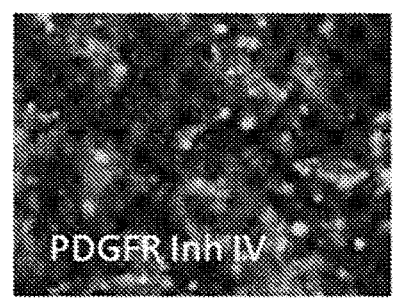
FIG. 4 – cont.

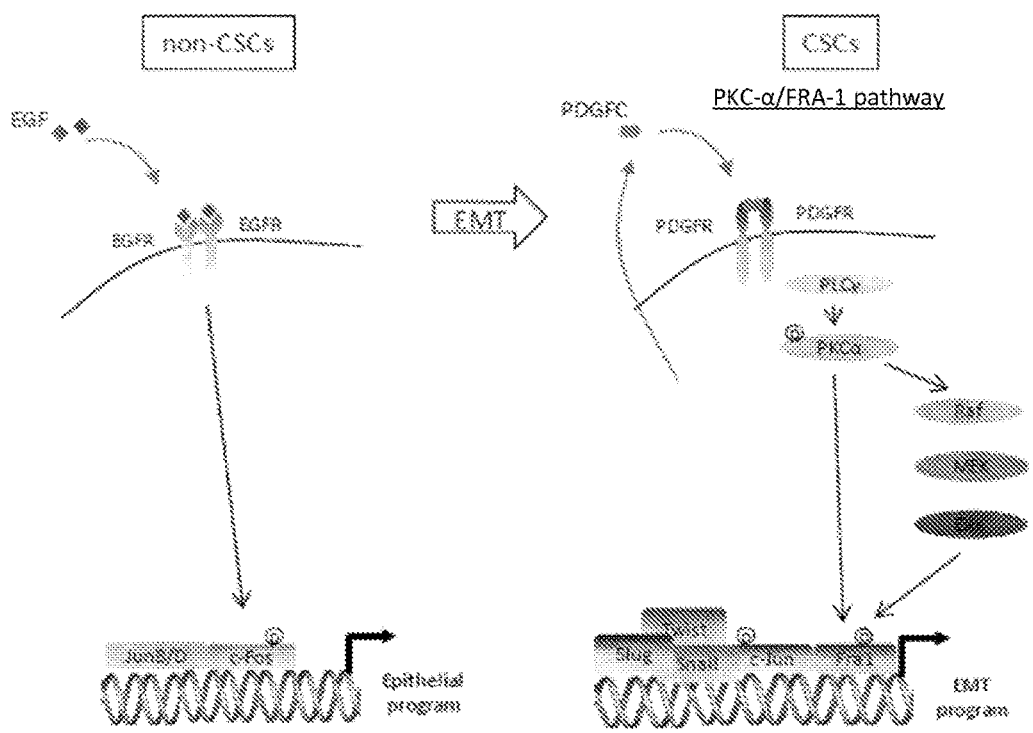
FIG. 4 – cont.

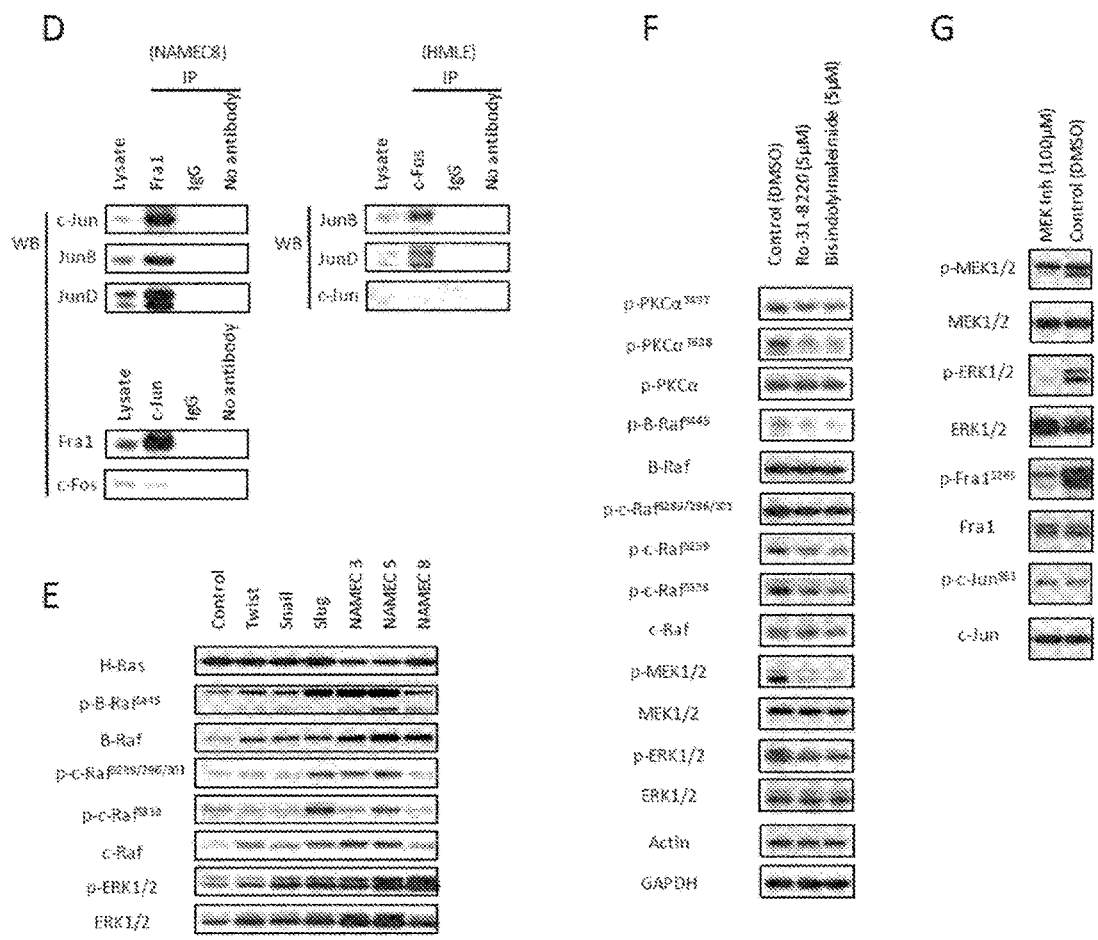
FIG. 5 - cont.

E
Fra1
| | Absent/Weak | Moderate | Strong |
|---|---|---|---|
| Grade 1 | 39 | 7 | 1 |
| Grade 2 | 45 | 9 | 3 |
| Grade 3 | 18* | 23* | 15* |
| Normal | 26 | 0 | 1 |
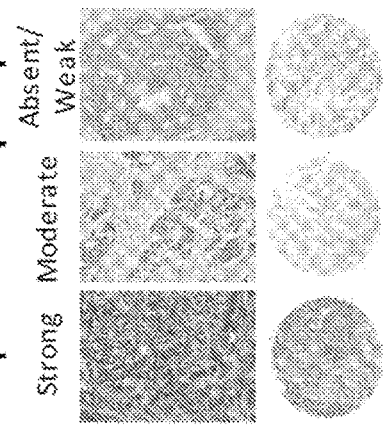
PKCα
| | Absent/Weak | Moderate | Strong |
|---|---|---|---|
| Grade 1 | 28 | 17 | 3 |
| Grade 2 | 27 | 24 | 6 |
| Grade 3 | 19 | 21 | 16* |
| Normal | 23 | 3 | 1 |
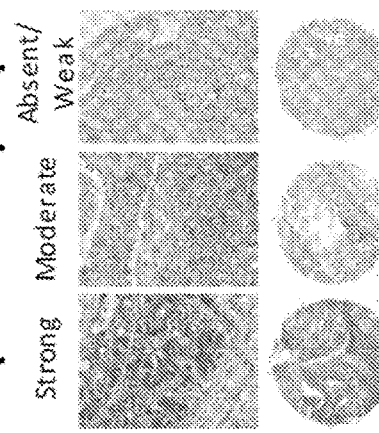
FIG. 7 - cont.

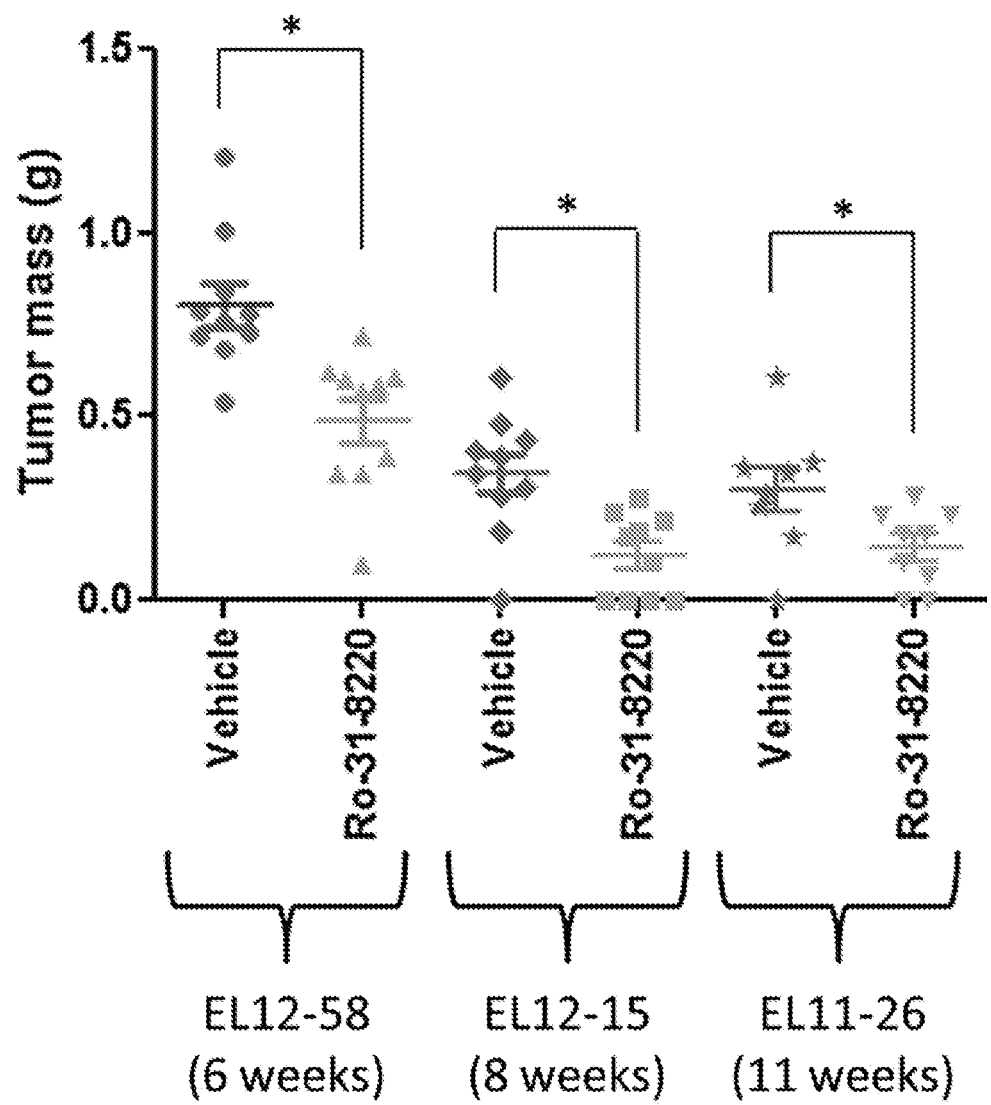
FIG. 7 - cont.

| Gene | RefSeq | Twist | Snail | Slug |
|---|---|---|---|---|
| FOSL1 | NM_005438.2 | 1.88 | 1.68 | 1.76 |
| ANXA2 | NM_001002857.1 | 1.43 | 1.87 | 1.46 |
| VCL | NM_003373.3 | 1.37 | 1.33 | 1.10 |
| GRK5 | NM_005308.2 | 1.18 | 1.42 | 1.70 |
| RALB | NM_002881.2 | 1.17 | 1.09 | 1.15 |
| ANXA4 | NM_001153.2 | 1.15 | 1.25 | 1.18 |
| FOSB | NM_006732.1 | 1.12 | 1.26 | 1.57 |
| LMNA | NM_005572.3 | 1.11 | 1.06 | 1.03 |
| CTNNB1 | NM_001098209.1 | 1.10 | 0.78 | 0.82 |
| TNNT2 | NM_001001431.1 | 1.07 | 1.09 | 1.04 |
| NR1H4 | NM_005123.1 | 1.07 | 1.03 | 0.98 |
| HMGB1 | NM_002128.4 | 1.05 | 1.04 | 1.28 |
| FOSL2 | NM_005253.3 | 1.04 | 1.08 | 1.02 |
| FXYD1 | NM_021902.2 | 1.03 | 1.01 | 0.97 |
| GRLF1 | NM_004491.4 | 1.02 | 1.01 | 0.91 |
| RPS6 | NM_001010.2 | 1.02 | 0.98 | 0.92 |
| TUBA1C | NM_032704.2 | 1.02 | 1.03 | 1.00 |
| ADRBK1 | NM_001619.2 | 1.00 | 1.01 | 0.94 |
| MARCKS | NM_002356.5 | 1.00 | 0.90 | 1.28 |
| KIT | NM_000222.1 | 1.00 | 1.06 | 0.97 |
| LMNA | NM_005572.3 | 0.97 | 1.03 | 1.07 |
| PDE3A | NM_000921.3 | 0.96 | 0.93 | 0.99 |
| TRPC6 | NM_004621.4 | 0.96 | 0.99 | 0.95 |
| PRKG1 | NM_006258.1 | 0.95 | 0.97 | 0.95 |
| CACNA1C | NM_000719.5 | 0.95 | 0.98 | 0.92 |
| KCNJ1 | NM_153766.1 | 0.95 | 0.95 | 0.89 |
| MBP | NM_001025100.1 | 0.93 | 0.34 | 0.65 |
| TP53 | NM_000546.3 | 0.91 | 0.83 | 0.83 |
| DNM1 | NM_001005336.1 | 0.89 | 0.93 | 0.98 |
| RAF1 | NM_002880.2 | 0.88 | 0.94 | 1.10 |
| ITGB4 | NM_001005731.1 | 0.88 | 0.54 | 0.45 |
| LMNB1 | NM_005573.2 | 0.87 | 0.74 | 0.85 |
| THOC5 | NM_001002878.1 | 0.84 | 0.96 | 1.00 |
| PLD1 | NM_002662.2 | 0.84 | 0.76 | 0.72 |
| ELAVL1 | NM_001419.2 | 0.79 | 0.78 | 0.90 |
| PICK1 | NM_012407.3 | 0.59 | 0.40 | 0.55 |
| MARCKSL1 | NM_023009.4 | 0.59 | 1.64 | 1.37 |
| FOS | NM_005252.2 | 0.46 | 0.35 | 0.41 |

FIG. 14

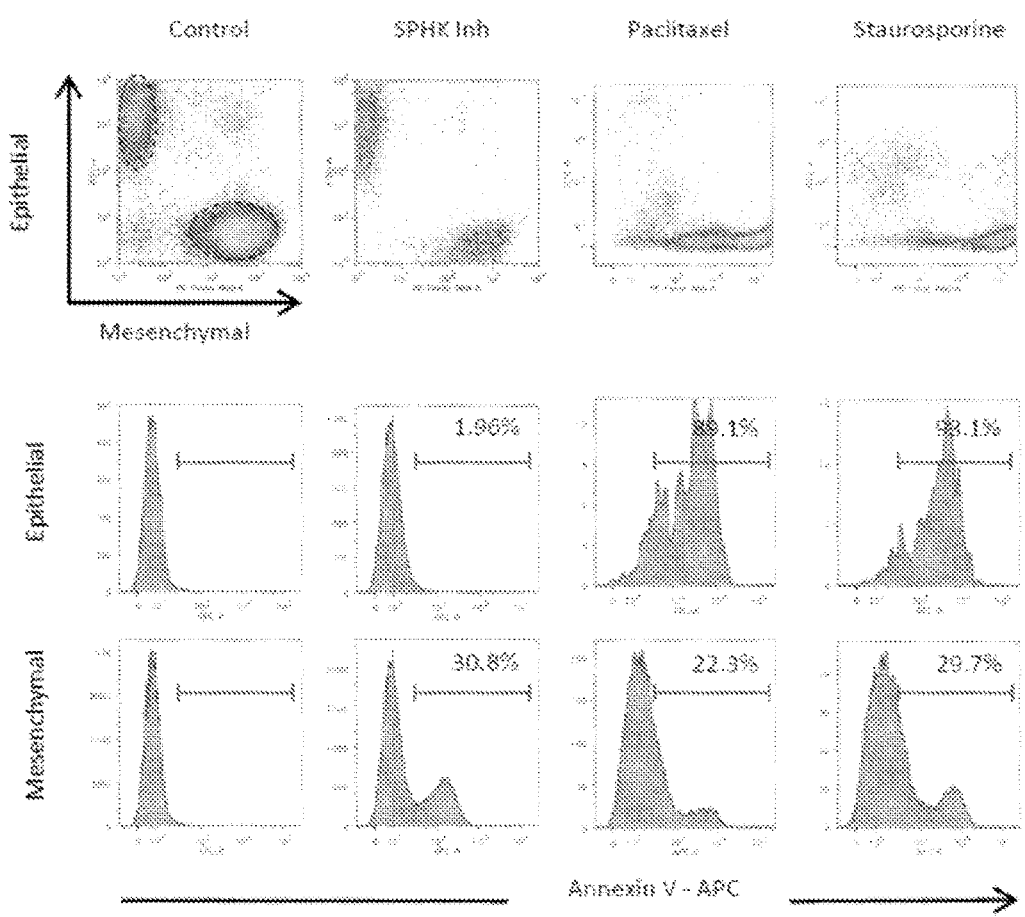
FIG. 21 - cont.

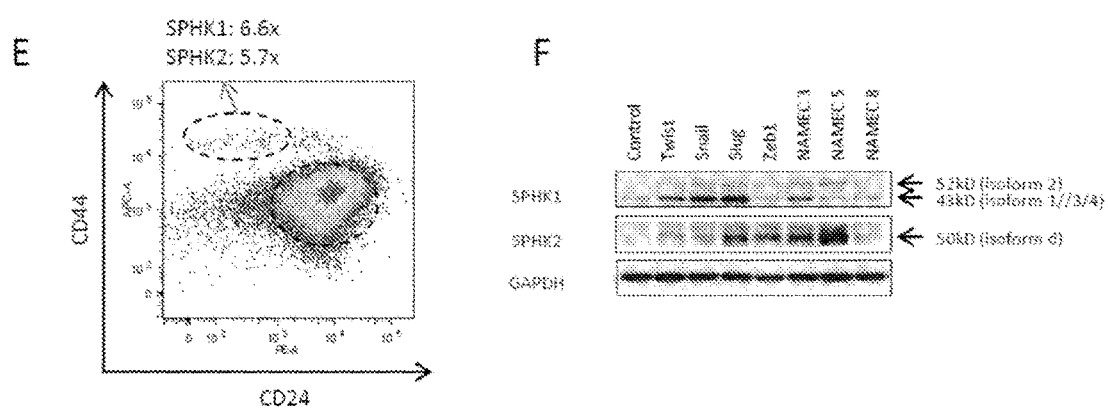
FIG. 21 - cont.

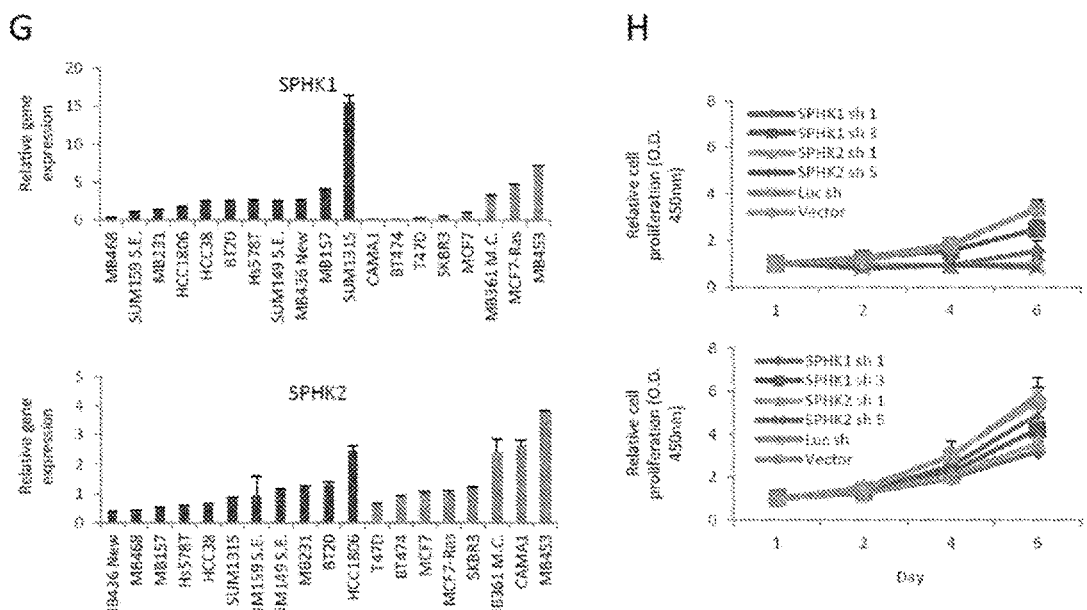
FIG. 21 - cont.

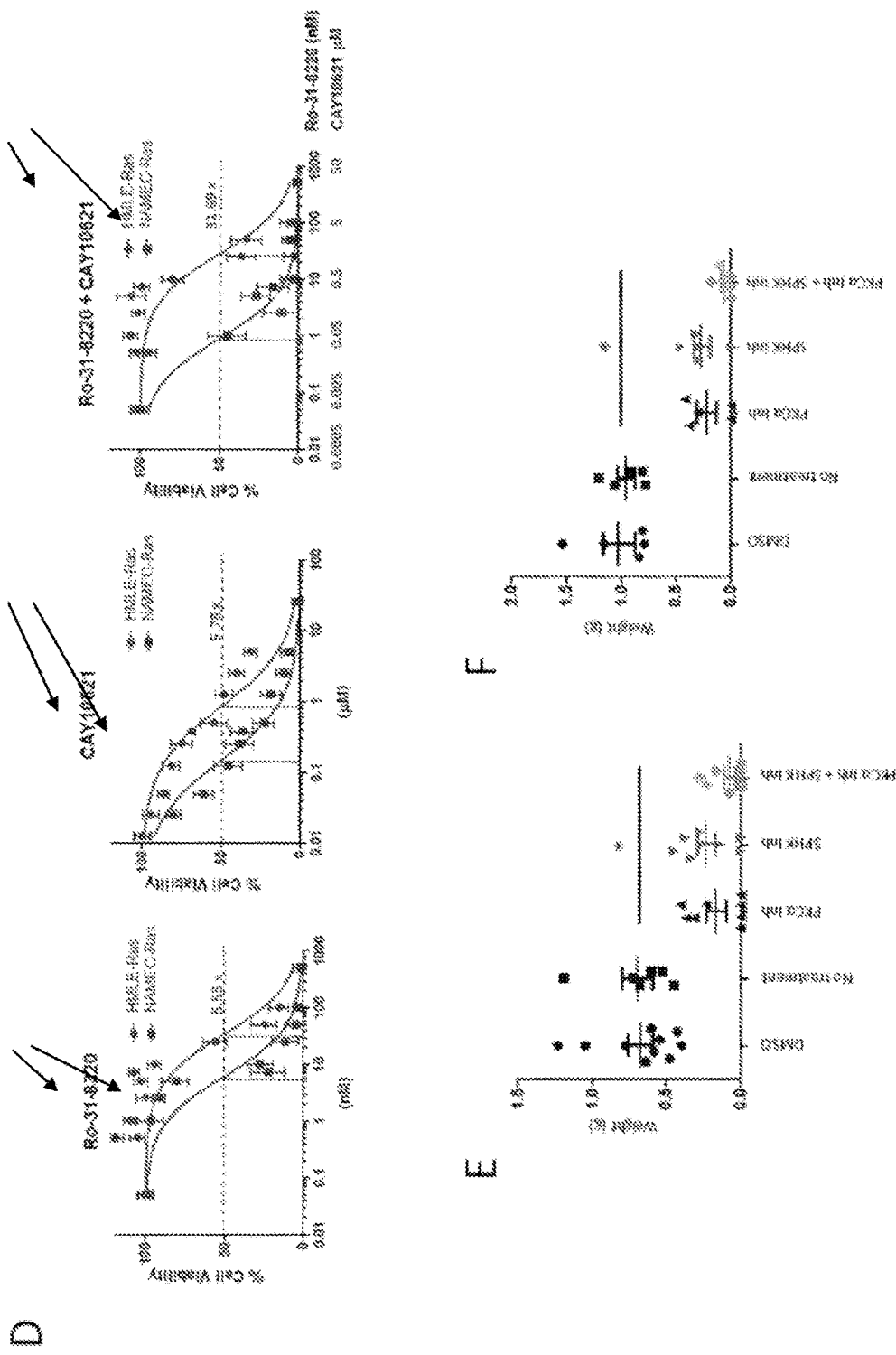
FIG. 22 - cont.

A

B

C
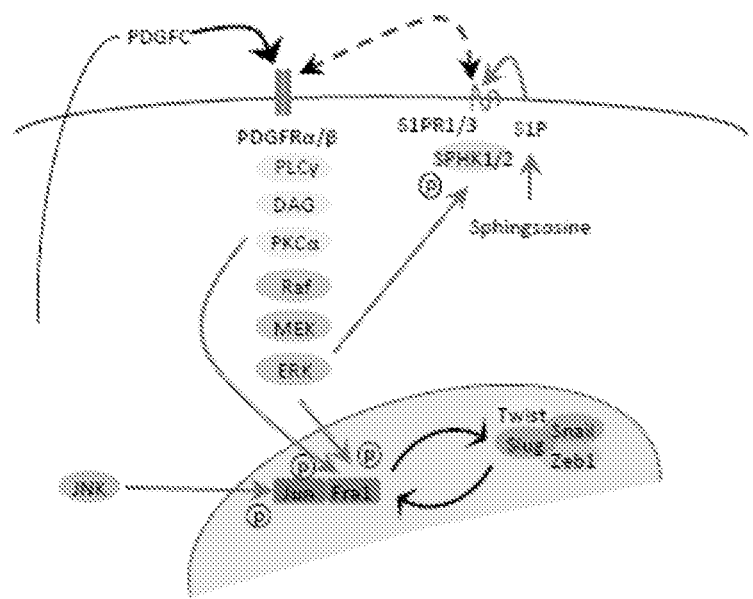
FIG. 23 - cont.

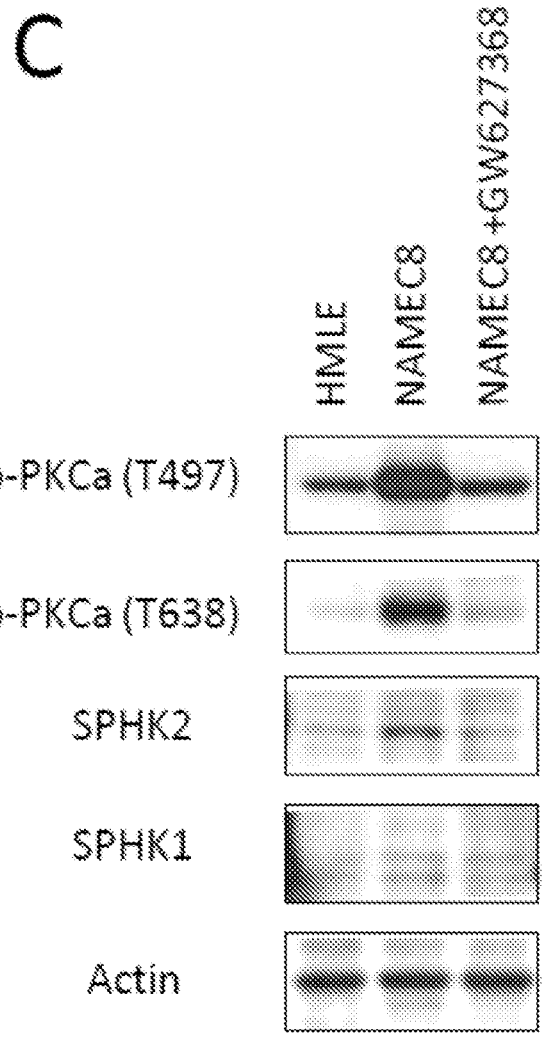
FIG. 25 - cont.

SELECTIVE TARGETING OF CANCER STEM CELLS

RELATED APPLICATION

This application is a national stage filing under U.S.C. § 371 of PCT International Application PCT/US2013/069121, entitled "SELECTIVE TARGETING OF CANCER STEM CELLS" with an international filing date of Nov. 8, 2013, which claims priority under 35 U.S.C. § 119(e) to U.S. Provisional Application Ser. No. 61/724,249, entitled "SELECTIVE TARGETING OF CANCER STEM CELLS" filed on Nov. 8, 2012, which are herein incorporated by reference in their entirety.

FEDERALLY SPONSORED RESEARCH

This invention was made with United States Government support under grants P01-CA080111 and R01-CA078461 awarded by the National Institutes of Health (NIH). The United States government has certain rights in the invention.

BACKGROUND OF INVENTION

Current cancer therapeutics often disrupt tumor growth by inhibiting rapidly proliferating cells, doing so via a variety of cytotoxic mechanisms. In fact, cells within many types of solid tumors often exhibit considerable phenotypic heterogeneity, and in some cases a certain subpopulation of cells appear to be responsible for driving tumor growth, recurrence and metastasis. The epithelial-mesenchymal transition (EMT) represents a cell-biological program that becomes activated during malignant progression and is associated with generation of invasive and cancer stem-like cells arising in epithelial tumors.

Cancer stem cells (CSCs), which possess tumor-initiating properties, have been identified within certain breast, colon, head and neck, lung and prostate carcinomas. In experimental models of cancer development, treatment of bulk cancer cells within tumors or cancer cells lines with chemo- or radiotherapy has been shown to select for the outgrowth of therapy-resistant subpopulations of cancer cells that are more tumorigenic, invasive and stem-like. Conventional cancer therapeutics tend to preferentially eliminate the non-CSCs in a tumor, leaving behind residues of CSCs that can subsequently generate clinical relapses.

SUMMARY OF INVENTION

Aspects of the invention are based in part on a recognition that effective treatment of carcinomas can be achieved by selectively targeting CSCs by inhibiting certain signaling pathways activated in CSCs but not in non-CSCs. Certain aspects of the invention are based on the discovery of regulatory genes uniquely associated with mesenchymal characteristics of an EMT whose expression is elevated in CSCs. In some embodiments, protein kinases are identified that are differentially utilized between different cellular states. These protein kinases provide therapeutic targets for inhibiting the growth and tumorigenic potential of CSCs.

In some embodiments, it has been found that inhibition of protein kinase Cα (PKCα)-Fos-related antigen 1 (FRA1) pathway signaling specifically targets cells that have undergone an EMT and are enriched for CSC properties, but has little discernible effect on the non-CSCs both in vitro and in vivo. In some embodiments, it has been found that formation of CSCs from non-stem cells involves a shift from epidermal growth factor receptor (EGFR) to platelet-derived growth factor receptor (PDGFR) signaling, which leads in turn to PKCα-dependent activation of downstream substrates that include the FRA1 subunit of the activator protein 1 (AP-1) transcription factor, as well as components of the extracellular-signal regulated kinase (ERK) signaling pathway. Accordingly, in some embodiments, methods are provided for inhibiting formation and growth of cancer stem cells that involve contacting CSCs with inhibitors of EGFR and/or PDGFR.

In some embodiments, it has been found that expression of PKCα and FRA1 are strongly induced upon passage through an EMT and in CSCs. In some embodiments, it has been found that expression of PKCα and FRA1 are clinically associated with more aggressive basal-like or triple-negative breast cancers. In some embodiments, loss of FRA1 expression in basal-like breast cancer cells that tend to bear mesenchymal features, brings about reversal of the EMT program, yielding a mesenchymal-epithelial transition (MET) and loss of tumor-initiating ability. Thus, in some embodiments, the identification of distinct molecular features that shift during the EMT cell-state transition and result in the enrichment of CSCs is exploited to provide a therapeutic window for targeting signaling components specifically active in CSCs. In some embodiments, methods are provided for inhibiting growth of cancer stem cells that involve contacting CSCs with inhibitors of FRA1. In some embodiments, it has been found that activity of the Sphingosine kinase (SPHK) pathway is increased in conjunction with PKCα upon passage through an EMT, and that inhibiting these signalling pathways in combination leads to synergistic elimination of CSCs.

Certain aspects of the invention relate to methods of inhibiting growth of carcinoma cells. In some embodiments, the methods comprise determining that carcinoma cells comprise cancer stem cells; and contacting the carcinoma cells with a PKC-α/FRA1 pathway inhibitor. In some embodiments, the methods comprise contacting the carcinoma cells with a PKC-α/FRA1 pathway inhibitor; and contacting the carcinoma cells with a sphingosine kinase pathway inhibitor. In some embodiments, the methods comprise contacting the carcinoma cells with a PKC-α inhibitor; and contacting the carcinoma cells with an EGFR inhibitor. In some embodiments, the methods comprise contacting the carcinoma cells with an inhibitor of a kinase listed in Table 6. In some embodiments, the methods comprise contacting the carcinoma cells with an inhibitor of PKCη, CLK1, CDK6 or JAK1. In some embodiments, the methods comprise contacting the carcinoma cells with an EGFR inhibitor. In some embodiments, the methods comprise contacting the cells with a sphingosine kinase pathway inhibitor. In some embodiments, the sphingosine kinase pathway inhibitor is a sphingosine kinase 1 inhibitor or sphingosine kinase 2 inhibitor. In some embodiments, the sphingosine kinase pathway inhibitor is a sphingosine-1-phosphate receptors 1 and 3 (S1PR1/3) antagonist, optionally which is VPC23019. In some embodiments, the carcinoma cells comprise basal-like breast cancer cells. In some embodiments, the carcinoma cells comprise cells arising from the airway epithelium, pancreas ductal epithelium, intestinal epithelium, prostate epithelium or breast epithelium. In some embodiments, the carcinoma cells are breast carcinoma cells characterized as $Her2^{neg}$, $ER^{neg}$, and $PR^{neg}$. In some embodiments, the methods further comprise determining the status of PKCα phosphorylation, wherein a reduction of PKCα phosphorylation at Serine 497 or Threonine 638 compared with an appropriate control indicates effectiveness of the PKC-α/FRA1 pathway inhibitor. In some embodiments, the methods further comprise determining the status of FRA1 phosphorylation, wherein a reduction of FRA1 phosphorylation at Serine 265 compared with an appropriate control indicates effectiveness of the PKC-α/FRA1 pathway inhibitor. In some embodiments, the methods further comprise determining the status of PLCγ phosphorylation, wherein a reduction of PLCγ phosphorylation at Tyrosine 783 or Tyrosine 1217 compared with an appropriate control indicates effectiveness of the PKC-α/FRA1 pathway inhibitor. In some embodiments, the methods further comprise determining the phosphorylation status of B-Raf, c-Raf, MEK1/2 or ERK1/2, wherein a reduction of phosphorylation B-Raf, c-Raf, MEK1/2 or ERK1/2 compared with an appropriate control indicates effectiveness of the PKC-α/FRA1 pathway inhibitor.

Certain aspects of the invention relate to methods of treating a subject having a carcinoma. In some embodiments, the methods comprise determining that the carcinoma comprises cancer stem cells; and administering to the subject an effective amount of a PKC-α/FRA1 pathway inhibitor. In some embodiments, the methods comprise administering to the subject an EGFR inhibitor or a sphingosine kinase pathway inhibitor. In some embodiments, the methods comprise administering to the subject an effective amount of a PKC-α/FRA1 pathway inhibitor; and administering to the subject an effective amount of a sphingosine kinase pathway inhibitor. In some embodiments, the methods comprise administering to the subject an effective amount of a PKC-α inhibitor; and administering to the subject an effective amount of an EGFR inhibitor. In some embodiments, the methods comprise determining that the carcinoma comprises cancer stem cells; and administering to the subject an effective amount of an EGFR inhibitor or a sphingosine kinase pathway inhibitor, and optionally administering to the subject a PKC-α/FRA1 pathway inhibitor. In some embodiments, the methods further comprise administering a non-CSC selective anti-cancer treatment to the subject. In some embodiments, the non-CSC selective anti-cancer treatment comprises surgery, radiation therapy, and/or a non-CSC selective chemotherapeutic agent. In some embodiments, the non-CSC selective chemotherapeutic agent has selective activity against non-CSC carcinoma cells. In some embodiments, the methods comprise (a) administering to the subject a therapy effective against non-CSC carcinoma cells; and (b) administering to the subject an EGFR inhibitor, a sphingosine kinase pathway inhibitor, and/or a PKC-α/FRA1 pathway inhibitor. In some embodiments, step (a) comprises administering to the subject radiation therapy or a non-CSC selective chemotherapeutic agent having selective activity against non-CSC carcinoma cells. In some embodiments, the at least one chemotherapeutic agent is a spindle poison, optionally which is paclitaxel, or a DNA replication inhibitor, optionally which is doxorubicin, or an alkylating agent, or a broad spectrum kinase inhibitor, optionally which is staurosporine, or a platinum-based compound, optional which is cisplatin. In some embodiments, the non-CSC selective chemotherapeutic agent has selective activity against non-CSC carcinoma cells. In some embodiments, the therapy effective against non-CSC carcinoma cells and the EGFR inhibitor, sphingosine kinase pathway inhibitor, and/or PKC-α/FRA1 pathway inhibitor are administered sequentially. In some embodiments, the therapy effective against non-CSC carcinoma cells and the EGFR inhibitor, sphingosine kinase pathway inhibitor, and/or PKC-α/FRA1 pathway inhibitor are administered sequentially within 1 hour, 1 day, 1 week, or 1 month of one another. In some embodiments, the therapy effective against non-CSC carcinoma cells and the EGFR inhibitor, sphingosine kinase pathway inhibitor, and/or PKC-α/FRA1 pathway inhibitor are administered concomitantly. In some embodiments, prior to one or both administrations the carcinoma is determined to contain basal-like cancer cells. In some embodiments, prior to one or both administrations the carcinoma is determined to be Her2$^{neg}$, ER$^{neg}$, and/or PR$^{neg}$. In some embodiments, prior to one or both administrations the carcinoma is determined to be metastatic. In some embodiments, prior to one or both administrations the carcinoma is determined to be metastatic. In some embodiments, prior to one or both administrations the carcinoma is determined to be resistant to at least one chemotherapeutic agent.

Certain aspects of the invention relate to methods of inhibiting the tumorigenic potential of cancer cells. In some embodiments, the methods comprise determining that the cancer cells comprise cancer stem cells; and contacting the cancer cells with a PKC-α/FRA1 pathway inhibitor. In some embodiments, the PKC-α/FRA1 pathway inhibitor is a FRA1 inhibitor. In some embodiments, the FRA1 inhibitor is a small interfering nucleic acid comprising a region of complementary with FRA1 mRNA that inhibits expression of FRA1 protein. In some embodiments, the small interfering nucleic acid is an antisense oligonucleotide, miRNA, shRNA or siRNA that targets FRA1 mRNA. In some embodiments, the methods further comprise determining the presence of basal-like cells among the cancer cells.

Certain aspects of the invention relate to methods of assessing a subject having a carcinoma. In some embodiments, the methods comprise obtaining a sample of the carcinoma from the subject; and determining the levels of FRA1 expression in the sample, wherein relatively high FRA1 expression in sample compared with an appropriate control indicates that the subject is likely to have a poor distant metastasis-free survival. In some embodiments, the methods further comprise determining the levels of PKCα expression in the sample, in which relatively high PKCα expression in the sample compared with an appropriate control further indicates that the subject is likely to have a poor distant metastasis-free survival (DMFS). In some embodiments, the carcinoma is Her2$^{neg}$, ER$^{neg}$ and/or PR$^{neg}$. In some embodiments, the carcinoma contains cells having BRCA1 mutations and/or p53 mutations.

Certain aspects of the invention relate to compositions comprising a non-CSC carcinoma cells and at least one of a EGFR inhibitor, a sphingosine kinase pathway inhibitor, and a PKC-α/FRA1 pathway inhibitor. In some embodiments, the compositions comprise at least two of a EGFR inhibitor, a sphingosine kinase pathway inhibitor, and a PKC-α/FRA1 pathway inhibitor. In some embodiments, the compositions comprise a EGFR inhibitor, a sphingosine kinase pathway inhibitor, and a PKC-α/FRA1 pathway inhibitor.

In some embodiments of the methods and compositions, the PKC-α/FRA1 pathway inhibitor is a Protein Kinase C-alpha (PKC-α) inhibitor. In some embodiments, the PKC-α inhibitor is PKC 20-28, Ro-31-8220, Ro-32-0432 or bisindolylmaleimide I. In some embodiments, the PKC-α inhibitor is a small interfering nucleic acid comprising a region of complementarity with PKC-α mRNA that inhibits expression of PKC-α protein. In some embodiments, the small interfering nucleic acid is an antisense oligonucleotide, miRNA, shRNA or siRNA that targets PKC-α mRNA. In some embodiments, the PKC-α/FRA1 pathway inhibitor is an inhibitor of PDGFRα or PDGFRβ. In some embodiments, the inhibitor of PDGFRα or PDGFRβ is imatinib. In some embodiments, the PKC-α/FRA1 pathway inhibitor is a PDGFR neutralizing antibody or PDGFR inhibitor. In some embodiments, the PKC-α/FRA1 pathway inhibitor is a FRA1 inhibitor. In some embodiments, the FRA1 inhibitor is a small interfering nucleic acid comprising a region of complementary with FRA1 mRNA that inhibits expression of FRA1 protein. In some embodiments, the small interfering nucleic acid is an antisense oligonucleotide, miRNA, shRNA or siRNA that targets FRA1 mRNA. In some embodiments, the PKC-α/FRA1 pathway inhibitor is an ERK inhibitor.

Certain aspects of the invention relate to methods of identifying a candidate compound for selectively inhibiting growth of cancer stem cells. In some embodiments, the methods comprise contacting test cells with a test compound, in which the test cells are cells that have spontaneously undergone an epithelial to mesenchymal transition and have been collected through differential detachment from a culture surface, or progeny cells thereof; and determining whether the test compound selectively inhibits growth of the test cells, wherein inhibition of growth indicates that the test compound is a candidate compound for selectively inhibiting growth of cancer stem cells. In some embodiments, the cells that have spontaneously undergone an epithelial to mesenchymal transition are obtained according to methods disclosed herein. In some embodiments, the methods further comprise co-culturing the test cells with control cells of epithelial cell origin that have not undergone an epithelial to mesenchymal transition, and contacting the co-cultured test and control cells with the test compound. In some embodiments, the methods comprise (a) co-culturing test cells and control cells, wherein the test cells are cells of epithelial cell origin that have undergone an epithelial to mesenchymal transition, or progeny cells thereof, and wherein the control cells are cells of epithelial cell origin that have not undergone an epithelial to mesenchymal transition; (b) contacting the co-cultured test and control cells with the test compound; and (c) determining whether the test compound selectively inhibits growth of the test cells compared with the control cells in the co-culture, wherein inhibition of growth indicates that the test compound is a candidate compound for selectively inhibiting growth of cancer stem cells. In some embodiments, the test cells are engineered to express a first detectable marker and the controls cells are engineered to express a second detectable marker, wherein assaying growth of the test cells comprises determining the number of cells in the co-culture that express the first detectable marker and assaying the growth control cells comprises determining the number of cells in the co-culture that express the second detectable marker. In some embodiments, the first and second detectable markers are fluorescent proteins having sufficiently different excitation and emission spectra to permit selective detection of each marker by fluorescence microscopy and/or fluorescence activated cell sorting (FACS). In some embodiments, the test compound is a kinase inhibitor. In some embodiments, the test compound is a Protein Kinase C (PKC) inhibitor. In some embodiments, the test compound is a protein kinase C (PKCα) inhibitor, an inhibitor of PDGFR, or an inhibitor of FRA-1. In some embodiments, the test compound is an inhibitor of CDC-like kinase 1 (CLK1), PI-3-kinase-related kinase SMG1, ephrin type-A receptor 2 (EphA2), nucleoside-diphosphate kinase 7 (NME7), protein kinase Cα (PKCα), serum/glucocorticoid regulated kinase 1 (SGK1), sphingosine kinase 1 (SPHK1), sphingosine kinase 2 (SPHK2) or cyclin-dependent kinase 6 (CDK6).

Certain aspects of the invention relate to methods of obtaining cells that have undergone an epithelial to mesenchymal transition. In some embodiments, the methods comprise (a) expanding a population of cells of epithelial origin on a culture surface under conditions that permit at least a subset of the cells to spontaneously undergo an epithelial to mesenchymal transition; and (b) obtaining cells of the subset that have undergone an epithelial to mesenchymal transition by differentially detaching cells that have undergone an epithelial to mesenchymal transition from the culture surface and collecting the detached cells. In some embodiments, the methods further comprise determining the presence of one or more markers of an EMT in the cells obtained in step (b). In some embodiments, the methods further comprise determining the presence of one or more markers of cancer stems cells in the cells obtained in step (b), wherein presence of the one or more markers of cancer stems cells in the detached cells indicates that the cells have undergone an epithelial to mesenchymal transition. In some embodiments, differentially detaching in step (b) comprises contacting the cells with at least one protease. In some embodiments, the at least one protease is a serine protease, optionally which is trypsin. In some embodiments, step (b) comprises contacting the cells with a medium comprising up to 0.1% of the protease. In some embodiments, the cells are collected in step (b) following contact with the protease for up to 2 minutes. In some embodiments, step (b) further comprises removing a medium containing the detached cells from the culture surface.

In some embodiments, the one or more markers of cancer stem cells comprise higher levels of expression of one or more of: Twist, Snail, Slug, Zeb1, Zeb2, vimentin, N-cadherin, fibronectin, and CD44, compared with the level of expression of the one or more markers in an appropriate control epithelial cell. In some embodiments, the one or more markers of cancer stem cells comprise lower levels of expression of E-cadherin or CD24, compared with the level of expression of the marker in an appropriate control epithelial cell. In some embodiments, the one or more markers of cancer stem cells comprise the cells exhibiting a fibroblast-like morphology. In some embodiments, the fibroblast-like morphology persists for multiple passages of cells. In some embodiments, the conditions that permit the cells to spontaneously undergo an epithelial to mesenchymal transition comprise the cells being at a confluence of at least 30% on the culture surface. In some embodiments, the conditions that permit the cells to spontaneously undergo an epithelial to mesenchymal transition comprise the cells being at a confluence of 30% to 70% on the culture surface. In some embodiments, the cells of epithelial origin comprise immortalized cells. In some embodiments, the immortalized cells are engineered to express SV40 large-T antigen and/or SV40 small-T antigen and/or telomerase reverse transcriptase and/or H-Ras (G12V). In some embodiments, the cells of epithelial origin comprises airway epithelial cells, pancreas ductal epithelial cells, intestinal epithelial cells, prostate epithelial cells or breast epithelial cells.

According to some aspects of the invention, cell preparations are provided that comprise one or more cells obtained according to the method disclosed herein, or progeny cells thereof. According to some aspects of the invention, kits are provided that comprise a container housing such a cell preparation. In some embodiments, methods are provided that comprise steps of obtaining a cell preparation of the invention and maintaining the cell preparation under conditions that permit growth of the cells contained therein. In some embodiments, methods are provided that comprise a step of generating clonal cell lines from cells obtained according to methods disclosed herein, or progeny cells thereof. In some embodiments, methods for generating clonal cell lines comprise obtaining an individual cell from cells obtained according to the methods disclosed herein, or progeny cells thereof, and expanding the individual cell to produce the cell line. In some embodiments, the individual cell is obtained using a limited dilution protocol or flow cytometry. In some embodiments, the cells of epithelial origin are human cells. In some embodiments, the cells that have undergone an epithelial to mesenchymal transition are engineered to express a detectable marker, which optionally comprises a fluorescent protein. In some embodiments, the cells of epithelial origin are not engineered to cause them to undergo EMT. In some embodiments, the cells of epithelial origin are not engineered to express an EMT-inducing transcription factor or to have reduced or absent expression of E-cadherin.

BRIEF DESCRIPTION OF DRAWINGS

FIG. 14 Relative gene expression difference (fold change) in HMLE-Twist, HMLE-Snail and HMLE Slug cells for the expression of candidate PKCα substrates relative to HMLE control cells. Signal intensity of each gene from microarray was compared to HMLE control cells.

FIGS. 21A, 21B and 21C show effects of two inhibitors targeting SPHK1/2 in NAMEC-Tom cells and HMLE-GFP cells. FIG.

21D shows effects of inhibitors, including paclitaxel and staurosporine, on cell apoptosis. FIG. 21E shows that SPHK1 and SPHK2 were upregulated in CD44hi/CD2410 cells. FIG. 21F shows kinase expression in cells that have undergone an EMT spontaneously. FIG. 21G shows SPHK1 expression in basal-like and luminal-like human breast cancer cell lines. FIG. 21H shows effects of depletion of SPHK1 or SPHK2 on NAMEC viability.

FIG. 22A shows that SPHK1/2 levels remained differentially regulated between NAMEC-Ras and HMLE-Ras cell populations in response to SPHK1/2 inhibitors. Bars from left to right are HMLE-Ras, Twist-Ras, Snail-Ras, Slug-Ras, NAMEC-Ras. FIG. 22B shows that similar to their immortalized, untransformed counterparts, NAMEC-Tom-Ras cells exhibited a heightened sensitivity to SPHK1/2 inhibitors relative to HMLE-GFP-Ras cells, and were more resistant to chemotherapy. FIG. 22C shows that consistent with NAMECs and HMLE cells cultured in vitro, NAMEC-Ras-derived xenografted tumors continued to express SPHK1 and SPHK2 whereas these proteins were largely absent in HMLE-Ras tumors. FIG. 22D provides results showing synergism of SPHK1/2 and PKCα inhibitors in targeting CSCs. FIG. 22E depict therapeutic benefits of PKCα and SPHK1/2 inhibitors. FIG. 22F shows that PKCα or SPHK1/2 inhibition decreased the tumor-initiation frequency and tumor size. FIG. 22G shows that combined treatment with PKCα and SPHK1/2 inhibitors treatment resulted in the smallest residual tumor masses compared with treatment using the inhibitors individually.

FIG. 23A shows that sphingosine-1-phosphate receptors 1 and 3 (S1PR1/3) are upregulated upon EMT. The first four bars from left to right are Control, Twist, Snail, Slug. FIG. 23B shows that treatment with a S1PR1/3 antagonist, VPC23019, selected against NAMEC-Tom-Ras cells (left bars) relative to HMLE-GFP-Ras cells (right bars) in a dose-dependent manner. FIG. 23C depicts signalling networks determined to be operating within CSCs in these examples.

DETAILED DESCRIPTION OF INVENTION

Figure 1:
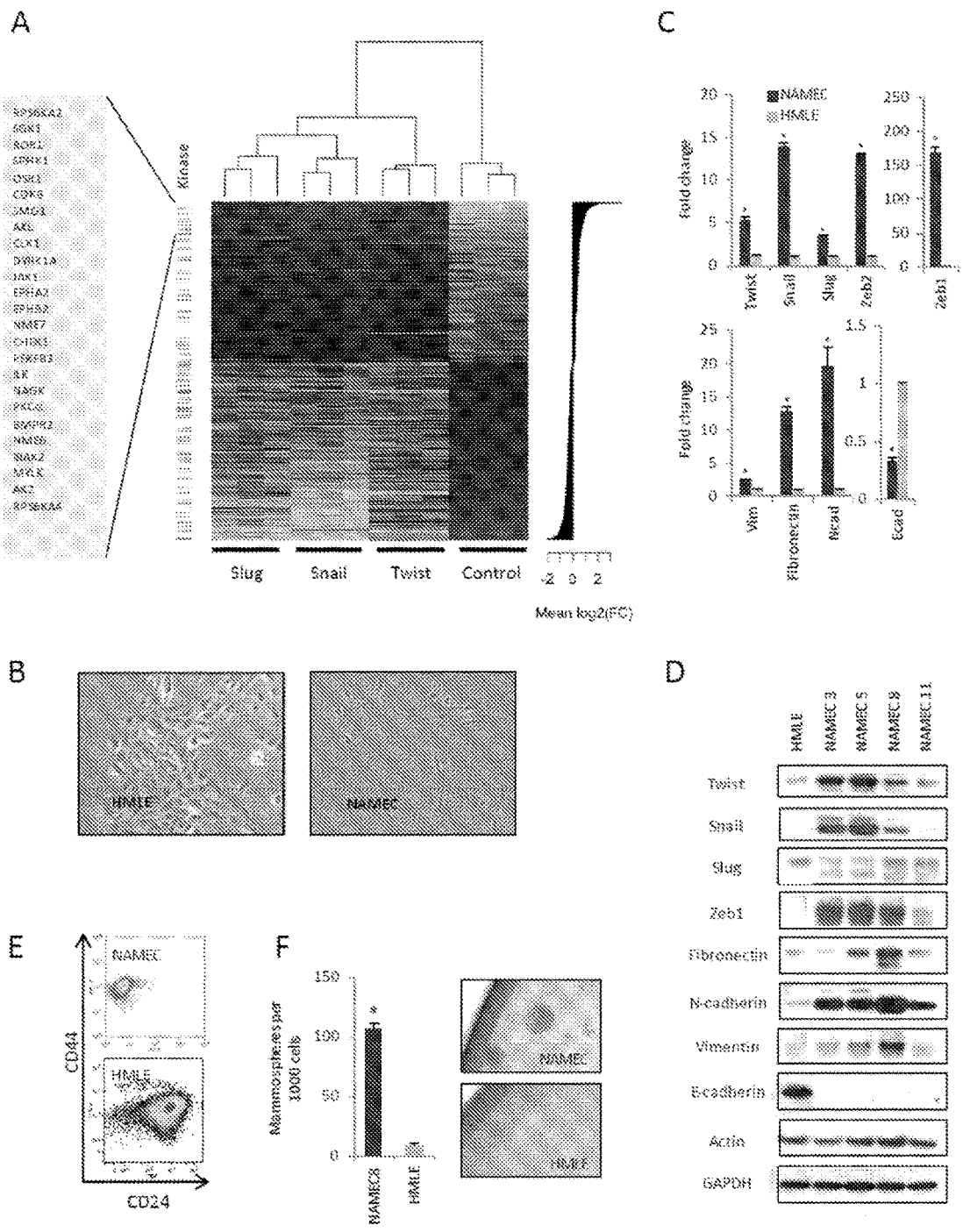
FIG. 1 depicts results of a global gene expression analysis. (A) Gene expression microarray was performed to identify the most differentially regulated genes between HMLE-Twist, HMLE-Snail, HMLE-Slug and control vector-HMLE cells. Red indicates larger and green represents lower value than the mean expression of this gene across all the samples (Twist, Snail, Slug and control, in triplicates). The most highly upregulated kinases are listed. (B) Wild-type parental HMLE cells formed epithelial, cobble stone-like islands which were largely immotile whereas NAMECs were fibroblastic, spindle-shaped, highly motile and demonstrated a loss of polarity. (C) Twist, Snail, Slug, Zeb1, Zeb2, vimentin, fibronectin and N-cadherin mRNAs were upregulated in NAMECs (left bars) relative to HMLE cells (right bars) while E-cadherin was repressed. Values were normalized to β-actin. * denotes significantly different from HMLE cells, p<0.05. Data presented as mean±s.e.m. (D) Twist, Snail, Slug, Zeb1, Zeb2, vimentin, fibronectin and N-cadherin proteins were markedly elevated, and E-cadherin was absent, in the various NAMEC cell lines whereas parental HMLE cells showed the opposite pattern. β-actin and GAPDH were used as loading control. (E) NAMECs were exclusively CD44$^{hi}$/CD24$^{lo}$ whereas HMLE cells were comprised of the minority stem-like CD44$^{hi}$/CD24$^{lo}$ and the majority non-stem cell CD44$^{lo}$/CD24$^{+}$ populations. (F) NAMECs were highly enriched for mammosphere-forming ability while HMLE cells were not. 500 cells were initially seeded into each well of a 96-well plate by FACS sorting and mammospheres were counted after 14 days. * denotes significantly different from HMLE cells, n=12, p<0.05. Data presented as mean±s.e.m.

Aspects of the invention are based on a recognition that effective treatment of carcinomas can be achieved by eliminating CSCs in addition to the majority non-CSCs in these tumors. In some embodiments, it has been found that PKCα inhibition can target CSCs selectively in vitro, as well as block tumor-initiation and growth arising from these CSCs in vivo. In some embodiments, it has been discovered that epithelial cells and mesenchymal cells selectively depend on EGF and PDGF receptors, respectively. Accordingly, in some embodiments, methods are provided that utilize a combination of PDGFR and EGFR inhibitors to kill tumor cells and reduce clinical relapse. In some embodiments, inhibition of SPHK pathway in combination with PKCα inhibition results in synergistic elimination of CSCs.

Certain aspects of the invention are based in part on a recognition that CSCs are generated in at least some carcinomas as one of the products of an EMT, indicating that these cells possess a more mesenchymal phenotype that is associated with highly aggressive traits. In some embodiments, molecular differences between populations enriched for CSCs and non-CSCs are provided that render CSCs susceptible to selective therapeutic attack. In some embodiments, these molecular differences are useful for identifying CSCs in a carcinoma. In some embodiments, these molecular differences provide the basis for a screen for identifying compounds that selectively target CSCs.

In some embodiments, methods are provided for distinguishing the effects of chemical inhibitors on CSCs (e.g., breast CSCs) from those affecting non-CSCs. Within epithelial cells (e.g., normal mammary epithelial cells), the forced expression of EMT-inducing transcription factors (EMT-TFs) endows cells with mesenchymal traits that include the gain of mesenchymal markers, vimentin, fibronectin and N-cadherin, accompanied by the loss of epithelial markers such as E-cadherin and ZO-1. These cells possess enhanced stem cell activity in vitro and in vivo. Likewise, in some embodiments, in populations of weakly or non-tumorigenic cancer cells, passage through the EMT program dramatically increases CSC frequency along with the acquisition of mesenchymal properties. These features include, in some embodiments, a distinctive $CD44^{hi}/CD24^{lo}$ cell-surface marker profile, mammosphere-forming ability, elevated resistance to certain chemotherapeutics, and/or greatly increased tumor-initiating ability upon engraftment in immune-compromised mice.

In certain embodiments, methods are provided that employ an EMT program (e.g., a spontaneously induced EMT program) to generate cells which are enriched for stem cell and CSC properties. In some embodiments, the generated cells and their progeny are useful for identifying signaling and transcriptional networks that are differentially utilized in cells that are products of an EMT. In some embodiments, functional molecular landmarks or markers within signaling networks that are associated with the EMT program are provided that are active in clinical specimens and enriched in the cancer stem-like state. For example, PKCα and FRA1 are provided as clinically useful markers for assessing the activity of an EMT program in tumors and predicting cancer progression.

In some embodiments, methods for producing genetically matched subpopulations of cells enriched for CSCs and non-CSCs are provided.

Other aspects of the invention in addition to the foregoing are described in greater detail below.

Methods of Inhibiting Growth and/or Tumorigenic Potential of Carcinoma Cells

Provided herein are methods for inhibiting growth and/or tumorigenic potential of carcinomas. Generally, the methods utilize compounds that selectively target cells that have undergone an EMT. Cells that have undergone an EMT exhibit one or more phenotypic characteristics of CSCs and are generally associated with increased tumorigenic potential of carcinomas. Several components of the PKC-α/FRA1 pathway are found to be active in CSCs of carcinomas, and activation of this pathway is found to be associated with poor prognosis in subjects having carcinomas. Moreover, expression of PKCα and FRA1 are strongly induced upon passage through an EMT. Thus, some aspects of the invention involve selectively inhibiting components of the PKC-α/FRA1 pathway resulting in depletion of CSCs in carcinomas and reduced tumorigenic potential of carcinomas.

In some embodiments, methods are provided that involve contacting carcinoma cells (in vitro or in vivo) with a PKC-α/FRA1 pathway inhibitor. As used herein, a "PKC-α/FRA1 pathway inhibitor" is a compound whose predominant mode of action is inhibition of a component of the PKC-α/FRA1 pathway of a cell. A PKC-α/FRA1 pathway inhibitor generally has relatively high selectivity for its target of the PKC-α/FRA1 pathway. The PKC-α/FRA1 pathway inhibitor may be at least 2-fold, 3-fold, 4-fold, 5-fold, 6-fold, 7-fold, 8-fold, 9-fold, 10-fold, 15-fold, 20-fold, or 50-fold more potent against its target (e.g., PKC-α, PDGFRα, PDGFRβ, FRA1, etc.) compared with an appropriate control molecule (e.g., a different member of the same protein family). For example, a PKC-α inhibitor may be at least 2-fold, 3-fold, 4-fold, 5-fold, 6-fold, 7-fold, 8-fold, 9-fold, 10-fold, 15-fold, 20-fold, or 50-fold more potent against PKC-α compared with PKC-β; a PDGFR-α inhibitor may be at least 2-fold, 3-fold, 4-fold, 5-fold, 6-fold, 7-fold, 8-fold, 9-fold, 10-fold, 15-fold, 20-fold, or 50-fold more potent against PDGFR-α compared with PDGFR-β; and a FRA1 inhibitor may be at least 2-fold, 3-fold, 4-fold, 5-fold, 6-fold, 7-fold, 8-fold, 9-fold, 10-fold, 15-fold, 20-fold, or 50-fold more potent against FRA1 compared with another Fos gene family member, e.g., FOS, FOSB, etc.; and so on.

Figure 4:
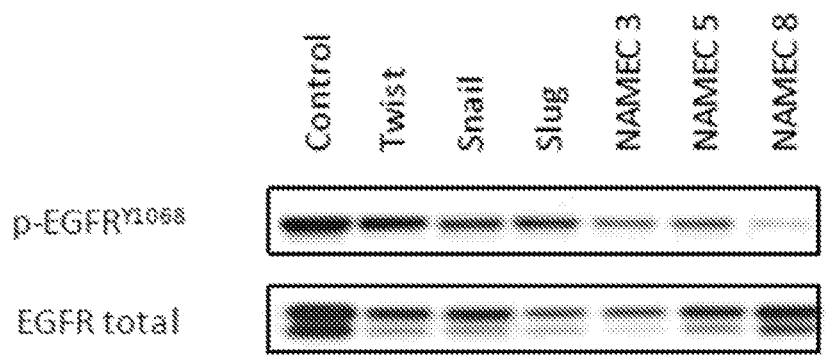
FIG. 4 depicts that EMT induces a switch from EGFR to PDGFR signaling. (A) Total and p-EGFR$^{Y1068}$ were downregulated in products of an EMT (HMLE-Twist, HMLE-Snail, HMLE-Slug, NAMEC3, NAMEC5 and NAMEC8 cells). p-EGFR$^{Y992}$ or p-EGFR$^{Y1045}$ was not detected (data not shown). (B) Dose response curves demonstrated that HMLE-Ras-GFP were more sensitive to EGFR inhibition (EGFR Inh and EGFR Inh III) than NAMEC-Ras-Tom cells. The difference in fold sensitivity between both cell types at $LC_{50}$ towards the agents is indicated. (C) Gene expression showed that PDGFRα, PDGFRβ and PDGFC were preferentially expressed in basal B (red) rather than basal A (orange) or luminal (green) subtypes of breast cancer cell lines. Relative gene expression was normalized to MCF7 cells. Data presented as mean±s.e.m. (D) Cells bearing mesenchymal traits (HMLE-Twist, HMLE-Snail, HMLE- Slug, NAMEC3, NAMEC5, NAMEC8 and NAMEC9) showed increased PDGFC expression relative to epithelial HMLE or HMLE-vector cells. Other PDGFR ligands that included PDGFA, PDGFB and PDGFD were not expressed (data not shown). * denotes significantly different from HMLE or HMLE-vector cells, p<0.005. Data presented as mean±s.e.m. (E) PDGFRα and PDGFRβ, along with their phosphorylated proteins, as well as PLCγ1 and PLCγ2, were upregulated in NAMECs and TF-induced EMT cells. (F) Treatment of NAMECs cultured in the absence of growth supplements with either a PDGFC neutralizing antibody (20 µg/ml) or a PDGFR inhibitor (1 µM) blocked the autocrinal activation of p-PDGFRβ$^{Y751}$. The addition of PDGFC (100 ng/ml) to growth factor-starved NAMEC activated PDGFRβ activity as measured by p-PDGFRβ$^{Y751}$. (G) Dose response curves demonstrated that NAMEC-Ras-Tom cells were more sensitive to PDGFR inhibitors (PDGFR Inh III and PDGFR Inh IV) than HMLE-Ras-GFP cells. The difference in fold sensitivity between both cell types at $LC_{50}$ towards the agents is indicated. (H) Schema depicting the differential utilization of signaling networks between epithelial and mesenchymal cell states upon the activation of an EMT program.
Figure 4:
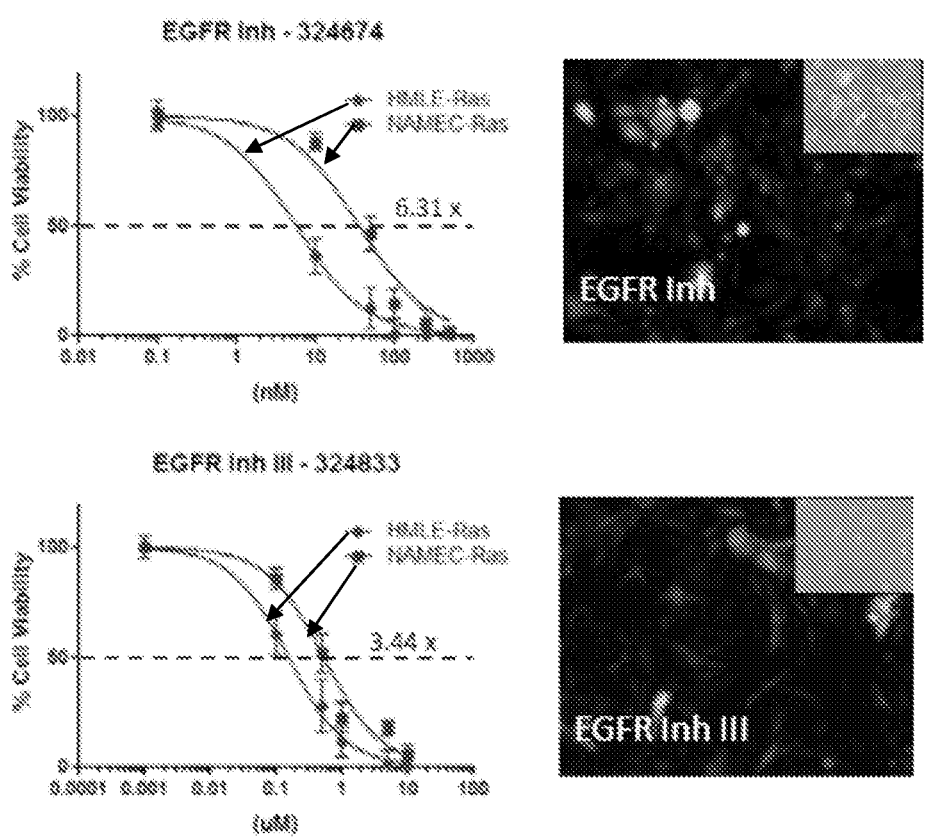

Exemplary components of the PKC-α/FRA1 pathway are depicted in FIG. 4H (right panel). It will be appreciated that certain agents act by binding to extracellular targets (e.g., protein domain or receptor) and certain agents act by binding to intracellular targets. In some embodiments, it has been found that formation of CSCs from non-stem cells involves activation of the PKC-α/FRA1 pathway. In some embodiments activity of the PKC-α/FRA1 pathway involves signaling through the platelet-derived growth factor receptor (PDGFR) which in turn leads to PKCα activation through PLCγ, and activation of downstream substrates of PKCα, including the FRA1 subunit of the activator protein 1 (AP-1) transcription factor and components of the extracellular-signal regulated kinase (ERK) signaling pathway, including Raf, MEK and ERK1/2. Thus, in some embodiments, a PKC-α/FRA1 pathway inhibitor is a compound whose predominant mode of action in a cell is inhibition of PKC-α, PLCγ, PDGFR, Raf, MEK, ERK1/2, or FRA-1. In some embodiments, where a PKC-α/FRA1 pathway inhibitor is a compound whose predominant mode of action in a cell is inhibition of PLCγ, reduction of PLCγ phosphorylation at Tyrosine 783 or Tyrosine 1217 or reduced activity of a downstream target of PLCγ compared with an appropriate control indicates effectiveness of the inhibitor.

The PKC-α/FRA1 pathway inhibitor may be a PKC-α inhibitor. The PKC-α inhibitor may be, for example, PKC 20-28, Ro-31-8220, Ro-32-0432 or bisindolylmaleimide I. The PKC-α inhibitor may alternatively be a small interfering nucleic acid comprising a region of complementarity with PKC-α mRNA that inhibits expression of PKC-α protein (e.g., an miRNA, shRNA or siRNA that selectively targets PKC-α mRNA). Further examples of PKC-α inhibitors are known in the art and may be used in methods, including, for example, PKC-α inhibitors disclosed in Lee J H, Nandy S K, Lawrence D S., A highly potent and selective PKCalpha inhibitor generated via combinatorial modification of a peptide scaffold. J Am Chem Soc. 2004 Mar. 24; 126(11): 3394-5; and Djung J F, Mears R J, Montalbetti C A, Coulter T S, Golebiowski A, Carr A N, Barker O, Greis K D, Zhou S, Dolan E, Davis G F. The synthesis and evaluation of indolylureas as PKCα inhibitors. Bioorg Med Chem. 2011 Apr. 15; 19(8):2742-50. Epub 2011 Feb. 26, the contents of each of which are incorporated herein by reference.

Effectiveness of a PKC-α inhibitor may be assessed by monitoring the status of PKCα phosphorylation. For example, a reduction of PKCα phosphorylation at Serine 497 or Threonine 638 compared with an appropriate control indicates effectiveness of the inhibitor. It will be understood that in various embodiments effectiveness of an inhibitor of a kinase, e.g., a PKC-α inhibitor, may be assessed by monitoring phosphorylation of any suitable substrate of such kinase in vitro (e.g., using a cell lysate containing a kinase or more highly purified kinase) or in a cell-based assay. Kinase assays and methods of performing them are known in the art. In some embodiments phosphorylation may be detected using a binding agent that specifically binds to a phosphorylated site on a substrate. For example, phosphorylation-site specific antibodies may be used in certain embodiments.

The PKC-α/FRA1 pathway inhibitor may be a FRA1 inhibitor. The FRA1 inhibitor may be a small interfering nucleic acid comprising a region of complementarity with FRA1 mRNA that inhibits expression of FRA1 protein (e.g., an miRNA, shRNA or siRNA that selectively targets FRA1 mRNA). Further examples of FRA1 inhibitors are known in the art and may be used in methods, including, for example, FRA1 inhibitors disclosed in U.S. Pat. No. 6,124,133, entitled ANTISENSE INHIBITION OF FRA-1 EXPRESSION, filed Oct. 15, 1999, the contents of which are incorporated herein by reference.

Effectiveness of a FRA1 inhibitor may be assessed by monitoring the status of FRA1 phosphorylation. For example, a reduction of FRA1 phosphorylation at Serine 265 compared with an appropriate control indicates effectiveness of the inhibitor. Alternately or additionally, effectiveness of a FRA1 inhibitor may be assessed by monitoring expression of a FRA1 target gene, which in some embodiments may comprise a reporter gene containing a DNA binding site for an AP-1 transcription factor comprising FRA1.

The PKC-α/FRA1 pathway inhibitor may be an inhibitor of PDGFRα or PDGFRβ, such as, for example, imatinib or sorafenib. The PKC-α/FRA1 pathway inhibitor may alternatively be a PDGFR neutralizing antibody. Further PDGFR inhibitors that may be used in the methods are known in the art, including those listed below.

| Agent | Target | Class |
|---|---|---|
| H-8650 | PDGF-R α & β Antagonist | Small Molecule |
| ab61219 | PDGF-R α | Antibody |
| PR292 | PDGF-R | Antibody |
| PDGFR-B1 | PDGF-R | Antibody |
| PDGFR-B2 | PDGF-R | Antibody |
| Imatinib (STI571) | PDGF-R | Small Molecule |
| Anti-PDGFR-β, clone 4A56 (Calbiochem) | PDGFR-β | Antibody |
| Anti-PDGFR Antibody, clone CH-3 (Calbiochem) | PDGFR | Antibody |
| Antt9-PDGFR α (550-end, V561D), (Calbiochem) | PDGFR α | Antibody |

-continued

| Agent | Target | Class |
|---|---|---|
| PDGFR Tyrosine Kinase Inhibitor III, (Calbiochem) | PDGFR | Small Molecule |
| PDGFR Tyrosine Kinase Inhibitor V, (Calbiochem) | PDGFR | Small Molecule |
| PDGFR Tyrosine Kinase Inhibitor IV, (Calbiochem) | PDGFR | Small Molecule |
| Sorafenib | PDGFR | Small Molecule |
| KN2941 (4-(6.7-dimethoxy-4-quinazolinyl)-N-(3,4-methylenedioxybenzyl)-1-piperazi- nethiocarboxamide) | PDGFR | Small Molecule |

The PKC-α/FRA1 pathway inhibitor may be an ERK (e.g., ERK1 or ERK2) inhibitor. ERK inhibitors that may be used in the methods are disclosed in the Examples. Additional ERK inhibitors that may be used are known in the art, including those listed below.

| Agent | Target | Class |
|---|---|---|
| FR180204 | ERK | Small Molecule |
| 3-(2-Aminoethyl)-5-((4-ethoxyphenyl)methylene)-2,4-thiazolidinedione | ERK | Small Molecule |
| (3R,4R)-4-(3,4-Dimethoxybenzyl)-3-(4-hydroxy-3-methoxybenzyl)dihydrofuran-2(3H)-one | ERK | Small Molecule |
| 2-[(2-chloro-4-iodophenyl)amino]-N-(cyclopropylmethoxy)-3,4-difluorobenzamide | ERK | Small Molecule |
| 2-(4-chloro-2-fluoro-anilino)-N-(2-hydroxyethoxy)-1,5-dimethyl-6-oxo-pyridine-3-carboxamide | ERK | Small Molecule |
| 2-[(2-fluoro-4-iodophenyl)amino]-N-(2-hydroxyethoxy)-1,5-dimethyl-6-oxo-1,6-dihydropyridine-3-carboxamide | ERK | Small Molecule |
| 5-[(4-bromo-2-chlorophenyl)amino]-4-fluoro-N-(2-hydroxyethoxy)-1-methyl-1H-benzimidazole-6-carboxamide | ERK | Small Molecule |
| (2Z,3Z)-bis{amino[(2-aminophenyl)sulfanyl]methylidene}butanedinitrile | ERK | Small Molecule |
| 2-(2-amino-3-methoxyphenyl)-4H-chromen-4-one | ERK | Small Molecule |
| (2Z)-3-amino-3-[(4-aminophenyl)sulfanyl]-2-[2-(trifluoromethyl)phenyl]prop-2-enenitrile | ERK | Small Molecule |
| N-methyl-3-phenyl-3-[4-(trifluoromethyl)phenoxy]propan-1-amine fluoxetine, and 2-chloro-4-{[2-{[(2R)-1-hydroxy-3-methylbutan-2-yl]amino}-9-(propan-2-yl)-9H-purin-6-yl]amino}benzoic acid | ERK | Small Molecule |
| GW5074 | ERK | Small Molecule |
| Pluripotin (Erk Inhibtor VII) | ERK | Small Molecule |
| PD173074 | ERK | Small Molecule |
| SL327 | ERK | Small Molecule |
| hypericin | ERK | Small Molecule |
| AG 99 | ERK | Small Molecule |
| CAY10561 | ERK | Small Molecule |
| ISIS 5132 | ERK | Antisense Oligonucleotide |
| Apigenin | ERK | Small Molecule |
| SP600125 | ERK | Small Molecule |
| SU4984 | ERK | Small Molecule |
| SB203580 | ERK | Small Molecule |
| 3-cyano-4-(phenoxyanilno) quinolines | ERK | Small Molecules |
| Quinolones, pyrazole compositions and isoxazole compositions | ERK | Small Molecules |

Effectiveness of the inhibitors may be determined by assessing the phosphorylation status of components of the ERK signaling cascade, including B-Raf, c-Raf, MEK1/2 or ERK1/2, in which a reduction of phosphorylation B-Raf, c-Raf, MEK1/2 or ERK1/2 compared with an appropriate control indicates effectiveness of the pathway inhibitor.

However, in some embodiments, methods further comprising contacting a CSC with a compound whose predominant mode of action in a cell is inhibition of PKCη, CLK1, CDK6 or JAK1. Effectiveness of a particular inhibitor may be assessed by monitoring the status of phosphorylation of the target of that inhibitor.

In some embodiments, a PKC-α/FRA1 pathway inhibitor is more potent against CSCs or cells that have undergone an EMT compared with an appropriate control cell (e.g., epithelial cells, non-CSC cancer cells, cells that have not undergone an EMT or that otherwise do not exhibit characteristics of a cell that has undergone an EMT). It should be appreciated that degree of potency of a PKC-α/FRA1 pathway inhibitor against an appropriate test cell can be evaluated through, for example, a dose response study. Sensitivity of test cells to a PKC-α/FRA1 pathway inhibitor can be determined by evaluating one or more parameters that quantify sensitivity of the test cells to the inhibitor such as, for example, an $LC_{50}$ or $EC_{50}$ parameter. In some embodiments, a PKC-α/FRA1 pathway inhibitor is at least 2-fold, 3-fold, 4-fold, 5-fold, 6-fold, 7-fold, 8-fold, 9-fold, 10-fold, 15-fold, 20-fold, 50-fold more potent against CSCs or cells that have undergone an EMT (e.g., as determined by a cell viability assays) than non-CSCs or cells that have not undergone an EMT or that otherwise do not exhibit characteristics of a cell that has undergone an EMT.

EGFR and PKC-α/FRA1

In some embodiments, it has been found that formation of CSCs from non-stem cells involves a shift from epidermal growth factor receptor (EGFR) to platelet-derived growth factor receptor (PDGFR) signaling, which leads in turn to PKCα-dependent activation of downstream substrates that include the FRA1 subunit of the activator protein 1 (AP-1) transcription factor, as well as components of the extracellular-signal regulated kinase (ERK) signaling pathway. Accordingly, in some embodiments, methods of inhibiting growth of carcinoma cells involve contacting the carcinoma cells with a PKC-α/FRA1 pathway inhibitor and with an EGFR inhibitor. In some embodiments, methods are provided for inhibiting growth of cancer stem cells that involve contacting carcinomas containing CSCs with inhibitors of EGFR and PDGFR. In some embodiments, methods of inhibiting formation of CSCs are provided. For example, in some embodiments formation of CSCs is inhibited by contacting carcinoma cells with an EGFR inhibitor, optionally in combination with a PDGFR inhibitor. In some embodiments formation of CSCs is inhibited by contacting a carcinoma with an EGFR inhibitor, optionally in combination with a PDGFR inhibitor. Examples of inhibitors of PDGFR and EGFR are disclosed elsewhere herein. Further EGFR inhibitors that may be used in the methods are known in the art, including those listed below.

| Agent | Target | Class |
|---|---|---|
| Trastuzumab (Herceptin; Genentech Inc) | EGFR | Antibody |
| Cetuximab (Erbitux; Bristol-Myers Squibb Corporation) | EGFR | Antibody |
| Panitumumab (Vectabix) | EGFR | Antibody |
| Gefitinib (Iressa; AstraZeneca) | EGFR | Small Molecule |
| Erlotinib (Tarceva; Genentech/Roche) | EGFR | Small Molecule |
| anti-EGFR immunoliposomes (Hermes Biosciences Inc.) | EGFR | Antibody-based Molecule |
| TP-38 (IVAX) | EGFR | Small Molecule |
| Vandetanib (Caprelsa, AstraZeneca) | EGFR | Small Molecule |
| Lapatinib (GSK) | EGFR | Small Molecule |

Sphingosine Kinase Pathway Inhibitors

In some embodiments, it has been found that activity of the Sphingosine kinase (SPHK) pathway is increased in conjunction with PKCα upon passage through an EMT, and their combined inhibition (i.e., inhibition of SPHK pathway and PKCα pathway) leads to synergistic elimination of CSCs. SPHK is a conserved lipid kinase that catalyzes formation sphingosine-1-phosphate (S1P) from the precursor sphingolipid sphingosine. Sphingolipid metabolites, such as ceramide, sphingosine and sphingosine-1-phosphate, are lipid second messengers involved in downstream cellular processes. There are two forms of SPHK, SPHK1 and SPHK2. SPHK1 is generally localized in the cytosol of cells, and migrates to the plasma membrane upon activation. SPHK2 is generally localized to the nucleus.

Activated SPHK1/2 converts sphingosine to sphingosine-1-phosphate (S1P) which activates its own receptors in an autocrine fashion. It has been found that cells that have activated an EMT program are sensitive to inhibition of the SPHK pathway, indicating that SPHK signalling modulates EMT-driven cancer progression. In some embodiments, it has been found that sphingosine-1-phosphate receptors 1 and 3 (S1PR1/3) are upregulated upon EMT. Moreover, treatment with a S1PR1/3 antagonist, VPC23019, selectively inhibits cells that have undergone an EMT in a dose-dependent manner. Two inhibitors targeting SPHK1/2 also selectively inhibited cells that have undergone an EMT in a dose-dependent manner. SPHK1 and SPHK2 were upregulated in CD44$^{hi}$/CD24$^{lo}$ CSCs, and SPHK is also highly expressed in basal-like, and not luminal-like, human breast cancer cell lines.

Accordingly, in some embodiments, the methods involve contacting cells with a PKC-α/FRA1 pathway inhibitor and a SPHK inhibitor. In some embodiments, the SPHK is a SPHK1 inhibitor or SPHK2 inhibitor. In some embodiments, the sphingosine kinase pathway inhibitor is a sphingosine-1-phosphate receptors 1 and 3 (S1PR1/3) antagonist, such as VPC23019. In some embodiments, lower doses of PKC-α/FRA1 and SPHK inhibitors are effective in killing cancer stem cells when the inhibitors are used in combination, compared with when the compounds are used separately. In some embodiments, the effective dose of a PKC-α/FRA1 inhibitor when used in combination with a SPHK inhibitor is less than or equal to 0.01%, 0.05%, 0.1%, 0.5%, 1%, 2%, 5%, 10%, 25%, or 50%, or 75% of the effective dose of the PKCα inhibitor when used without the SPHK inhibitor. In some embodiments, the effective dose of a PKCα inhibitor when used in combination with a SPHK inhibitor is in a range of 0.01% to 0.05%, 0.01% to 0.5%, 0.1% to 2%, 0.5% to 5%, 1% to 10%, 5% to 25%, 15% to 50%, or 25% to 75% of the effective dose of the PKCα inhibitor when used without the SPHK inhibitor.

Similarly, in some embodiments, the effective dose of a SPHK pathway inhibitor when used in combination with a PKC-α/FRA1 inhibitor is less than or equal to 0.01%, 0.05%, 0.1%, 0.5%, 1%, 2%, 5%, 10%, 25%, 50%, or 75% of the effective dose of the SPHK pathway inhibitor when used without the PKC-α/FRA1 inhibitor. In some embodiments, the effective dose of a SPHK inhibitor when used in combination with a PKC-α/FRA1 inhibitor is in a range of 0.01% to 0.05%, 0.01% to 0.5%, 0.1% to 2%, 0.5% to 5%, 1% to 10%, 5% to 25%, 15% to 50%, or 25% to 75% of the effective dose of the SPHK inhibitor when used without the PKC-α/FRA1 inhibitor.

Examples of SPHK inhibitors that may be used in the methods are known in the art, including, for example, as disclosed in Pitman M R, Pitson S M., *Inhibitors of the sphingosine kinase pathway as potential therapeutics*. Curr Cancer Drug Targets. 2010 June; 10(4):354-67; Kevin J. French, John J. Upson, Staci N. Keller, Yan Zhuang, Jong K. Yun, and Charles D. Smith, *Antitumor Activity of Sphingosine Kinase Inhibitors*. J Pharmacol Exp Ther. 2006 August; 318(2): 596-603; Susan Pyne, Robert Bittman, and Nigel J. Pyne. *Sphingosine Kinase Inhibitors and Cancer: Seeking the Golden Sword of Hercules*. Cancer Res. 2011 Nov. 1; 71(21):6576-82. Epub 2011 Sep. 22; Lim K G, Tonelli F, Li Z, Lu X, Bittman R, Pyne S, Pyne N J. *FTY720 analogues as sphingosine kinase 1 inhibitors: enzyme inhibition kinetics, allosterism, proteasomal degradation, and actin rearrangement in MCF-7 breast cancer cells*. J Biol Chem. 2011 May 27; 286(21):18633-40. Epub 2011 Apr. 4; and Tonelli F, Lim K G, Loveridge C, Long J, Pitson S M, Tigyi G, Bittman R, Pyne S, Pyne N J. *FTY720 and (S)-FTY720 vinylphosphonate inhibit sphingosine kinase 1 and promote its proteasomal degradation in human pulmonary artery smooth muscle, breast cancer and androgen-independent prostate cancer cells*. Cell Signal. 2010 October; 22(10):1536-42. Epub 2010 Jun. 4, the contents of which are incorporated herein by reference in their entireties. Further examples of SPHK inhibitors are disclosed elsewhere herein or otherwise known in the art.

In some embodiments an inhibitor comprises a polypeptide comprising at least a ligand binding domain of a receptor. Such polypeptides may act as "traps" for one or more ligand(s) of the respective receptor. For example, a polypeptide comprising at least a portion of an extracellular domain of a receptor (e.g., EGFR, PDGFR) may be used in certain embodiments. In some embodiments a soluble portion of an extracellular domain is used. In some embodiments a polypeptide is bifunctional in that it comprises a first portion capable of binding to a first ligand (e.g., EGF) and a second portion capable of binding to a second ligand (e.g., PDGF). It will be understood that the polypeptide need not be identical to the naturally occurring ligand binding domain. For example, a polypeptide may in some embodiments be at least about 90%, 95%, 96%, 97%, 98%, 99%, or more identical to a naturally occurring ligand binding domain. In some embodiments an inhibitor comprises a compound that inhibits endogenous synthesis of a ligand of a receptor of interest herein. Such an inhibitor may, for example, inhibit an enzyme involved in a synthesis pathway for such a ligand.

Tumor Prognosis

In some aspects, methods of tumor prognosis are provided. In some aspects, such methods comprise measuring expression of a PKC-α/FRA1 pathway component in the tumor or a sample obtained from the tumor, wherein increased expression as compared with a suitable control is indicative of an increased likelihood of poor outcome. In some embodiments, high Fra1 expression is significantly correlated with poor distant metastasis-free survival (DMFS). In some embodiments high c-Fos or FosB expression is associated with better survival prognosis. In some embodiments, prognostic information obtained according to the present invention may be used in selecting a therapy or therapeutic regimen for a subject. For example, a subject identified as having a poor prognosis (e.g., increased likelihood of poor outcome), may be treated using a more aggressive therapeutic regimen (e.g., higher dose, additional agents, longer treatment period, etc.) than if the subject is not determined to have a poor prognosis. In some embodiments a treatment regimen comprising a CSC-selective agent may be selected. In some aspects, a kit comprising a detection agent suitable for detecting a PKC-α/FRA1 pathway component in a tumor or tumor sample is provided. It will be appreciated that a sample may be processed. For example, cells may be lysed or permeabilized; RNA may be isolated, reverse transcribed, amplified, etc. A kit may comprise, e.g., an agent (e.g., an antibody) that specifically binds to a protein or to an activated form of the protein or a nucleic acid that binds to RNA encoding the protein (or to its complement). In some embodiments detection comprises detecting a protein. In some embodiments detection comprises detecting mRNA. In some embodiments detection may comprise performing immunohistochemistry, e.g., on a tumor section. The kit may comprise one or more additional items such as a secondary detection agent (e.g., a secondary antibody) or control. In some embodiments the detection agent or kit may be validated for use in a method of tumor prognosis or treatment selection.

Methods of Treatment

Methods of treating a subject having a carcinoma are also provided herein. In some embodiments, the methods involve administering to the subject an effective amount of a PKC-α/FRA1 pathway inhibitor. The methods may also involve administering to the subject an EGFR inhibitor or a sphingosine kinase pathway inhibitor. In some embodiments, the methods involve administering to the subject an effective amount of a PKC-α inhibitor; and administering to the subject an effective amount of an EGFR inhibitor. In some embodiments, the methods involve administering to the subject an effective amount of a PKC-α inhibitor; and administering to the subject an effective amount of an sphingosine kinase pathway inhibitor.

In some embodiments, the methods involve administering an EGFR inhibitor or a sphingosine kinase pathway inhibitor when the carcinoma has been identified as comprising cancer stem cells, basal-like cells or cells expressing one or more markers indicated of a EMT. Thus, in some embodiments, the methods further involve determining that the carcinoma comprises cancer stem cells, basal-like cells or cells expressing one or more markers indicative of an EMT.

In some embodiments, the methods involve administering a non-CSC selective anti-cancer treatment to the subject in combination with a CSC selective treatment (e.g., a PKC-α/FRA1 pathway inhibitor). In some embodiments, the non-CSC selective anti-cancer treatment comprises surgery, radiation therapy, and/or a non-CSC selective chemotherapeutic agent. The chemotherapeutic agent may be a spindle poison, such as paclitaxel, or a DNA replication inhibitor, such as doxorubicin, topoisomerase inhibitors and antimetabolites, or an alkylating agent, or a broad spectrum kinase inhibitor, such as staurosporine, or a platinum-based compound, such as cisplatin, or another agent.

In some embodiments, the non-CSC selective chemotherapeutic agent has selective activity against non-CSC carcinoma cells. For example, the methods may involve administering to a subject a therapy effective against non-CSC carcinoma cells and administering to the subject an EGFR inhibitor, and/or a sphingosine kinase pathway inhibitor, and/or a PKC-α/FRA1 pathway inhibitor. A therapy effective against non-CSC carcinoma cells may be radiation therapy or a non-CSC selective chemotherapeutic agent having selective activity against non-CSC carcinoma cells.

A therapy effective against non-CSC carcinoma cells and an EGFR inhibitor, sphingosine kinase pathway inhibitor and/or PKC-α/FRA1 pathway inhibitor may be administered sequentially or concomitantly. A therapy effective against non-CSC carcinoma cells and an EGFR inhibitor, sphingosine kinase pathway inhibitor, and/or PKC-α/FRA1 pathway inhibitor may be administered sequentially within 1 hour, 2 hours, 12 hours, 18 hours, 1 day, 2, days, 1 week, 2 weeks, 3 weeks or 1 month of one another. In some embodiments a non-CSC selective therapy is administered to eliminate a substantial fraction of the bulk tumor cell population (e.g., at least 80%, 90%, 95%, 98%, or more of the tumor cells). In some embodiments such therapy may render the tumor undetectable using, e.g., standard methods such as imaging or PET scan. In some embodiments a CSC-selective therapy may be administered to inhibit growth of residual CSCs and/or inhibit formation of CSCs from remaining residual non-CSC tumor cells.

In some embodiments, the carcinoma is evaluated for one or more markers of a cancer stem cell. The carcinoma may be evaluated prior to administration of a compound to treat the carcinoma or after administration. For example, the carcinoma may be assessed to determine whether it contains basal-like cancer cells. The carcinoma may be assessed to determine whether it is $Her2^{neg}$, $ER^{neg}$, and/or $PR^{neg}$. The carcinoma may be assessed to determine whether it is metastatic. The carcinoma may be assessed to determine whether it is resistant to at least one chemotherapeutic agent.

In some embodiments, methods for assessing a subject having a carcinoma are provided. The methods may be used to determine if the subject is a candidate for a particular treatment, to monitor progression of the carcinoma, or to monitor effectiveness of the treatment. The methods may involve obtaining a sample of the carcinoma from the subject and determining the levels or phosphorylation status of one or more components of the PKCα/FRA1 pathway in the sample. In some embodiments, the methods involve determining the levels or phosphorylation status of one or more components of PKC-α, PDGFR, Raf, MEK, ERK1/2, FRA-1, PLCγ, PKCη, CLK1, CDK6 or JAK1. For example, the methods may involve assessing the levels of FRA1 expression in the sample, in which relatively high FRA1 expression in the sample compared with an appropriate control indicates that the subject is likely to have a poor distant metastasis-free survival (DMFS). In another example, the methods may involve assessing the levels of PKCα expression in the sample, in which relatively high PKCα expression in the sample compared with an appropriate control indicates that the subject is likely to have a poor DMFS. The methods may similarly involve assessments of the phosphorylation status of these proteins or the indicator of the activation status of the proteins and PKCα/FRA1 pathway.

Methods described herein have broad application to treating disorders, such as cancer, that are associated with cancer stem cells. Cancer is a disease characterized by uncontrolled or aberrantly controlled cell proliferation and other malignant cellular properties. As used herein, the term cancer includes, but is not limited to, the following types of cancer: breast cancer; biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor.

In certain embodiments, cancer is a colon carcinoma, a pancreatic cancer, a breast cancer, an ovarian cancer, a prostate cancer, a squamous cell carcinoma, a cervical cancer, a lung carcinoma, a small cell lung carcinoma, a bladder carcinoma, a squamous cell carcinoma, a basal cell carcinoma, an adenocarcinoma, a sweat gland carcinoma, a sebaceous gland carcinoma, a papillary carcinoma, a papillary adenocarcinoma, a cystadenocarcinoma, a medullary carcinoma, a bronchogenic carcinoma, a renal cell carcinoma, a hepatocellular carcinoma, a bile duct carcinoma, a choriocarcinoma, a seminoma, a embryonal carcinoma, a Wilms' tumor, or a testicular tumor. In one embodiment, cancer is a lung carcinoma. In some embodiments, cancer is a breast carcinoma. Other appropriate cancers, particularly carcinomas, will be known to one of ordinary skill in the art.

Some aspects of the invention are methods for treating a subject having, or suspected of having, cancer comprising administering to the subject an effective amount of a compound that selectively targets cancer stem cells, e.g., by targeting the PKC-α/FRA1 pathway. In some embodiments, the treatment methods of the invention involve treatment of a subject having (e.g., harboring) or at risk of having a cancer stem cell (CSC) and/or a CSC-dependent tumor. In some embodiments, the subject has a tumor of epithelial origin (i.e., a carcinoma).

As used herein, a subject is a mammal, including but not limited to a dog, cat, horse, cow, pig, sheep, goat, chicken, rodent, or primate. Preferred subjects are human subjects. The human subject may be a pediatric or adult subject. In some embodiments the adult subject is a geriatric subject. Whether a subject is deemed "at risk" of having a tumor is a determination that may be within the discretion of the skilled practitioner caring for the subject. Any suitable diagnostic test and/or criteria can be used. For example, a subject may be considered "at risk" of having a tumor if (i) the subject has a mutation, genetic polymorphism, gene or protein expression profile, and/or presence of particular substances in the blood, associated with increased risk of developing or having cancer relative to other members of the general population not having mutation or genetic polymorphism; (ii) the subject has one or more risk factors such as having a family history of cancer, having been exposed to a carcinogen or tumor-promoting agent or condition, e.g., asbestos, tobacco smoke, aflatoxin, radiation, chronic infection/inflammation, etc., advanced age; (iii) the subject has one or more symptoms of cancer, etc. In some embodiments, if the compound is one that has been previously (prior to the instant invention) administered to subjects for purposes other than treating cancer, e.g., for treatment of a condition other than cancer, the subject is not one to whom the compound would normally be administered for such other purpose and/or the compound is administered in a formulation or at a dose distinct from that known in the art to be useful for such other purpose.

Moreover, as used herein treatment or treating includes amelioration, cure, and/or maintenance of a cure (i.e., the prevention or delay of relapse) of a disorder (e.g., a tumor). Treatment after a disorder has started aims to reduce, ameliorate or altogether eliminate the disorder, and/or its associated symptoms, to prevent it from becoming worse, to slow the rate of progression, or to prevent the disorder from re-occurring once it has been initially eliminated (i.e., to prevent a relapse). A suitable dose and therapeutic regimen may vary depending upon the specific compound used, the mode of delivery of the compound, and whether it is used alone or in combination.

As used herein, a therapeutically effective amount generally refers to an amount of a compound that inhibits formation, progression, growth and/or spread (e.g., metastasis) of a tumor or cell. In some embodiments, therapeutically effective amount is an amount of a compound sufficient to inhibit growth of a cell. A therapeutically effective amount can refer to any one or more of the compounds or compositions described herein, or discovered using the methods described herein, that inhibit the growth and/or survival of cells, e.g., CSCs. In some embodiments, a therapeutically effective amount is an amount sufficient to inhibit PKC-α/FRA1 pathway activity in a cell. In some embodiments, a therapeutically effective amount is an amount sufficient to inhibit PDGFR pathway activity in a cell. In some embodiments, a therapeutically effective amount is an amount sufficient to inhibit EGFR pathway activity in a cell. In some embodiments, a therapeutically effective amount is an amount sufficient to inhibit SPHK pathway activity in a cell.

Methods for establishing a therapeutically effective amount for any compounds or compositions described herein will be known to one of ordinary skill in the art. As used herein, pharmacological compositions comprise compounds or compositions that have therapeutic utility, and a pharmaceutically acceptable carrier, e.g., that facilitate delivery of compounds or compositions, in a therapeutically effective amount. The effective amount for any particular application can also vary depending on such factors as the cancer being treated, the particular compound being administered, the size of the subject, or the severity of the disease or condition. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned with the goal of avoiding substantial toxicity and yet effective to treat the particular subject. In some embodiments a useful compound increases the average length of survival, increases the average length of progression-free survival, and/or reduces the rate of recurrence, of subjects treated with the compound in a statistically significant manner.

Subject doses of the compounds described herein typically range from about 0.1 µg to 10,000 mg, more typically from about 1 µg to 8000 mg, e.g., from about 10 µg to 100 mg once or more per day, week, month, or other time interval. Stated in terms of subject body weight, typical dosages in certain embodiments of the invention range from about 0.1 µg to 20 mg/kg/day, e.g., from about 1 to 10 mg/kg/day, e.g., from about 1 to 5 mg/kg/day. In certain embodiments reduced dose may be used when different pathway inhibitors (e.g., PKC-α/FRA-1 pathway and SPHK pathway inhibitors) are administered in combination either concomitantly or sequentially. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. It is often the case that a maximum dose be used, that is, the highest safe dose according to sound medical judgment.

The dose used may be the maximal tolerated dose or a sub-therapeutic dose or any dose there between. Multiple doses of the molecules of the invention are also contemplated. When the molecules of the invention are administered in combination a sub-therapeutic dosage of either of the molecules, or a sub-therapeutic dosage of both, may be used in the treatment of a subject having, or at risk of developing, cancer. When the two classes of drugs are used together, the cancer medicament may be administered in a sub-therapeutic dose to produce a desirable therapeutic result. A "sub-therapeutic dose" as used herein refers to a dosage which is less than that dosage which would produce a therapeutic result in the subject if administered in the absence of the other agent. Thus, the sub-therapeutic dose of a cancer medicament is one which would not produce the desired therapeutic result in the subject in the absence of the administration of the molecules of the invention. Therapeutic doses of cancer medicaments are well known in the field of medicine for the treatment of cancer. These dosages have been extensively described in references such as Remington's Pharmaceutical Sciences; as well as many other medical references relied upon by the medical profession as guidance for the treatment of cancer.

The compositions disclosed herein may be administered by any suitable means such as orally, intranasally, subcutaneously, intramuscularly, intravenously, intra-arterially, parenterally, intraperitoneally, intrathecally, intratracheally, ocularly, sublingually, vaginally, rectally, dermally, or as an aerosol. Depending upon the type of condition (e.g., cancer) to be treated, compounds of the invention may, for example, be inhaled, ingested or administered by systemic routes. Thus, a variety of administration modes, or routes, are available. The particular mode selected will depend, of course, upon the particular compound selected, the particular condition being treated and the dosage required for therapeutic efficacy. The methods of this invention, generally speaking, may be practiced using any mode of administration that is medically acceptable, meaning any mode that produces acceptable levels of efficacy without causing clinically unacceptable adverse effects. Preferred modes of administration are parenteral and oral routes. The term "parenteral" includes subcutaneous, intravenous, intramuscular, intraperitoneal, and intrasternal injection, or infusion techniques. In some embodiments, inhaled medications are of particular use because of the direct delivery to the lung, for example in lung cancer patients. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. Other appropriate routes will be apparent to one of ordinary skill in the art.

According to the methods of the invention, the compounds may be administered in a pharmaceutical composition. Administering the pharmaceutical composition of the present invention may be accomplished by any means known to the skilled artisan. In addition to the active agent, the pharmaceutical compositions of the present invention typically comprise a pharmaceutically-acceptable carrier. The term "pharmaceutically-acceptable carrier", as used herein, means one or more compatible solid or liquid filler diluents or encapsulating substances which are suitable for administration to a human or lower animal. In preferred embodiments, a pharmaceutically-acceptable carrier is a non-toxic material that does not interfere with the effectiveness of the biological activity of the active ingredients. The term "compatible", as used herein, means that the components of the pharmaceutical compositions are capable of being comingled with the compound of the present invention, and with each other, in a manner such that there is no interaction which would substantially reduce the pharmaceutical efficacy of the pharmaceutical composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils such as peanut oil, cottonseed oil, sesame oil, olive oil, corn oil and oil of theobrama; polyols such as propylene glycol, glycerin, sorbitol, mannitol, and polyethylene glycol; sugar; alginic acid; pyrogen-free water; isotonic saline; phosphate buffer solutions; cocoa butter (suppository base); emulsifiers, such as the Tweens; as well as other non-toxic compatible substances used in pharmaceutical formulation. Wetting agents and lubricants such as sodium lauryl sulfate, as well as coloring agents, flavoring agents, excipients, tableting agents, stabilizers, antioxidants, and preservatives, can also be present.

The pharmaceutically-acceptable carrier employed in conjunction with the compounds of the present invention is used at a concentration sufficient to provide a practical size to dosage relationship. The pharmaceutically-acceptable carriers, in total, may comprise from about 60% to about 99.99999% by weight of the pharmaceutical compositions of the present invention, e.g., from about 80% to about 99.99%, e.g., from about 90% to about 99.95%, from about 95% to about 99.9%, or from about 98% to about 99%.

Pharmaceutically-acceptable carriers suitable for the preparation of unit dosage forms for oral administration and topical application are well-known in the art. Their selection will depend on secondary considerations like taste, cost, and/or shelf stability, which are not critical for the purposes of the subject invention, and can be made without difficulty by a person skilled in the art.

Pharmaceutically acceptable compositions can include diluents, fillers, salts, buffers, stabilizers, solubilizers and other materials which are well-known in the art. The choice of pharmaceutically-acceptable carrier to be used in conjunction with the compounds of the present invention is basically determined by the way the compound is to be administered. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. It will also be understood that the compound can be provided as a pharmaceutically acceptable pro-drug, or an active metabolite can be used. Furthermore it will be appreciated that agents may be modified, e.g., with targeting moieties, moieties that increase their uptake, biological half-life (e.g., pegylation), etc.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

When the compounds described herein are used therapeutically, in certain embodiments a desirable route of administration may be by pulmonary aerosol. Techniques for preparing aerosol delivery systems containing compounds are well known to those of skill in the art. Generally, such systems should utilize components which will not significantly impair the biological properties of the peptides (see, for example, Sciarra and Cutie, "Aerosols," in Remington's Pharmaceutical Sciences). Those of skill in the art can readily determine the various parameters and conditions for producing aerosols without resort to undue experimentation.

The compounds of the invention may be administered directly to a tissue. Preferably, the tissue is one in which the cancer cells are found. Alternatively, the tissue is one in which the cancer is likely to arise. Direct tissue administration may be achieved by direct injection. The peptides may be administered once, or alternatively they may be administered in a plurality of administrations. If administered multiple times, the peptides may be administered via different routes. For example, the first (or the first few) administrations may be made directly into the affected tissue while later administrations may be systemic.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration. For buccal administration, the compositions may take the form of tablets or lozenges formulated in conventional manner.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In yet other embodiments, the preferred vehicle is a biocompatible microparticle or implant that is suitable for implantation into the mammalian recipient. Exemplary bioerodible implants that are useful in accordance with this method are described in PCT International Application Publication No. WO 95/24929, entitled "Polymeric Gene Delivery System", which reports on a biodegradable polymeric matrix for containing a biological macromolecule. The polymeric matrix may be used to achieve sustained release of the agent in a subject. In accordance with one aspect of the instant invention, the agent described herein may be encapsulated or dispersed within the biocompatible, preferably biodegradable polymeric matrix. The polymeric matrix preferably is in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents of the invention may be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly (ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the peptide, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for prophylactic treatment of subjects at risk of developing a recurrent cancer. Long-term release, as used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

Cell Culture-Based Method for the Generation of Cells with Properties of Cancer Stem Cells.

Aspects of the invention provide cells that have spontaneously undergone an EMT. In some embodiments, the cells reside stably in the mesenchymal state and do not spontaneously differentiate into epithelial derivatives in culture. For example, in some embodiments the cells reside stably in the mesenchymal state for at least 10, 20, 30, 35, 40, 45, 50, 60, 70, 80, or more population doublings or passages. In some embodiments, such cells are referred to herein as Naturally Arising MEsenchymal Cells (NAMECs). These cells are formed in the absence of introduced exogenous EMT-inducing master transcription factors (EMT-TFs), such as Twist, Snail and Slug and/or in the absence of genetic modification that inhibits E-cadherin expression. In some embodiments NAMECs are formed from cells that are free of genetic modification that would cause such cells to undergo an EMT. In some embodiments NAMECs are formed from cells that are free of genetic modification provided, however, that in some embodiments such cells contain a genetic modification to immortalize such cells, a genetic modification to cause them to express a detectable marker, and/or a genetic modification to cause them to express an oncogene or have reduced or absent expression of a tumor suppressor gene. In some embodiments NAMECs express elevated levels of one or more endogenous EMT-TFs (e.g., Twist, Snail, Slug, Zeb1 and/or Zeb2).

In some embodiments NAMECs express elevated levels of one or more associated EMT markers (e.g., vimentin, N-cadherin and fibronectin). In some embodiments NAMECs express reduced levels of the epithelial adherens junction protein, E-cadherin. In some embodiments, NAMECs are characterized as $CD44^{hi}/CD24^{lo}$, similar to mammary epithelial stem cells that are naturally present within HMLE populations. In some embodiments, NAMECs have relatively high mammosphere-forming ability compared with corresponding epithelial cells that have not undergone an EMT. In some embodiments NAMECs are characterized as having elevated (e.g., high) expression of any one or more markers characteristic of epithelial stem cells, e.g., epithelial stem cells found in or originating from a particular organ or tissue type. In some embodiments NAMECs are characterized as having elevated (e.g., high) expression of any one or more markers characteristic of cancer stem cells, e.g., CSCs originating found in a particular organ or tissue type or originating from epithelial cells from a particular organ or tissue type. In some embodiments a marker of epithelial stem cells or CSCs comprises a physical property such as differential light scattering, dye exclusion, etc., as compared with non-stem cells.

In some embodiments, NAMECs are isolated by differentially detaching spontaneously arising mesenchymal-like cells that are less adherent than epithelial cells to tissue culture surfaces (e.g., standard plastic tissue culture surfaces). In some embodiments, epithelial cells (e.g., HMLEs) are grown to between 30% and 70% confluence (e.g., 50% confluence) and then actively detached from the tissue culture surface. In some embodiments, the cells are actively detached by contacting cells with a chelating agent (e.g., EDTA). In some embodiments, the cells are active detachment of the cells does not involve the use of a chelating agent (e.g., EDTA). In some embodiments, the cells are actively detached by impacting the culture surface with a mechanical force of sufficient magnitude to selectively detach mesenchymal-like cells that are less adherent than epithelial cells to tissue culture surface. In some embodiments a culture vessel may be tapped, for example. In some embodiments, the cells are actively detached by contacting cells with a protease (e.g., trypsin). The digestion may be for a duration of up to 30 sec, up to 1 minute, up to 2 minutes or more in some cases. The digestion may be for a duration of about 15 seconds, about 30 seconds, about 45 seconds, about 60 seconds, about 120 seconds, or more. The protease may be trypsin at a concentration of up to 0.01%, up to 0.025%, up to 0.05%, up to 0.05%, up to 0.1%, or more. The concentration and/or exposure time may be lower than a standard concentration and/or exposure time typically employed for passaging cells. It will be understood that in certain embodiments other enzymes may be used instead of or in addition to trypsin. In some embodiments collagenase is used. A variety of cell detachment solutions are commercially available and may be used in certain embodiments. An appropriate enzyme (or combination or solution thereof), concentration, duration, and, in some embodiments, mechanical means, may be selected so as to selectively detach NAMECs. In some embodiments a detachment agent or combination is selected for a particular epithelial cell type of interest. In some embodiments, cells that are selectively detached from a culture surface are up to 10%, up to 20%, up to 30%, up to 40%, up to 50%, up to 60%, up to 70%, up to 80% or up to 90% of the total population of cells. In some embodiments, a protocol for isolating NAMECs may include use of an agent that inhibits (e.g., at least partly inactivates) a protease. For example, in some embodiments a brief exposure to a standard concentration of an enzyme may be employed, followed by application of an agent that inhibits the enzyme. Suitable agents are known in the art. For example, Trypsin Neutralizing Solution, e.g., for use in tissue culture is available. In some embodiments an isolation procedure results in a population that is enriched for NAMECs by at least a factor of 2, 5, 10, 20, 50-fold, or more, relative to the starting population. It should be appreciated that one or more additional separation/selection methods may be applied to further enrich for NAMECs, if desired. For example, cells can be selectively enriched for or depleted for (e.g., removing non-NAMECs that may be detached) by contacting with a binding agent such as an antibody that binds to a cell surface marker, optionally followed by FACS.

Actively detached cells may be collected, re-plated and expanded, e.g., to assess for the presence one or more markers of an EMT, including, for example, the presence of a morphologically mesenchymal phenotype that can be stably propagated, and/or for use in a method described herein. Clonal and/or non-clonal NAMEC cell lines may be generated using, for example, a limited dilution protocol, flow cytometry, or other appropriate method. In some aspects, such cell lines, cells, and populations of cells of such cell lines are provided herein. In some embodiments such a cell, cell line, or population of cells is genetically modified following isolation. For example, such a cell line, cell, or population of cells may be genetically engineered to comprise a detectable marker, to express an oncogene, and/or to have reduced or absent expression of a tumor suppressor gene.

In some embodiments NAMECs are provided for use or used in a screen to identify agents capable of inhibiting survival and/or proliferation of CSCs. In some embodiments such a screen is conducted to identify agents that selectively inhibit survival and/or proliferation of CSCs as compared with their effect on non-CSCs or a nonselected population of cancer cells. Examples of such screens are provided herein. In some embodiments NAMECs are provided for use or used to produce a non-human animal tumor model. For example, NAMECs may be introduced into a non-human mammal, e.g., a rodent (e.g., a mouse or rat). The non-human animal may be used as a test animal, e.g., for testing the effect of a test agent on tumor formation or growth. In some embodiments the non-human animal may be used in the identification or characterization of a CSC-selective agent. In some embodiments NAMECs may be cultured or introduced into a non-human animal host in combination with non-CSCs or in combination with non-tumor cells. For example, NAMECs may be cultured or introduced into a non-human animal host in combination with stromal cells, e.g., fibroblasts. In some embodiments such non-human animals are provided herein.

The extent to which a cell that has undergone an EMT exhibits an increase or decrease in the expression of one or more proteins or an increase in one or more functional properties of a cancer stem cell may be assessed by performing a comparison with a control cell, e.g., a cell that has not undergone an EMT (a negative control cell) or a cell that has undergone an EMT (a positive control cell), e.g., a cancer stem cell.

Examples of proteins for which increased expression in a cell that has undergone an EMT, compared with a cell that has not undergone an EMT, is indicative of the EMT includes N-cadherin, Vimentin, Fibronectin, Snail1 (Snail), Snail2 (Slug), Twist, Goosecoid, FOXC2, Sox10, MMP-2, MMP-3, MMP-9, Integrin vl36, CD44, and ESA. Examples of proteins for which decreased expression in a cell that has undergone an EMT, compared with a cell that has not undergone an EMT, is indicative of the EMT includes E-cadherin, Desmoplakin, Cytokeratin, Occludin, and CD24. The extent to which a epithelial cell has undergone an EMT may be assessed by determining the expression of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or more proteins. The expression of such proteins may be determined using a variety of assay methods including those disclosed herein and others which are known in the art. It is to be understood that some proteins whose expression levels are indicative of an EMT in a cell are also proteins that may cause the EMT to occur. For example, overexpression of Twist in an epithelial cell causes the cell to undergo an EMT. Similarly, a reduction in expression of E-cadherin in an epithelial cell causes the cell to undergo an EMT. Thus, when an EMT is brought about by increasing (e.g., by cDNA mediated overexpression) the expression of a protein such as Twist or decreasing (e.g., by RNAi mediated inhibition) the expression of a protein such as E-cadherin alterations in the expression of other proteins (e.g., CD44, Desmoplakin) may serve as suitable indicators of the EMT.

It is to be understood that functional properties of cancer or non-cancer stem cells that have or have not undergone an EMT may be assessed using a variety of methods known in the art. Growth in suspension cultures, for example, may be assessed by growing in a spinner flask cells that have undergone an EMT and measuring the change in cell number in the spinner flask over time. This change in cell number may be compared with the change in cell number of control cells that have not undergone an EMT and which have been grown under same or similar conditions. Up to a 10%, 20%, 30%, 40%, 50%, 60%, 70%, 80%, 90%, 100%, or more increase in doubling time of cells grown in suspension culture that have undergone an EMT compared with control cells grown under the same or similar conditions, but that have not undergone an EMT, may be indicative of an increased ability to grow in suspension.

The ability of cells that have undergone an EMT to form tumors in vivo at low cell seeding numbers may be assessed by a comparison with control cells that have not undergone an EMT. The ability to form tumors in vivo at low cell seeding numbers depends on a variety of factors which will be apparent to the skilled artisan, including for example the type of animal (e.g., a mouse) in which the cells are injected, the location where the cells are seeded (e.g., injected), and the ability of the animal to mount an immune response against the cells. As used herein, "low cell seeding numbers" means seeding of up to $10^0$, up to $10^1$, up to $10^2$, up to $10^3$, up to $10^4$, up to $10^5$, up to $10^6$ or more cells. The number of tumors formed in vivo following seeding of cells (e.g., a one or more locations or in one or more animals) is an exemplary parameter by which this comparison with a control may be made. The size (e.g., volume) of tumors formed in vivo following seeding of cells is another exemplary parameter by which this comparison with a control may be made. Up to a 10%, 20%, 30%, 40%, 50%, 60%, 70%, 80%, 90%, 100%, or more increase in tumor incidence or size, for example, may be indicative of an increased ability to form tumors in vivo at low cell seeding numbers.

In certain embodiments, the epithelial to mesenchymal transition is brought about by inhibiting the expression or activity of E-Cadherin in the cell. The expression or activity of E-Cadherin can be inhibited by using methods known to one of ordinary skill in the art. Exemplary methods for inhibiting E-cadherin expression or activity include contacting a cell with a small interfering nucleic acid complementary to E-Cadherin mRNA, contacting a cell with a blocking antibody to E-cadherin; inducing the expression of dysadherin, for example by cDNA-based overexpression of dysadherin, in a cell; and interfering with cell-polarity genes in the cell. For example, depletion of Scribble disrupts E-cadherin-mediated cell-cell adhesion and induces EMT (Qin Y, et al., J Cell Biol 2005; 171:1061-71). Thus, in some embodiments, inhibition of Scribble, such as by RNA interference, can induce an EMT. Also, genetic screens in *Drosophila* identified a number of genes affecting cell polarity whose inactivation results in loss of E-cadherin expression (Pagliarini R A, et al., Science 2003; 302:1227-31). Other exemplary methods for interfering with cell polarity genes to induce EMT are known in the art.

In certain embodiments, the activity of E-cadherin is inhibited by RNA interference. Methods for inhibiting gene expression, such as E-cadherin expression, by RNA interference are disclosed herein and known in the art. In some embodiments, a cell is transfected with a small interfering nucleic acid complementary to E-Cadherin mRNA in the cell to inhibit E-cadherin activity in the cell. Exemplary small interfering nucleic acids are disclosed herein and are known to persons skilled in the art. Methods for transfection of small interfering nucleic acids (e.g., siRNA) are well known in the art and examples are disclosed herein. In some embodiments, the cell has a stably integrated transgene that expresses a small interfering nucleic acid (e.g., shRNA, miRNA) that is complementary to E-Cadherin mRNA and that causes the downregulation of E-Cadherin mRNA through the RNA interference pathway.

Various strategies for gene knockdown known in the art can be used to inhibit the expression of any gene of interest disclosed, for example E-cadherin and others disclosed herein that are useful for inducing EMT or that are useful for targeting CSCs or other cells, such as targets of the PKCα/FRA1 pathway. For example, gene knockdown strategies may be used that make use of RNA interference (RNAi) and/or microRNA (miRNA) pathways including small interfering RNA (siRNA), short hairpin RNA (shRNA), double-stranded RNA (dsRNA), miRNAs, and other nucleotide-based molecules known in the art. In one embodiment, vector-based RNAi modalities (e.g., shRNA or shRNA-mir expression constructs) are used to reduce expression of a gene (e.g., E-cadherin) in a cell. It will be appreciated that exemplary sequences of the various proteins of interest (and nucleic acids encoding them) may be found, e.g., in public databases such as those available at the NCBI (e.g., RefSeq), Uniprot, etc. Typically, the small interfering nucleic acid has a region of complementarity with its target of at least 6, e.g., at least 7, at least 8, at least 9, at least 10, at least 15 or more consecutive nucleotides in length.

A broad range of RNAi-based modalities could be also employed to inhibit expression of a gene in a cell, such as siRNA-based oligonucleotides and/or altered siRNA-based oligonucleotides. Altered siRNA based oligonucleotides are those modified to alter potency, target affinity, safety profile and/or stability, for example, to render them resistant or partially resistant to intracellular degradation. Modifications, such as phosphorothioates, for example, can be made to oligonucleotides to increase resistance to nuclease degradation, binding affinity and/or uptake. In addition, hydrophobization and bioconjugation enhances siRNA delivery and targeting (De Paula et al., RNA. 13(4):431-56, 2007) and siRNAs with ribo-difluorotoluyl nucleotides maintain gene silencing activity (Xia et al., ASC Chem. Biol. 1(3): 176-83, (2006)). siRNAs with amide-linked oligoribonucleosides have been generated that are more resistant to S1 nuclease degradation than unmodified siRNAs (Iwase R et al. 2006 Nucleic Acids Symp Ser 50: 175-176). In addition, modification of siRNAs at the 2'-sugar position and phosphodiester linkage confers improved serum stability without loss of efficacy (Choung et al., Biochem. Biophys. Res. Commun. 342(3):919-26, 2006).

Other molecules that can be used to inhibit expression of a gene (e.g., a gene, such as E-Cadherin, that negatively regulates EMT) include sense and antisense nucleic acids (single or double stranded), ribozymes, peptides, DNAzymes, peptide nucleic acids (PNAs), triple helix forming oligonucleotides, antibodies, and aptamers and modified form(s) thereof directed to sequences in gene(s), RNA transcripts, or proteins. Antisense and ribozyme suppression strategies have led to the reversal of a tumor phenotype by reducing expression of a gene product or by cleaving a mutant transcript at the site of the mutation (Carter and Lemoine Br. J. Cancer. 67(5):869-76, 1993; Lange et al., Leukemia. 6(11):1786-94, 1993; Valera et al., J. Biol. Chem. 269(46):28543-6, 1994; Dosaka-Akita et al., Am. J. Clin. Pathol. 102(5):660-4, 1994; Feng et al., Cancer Res. 55(10): 2024-8, 1995; Quattrone et al., Cancer Res. 55(1):90-5, 1995; Lewin et al., Nat Med. 4(8):967-71, 1998). Ribozymes have also been proposed as a means of both inhibiting gene expression of a mutant gene and of correcting the mutant by targeted trans-splicing (Sullenger and Cech Nature 371(6498):619-22, 1994; Jones et al., Nat. Med. 2(6):643-8, 1996). Ribozyme activity may be augmented by the use of, for example, non-specific nucleic acid binding proteins or facilitator oligonucleotides (Herschlag et al., Embo J. 13(12):2913-24, 1994; Jankowsky and Schwenzer Nucleic Acids Res. 24(3):423-9, 1996). Multitarget ribozymes (connected or shotgun) have been suggested as a means of improving efficiency of ribozymes for gene suppression (Ohkawa et al., Nucleic Acids Symp Ser. (29):121-2, 1993).

In some embodiments, EMT is brought about by modulating the activity of a transcription factor (e.g., a transcription factor that modulates E-cadherin activity). The directionality of the modulation (e.g., inhibiting the activity or inducing the activity of the transcription factor) to induce EMT can be determined or confirmed by a skilled artisan using routine experimentation. In cases where it is desirable to inhibit the activity of a transcription factor, RNA interference is useful. For example, a small interfering nucleic acid, as disclosed herein, complementary to mRNA of a transcription factor can be used to inhibit the activity of the transcription factor. In some embodiments, EMT is brought about by inducing the activity of a transcription factor selected from: Snail1, Snail2, Goosecoid, FoxC2, TWIST, E2A, SIP-1/Zeb-2, dEF1/ZEb1, LEF1, Myc, HMGA2, TAZ, Klf8, HIF-1, HOXB7, SIM2s, and Fos. Exemplary methods for inducing the activity of transcription factors are known in the art. In some cases where it is desirable to induce the activity of a transcription factor exogenous expression of the transcription factor is useful. For example, induction of TWIST expression in a cell is known in the art to inhibit the activity of E-cadherin in the cell and induce EMT. In one embodiment, TWIST is induced in a cell by transfecting the cell with an expression vector encoding TWIST, thereby exogenously expressing TWIST in the cell. In some embodiments, a cell has a stably integrated transgene that expresses a transcription factor, such as TWIST, that causes an EMT in the cell.

Cells

A variety of cell (including primary cells) have the potential for the generation of naturally-arising mesenchymal cell populations bearing properties of stem cells or cancer stem cells. Epithelial cells arising from epithelium may undergo an EMT in response to cell-extrinsic signaling ligands such as TGFβ or Wnt, and through the forced overexpression of EMT transcription factors such as Twist or Snail. As these cells undergo senescence naturally after multiple rounds of cell division and cannot be passaged for prolonged periods, it is often advantageous to immortalize them with hTert and, in some embodiments, subsequently transform them with a SV40-LargeT antigen to allow for their long-term maintenance in vitro. These cells can subsequently be tested for their ability to undergo an epithelial-mesenchymal transition (EMT) and assayed for the gain of stem cell properties. Further introduction of an oncogenic H-Ras (G12V) can confer these cells with tumorigenic potential including the generation of cancer stem cells. Thus, it is possible to generate populations of cancer stem cells and non-CSCs for the purpose of therapeutic screening. Non-limiting examples of cells that are useful for generating naturally-arising mesenchymal cell populations bearing properties of stem cells or cancer stem cells, include: NHBE (Lonza, CC-2540): normal human bronchial/tracheal epithelial cells (for the study of lung cancer); PrEC (Lonza, CC-2555): human prostate epithelial cells (for the study of prostate cancer); InEpC (Lonza, CC-2931): human intestinal epithelial cells (for the study of gastrointestinal cancers); and HPNE-hTert (ATCC, CRL-4023): human pancreas ductal epithelial cells (for the study of pancreatic cancer). Further examples, e.g., HMLE cells, are disclosed in International Application Publication Number, WO/2009/126310, entitled, METHODS FOR IDENTIFICATION AND USE OF AGENTS TARGETING CANCER STEM CELLS, the contents of which are incorporated herein by reference.

In some embodiments, carcinoma cells are provided that comprise basal-like cancer cells. In some embodiments, carcinoma cells arise from the airway epithelium, pancreas ductal epithelium, intestinal epithelium, prostate epithelium or breast epithelium. In some embodiments, the carcinoma cells are carcinoma cells (e.g., from breast epithelium) characterized as Her2$^{neg}$, ER$^{neg}$, and/or PR$^{neg}$.

Aspects of the invention provide test cells and control cells, for example test and control cells that are useful for identifying compounds that specifically target cancer stem cells. As described herein, test or control cells can be primary cells, non-immortalized cell lines, immortalized cell lines, transformed immortalized cell lines, benign tumor derived cells or cell lines, malignant tumor derived cells or cell lines, transgenic cell lines, etc. In some embodiments the tumor is a metastatic tumor, in which case the cells may be derived from the primary tumor or a metastasis. In preferred embodiments, test cells are cells that have undergone an epithelial to mesenchymal transition. Control cells can include both positive and negative controls cells. In one embodiment, a positive control cell is a cancer stem cell, optionally which expresses one or more cancer stem cell biomarker(s). In certain embodiments, a cancer stem cell biomarker is selected from E-Cadherin, TWIST, and a CD44$^+$CD24$^-$ marker profile. Non limiting cancer stem cell biomarkers include: CD20, CD24, CD34, CD38, CD44, CD45, CD105, CD133, CD166, EpCAM, ESA, SCA1, Pecam, Stro1, FOXC2$^{pos}$, N-cadherin$^{high}$, E-cadherin$^{low/neg}$, alpha-catenin$^{low/neg}$, gamma-catenin$^{low/neg}$, vimentin$^{pos}$, and fibronectin$^{pos}$. Other exemplary cancer stem cell markers will be apparent to one of ordinary skill in the art. In some embodiments, a positive control cell is a cell that has undergone an EMT, for example a cell that has reduced E-Cadherin expression.

In some embodiments, a negative control cell is a cancer cell that is not a cancer stem cell, optionally which does not exhibit detectable expression of one or more cancer stem cell biomarker(s). More than one set of control cells may be provided, such as cancer cells that are not cancer stem cells and non-cancer cells. Cells (test or control) may be subjected to one or more genetic or chemical perturbations (e.g., siRNA treatment or other treatment) and then incubated for a predetermined time. The predetermined time is a time sufficient to produce a desired effect in a control cell (e.g., inhibit the growth and/or survival thereof).

In some embodiments the cells are mammalian cells, e.g., human cells or non-human animal cells, e.g., cells of non-human primate, rodent (e.g., mouse, rat, guinea pig, rabbit), origin, or interspecies hybrids. In certain embodiments the test and control cells are obtained from a biopsy (e.g., tissue biopsy, fine needle biopsy, etc.) or at surgery for a cancerous or noncancerous condition.

In some embodiments, cells (e.g., test cells, controls cells) of the invention may be derived from a cancer (e.g., naturally occurring cancer). In some embodiments, cells (e.g., test cells, controls cells) of the invention may be derived from a cancer of epithelial origin (e.g., breast cancer). In some embodiments, the cancer from which cells are derived is a colon carcinoma, a pancreatic cancer, a breast cancer, an ovarian cancer, a prostate cancer, a squamous cell carcinoma, a cervical cancer, a lung carcinoma, a small cell lung carcinoma, a bladder carcinoma, a squamous cell carcinoma, a basal cell carcinoma, an adenocarcinoma, a sweat gland carcinoma, a sebaceous gland carcinoma, a papillary carcinoma, a papillary adenocarcinoma, a cystadenocarcinoma, a medullary carcinoma, a bronchogenic carcinoma, a renal cell carcinoma, a hepatocellular carcinoma, a bile duct carcinoma, a choriocarcinoma, a seminoma, a embryonal carcinoma, a Wilms' tumor, melanoma, or a testicular tumor. In one embodiment, cancer is a lung carcinoma. In one embodiment, cancer is a breast carcinoma. Other cancers will be known to one of ordinary skill in the art. In some embodiments the cancer is a spontaneously arising cancer. In some embodiments the cancer is a cancer associated with a known or characteristic genetic mutation or polymorphism. In some embodiments the cancer is an experimentally produced cancer. In some embodiments the cancer is a hormone-responsive cancer. In some embodiments the cells are derived from an early stage cancer or precancerous lesion, e.g., a papilloma, adenoma, dysplastic lesion, etc., or a carcinoma in situ. In some embodiments the cancer is one that is responsive to a chemotherapeutic agent or combination thereof (e.g., any one or more of the chemotherapeutic agents discussed below). In some embodiments the cancer is one that is resistant to a chemotherapeutic agent or combination thereof.

In some embodiments, cancer cells are experimentally produced. Cancer cells can be experimentally produced by a number of methods known in the art that result in transformation of a non-cancer cell (non-transformed cell) to a cancer cell (transformed cell). Such experimentally produced cancer cells may be metastatic or non-metastatic.

In some cases, cancer cells are produced from non-cancer cells by transfecting the non-cancer cells (transiently or stably) with one or more expression vector(s) encoding an oncogene. Such oncogenes, when expressed, lead to neoplastic or hyperplastic transformation of a cell. The oncogene may be a complete sequence of the oncogene, preferably an oncogenic form of the oncogene, or it may be a fragment of the oncogene that maintains the oncogenic potential of the oncogene. Exemplary oncogenes include MYC, SRC, FOS, JUN, MYB, RAS, ABL, BCL2, HOXI1, HOX1 IL2, TAL1/SCL, LMO1, LMO2, EGER, MYCN, MDM2, CDK4, GLI1, IGF2, activated EGFR, mutated genes, such as FLT3-ITD, mutated of TP53, PAX3, PAX7, BCR/ABL, HER2/NEU, FLT3R, FLT3-ITD, SRC, ABL, TAN1, PTC, B-RAF, PML-RAR-alpha, E2A-PBX1, and NPM-ALK, as well as fusion of members of the PAX and FKHR gene families. Other exemplary oncogenes are well known in the art and several such examples are described in, for example, The Genetic Basis of Human Cancer (Vogeistein. B. and Kinzier, K. W. eds. McGraw-Hill, New York, N.Y., 1998). Homologues of such genes can also be used.

In some cases, cancer cells can be produced from non-cancer cells by transfecting the non-cancer cells (transiently or stably) with one or more expression vector(s) encoding an inhibitory molecule (e.g., shRNA, mirRNA) capable of inhibiting the expression of a tumor suppressor gene. Such inhibitory molecules, when expressed, lead. to neoplastic or hyperplastic transformation of a cell. Exemplary tumor suppressor genes include RB, TP53, APC, NF-1, BRCA-1, BRCA-2 and WT-1. Other exemplary tumor suppressor genes are well known in the art.

In some cases, cancer cells can be produced from non-cancer cells by transfecting the non-cancer cells (transiently or stably) with one or more expression vector(s) encoding an inhibitory molecule (e.g., shRNA) capable of inhibiting the expression of a tumor suppressor gene and one or more expression vector(s) encoding an oncogene.

In some embodiments, cells (e.g., test cells, control cells) of the invention are derived from noncancerous tissue. For example, the cells may be derived from any epithelial tissue. One of skill in the art will appreciate that "epithelium" refers to layers of cells that line the cavities and surfaces of structures throughout the body and is also the type of tissue of which many glands are at least in part formed. Such tissues include, for example, tissues found in the breast, gastrointestinal tract (stomach, small intestine, colon), liver, biliary tract, bronchi, lungs, pancreas, kidneys, ovaries, prostate, skin, cervix, uterus, bladder, ureter, testes, exocrine glands, endocrine glands, blood vessels, etc. In some embodiments the epithelium is endothelium or mesothelium. In certain embodiments the cells are human breast epithelial cells. In certain embodiments the cells are noncancerous human breast cells obtained from a reduction mammoplasty. In certain embodiments, the test and control cells are derived from any cell type that normally expresses E-cadherin. In certain embodiments, the test and control cells are of a cell type that does not normally express N-cadherin. In certain embodiments, the test and control cells are of a cell type that normally expresses E-cadherin at levels at least 5, 10, 20, 50, or 100-fold higher levels, on average, than those at which it expresses N-cadherin.

In some embodiments the cells (test and/or control) have been modified, e.g., genetically modified, so as to express, inhibit, or delete one or more oncogenes or tumor suppressor genes. In some embodiments such modification immortalizes the cells. In some embodiments such modification transforms the cells to tumorigenic cells. For example, in certain embodiments test and/or control cells are immortalized by expressing telomerase catalytic subunit (e.g., human telomerase catalytic subunit; hTERT) therein. In certain embodiments test and/or control cells are transformed by expressing SV40 (e.g., early region) or Ras, optionally activated Ras such as H-rasV12, therein. In some embodiments cells are modified or treated so as to have reduced or essentially absent expression and/or functional activity of cell cycle checkpoint or DNA damage sensing proteins, e.g., p16, e.g., $p16^{INK4a}$, p53 and/or retinoblastoma (Rb) proteins. For example, cells can be modified to express a shRNA targeted to one or more of these genes, or to express a viral protein that binds to one or more of these proteins. Combinations of such modifications can be used. For example, cells may be modified to express SV40 large T (LT), hTERT, and H-rasV12. Other means of immortalizing and/or transforming cells are known in the art and are within the scope of the invention.

In certain embodiments of the invention the test cells and control cells are derived from an initial population of substantially identical cells that have not undergone an EMT. Certain of these cells are manipulated so as to render them suitable for use as test cells, e.g., by modifying them so as to be able to induce EMT in a controlled manner and then inducing EMT or by treating them with an agent that induces EMT, e.g., as described above. In certain embodiments such as these the test and control cells are genetically matched but have one or several defined genetic differences such as those described herein that result in the test cells having undergone EMT while the control cells have not undergone EMT. In certain embodiments, two populations of cells derived from the same starting population, wherein one population has been modified by introducing a vector and the other population has not been so modified. In certain embodiments, two populations of cells derived from the same starting population, wherein one population has been modified by introducing an expression construct encoding an inhibitory nucleic acid or protein element and the other population has been modified by introducing a expression construct encoding a control nucleic acid or protein element (e.g., one that would not be expected to inhibit an endogenous cellular gene or protein). Typically the expression constructs are otherwise similar or identical. In certain embodiments of the invention, the test cells and control cells are genetically matched and contain an expression construct (optionally integrated into the genome) comprising a sequence encoding a short interfering RNA capable of inducing EMT (such as a shRNA or miRNA targeted to E-cadherin), wherein the sequence is operably linked to a regulatable (e.g., inducible or repressible) promoter. In certain embodiments of the invention, the test cells and control cells are genetically matched and contain an expression construct (optionally integrated into the genome) comprising a sequence encoding a protein capable of inducing EMT, wherein the sequence is linked to a regulatable (e.g., inducible or repressible) promoter. Regulatable expression systems are known in the art and include, e.g., systems utilizing promoters that are inducible by heavy metals, small molecules, etc. Drug-regulatable promoters that are suited for use in mammalian cells include the tetracycline/doxycycline regulatable promoter systems.

"Genetically matched" includes cells or populations of cells that have largely identical genomes, e.g., their genomes are at least 95%, 98%, 99%, 99.5%, 99.9%, 99.99% identical, or more. Typically, genetically matched cells are derived from the same subject or, in the case of certain species such as mice or rats, from different subjects belonging to a particular inbred strain. In some embodiments genetically matched cells are derived from the same tissue sample. In some embodiments of the invention, test and control cells will have been derived from the same initial population of genetically matched cells and will have undergone no more than 2, 5, 10, 15, 20, 25, 30, 35, 40, 50, 60, 70, 80, 90, or 100 rounds of cell division before being used in an inventive method. In some embodiments two or more cells or cell lines may be identified as having originated from the same sample or subject. If desired, cells may be tested to confirm whether they are derived from a single subject, sample, or a particular cell line by any of a variety of methods known in the art such as DNA fingerprinting (e.g., short tandem repeat (STR) analysis) or single nucleotide polymorphism (SNP) analysis (which may be performed using, e.g., SNP arrays (e.g., SNP chips) or sequencing).

The invention provides genetically matched test cells (or cells that can be induced to undergo an EMT and thereby become suitable for use as test cells) and control cells and kits containing such cells (e.g., test cells, control cells, or both test cells and control cells, e.g., in separate containers). In some embodiments, test cells comprise NAMECs. In some embodiments a kit comprises NAMECs and further comprises parental cells of a cell line from which such NAMECs were originally isolated. In some embodiments the test cells and control cells express different detectable markers. In some embodiments, cells may be provided as a frozen vial containing cells, e.g., in a suitable medium. The medium may comprise one or more agents for cryopreservation. Without wishing to be bound by any theory and without limiting the invention in any way, by using test and control cells that are genetically matched and differ primarily or essentially in that the test cells have undergone an EMT and the control cells have not, the invention allows identification of compounds that differentially affect the test cells versus the control cells (e.g., compounds that inhibit growth of the test cells to a significantly greater extent than the extent to which they inhibit growth of the control cells) as a result of differences in the test cells and control cells that arise as a consequence of the differentiation state of the cells e.g., as a consequence of the test cells having undergone an EMT (associated with acquiring cancer stem cell-like properties) rather than because of other, possibly unknown, genetic or epigenetic differences in the test and control cells.

Methods for Identifying Compounds that Differentially Target CSCs

In some embodiments, methods are provided for identifying candidate compounds or compositions that differentially target CSCs. In some embodiments, screening may be carried out in vitro or in vivo using any of the assays disclosed herein, or any assay known to one of ordinary skill in the art to be suitable for contacting a test cell with a test compound and assaying for alterations in the growth and/or survival of the test cell.

In some embodiments, methods of identifying a candidate compound for selectively inhibiting growth of cancer stem cells involve contacting test cells with a test compound, in which the test cells are cells that have spontaneously undergone an epithelial to mesenchymal transition and have been collected through differential detachment from a culture surface, or progeny cells thereof; and determining whether the test compound selectively inhibits growth of the test cells, in which inhibition of growth indicates that the test compound is a candidate compound for selectively inhibiting growth of cancer stem cells.

The methods may involve co-culturing test cells and control cells, in which the test cells are cells of epithelial cell origin that have undergone an epithelial to mesenchymal transition, or progeny cells thereof, and the control cells are cells of epithelial cell origin that have not undergone an epithelial to mesenchymal transition. Methods employing co-culture systems may involve contacting the co-cultured test and control cells with a test compound; and determining whether the test compound selectively inhibits growth of the test cells compared with the control cells in the co-culture, in which inhibition of growth indicates that the test compound is a candidate compound for selectively inhibiting growth of cancer stem cells. In some cases, particularly in co-culture based methods, test cells are engineered to express a first detectable marker and the controls cells are engineered to express a second detectable marker. Here, assaying growth of the test cells comprises determining the number of cells in the co-culture that express the first detectable marker and assaying the growth control cells comprises determining the number of cells in the co-culture that express the second detectable marker. The first and second detectable markers may be fluorescent proteins having sufficiently different excitation and emission spectra to permit selective detection of each marker by fluorescence microscopy and/or fluorescence activated cell sorting (FACS).

In one aspect compounds are contacted with test cells (and optionally control cells) at a predetermined dose. In one embodiment the dose may be about up to 1 nM. In another embodiment the dose may be between about 1 nM and about 100 nM. In another embodiment the dose may be between about 100 nM and about 10 uM. In another embodiment the dose may be at or above 10 uM. Following incubation for an appropriate time, optionally a predetermined time, the effect of compounds or composition on the growth and/or survival of the test cell is determined by an appropriate method known to one of ordinary skill in the art. Cells can be contacted with compounds for various periods of time. In certain embodiments cells are contacted for between 12 hours and 20 days, e.g., for between 1 and 10 days, for between 2 and 5 days, or any intervening range or particular value. Cells can be contacted transiently or continuously.

If desired, compound can be removed prior to assessing growth and/or survival of the test cell. As used herein, "suppress", "inhibit", or "reduce" may, or may not, be complete. For example, cell proliferation, may, or may not, be decreased to a state of complete arrest for an effect to be considered one of suppression, inhibition or reduction of cell proliferation. Similarly, gene expression may, or may not, be decreased to a state of complete cessation for an effect to be considered one of suppression, inhibition or reduction of gene expression. Moreover, "suppress", "inhibit", or "reduce" may comprise the maintenance of an existing state and the process of affecting a state change. For example, inhibition of cell proliferation may refer to the prevention of proliferation of a non-proliferating cell (maintenance of a non-proliferating state) and the process of inhibiting the proliferation of a proliferating cell (process of affecting a proliferation state change). Similarly, inhibition of cell survival may refer to killing of a cell, or cells, such as by necrosis or apoptosis, and the process of rendering a cell susceptible to death, such as by inhibiting the expression or activity of an anti-apoptotic regulatory factor. The suppression, inhibition, or reduction may be at least about 5%, 10%, 15%, 20%, 25%, 30%, 35%, 40%, 45%, 50%, 55%, 60%, 65%, 70%, 75%, 80%, 85%, 90%, 95%, 99% of a reference level (e.g., a control level).

In some cases the level of modulation (e.g., suppression, inhibition, or reduction) compared with a control level is statistically significant. As used herein, "statistically significant" refers to a p-value of less than 0.05, e.g., a p-value of less than 0.025 or a p-value of less than 0.01, using an appropriate statistical test (e.g, ANOVA, t-test, etc.).

In certain embodiments, the growth and/or survival of the test cell and/or control cell is determined by an assay selected from: a cell counting assay, a replication labeling assay, a cell membrane integrity assay, a cellular ATP-based viability assay, a mitochondrial reductase activity assay, a caspase activity assay, an Annexin V staining assay, a DNA content assay, a DNA degradation assay, and a nuclear fragmentation assay. Other exemplary assays include BrdU, EdU, or H3-Thymidine incorporation assays; DNA content assays using a nucleic acid dye, such as Hoechst Dye, DAPI, Actinomycin D, 7-aminoactinomycin D or Propidium Iodide; Cellular metabolism assays such as AlamarBlue, MTT, XTT, and CellTitre Glo; Nuclear Fragmentation Assays; Cytoplasmic Histone Associated DNA Fragmentation Assay; PARP Cleavage Assay; TUNEL staining; and Annexin staining.

In one embodiment, gene expression analysis (e.g., microarray, cDNA array, quantitative RT-PCR, RNAse protection assay) is employed to examine the expression of genes whose products mediate cell cycle/growth and/or survival.

In other embodiments, alterations in the growth and/or survival of the test cell and/or control cell is/are assessed by examining protein levels, for example the level of protein encoded by a foregoing cell cycle/growth and/or survival gene. Protein levels can be assessed by an appropriate method known to one of ordinary skill in the art, such as western analysis. Other methods known to one of ordinary skill in the art could be employed to analyze proteins levels, for example immunohistochemistry, immunocytochemistry, ELISA, radioimmunoassays, proteomics methods, such as mass spectroscopy or antibody arrays.

Still other parameters disclosed herein that are relevant assessing cell growth and/or survival can provide assays for screening for compounds. For example, high-content imaging or Fluorescence-activated cell sorting (FACS) of cells may be used. In one embodiment, the effect of a compound on a test cell and/or control cell can be assessed by evaluating the apoptotic state of the test cell using automated microscopic imaging or FACS (See for example United States Patent Publication 20070172818). In some cases, fluorescence-based TUNEL staining (e.g., using a FITC-dUTP with standard TUNEL methods known in the art) can reveal apoptosis in a test cell and/or control cell. Other methods include immunocytochemistry using an antibody (e.g., cleaved PARP, cleaved Lamin A, etc.) to detect caspase activity. In other embodiments, an image-based cell cycle/growth marker can be used, such as one or more of those exemplified in Young D W, et al., Nat Chem Biol. 2008 January; 4(1):59-68. These examples of imaging are not intended to be limiting, and other similar methods will be readily apparent to one of ordinary skill in the art.

In other embodiments, the activity of a cell growth and/or survival gene, such as those disclosed herein, can be assayed in a compound screen. In one embodiment, the assay comprises an expression vector that includes a regulatory region of a gene of interest operably linked to a sequence that encodes a reporter gene product (e.g., a luciferase enzyme), wherein expression of the reporter gene is correlated with the activation of the gene. In this embodiment assessment of reporter gene expression (e.g., luciferase activity) provides an indirect method for assessing cell growth and/or survival. This and other similar assays will be well known to one of ordinary skill in the art. The reporter gene product could be, without limitation, a fluorescent or luminescent protein, enzyme, or other protein amenable to convenient detection and, optionally, quantitation. Examples include GFP, RFP, BFP, YFP, CYP, SFP, reef coral fluorescent protein, mFruits such as mCherry, luciferase, aequorin and derivatives of any of the foregoing. Enzyme reporter proteins such as beta-galactosidase, alkaline phosphatase, chloramphenicol acetyltransferase, etc., are also of use. In other embodiments, chromatin immunoprecipitation assays could be used to assess the binding of transcription factors at a regulatory DNA region of cell growth and/or survival gene(s).

The foregoing assay methods of the invention are amenable to high-throughput screening (HTS) implementations. In some embodiments, the screening assays of the invention are high throughput or ultra high throughput (e.g., Fernandes, P. B., Curr Opin Chem Biol. 1998 2:597; Sundberg, S A, Curr Opin Biotechnol. 2000, 11:47). HTS refers to testing of up to, and including, 100,000 compounds per day. Whereas ultra high throughput (uHTS) refers to screening in excess of 100,000 compounds per day. The screening assays of the invention may be carried out in a multi-well format, for example, a 96-well, 384-well format, or 1,536-well format, and are suitable for automation. In the high throughput assays of the invention, it is possible to screen several thousand different compounds or compositions in a single day. In particular, each well of a microtiter plate can be used to run a separate assay against a selected test compound, or, if concentration or incubation time effects are to be observed, a plurality of wells can contain test samples of a single compound. It is possible to assay many plates per day; assay screens for up to about 6,000, 20,000, 50,000, or more than 100,000 different compounds are possible using the assays of the invention. Typically, HTS implementations of the assays disclosed herein involve the use of automation. In some embodiments, an integrated robot system consisting of one or more robots transports assay microplates between multiple assay stations for compound, cell and/or reagent addition, mixing, incubation, and finally readout or detection. In some aspects, an HTS system of the invention may prepare, incubate, and analyze many plates simultaneously, further speeding the data-collection process. High throughput screening implementations are well known in the art. Exemplary methods are also disclosed in High Throughput Screening: Methods and Protocols (Methods in Molecular Biology) by William P. Janzen (2002) and High-Throughput Screening in Drug Discovery (Methods and Principles in Medicinal Chemistry) (2006) by Jörg Hüser, the contents of which are both incorporated herein by reference in their entirety.

As described above, compounds or compositions that substantially affect the growth and/or survival of a test cell and/or control cell, and/or that are candidate modulators of the EMT program can be uncovered using the disclosed test methods. Examples of types of compounds or compositions that may be tested include, but are not limited to: anti-metastatic agents, cytotoxic agents, cytostatic agents, cytokine agents, anti-proliferative agents, immunotoxin agents, gene therapy agents, angiostatic agents, cell targeting agents, HDAC inhibitory agents, etc. In some embodiments, the test compound is a kinase inhibitor. In some embodiments, the test compound is a Protein Kinase C (PKC) inhibitor. In some embodiments, the test compound is a protein kinase C (PKCα) inhibitor, an inhibitor of PDGFR, or an inhibitor of FRA-1. In some embodiments, the test compound is an inhibitor of CDC-like kinase 1 (CLK1), PI-3-kinase-related kinase SMG1, ephrin type-A receptor 2 (EphA2), nucleoside-diphosphate kinase 7 (NME7), protein kinase C α (PKCα), serum/glucocorticoid regulated kinase 1 (SGK1), sphingosine kinase 1 (SPHK1), sphingosine kinase 2 (SPHK2) or cyclin-dependent kinase 6 (CDK6). As used herein, compounds or compositions may in some cases be referred to as test agents. In some embodiments a first screen is performed in a cell-free system to identify a compound capable of inhibiting a target of interest, e.g., a kinase described herein. In some embodiments the effect of an identified compound on CSCs, non-CSCs, or a combination thereof may be assessed. In some embodiments the effect of an identified compound on test cells, control cells, or a combination thereof may be assessed. A compound that exhibits a desired effect, e.g., inhibition, e.g., selective inhibition, of survival and/or proliferation of CSCs may be identified.

The following provides further examples of test compounds and is not meant to be limiting. Those of ordinary skill in the art will recognize that there are numerous additional types of suitable test compounds that may be tested using the methods, cells, and/or animal models of the invention. Test compounds can be small molecules (e.g., compounds that are members of a small molecule chemical library). The compounds can be small organic or inorganic molecules of molecular weight below about 3,000 Daltons. The small molecules can be, e.g., from at least about 100 Da to about 3,000 Da (e.g., between about 100 to about 3,000 Da, about 100 to about 2,500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The small molecules can be natural products, synthetic products, or members of a combinatorial chemistry library. A set of diverse molecules can be used to cover a variety of functions such as charge, aromaticity, hydrogen bonding, flexibility, size, length of side chain, hydrophobicity, and rigidity. Combinatorial techniques suitable for synthesizing small molecules are known in the art (e.g., as exemplified by Obrecht and Villalgrodo, Solid-Supported Combinatorial and Parallel Synthesis of Small-Molecular-Weight Compound Libraries, Pergamon-Elsevier Science Limited (1998)), and include those such as the "split and pool" or "parallel" synthesis techniques, solid-phase and solution-phase techniques, and encoding techniques (see, for example, Czarnik, A. W., Curr. Opin. Chem. Biol. (1997) 1:60). In addition, a number of small molecule libraries are publicly or commercially available (e.g., through Sigma-Aldrich, TimTec (Newark, Del.), Stanford School of Medicine High-Throughput Bioscience Center (HTBC), and ChemBridge Corporation (San Diego, Calif.).

Compound libraries screened using the new methods can comprise a variety of types of test compounds. A given library can comprise a set of structurally related or unrelated test compounds. In some embodiments, the test compounds are peptide or peptidomimetic molecules. In some embodiments, test compounds include, but are not limited to, peptide analogs including peptides comprising non-naturally occurring amino acids, phosphorous analogs of amino acids, amino acids having non-peptide linkages, or other small organic molecules. In some embodiments, the test compounds are peptidomimetics (e.g., peptoid oligomers, e.g., peptoid amide or ester analogues, D-peptides, L-peptides, oligourea or oligocarbamate); peptides (e.g., tripeptides, tetrapeptides, pentapeptides, hexapeptides, heptapeptides, octapeptides, nonapeptides, decapeptides, or larger, e.g., 20-mers or more); cyclic peptides; other non-natural peptide-like structures; and inorganic molecules (e.g., heterocyclic ring molecules). In some embodiments a polypeptide comprises an affibody, adnectin, DARPin, knottin, anticalins, or steffin. The polypeptide, e.g., affibody, adnectin, DARPin, knottin, anticalins, or steffin, may be designed or selected to bind to a target of interest. Test compounds can also be nucleic acids.

The test compounds and libraries thereof can be obtained by systematically altering the structure of a first "hit" compound, also referred to as a lead compound, that has a chemotherapeutic (e.g., anti-CSC) effect, and correlating that structure to a resulting biological activity (e.g., a structure-activity relationship study).

Such libraries can be obtained using any of the numerous approaches in combinatorial library methods known in the art, including: peptoid libraries (libraries of molecules having the functionalities of peptides, but with a novel, non-peptide backbone which are resistant to enzymatic degradation but which nevertheless remain bioactive; see, e.g., Zuckermann, et al., J. Med. Chem., 37:2678-85 (1994)); spatially addressable parallel solid phase or solution phase libraries; synthetic library methods requiring deconvolution; the "one-bead on e-Compound" library method; and synthetic library methods using affinity chromatography selection (Lam, Anticancer Drug Des. 12:145 (1997)). Examples of methods for the synthesis of molecular libraries can be found in the art, for example in: DeWitt et al., Proc. Natl. Acad. Sci. USA, 90:6909 (1993); Erb et al., Proc. Natl. Acad. Sci. USA, 91:11422 (1994); Zuckermann et al., J. Med. Chem., 37:2678 (1994); Cho et al., Science, 261:1303 (1993); Carrell et al., Angew. Chem. Int. Ed. Engl., 33:2059 (1994); Carell et al., Angew. Chem. Int. Ed. Engl., 33:2061 (1994); and in Gallop et al., J. Med. Chem., 37:1233 (1994). Libraries of compounds can be presented in solution (e.g., Houghten (1992) Biotechniques, 13:412-421), or on beads (Lam (1991) Nature, 354:82-84), chips (Fodor (1993) Nature, 364:555-556), bacteria (Ladner, U.S. Pat. No. 5,223,409), spores (Ladner, U.S. Pat. No. 5,223,409), plasmids (Cull et al. (1992) Proc. Natl. Acad. Sci. USA, 89:1865-1869) or on phage (Scott and Smith (1990) Science, 249: 386-390; Devlin (1990) Science, 249:404-406; Cwirla et al. (1990) Proc. Natl. Acad. Sci. USA, 87:6378-6382; Felici (1991) J. Mol. Biol., 222:301-310; Ladner, supra.).

In some embodiments, the methods of the invention are used to screen "approved drugs". An "approved drug" is any compound (which term includes biological molecules such as proteins and nucleic acids) which has been approved for use in humans by the FDA or a similar government agency in another country, for any purpose.

Applicants reserve the right to exclude any particular compound, compounds, or compound class from the scope of "test compound" and/or from the compositions and methods of the invention. In some embodiments the "test compound" is not a compound found in, or known in the art as an ingredient of, tissue culture medium, e.g., a compound provided for purposes of culturing the cells. In some embodiments the test compound may be one found in, or known in the art as an ingredient of, tissue culture medium, but is used as a test compound at concentrations differing from those at which it is typically used as an ingredient of tissue culture medium. In some embodiments the compound is not a compound known in the art as being useful for treating cancer and/or for reducing side effects associated with chemotherapy.

Certain results of the compound identification and characterization methods disclosed herein may be clinically beneficial, such as if the compound is a PKC-α/FRA1 inhibitor or SPHK inhibitors as those disclosed herein. Still other clinically beneficial results include: (a) inhibition or arrest of primary tumor growth, (b) inhibition of metastatic tumor growth and (c) extension of survival of a test subject. Compounds with clinically beneficial results are potential chemotherapeutics, and may be formulated as such.

Compounds identified as having a chemotherapeutic or anti-CSC effect may be referred to herein as lead compounds and can be selected and systematically altered, e.g., using rational design, to optimize binding affinity, avidity, specificity, or other parameters. Such optimization can also be screened for using the methods described herein. Thus, one can screen a first library of small molecules using the methods described herein, identify one or more compounds that are "hits" or "leads" (by virtue of, for example, their ability to inhibit the growth and/or survival of a test cell and/or cancer stem cell and/or their ability to reduce the size and/or number of CSC dependent tumors, e.g., at the original site of implantation and at metastasis sites), and subject those hits to systematic structural alteration to create a second library of compounds (e.g., refined lead compounds) structurally related to the hit. The second library can then be screened using the methods described herein. A refined lead compound can be produced by modifying the lead compound to achieve (i) improved potency, (ii) decreased toxicity (improved therapeutic index); (iii) decreased side effects; (iv) modified onset of therapeutic action and/or duration of effect; and/or (v) modified pharmacokinetic parameters (absorption, distribution, metabolism and/or excretion). The lead compound could be, e.g., purified from natural sources or chemically synthesized. Modifications could be made directly to the lead compound, or refined lead compounds (e.g., derivatives) could be synthesized from suitable starting materials.

In certain embodiments of the invention a compound identified using the inventive methods displays selective activity (e.g., inhibition of proliferation, inhibition of tumorigenesis, toxicity) against test cells relative to its activity against control cells. For example, the IC50 of a compound may be about 2, 5, 10, 20, 50, 100, 250, 500, or 1000-fold lower for test cells versus control cells. In some embodiments, the IC50 of a compound may be about 2, 5, 10, 20, 50, 100, 250, 500, or 1000-fold lower for cells that have undergone EMT than for genetically matched cells that have not undergone EMT. In some embodiments, the IC50 of a compound may be about 2, 5, 10, 20, 50, 100, 250, 500, or 1000-fold lower for CSCs than for non-CSC cancer cells. In some embodiments, the IC50 of a compound may be about 2, 5, 10, 20, 50, 100, 250, 500, or 1000-fold lower for CSCs than for normal (non-cancerous) cells that have not undergone EMT.

In some cases it is desirable to determine the potency of a compound of the invention using a dose response assay. Methods for determining the potency of compounds or compositions are well known in the art. In some embodiments, potency is characterized as a half maximal effective concentration (EC50) of a compound. As used herein, the term half maximal effective concentration (EC50) refers to the concentration of a compound that induces a response in a biological system (e.g., one or more cells) halfway between the baseline response (e.g., no compound) and the maximal response. EC50 is commonly used in the art as a measure of compound potency (e.g., drug potency). The EC50 of a dose response curve represents the concentration of a compound where 50% of its maximal effect (also referred to as maximal response) is observed. EC50 is related to the half maximal inhibitory concentration (IC50), which is often used as a measure of inhibition by a compound (50% inhibition) in a biochemical assays, for example competitive binding assays and functional agonist/antagonist assays. Methods for determining EC50/IC50 values are well known in the art.

A variety of techniques useful for determining the structures of compounds are known and can be used in the methods described herein (e.g., NMR, mass spectrometry, gas chromatography equipped with electron capture detectors, fluorescence, and absorption spectroscopy).

Assays of chemotherapeutic activity of test compounds may be conducted in vitro or ex vivo and/or in vivo using cells (e.g., test cells that have undergone an epithelial to mesenchymal transition, cancer stem cells identified or generated using any suitable method, cancer cells, cancer cell lines, etc.) and methods of the invention or any suitable system for testing efficacy. For example, a test compound may be administered to a nonhuman subject to which has been administered (e.g., implanted or injected with) a plurality of the test cells described herein, e.g., a number of cancer stem cells sufficient to induce the formation of one or more tumors (e.g., CSC-dependent tumors), a tumor xenograft, etc. The nonhuman subject can be, e.g., a rodent (e.g., a mouse). Optionally the nonhuman subject is immunocompromised, e.g., a Nude, SCID, NOD-SCID, Rag1−/−, and Rag2−/− mouse. In some embodiments the test subject is a cancer-prone animal, e.g., an animal model harboring an activated oncogene and/or lacking a tumor suppressor gene, or an animal that has been exposed to a condition, compound, or stimulus that renders the animal prone to develop cancer. As used herein, a non-human test subject may also be referred to as an animal host.

The test compound can be administered to the subject by any regimen known in the art. For example, the test compound can be administered prior to, concomitant with, and/or following the administration of cancer stem cells of the invention. A test compound can also be administered regularly throughout the course of the method, for example, one, two, three, four, or more times a day, weekly, bi-weekly, or monthly, beginning before or after cells of the invention have been administered. In other embodiments, the test compound is administered continuously to the subject (e.g., intravenously or by release from an implant, pump, sustained release formulation, etc.). The dose of the test compound to be administered can depend on multiple factors, including the type of compound, weight of the subject, frequency of administration, etc. Determination of dosages is routine for one of ordinary skill in the art. Typical dosages are 0.01-200 mg/kg (e.g., 0.1-20 or 1-10 mg/kg).

The size and/or number of tumors in the subject can be determined following administration of the tumor cells and the test compound. The size and/or number of tumors can be determined non-invasively by any means known in the art. For example, tumor cells that are fluorescently labeled (e.g., by expressing a fluorescent protein such as GFP) can be monitored by various tumor-imaging techniques or instruments, e.g., non-invasive fluorescence methods such as two-photon microscopy. The size of a tumor implanted subcutaneously can be monitored and measured underneath the skin.

To determine whether a compound affects the growth of cells, the size and/or number of tumors in the subject can be compared to a reference standard (e.g., a control value). A reference standard can be a control subject which has been given the same regimen of administration of cancer stem cells and test compound, except that the test compound is omitted or administered in an inactive form. Alternately, a compound believed to be inert in the system can be administered. A reference standard can also be a control subject which has been administered cancer cells that are not cancer stem cells and test compound, cancer cells that are not cancer stem cells and no test compound, or cancer cells that are not cancer stem cells and an inactive test compound. The reference standard can also be a numerical figure(s) or range of figures representing the level of a biomarker or the size and/or number of tumors expected in an untreated subject. This numerical figure(s) or range of figures can be determined by observation of a representative sample of untreated subjects. A reference standard may also be the test animal before administration of the compound.

In some cases the activity of a compound (e.g., a lead compound) can be tested by contacting control cells and test cells that are grown in a co-culture. Co-cultures enable evaluation of the selective growth and/or survival properties of two or more populations of cells (e.g., control and test cells) in contact with a compound in a common growth chamber. Typically, each population of cells grown a co-culture will have an identifying characteristic that is detectable and distinct from an identifying characteristic of the other population(s) of cells in the co-culture. In some embodiments, the identifying characteristic comprises a level of expression of GFP protein or other reporter protein such as those mentioned above and/or a biomarker of EMT's or of activity of the PKC-α/FRA1 pathway or the SPHK pathway. However, the invention is not so limited and other identifying characteristics known in the art may be suitable, provided that the identifying characteristic enables measurement (e.g., by FACS or other suitable assay method disclosed herein) of a parameter of interest (e.g., PKC-α/FRA1 pathway activity, SPHK pathway activity, cell growth, cell survival) of each of the two or more populations of cells in the co-culture. Compositions, e.g., co-cultures, comprising at least some test cells (e.g., between 1 and 99% test cells) and at least some control cells (e.g., between 1 and 99% control cells), are an aspect of the invention. In some embodiments the percentage of test cells is between 10% and 90%. In other embodiments the percentage of test cells is between 20% and 80%. In some embodiments the percentage of test cells is between 30% and 70%. In some embodiments the percentage of test cells is between 40% and 60%, e.g., about 50%. In some embodiments the composition further comprises a test agent.

In other embodiments, test cells and control cells are maintained in separate vessels (e.g., separate wells of a microwell plate) under substantially identical conditions.

Assay systems comprising test cells, control cells, and one or more test compounds, e.g., 10, 100, 1000, 10,000, or more test compounds, wherein the cells and test agents are arranged in one or more vessels in a manner suitable for assessing effect of the test compound(s) on the cells, are aspects of the invention. Typically the vessels contain a suitable tissue culture medium, and the test compounds are present in the tissue culture medium. One of skill in the art can select a medium appropriate for culturing a particular cell type. In some embodiments, a medium is free or essentially free of serum or tissue extracts while in other embodiments such a component is present. In some embodiments, cells are cultured on a plastic or glass surface. In some embodiments cells are cultured on or in a material comprising collagen, laminin, Matrigel®, or a synthetic material, e.g., a synthetic hydrogel, intended to provide an environment that resembles in at least some respects the extracellular environment found in many tissues. In some embodiments test and/or control cells are cultured with non-cancerous stromal cells. In some embodiments test and/or control cells are cultured with fibroblasts. In some embodiments test and/or control cells are cultured in three-dimensional culture matrix.

As used herein, the terms "approximately" or "about" in reference to a number are generally taken to include numbers that fall within a range of 1%, 5%, 10%, 15%, or 20% in either direction (greater than or less than) of the number unless otherwise stated or otherwise evident from the context (except where such number would be less than 0% or exceed 100% of a possible value).

All references described herein are incorporated by reference for the purposes described herein.

Exemplary embodiments of the invention will be described in more detail by the following examples. These embodiments are exemplary of the invention, which one skilled in the art will recognize is not limited to the exemplary embodiments.

EXAMPLES

Experimental Methods and Materials

Kinase Inhibitor Screen

Kinase inhibitors and other chemical compounds were obtained from various sources listed below. These were dissolved or diluted in DMSO. To set up the screen, 75,000 NAMEC-Tom and 15,000 HMLE-GFP cells were seeded into each well of a 6-well tissue culture plate. The following day, spent media was replaced with 3 ml of fresh media. Inhibitors were added to achieve the desired range of concentrations. For control treatment, DMSO was added. Fresh media containing inhibitors were replaced daily during the six day period. For analysis, cells were trypsinized with 1 ml 0.15% trypsin, diluted with 1 ml serum-containing media and fixed with 1 ml of 4% paraformaldehyde. FACS analysis was performed to analyze the proportion of surviving cells relative to DMSO-treated control for NAMEC-Tom or HMLE-GFP cells. To test the effects of these inhibitors on CSCs and non-CSCs, NAMEC-Ras-Tom and HMLE-Ras-Tom were used in similar co-mixed experiments.

The list of compounds used in the kinase inhibitor screen to identify those selective against mesenchymal but not epithelial cells is provided herein.

Cell Lines and Cell Culture

All cell cultures were maintained at 37° C. with 5% $CO_2$. HMLE cells and NAMECs were maintained in MEGM (Lonza). MCF7, MDA-MB-231, CAMA1, MDA-MB-436, SKBR3, T47D, SUM 159 were maintained using standard methods. Human mammary epithelial cell lines (HMLE) were generated as described and immortalized using retroviral vectors to express the catalytic subunit of the human telomerase enzyme, hTERT and the SV-40 Large T antigen (Elenbaas et al., 2001).

NAMECs were isolated based on the observation that mesenchymal cells were less adherent than epithelial cells to tissue culture surfaces. HMLE cells were grown to 50% confluence, followed by differential trypsinization for one minute with 0.05% trypsin. Detached cells were carefully collected and re-plated at approximately 200 cells per well of a 24-well plate. Upon expansion, wells were screened for populations which were morphologically mesenchymal and can be stably propagated. We generated clonal and non-clonal NAMEC cell lines. Clonal cells lines (NAMEC 1-5) were derived from a single mesenchymal cell plated into a 96-well plate by FACS. Non-clonal lines (NAMEC 6-11) were derived from at least 200 mesenchymal cells. These lines were assessed for mesenchymal properties by analyses of their protein and mRNA expression and CD44/CD24 profile.

HMLE-Twist-ER and HMLE-Snail-ER cells were generated as described (Casas et al., 2011). For EMT-induction, 100 nM of hydroxytamoxifen (Sigma) in ethanol was added to the culture medium every 24 h for a total duration of 12 days. Control cells were treated with ethanol. To generate stable EMT TF-induced cells, HMLE cells were infected with constitutive pBabePuro-Twist, pBabePuro-Snail and pWPXL-hSlug (Guo et al., 2012; Mani et al., 2008).

To generate tumorigenic cells, cells were infected with pWZL-Blast-Ras (Elenbaas et al., 2001). pLL3.7-GFP and pLV-tdTomato lentivirus were used to generate GFP$^+$ and Tom$^+$ cells, respectively. For stable knockdown of target genes, pLK0.1-Puro shRNAs were used (Dana Farber Cancer Institute RNAi Facility). Production of virus and infection of target cells were performed using standard methods. Infected cells were selected with 2 mg/ml puromycin, 200 mg/ml hygromycin, or 200 mg/ml neomycin.

For mammosphere culture, cells were seeded onto 96-well ultralow-adherence plates at 500 cells/well in Mammocult medium (Stem Cell Technologies) supplemented with heparin, hydrocortisone and methylcellulose. Spheres were counted at 12-14 days later.

Kinase Inhibitor Screen II

Kinase inhibitors and other chemical compounds were obtained from various sources listed below. These were dissolved or diluted in DMSO. To set up the screen, 75,000 NAMEC-Tom and 15,000 HMLE-GFP cells were seeded into each well of a 6-well tissue culture plate. The following day, spent media was replaced with 3 ml of fresh media. Inhibitors were added to achieve the desired range of concentrations. For control treatment, DMSO was added. Fresh media containing inhibitors were replaced daily during the six day period. For analysis, cells were trypsinized with 1 ml 0.15% trypsin, diluted with 1 ml serum-containing media and fixed with 1 ml of 4% paraformaldehyde. FACS analysis was performed to analyze the proportion of surviving cells relative to DMSO-treated control for NAMEC-Tom or HMLE-GFP cells. To test the effects of these inhibitors on CSCs and non-CSCs, NAMEC-Ras-Tom and HMLE-Ras-Tom were used in similar co-mixed experiments. To assess the fraction of cells undergoing apoptosis, cells were exposure to agents for three days without fresh media and then analyzed with Annexin V-APC (BD Biosciences).

TABLE 1

The following compounds were used in the kinase inhibitor screen to identify those selective against mesenchymal but not epithelial cells.

| Inhibitors | Catalogue number | Company |
|---|---|---|
| Ro 31-8220 | 13334 | Cayman Chemical |
| Paclitaxel | 89164-960 | VWR |
| CAY10621 | 13371 | Cayman Chemical |
| PD0332991 | S1116 | Selleck |
| Bisindolylmaleimide I | 13298 | Cayman Chemical |
| Staurosporine | ALX-380-014-M005 | Enzo |
| PKC Inhibitor 20-28 | 476480 | EMD Biosciences |
| GSK 650394 | 3572 | Tocris |
| PKCη Pseudosubstrate | 539604 | EMD Biosciences |
| TG003 | 219479 | EMD Biosciences |
| Calmidazolium Chloride (R24571) | sc-201494 | SCBT |
| W-7 | sc-201501 | SCBT |
| Fluphenazine-N-2-chloroethane-2HC1 | sc-201502 | SCBT |
| RO-32-0432 | 80057-472 | VWR |
| PD-98059 | BML-EI360-0005 | Enzo |
| U0126 | 70970 | Cayman Chemical |
| SP600125 | BML-EI305-0010 | Enzo |
| EGFR Inhibitor | 324674 | EMD Biosciences |
| EGFR Inhibitor III-TKS050 | 324833 | EMD Biosciences |
| PDGFR Tyrosine Kinase Inhibitor III | 521232 | EMD Biosciences |
| PDGFR Tyrosine Kinase Inhibitor IV | 521233 | EMD Biosciences |

Protein Extraction and Western Blotting

To obtain protein extracts, cells were scraped from culture dishes in chilled PBS, centrifuged at 450×g for 4 min at 4° C., washed again in PBS, and incubated for 20 min in ice cold lysis buffer containing freshly added protease inhibitors (0.5 mM phenylmethylsulfonyl fluoride, 10 μg/ml leupeptin, 2 μg/ml aprotonin). Lysates were cleared by centrifugation at 12,100×g, 4° C. for 10 min and the supernatant was snap frozen in liquid nitrogen. Protein concentrations were determined using Bradford Dye (Bio-Rad). 30 μg total protein was separated by SDS-PAGE on NuPAge gels (Invitrogen), and transferred to Hybond-P PVDF membrane (GE Healthcare). The membrane was probed with specific primary antibodies and antibody-protein complex detected by HRP-conjugated antibodies and ECL-Plus (Amersham Biosciences).

Antibodies.

TABLE 2

The listed antibodies were used in the following applications.

| Antibody | Catalogue number | Company | Applications |
|---|---|---|---|
| p-MEK1/2 (Ser217/221) | 9154 | CST | WB |
| p44/42 MAPK (Erk1/2) | 4695 | CST | WB |
| p-p44/42 MAPK (pErk1/2) (T202/Y204) | 4370 | CST | WB |
| MEK1/2 | 9122 | CST | WB |
| p-A-Raf (Ser299) | 4431 | CST | WB |
| p-c-Raf (Ser289/296/301) | 9431 | CST | WB |
| p-c-Raf (Ser338) | 9427 | CST | WB |
| c-Raf | 9422 | CST | WB |
| B-Raf | 9434 | CST | WB |
| p-B-Raf (Ser445) | 2696 | CST | WB |
| PDGFRα | 3174 | CST | WB |
| p-PDGFRα (Tyr849) | 3170 | CST | WB |
| PDGFRβ | 3169 | CST | WB |
| p-PDGFRβ (Tyr1021) | 2227 | CST | WB |
| p-PDGFRβ (Tyr751) | 4549 | CST | WB |
| β-Actin | 4970 | CST | WB |
| GAPDH | 5174 | CST | WB |
| H-Ras | sc520 | SCBT | WB |
| PKCα (c-term) | 1510-1 | Epitomics | WB, IHC |
| p-PKCα (T497) | 2378-1 | Epitomics | WB, IHC |
| p-PKCα (T638) | 1195-1 | Epitomics | WB, IHC |
| p-PKCα (S657) | sc12356 | SCBT | WB, IHC |
| p-EGFR (Tyr 992) | 2235 | CST | WB |
| p-EGFR (Tyr 1045) | 2237 | CST | WB |
| p-EGFR (Tyr 1068) | 3777 | CST | WB |
| EGFR | 4267 | CST | WB |
| p-SAPK/JNK (T183/185) | 9255 | CST | WB |
| SAPK/JNK | 9258 | CST | WB |
| p-c-Jun | 2361S | CST | WB, IHC |
| c-Jun | 9165S | CST | WB, IHC |
| JunB | 3753 | CST | WB |
| JunD | 5226-1 | Epitomics | WB |
| FosB | 2251 | CST | WB |
| FRA1 | 5281 | CST | WB, IHC |
| p-FRA1 (S265) | 5841 | CST | WB, IHC |
| c-Fos | 2250 | CST | WB |
| p-c-Fos (S63) | 5348 | CST | WB |
| Twist | ab50887 | Abcam | WB, IHC, IF, ChIP |
| Snail | 3879 | CST | WB, IHC, IF, ChIP |
| Slug | 9585 | CST | WB, IHC, IF |
| Zeb1 | sc25388 | SCBT | WB, IHC |
| PLCγ1 | 5690 | CST | WB |
| PLCγ2 | 3872 | CST | WB |
| p-PLCγ1 (Tyr783) | 2821 | CST | WB |
| p-PLCγ2 (Tyr1217) | 3871 | CST | WB |
| p-PLCγ2 (Tyr759) | 3874 | CST | WB |
| E-cadherin | 610182 | BD Biosciences | WB, IF |
| Fibronectin | 610078 | BD Biosciences | WB, IF |
| Vimentin | MS-129-P1 | Thermo Scientific | WB, IF |
| N-cadherin | 610921 | BD Biosciences | WB, IF |
| CD44-APC | 55942 | BD Biosciences | FACS |
| CD24-PE | 555428 | BD Biosciences | FACS |
| GST | 2625 | CST | ChIP |
| Annexin V-APC | 561012 | BD Biosciences | FACS |
| PDGFC neutralizing antibody | AF1560 | R&D | Neutralizing Ab |

RNA Isolation, Reverse Transcription and Real-Time PCR Analysis

Cells were rinsed twice in ice-cold PBS. Total RNA was extracted using Trizol (Invitrogen) and column-purified with RNeasy kits (Qiagen). cDNA synthesis was performed with 1 μg of total RNA at 37° C. for 2 h using the High Capacity cDNA Archive Kit (Applied Biosystems), and subsequently diluted 10 times. mRNA levels were measured with gene-specific primers listed below using the ABI Prism 7900HT Sequence Detection System 2.2 (Applied Biosystems). Results were normalized to β-actin or GAPDH and analyzed using SDS 2.2 software.

Primers

TABLE 3

The following primers were used in quantitative PCR for measuring gene expression relative to β-actin or GAPDH.

| Gene | SEQ ID NO: | Forward | SEQ ID NO: | Reverse |
|---|---|---|---|---|
| hActin | 1 | GGATTCCTATGTGGGCGACGA | 50 | ACATGGCTGGGGTGTTGAAGG |
| hGAPDH | 2 | TGGCAAATTCCATGGCACCG | 51 | CGCCCCACTTGATTTTGGAGG |
| h/mTwist1 | 3 | CCTGCGCAAGATCATCCCCA | 52 | GCTGCAGCTTGCCATCTTGGA |
| hZeb2 | 4 | CGGTATTGCCAACCCTCTGGA | 53 | TTGTTGTGCCAGGGGTGTTCC |
| hSnai1 | 5 | CTGGGTGCCCTCAAGATGCA | 54 | CCGGACATGGCCTTGTAGCA |
| hSnai2 | 6 | TACCGCTGCTCCATTCCACG | 55 | CATGGGGTCTGAAAGCTTGG |
| hFoxc2 | 7 | TGTTCGAGAACGGCAGCTTCC | 56 | CACCTTGGTGATGACCGGCA |
| hEcad | 8 | TTGCACCGGTCGACAAAGGAC | 57 | TGGATTCCAGAAACGGAGGCC |
| hNcad | 9 | TGTCGGTGACAAAGCCCCTG | 58 | AGGGCATTGGGATCGTCAGC |
| hVimentin | 10 | ACCCGCACCAACGAGAAGGT | 59 | ATTCTGCTGCTCCAGGAAGCG |
| hFibronectin1 | 11 | GAGAATGGACCTGCAAGCCCA | 60 | AGTGCAAGTGATGCGTCCGC |
| hZeb1 | 12 | TGCACTGAGTGTGGAAAAGC | 61 | TGGTGATGCTGAAAGAGACG |
| hPDGFRa | 13 | GTCTGGAGCGTTTGGGAAGGT | 62 | GATCTGGCCGTGGGTTTTAGC |
| hPDGFRb | 14 | GGACATACCCCCGCAAAGAA | 63 | CTAACTCGGCACTGGGGATGT |
| hPDGF-C | 15 | ATATTAGGGCGCTGGTGTGGT | 64 | TGGCAAAGCTGAAGGGGGTAG |
| hS1PR1 | 16 | AGCGCGGACAAGGAGAACAG | 65 | GGCGGGAGTGAGCTTGTAGGT |
| hS1PR2 | 17 | CGCCTTCAGCATCCTCCTTC | 66 | GCTGCGCCACGTGTAGATGA |
| hS1PR3 | 18 | TCAGGGAGGGCAGTATGTTCG | 67 | AGAGGGGCAGGATGGTAGAGC |
| hS1PR4 | 19 | TGCTGAAGACGGTGCTGATGA | 68 | GTTGACCGCCGAGTTGAGGA |
| hS1PR5 | 20 | GCCGCTCACGCTGAAACTGT | 69 | TTGGCGTAGAGCGGCAAGAC |
| hFOSL1 | 21 | GGGCCTGTGCTTGAACCTGA | 70 | TCTCCGCTGCTGCTGCTACTC |
| hFOSB | 22 | GGCTTTCCCCGGAGACTACG | 71 | GGACTGGGCCATGGAAGAGAT |
| hFOS | 23 | GAGGGGCAAGGTGGAACAGT | 72 | CTTGCAGGCAGGTCGGTGAG |
| hJUN | 24 | TGCCCCAAGAACGTGACAGAT | 73 | GCCTGGGTTGAAGTTGCTGAG |
| hROR1 | 25 | TTGGCAACCGCACCGTCTAT | 74 | GGGAAGGAATGGCGAACTGAG |
| hRIOK1 | 26 | TGACTGGGACTGGGATGAAGG | 75 | GCTGAACTGCTGTCGGAGGTC |
| hRIOK2 | 27 | GGGAGCGTACCAAAACTGTCC | 76 | CTTTGCCAACACCCATCTGGT |
| hSPHK1 | 28 | GTCACGTGCAGCCCCTTTTG | 77 | CTCGTGCATCAGCCCGTCTC |
| hSPHK2 | 29 | TGGGGCTTCGTGTCAGATGT | 78 | AGTGGCGGGAGGTAGGAGA |
| hSMG1 | 30 | GGCAAAGGCACGATGATACCA | 79 | CCCAACGACTTCCGACCATAA |
| hCALM1 | 31 | GCGATGGCACCATCACAACA | 80 | CGGAATGCCTCACGGATTTCT |
| hCALM2 | 32 | TCTTGGGCAGAATCCCACAGA | 81 | TGGCGAAGTTCTGCAGCACTA |
| hJAK1 | 33 | CGGCTGGGCAGTGGAGAGTA | 82 | GTAGTGGAGCCGGAGGGACT |
| hILK | 34 | GGGGGCACGGATCAATGTAA | 83 | ATCTTCTCTGCCCGCTCTCG |
| hPLAU | 35 | AAAAGCCCTCCTCTCCTCCAG | 84 | TTCATCTCCCCTTGCGTGTTG |
| hPLAUR | 36 | GACCCTGAGCTATCGGACTGG | 85 | ACGGCTTCGGGAATAGGTGAC |

TABLE 3-continued

The following primers were used in quantitative PCR for measuring gene expression relative to β-actin or GAPDH.

| Gene | SEQ ID NO: | Forward | SEQ ID NO: | Reverse |
|---|---|---|---|---|
| hPRKCA | 37 | TGGTGTTGGGAAAGGGGAGTT | 86 | AGGAGTGCAGCTGCGTCAAGA |
| hPINK1 | 38 | CTGCTGCCTGGCTGATGAGAG | 87 | TGGCCGTAGAAGGGATTGACA |
| hAXL | 39 | TTCTCGTGGCCCTGGTGGTAT | 88 | CTTCTTTCGCCGGTGGACAA |
| hCDK6 | 40 | CACCCCAACGTGGTCAGGTT | 89 | AAGGCCGAAGTCAGCGAGTTT |
| hDYRK1A iso a | 41 | GAATCGCCCAGTGGCTGCTA | 90 | TTGGCGGGGATTGGAGTAGAC |
| hDYRK1A iso e | 42 | GCTGGGGAGTCAGGTCATACG | 91 | CATGGCGGGGCTTGTAGATAC |
| hNME7 | 43 | TGCTGGGACCTGCAAACTCTG | 92 | GGCCCACAACCTCCACTTGA |
| hNME6 | 44 | GCCAATCCGAGCCTACATCC | 93 | ACTGGGGCTCTTCCTCCTCAT |
| hPLK2 | 45 | TCCAGCCACCTACCACCACAG | 94 | TCCAGACATCCCCGAAGAACC |
| hSTK36 | 46 | ATTCCCACCGCATCCTACACC | 95 | CCGGGCAAATCCAAAGTCAC |
| hCERK | 47 | GGCGCTGCATATCGTTGTTG | 96 | TGTCCCCGTAGAAGCCGTAGC |
| hSGK1 | 48 | ATGCCAACCCTTCTCCTCCAC | 97 | CAGAACATTCCGCTCCGACAT |
| hJunB | 49 | GGTGGCGGCAGCTACTTTTCT | 98 | TGATCACGCCGTTGCTGTTG |

Table 4 & 5: The following promoting-spanning probes were used in quantitative PCR for accessing the occupancy of Twist or Snail on the FRA1 and c-Fos genomic loci.

| Probes | SEQ ID NO: | Forward | SEQ ID NO: | Reverse |
|---|---|---|---|---|
| FRA1 prom1 | 99 | tccacggatcatactgcctcaa | 111 | tggtgcctctcctttgcctttg |
| FRA1 prom2 | 100 | ccgcctcagcctccagaaca | 112 | agcccttacaccttcacagaca |
| FRA1 prom3 | 101 | cggctgtgacttggcaacctg | 113 | ggcttgtggccaccagacttgt |
| FRA1 prom4 | 102 | gtggccctgaattaaaactcgt | 114 | tcagcgcccctccaagtaag |
| FRA1 prom5 | 103 | tgccaccattttttgtaaccctg | 115 | acctccgtttctgctcccacaa |
| FRA1 prom6 | 104 | gcgcggcgaggaagttacac | 116 | tctcgggctgaaccactgcg |
| FRA1 prom7 | 105 | gccgtgtaccccgcagagc | 117 | ggttccccgctccagtccc |
| FRA1 prom8 | 106 | gcagcgggcagcagagacc | 118 | gaaagcgggcacggagacg |
| FRA1 prom9 | 107 | cctgcccacctctgacttctgc | 119 | ccctcaccccagcccagact |
| FRA1 prom10 | 108 | tggagtctgggctggggtgag | 120 | cggaggggcgaaggacagac |

Table 4 & 5: The following promoting-spanning probes were used in quantitative PCR for accessing the occupancy of Twist or Snail on the FRA1 and c-Fos genomic loci.

| Probes | SEQ ID NO: | Forward | SEQ ID NO: | Reverse |
|---|---|---|---|---|
| FRA1 prom11 | 109 | cgtccgttccgccgagtca | 121 | ggttgggatggggctcagtgt |
| FRA1 prom12 | 110 | cacgcaccaccacacccaacta | 122 | tttaacctccatgtgcctcagt |

| Probes | SEQ ID NO: | Forward | SEQ ID NO: | Reverse |
|---|---|---|---|---|
| c-Fos prom1 | 123 | ATGCTGGGGATGGGCTGTGT | 132 | GGGGATCCAAAAGTGAAAAGG |
| c-Fos prom2 | 124 | TAGTGGGGCAGGAGAGGGAGTC | 133 | GCCAGGCAACACAGAAGAAGG |
| c-Fos prom3 | 125 | CCCGAGGGCTGGAGGTTAGG | 134 | CGGCATCGAGTACAGGACCCC |
| c-Fos prom4 | 126 | CGCGAGCAGTTCCCGTCAAT | 135 | TTGGCGCGTGTCCTAATCTCG |
| c-Fos prom5 | 127 | CGGCGCCTCGTACTCCAACC | 136 | TGCTGCAGCGGGAGGATGA |
| c-Fos prom6 | 128 | GCATGGGCTCGCCTGTCAAC | 137 | AGAACGAACCTGCCTCCCGAAG |
| c-Fos prom7 | 129 | TCCGGGGAGGTGGCAGAAA | 138 | TGCGTTCCCGTTATCCCTTCAG |
| c-Fos prom8 | 130 | ACGTCGGCTTTCCCCTTCTGTT | 139 | GCGCTCGGCCTCCTGTCAT |
| c-Fos prom9 | 131 | TGCATTGTTGAGGTGGTCTGAA | 140 | TGGAACAATAAGCAAACAATG |

Immunofluorescence Microscopy of Cells.

Cell cultures were fixed in 4% paraformaldehyde and permeabilized with 0.25% Triton X-100, followed by blocking with 1% bovine serum albumin in PBS. Cells were incubated in specific primary antibodies, followed by the appropriate secondary antibodies conjugated with Alexa Fluor-488, -568, -594 or -633 (Molecular Probes).

Chromatin Immunoprecipitation and CHIP-Seq Assay.

ChIP assay was carried out using existing methods. Briefly, the cells were cross-linked with 1% formaldehyde for 10 min at room temperature, and formaldehyde was then inactivated by the addition of 125 mM glycine. Chromatin extracts containing DNA fragments with an average size of 200-500 bp were immunoprecipitated using anti-Twist or anti-Snail antibody. The ChIP-enriched DNA was then decrosslinked and analyzed by realtime PCR using the ABI PRISM 7900 sequence detection system and SYBR green master mix. Relative occupancy values were calculated by determining the apparent immunoprecipitation efficiency (ratios of the amount of immunoprecipitated DNA to that of the input sample) and normalized to the level observed.

Gene Expression Microarray and Analyses.

Cells were rinsed twice in ice-cold PBS. Total RNA was extracted using Trizol (Invitrogen) and column-purified with RNeasy kits (Qiagen). Expression profiling of coding genes was carried out using Illumina HumanRef-8 v2 BeadArrays as per manufacturer's instructions. Total chip data is deposited for public access with GEO repository accession number: updating in process. Gene expression data from Illumina array is normalized by quantile normalization. Differential genes are called using LIMMA with p value <0.05 and fold change >1.2.

Heatmap of differential genes are generated using R package gplots after the following steps. (i) Quantile normalization of all genes across all samples. (ii) Each gene is centered to zero across all the samples. Because the control is shared for Twist, Snail and Slug overexpressed samples, the weight of the control should be 3 instead of 1 when calculating the mean of each gene across all samples. (iii) Hierarchical clustering method is used when generate the cluster of the samples (columns).

Cell Lines and Cell Culture

Cell cultures were maintained at 37° C. with 5% $CO_2$. HMLE cells and NAMECs were maintained in MEGM (Lonza). MCF7, MDA-MB-231, CAMA1, MDA-MB-436, SKBR3, T47D, SUM 159 were maintained using standard methods. Human mammary epithelial cell lines (HMLE) were generated and immortalized using retroviral vectors to express the catalytic subunit of the human telomerase enzyme, hTERT and the SV-40 Large T antigen.

NAMECs were isolated based on the observation that mesenchymal cells were less adherent than epithelial cells to tissue culture surfaces. HMLE cells were grown to 50% confluency, followed by differential trypsinization for one minute with 0.05% trypsin. Detached cells were carefully collected and re-plated at approximately 200 cells per well of a 24-well plate. Upon expansion, wells were screened for populations which were morphologically mesenchymal and can be stably propagated. We generated clonal and non-clonal NAMEC cell lines. Clonal cells lines (NAMEC 1-5) were derived from a single mesenchymal cell plated into a 96-well plate by FACS. Non-clonal lines (NAMEC 6-11) were derived from at least 200 mesenchymal cells. These lines were assessed for mesenchymal properties by analyses of their protein and mRNA expression and CD44/CD24 profile.

HMLE-Twist-ER and HMLE-Snail-ER cells were generated using existing methods. For EMT-induction, 100 nM of hydroxytamoxifen (Sigma) in ethanol was added to the culture medium every 24 h for a total duration of 12 days. Control cells were treated with ethanol. To generate stable EMT TF-induced cells, HMLE cells were infected with constitutive pBabePuro-Twist, pBabePuro-Snail and pWPXL-hSlug. To generate tumorigenic cells, cells were infected with pWZL-Blast-Ras. pLL3.7-GFP and pLV-tdTomato lentivirus were used to generate GFP+ and Tom+ cells, respectively. For stable knockdown of target genes, pLKO.1-Puro shRNAs were used (Dana Farber Cancer Institute RNAi Facility). Production of virus and infection of target cells were performed using existing methods. Infected cells were selected with 2 mg/ml puromycin, 200 mg/ml hygromycin, or 200 mg/ml neomycin.

For mammosphere culture, cells were seeded onto 96-well ultralow-adherence plates at 500 cells/well in Mammocult medium (Stem Cell Technologies) supplemented with heparin, hydrocortisone and methylcellulose. Spheres were counted at 12-14 days later.

RNAi Constructs

Lentiviral shRNAs were obtained from the The RNAi Consortium (TRC) collection. The clone ID for the shRNAs used are:
FRA1 sh1, TRCN0000019539;
FRA1 sh2, TRCN0000019541;
PKCα sh1, TRCN0000001690;
PKCα sh2, TRCN0000001691;
c-Fos sh1, TRCN0000016003
c-Fos sh2, TRCN0000016004
Twist sh3, TRCN0000020541
Twist sh4, TRCN0000020542
Snail sh2, TRCN0000063819
Snail sh4, TRCN0000063821
Luciferase shRNA, TRCN0000072243

Co-Immunoprecipitation

NAMECs or HMLE cell lysates were harvested by adding 1 ml of immunoprecipitation (IP) buffer per plate of cells followed by scrapping. Cells were then sonicated on ice and spun down at 15000×g for 15 min to retrieve the supernatant. 5-10 µl of antibody (c-Jun, c-Fos or FRA1) were added to the lysates and incubated overnight at 4° C. on a rotator. As a control, IgG or no antibody was used. 50 µl of Protein G Dynabeads were prewashed with IP buffer were added the next day for 2 h and incubated at 4° C. Beads were washed with IP buffer once with 10 min incubation at 4° C. and subsequent twice more without incubation. IP buffer was prepared with 20 mM Tris, pH 7.5, 150, 300 or 500 mM NaCl, 5 mM $MgCl_2$, 0.1% NP40, 10% Glycerol, 1 mM DTT (added fresh), 0.5 mM PMSF (added fresh), 1x protease inhibitor (added fresh). After IP, beads were denatured in LDS buffer at 80° C. for 10 min and removed. Lysates were used for western blotting to identify protein-protein interactions.

Meta-Analysis of Oncogenomic Data

To evaluate the expression of genes (FRA1 and PKCα) in breast tumors classified according to molecular subtypes and mutations, we analyzed gene expression studies deposited in Oncomine. The $log_2$ median centered intensity for each gene was determined for each molecular subtype.

To test whether the expression of FRA1 or PKCα correlated with distant metastasis-free survival, the datasets (GSE2603, GSE17705, GSE21653, GSE16446, GSE17907, GSE19615 and GSE20685; n=1354) were analysed and Kaplan-Meier plots were generated using kmplot.com.

Proliferation Assays

To measure cell growth rates, 1000 cells were seeded onto 96-well plates in triplicate. Cell viability was measured using WST-1 reagent (Roche) according to the manufacturer's instructions.

Statistical Analyses

All data are presented as mean±standard error of mean except specified otherwise. Student t-test (two-tailed) was used to compare two groups and calculate p-values. p-value <0.05 was considered significant.

Tumor Xenografts

All research involving animals complied with protocols approved by the MIT Committee on Animal Care. The number of cells, the route if injection and the time for tumor growth are indicated in the figure legends. For subcutaneous injections, cells resuspended in 100111 PBS containing 50% Matrigel were injected into both flanks female NOD-SCID mice except for studies involving the in vivo administration of chemical inhibitors where only one flank was implanted. The tumor incidence and weight were measured between 4 and 12 weeks post-injection. For determining the frequency of cancer stem cells, the Extreme Limiting Dilution Analysis program was used (Hu and Smyth, 2009).

Promoter-Luciferase Reporters

FRA1-WT-BS, FRA1-MUT-BS and AP-1 promoter luciferase constructs were kindly provided by David Dornan, Genentech (Stinson et al., 2011). To perform the promoter-luciferase assays, cells were seeded 24 h before transfection at a density of $2.5 \times 10^4$ cells per well in 96-well culture plates. For RNAi and overexpression studies, shRNAs or overexpression constructs were co-transfected with promoter-luciferase (75 ng) and pRL-SV40 (1 ng) (Promega). Firefly and *Renilla luciferase* activities were measured with the Dual-Luciferase Reporter system (Promega) 48 h post-transfection. The data generated were expressed as relative to vector control transfection, after normalization to *Renilla luciferase* readings.

Immunohistochemistry of Tumor Samples

Formalin-fixed paraffin-embedded tumor tissues were obtained from US Biomax (BR2085a). Immunohistochemistry (IHC) of tissue microarray sections was performed using the PKCα and FRA1 primary antibodies and VECTASTAIN ABC kits (Vector Labs). For xenografted tumors arising from NAMEC-Ras or HMLE-Ras cells, tumors were extracted and formalin-fixed followed by paraffin-embedding. IHC was performed using the PKCα or PKCα$^{T497}$ primary antibodies and VECTASTAIN ABC kits (Vector Labs).

Ras Activation Assay

To measure the level of active GTP-bound Ras, protein lysates were prepared using existing methods. 200 μg of protein lysate for each sample was subject to pull-down with Raf-RBD beads (Cytoskeleton Inc.), and separated on a SDS-PAGE gel.

Patient-Derived Breast Cancer Xenograft Establishment and Therapy

Primary human breast cancer samples were obtained. Patient-derived breast tumor fragments (approximately 3×1×3 mm) were inserted bilaterally into the inguinal mammary fat pads of 6- to 8-week-old NOD-SCID-IL2Ryc-/- female mice for initial establishment of tumors within 2 hr of surgery and subsequently expanded in NOD-SCID mice once established. Established TNBC tumors (EL12-15, EL12-58, and EL11-26) were implanted into cohorts of 6- to 8-week-old female NOD-SCID mice. Treatment was initiated at the time of tumor implantation and the mice were randomized into two groups: vehicle (10% DMSO in saline) and treatment (Ro-31-8220, 5 mg/kg/day intraperitoneally). Tumors were collected and weighed after 6, 8, or 11 weeks.

Figure 8:
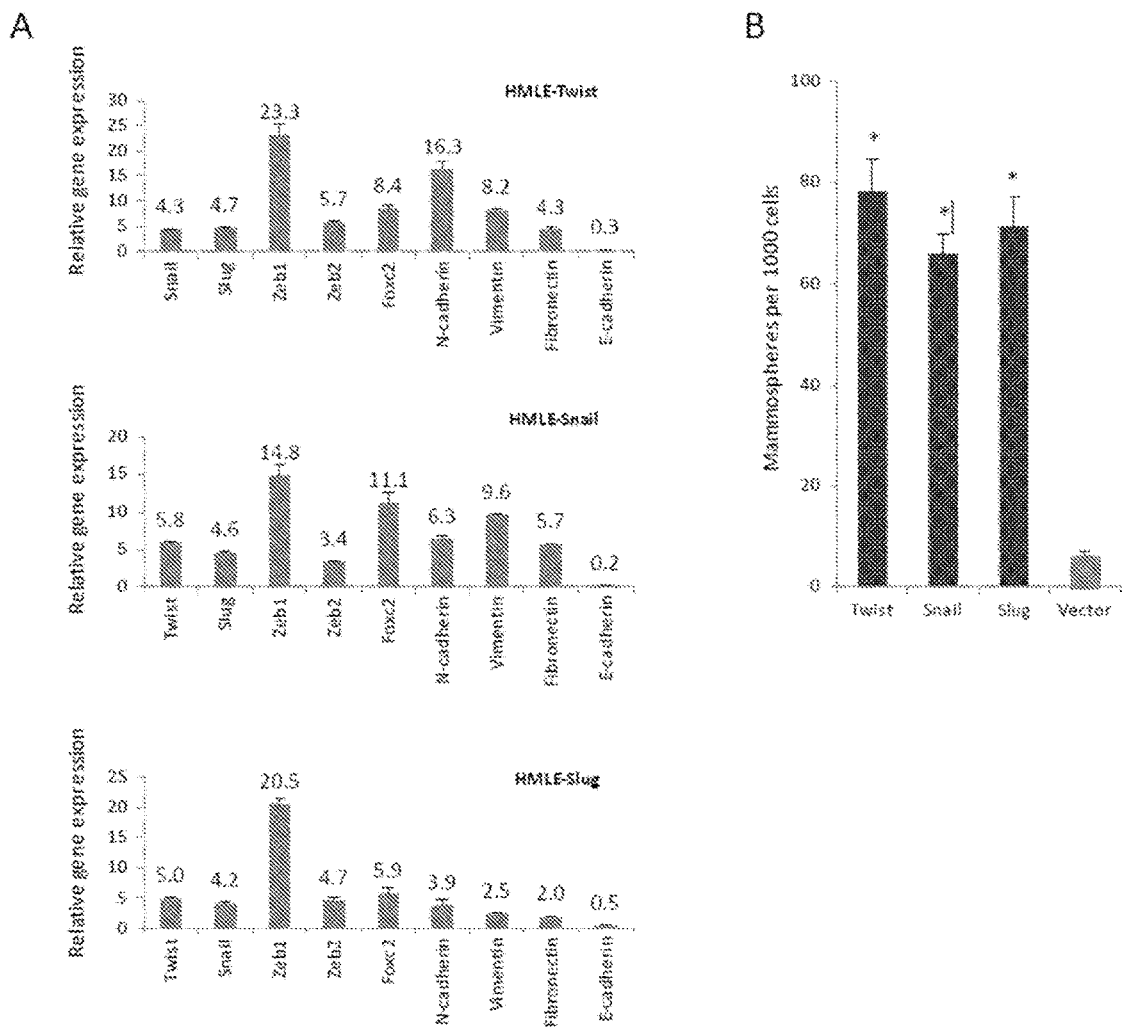
FIG. 8 depicts a series of graphs. (A) Expression of EMT markers in HMLE-Twist, HMLE-Snail and HMLE-Slug cells relative to HMLE-vector control cells. Values were normalized to β-actin. Data presented as mean±s.e.m. (B) HMLE cells transduced with Twist, Snail or Slug formed mammospheres more efficiently than control cells. Data presented as mean±s.e.m. *denotes significantly different from control HMLE cells, p<0.01.

Example 1: Identification of Kinases Expressed Differentially in EMT-Induced Cells To assess molecular changes associated with epithelial cells that have passed through an EMT, we transduced genes encoding the Twist, Snail and Slug EMT-inducing master transcription factors (EMT-TFs) into HMLE human mammary epithelial cells, which had previously been immortalized through the introduction of the hTERT and SV40 early-region genes. The resulting cells (HMLE-Twist, HMLE-Snail and HMLE-Slug) displayed a set of mesenchymal markers (FIG. 8A), and were judged by these criteria to have undergone an EMT. These cells resided predominantly in the CD44$^{hi}$/CD24$^{lo}$ marker state and formed mammospheres 10.3-14.9 times more efficiently than parental epithelial cells (FIG. 8B), indicating they were enriched for stem cell activity. EMT and stem cell programs in these cells closely resemble those operating in their transformed neoplastic derivatives.

Figure 9:
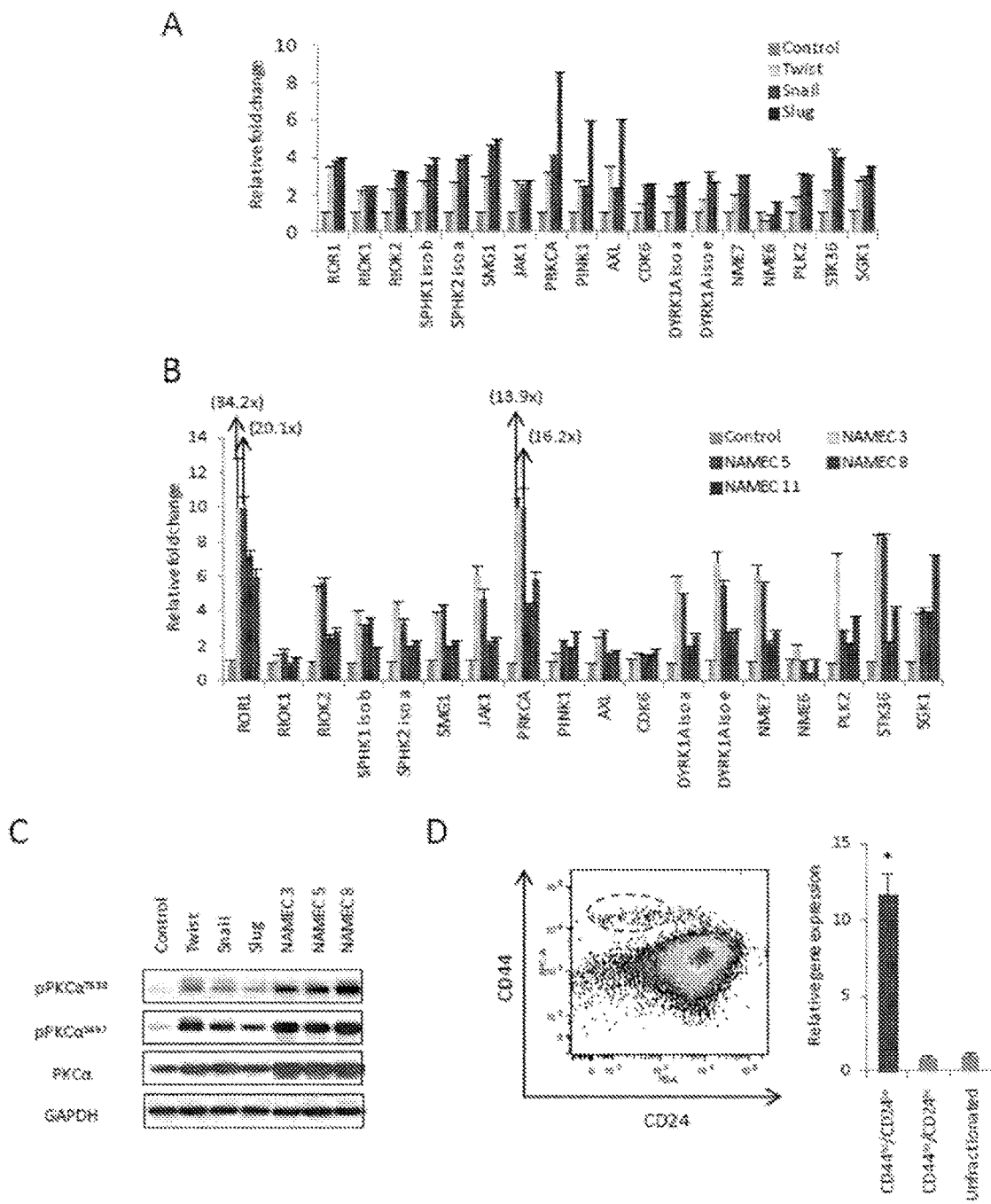
FIG. 9 (A) Quantitative PCR validation of differentially expressed kinases selected based on gene expression microarray. Values were normalized to β-actin. Data presented as mean±s.e.m. Bars from left to right for each kinase are Control, Twist, Snail, Slug. (B) Selected to-regulated kinases upregulated in TF-induced EMT were also increased in the various NAMEC cell lines relative to HMLE cells. Values were normalized to β-actin. Data presented as mean±s.e.m. Bars from left to right for each kinase are Control, NAMEC3, NAMEC5, NAMEC8, NAMEC11 (C) Protein expression of PKCα, PKCα$^{T638}$ and PKCα$^{S497}$ in HMLE, HMLE-Twist, HMLE-Snail, HMLE-Slug, NAMEC3, NAMEC5 and NAMEC8 cells. (D) Increased expression of PKCα mRNA in CD44$^{hi}$/CD24$^{lo}$ stem cell compartment of HMLE cells. *denotes significantly different from unfractioned or CD44$^{lo}$/CD24$^{hi}$ HMLE cells, p<0.01. Values were normalized to β-actin. Data presented as mean±s.e.m.

Using microarray gene expression analyses, we searched for kinase-encoding genes that exhibited the greatest difference in expression when comparing parental epithelial cells and the derived EMT-TF-induced cells. This yielded a group of kinase-encoding genes that were coordinately overexpressed at least two fold in HMLE-Twist, HMLE-Snail and HMLE-Slug cells relative to the HMLE parental epithelial population (FIG. 1A, FIG. 9A and Table 6). These kinases include, among others, CDC-like kinase 1 (CLK1), PI-3-kinase-related kinase SMG1, ephrin type-A receptor 2 (EphA2), nucleoside-diphosphate kinase 7 (NME7), protein kinase C α (PKCα), serum/glucocorticoid regulated kinase 1 (SGK1), sphingosine kinase 1 (SPHK1), sphingosine kinase 2 (SPHK2) and cyclin-dependent kinase 6 (CDK6). We validated the expression of the top 18 selected kinase mRNAs by quantitative PCR (qPCR), thereby confirming the differential gene expression initially obtained from microarray profiling (FIG. 9A). The distinctive changes in the expression patterns of these kinases occurring during the EMT cell-state transition indicated that the kinases were candidates for selective therapeutic intervention. The candidates were evaluated using validated kinase inhibitors.

Figure 10:
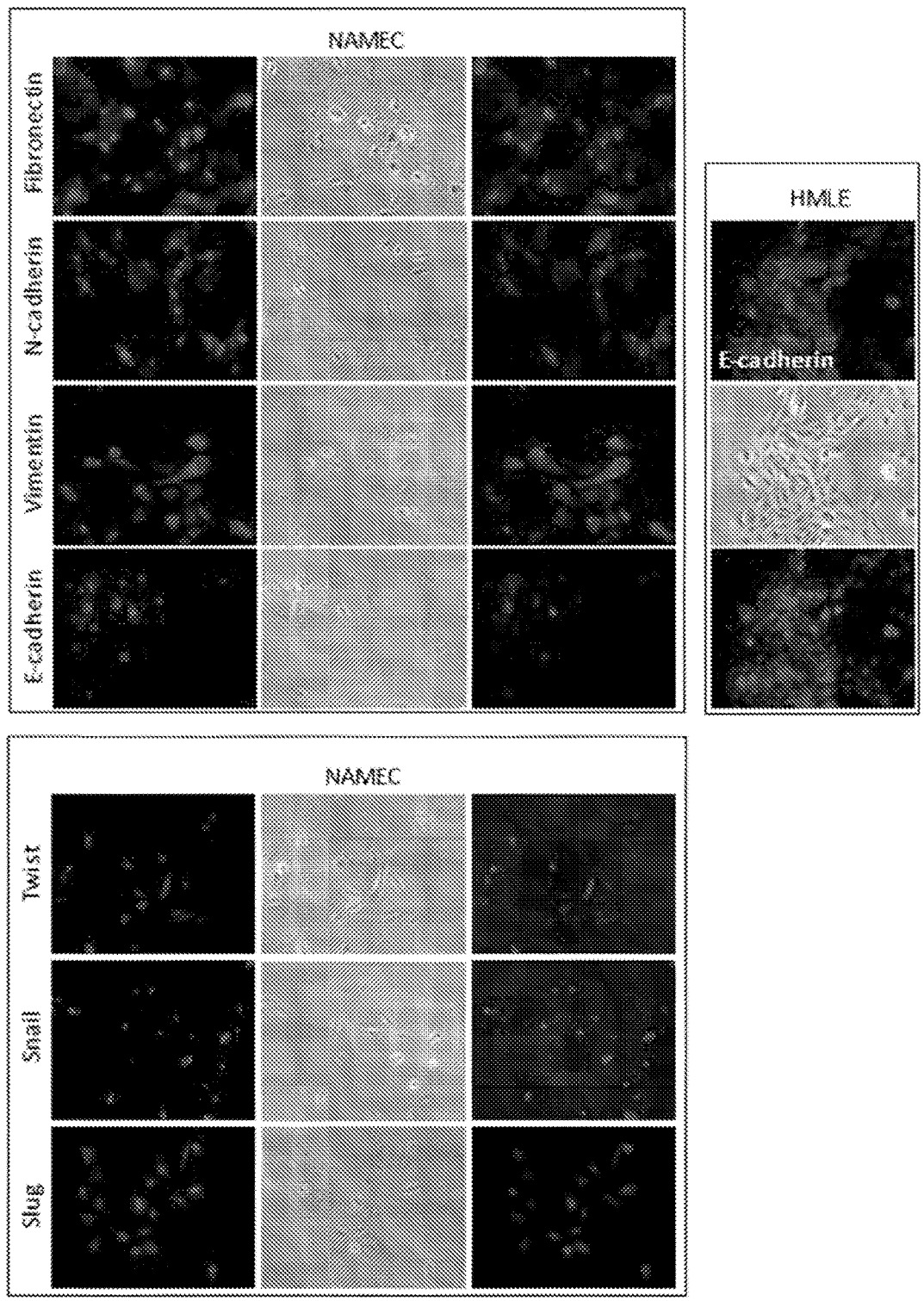
FIG. 10 Immunofluorescence staining showed the expression of mesenchymal markers, fibronectin, vimentin and N-cadherin in NAMECs and the absence of E-cadherin. The EMT-TFs, Twist, Snail and Slug were also expressed and localized to the nucleus of NAMECs. E-cadherin was expressed and localized to the adherens junction in HMLE cells.

We sought to derive populations of HMLE cells that had spontaneously undergone an EMT, thereafter residing stably in the mesenchymal state; such cells, which we succeeded in isolating, do not spontaneously differentiate into epithelial derivatives in culture (FIG. 1B and Supplementary Methods). Thus, in the absence of introduced exogenous EMT-TFs, the phenotypic state of these cells appeared to be controlled by endogenously expressed EMT-TFs (FIGS. 1C and D); these TFs, in turn, were ostensibly responsive to physiologic regulators, such as the paracrine and autocrine signals that play key roles in the induction and maintenance of the mesenchymal state. We derived 11 lines—five monoclonal and six polyclonal cell populations—all termed Naturally Arising MEsenchymal Cells (NAMECs), which derived from bulks cultures of the immortalized HMLE cells. Indeed, NAMECs expressed elevated levels of endogenous EMT-TFs (Twist, Snail, Slug, Zeb1 and Zeb2) and associated markers (vimentin, N-cadherin and fibronectin), as well as loss of the key epithelial adherens junction protein, E-cadherin (FIG. 1C, 1D and FIG. 10). Similar to EMT-TF-induced cells and the CD44$^{hi}$/CD24$^{lo}$ mammary epithelial stem cells that are naturally present within HMLE populations, NAMECs were also predominantly CD44$^{hi}$/CD24$^{lo}$ and, relative to HMLE cells, exhibited a 11.3 fold higher mammosphere-forming ability, an in vitro assay of stem cell activity (FIGS. 1E and F). Hence, NAMECs exhibited bona fide characteristics of cells that have passed through an EMT and differed greatly from the parental epithelial HMLE cells.

Inhibition of PKCα Depletes Stem-Like Cells in a Kinase Screen

We undertook to identify kinase inhibitors that selectively targeted mesenchymal-like cells including those with stem cell properties. To do so, we established a screen that measured the ability of candidate inhibitors to preferentially deplete NAMECs but not parental HMLE cells from cell cultures. Thus, we labeled NAMECs with the tdTomato red fluorescent protein (NAMEC-Tom) and the HMLE cells with the GFP green fluorescent protein (HMLE-GFP); we then attempted to reconstitute certain stem cell and non-stem cell interactions that might operate in vivo by mixing the two cell populations in 6-well adherent tissue culture plates. One day later, we challenged these cultures with a variety of kinase inhibitors (FIG. 2A).

Figure 11:
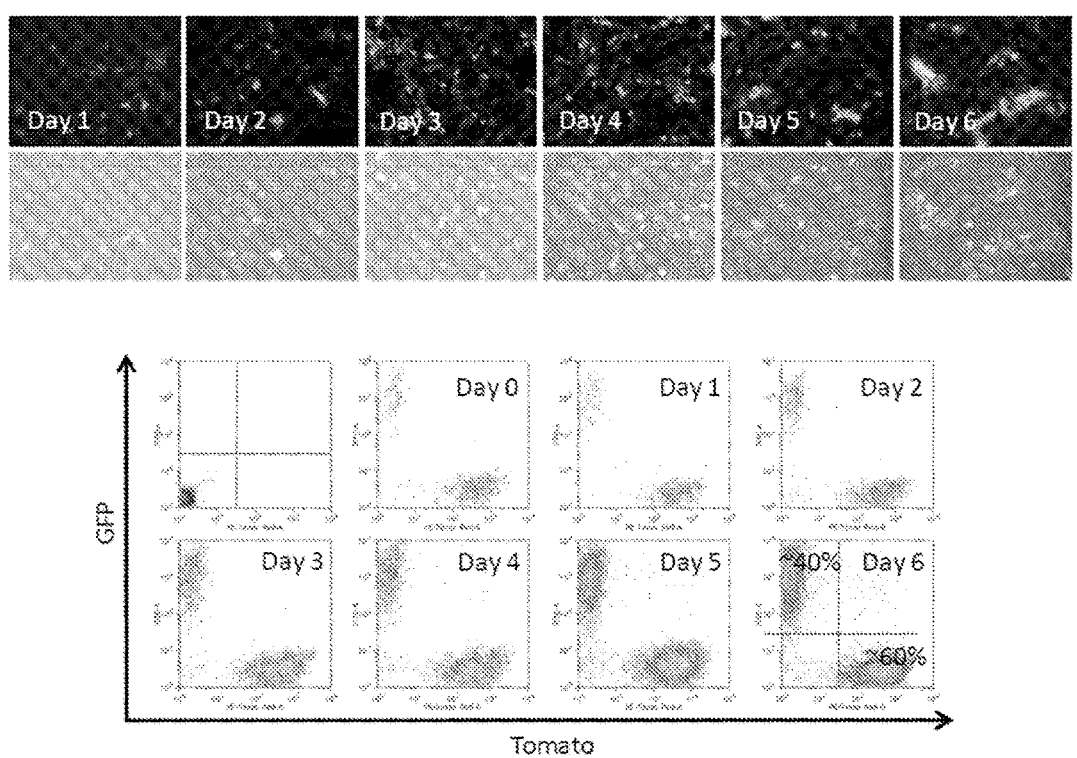
FIG. 11 Growth kinetics of co-mixed NAMECs and HMLE cells over six days. 75,000 HMLE-GFP cells and 15,00 NAMEC-Tom cells were seeded in a 6-well plate and the representative portion of each cell type was analyzed daily over a six day period. Day 0 represented the co-mixed cells prior to seeding.

The robustness of this screen, designed to identify mesenchymal cell-specific inhibitors, was enhanced by seeding NAMEC-Tom and HMLE-GFP cells in a 5:1 ratio. While NAMEC-Tom cells, like others that have passed through an EMT, proliferated marginally more slowly than their epithelial counterparts in culture, their initial advantage in seeding density was compensated over the course of the six day-long assays by the more rapid proliferation of the HMLE-GFP cells (FIG. 11). After six days of treatment, the relative proportions of NAMEC-Tom and HMLE-GFP cells were quantified with fluorescent-activated cell sorting (FACS) to determine the selective effects, if any, of these various inhibitors (FIG. 2A).

We targeted several proteins kinases (PKCα, PKCη, CDK6, CamK, CLK1, SGK1 and JAK1) that we had found to be expressed at elevated levels in HMLE-Twist, HMLE-Snail and HMLE-Slug cells relative to the parental HMLE epithelial population (FIGS. 1A, 9A & 9C and Table 6); this initial survey involved use of a panel of 13 commercially available kinase inhibitors. FIG. 2B illustrates the effects of kinase inhibitors on NAMEC-Tom and HMLE-GFP cells at the end of a six-day treatment period, presenting the relative proportion of surviving cells. The numbers of viable cells were quantified in each case with FACS in order to determine the proportion of NAMEC-Tom or HMLE-GFP cells in inhibitor-treated populations relative to DMSO-treated controls (FIG. 2C). In contrast to the behavior of most kinase inhibitors tested to date (Barr et al., 2008; Thomson et al., 2008), ten out of the 13 kinase inhibitors tested appeared to select against mesenchymal cells. We ensured these inhibitors operated over a broad range of concentrations by performing dose-response measurements of the mixed cell populations (FIG. 2D).

Figure 2:
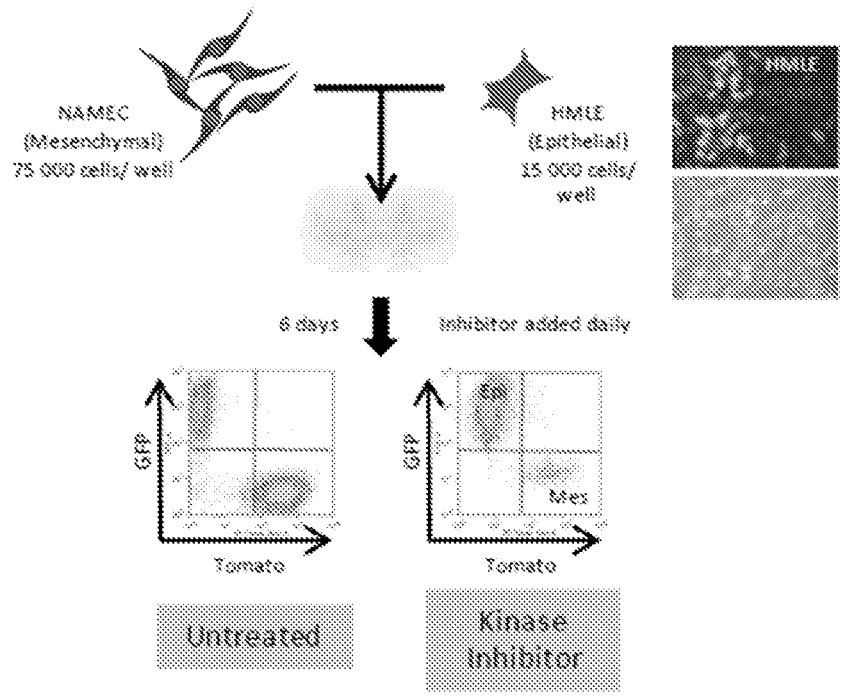
FIG. 2 depicts that PKCα inhibition selectively targets cells that have undergone an EMT and are enriched for stem cell properties. (A) The approach for establishing a kinase inhibitor screen which can identify stem cell-specific inhibitors. NAMEC-Tom and HMLE-GFP cells were co-mixed in a 5:1 ratio and seeded for 24 h prior to daily inhibitor treatment for six days. Remaining cells were trypsinized and analyzed by FACS to determine the proportion of NAMEC-Tom or HMLE-GFP cells relative to control DMSO treatment. (B) The proportion of surviving NAMEC-Tom and HMLE-GFP cells was visualized by florescence microscopy after six days of inhibitor treatment. (C) Cell frequency was quantification by FACS that segregated and counted NAMEC-Tom and HMLE-GFP cells normalized to DMSO-treated controls. PKCa inhibitors (PKC 20-28, Ro-31-8220 and bisindolylmalmide I) diminished NAMEC-Tom cells relative to HMLE-GFP cells. (D) Dose response curves of NAMEC-Tom and HMLE-GFP cells treated with PKCα inhibitors, paclitaxel or staurosporine over a range of concentrations. The difference in fold sensitivity between NAMEC-Tom and HMLE-GFP cells at $LC_{50}$ towards the inhibitors is indicated. Curves for each cell type were generated with data points using non-linear regression curve fit with the variable slope model. Graphpad Prism was used to generate the curves. (E) Measurement of apoptosis in co-mixed NAMEC-Tom and HMLE-GFP cells treated with chemical inhibitors for three days. NAMEC-Tom and HMLE-GFP cells were gated on PE-TexasRed and GFP, respectively, and then analyzed for Annexin V-APC staining.
Figure 2:
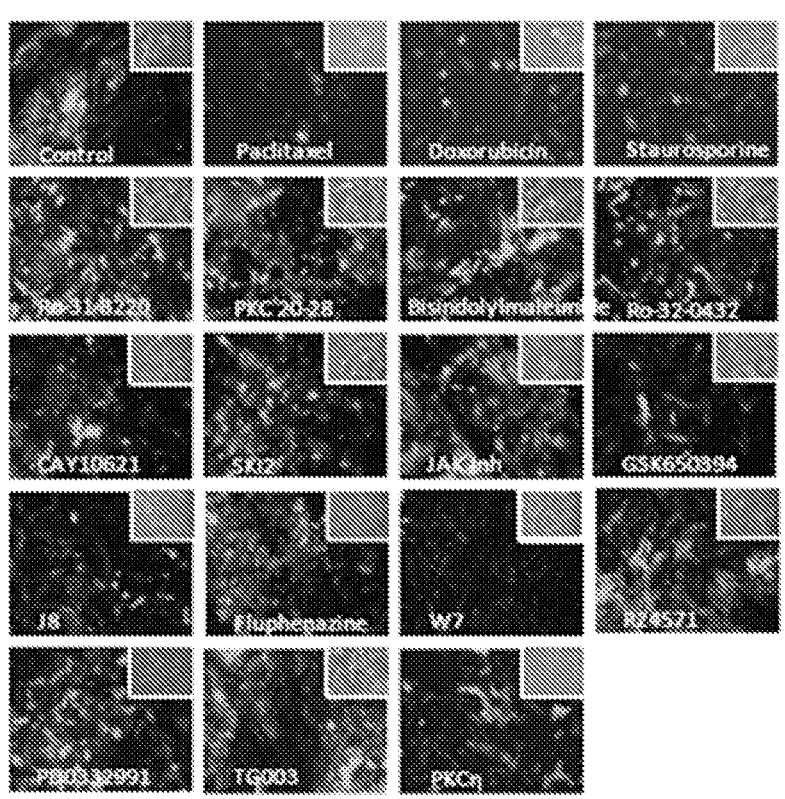

The four inhibitors targeting PKCα (PKC 20-28, Ro-31-8220, Ro-32-0432 and bisindolylmaleimide I) showed a 6.8- to 12.1-fold selectivity against NAMEC-Tom cells at $LC_{50}$ (lethal concentration, 50%) relative to HMLE-GFP cells (FIG. 2D). The inhibitors targeting PKCη, CLK1, CDK6 and JAK1 also appeared to deplete NAMEC-Tom cells preferentially (FIG. 2B). Three non-pathway-specific compounds, staurosporine (a broad spectrum kinase inhibitor), doxorubicin and paclitaxel (the latter two being agents used clinically) preferentially depleted the epithelial HMLE-GFP cells instead (FIGS. 2B and D). This indicated that non-cell state-specific inhibitors could enhance the representation of more aggressive cancer stem-like cells in the cell populations following treatment.

To assess how PKC inhibitors function in these cell populations, we tested whether they induced apoptosis. Thus, the mixed cell populations described above were treated with one of the inhibitors (Ro-31-8220) for three days and assessed with Annexin V, which marks apoptotic cells. 89% of NAMEC-Tom cells underwent apoptosis in comparison to 22.4% of the HMLE-GFP cells (FIG. 2E). Conversely, paclitaxel and staurosporine resulted in HMLE-GFP cell apoptosis of 89% and 98%, respectively, leaving NAMEC-Tom cells far less affected (paclitaxel: 22.3%; staurosporine: 29.7%) (FIG. 2E).

Figure 12:
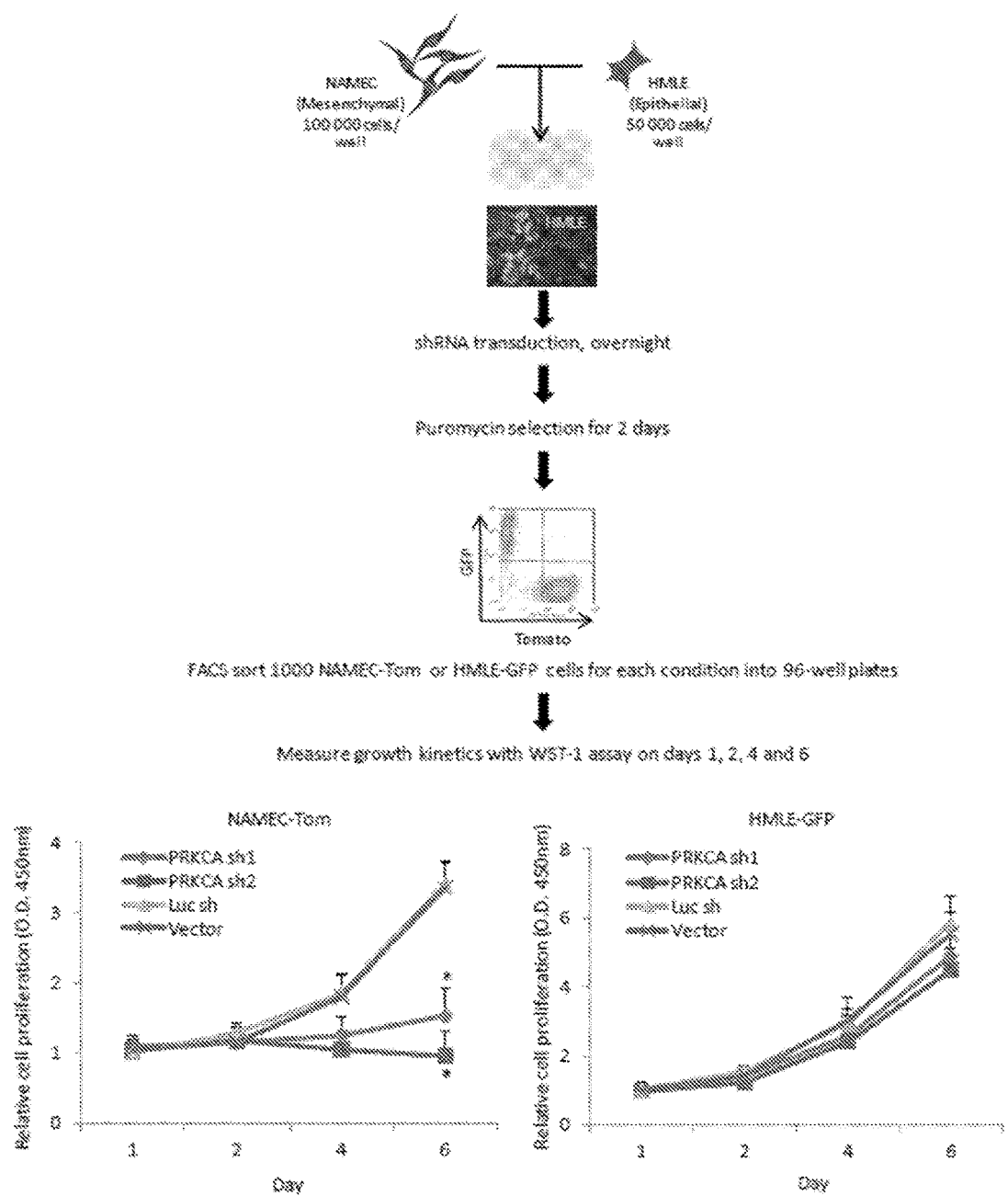
FIG. 12 Effect of PKCα RNAi on the growth kinetics of NAMEC-Tom and HMLE-GFP cells. Data presented as mean±s.e.m. *denotes significantly different from shLuc control, p<0.01

To assess specificity of the PKCα inhibitory effects, we depleted PKCα by gene silencing with RNAi. Co-mixed NAMEC-Tom and HMLE-GFP cells were infected with either of two different lentiviral vector-expressed shRNAs targeting PKCα (FIG. 12). These cells were then re-plated separately based on $Tom^+$ or $GFP^+$ expression at equal numbers by FACS into 96-well plates. Cell proliferation was measured over the course of six days. Consistent with the use of chemical inhibitors, depletion of PKCα resulted in the loss of NAMEC viability by 71% whereas HMLE cells were less affected (19%) (FIG. 12). These data indicated a greater dependence on signaling networks regulated by PKCα in cells that have passed through an EMT program.

Figure 3:
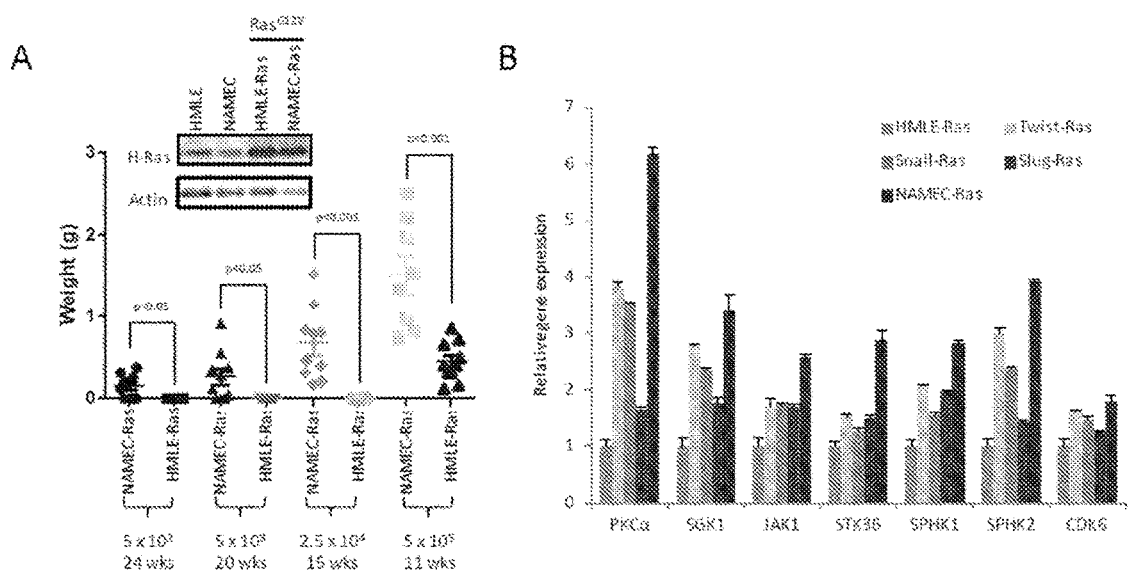
FIG. 3 depicts that cell state-specific kinase expression is conserved upon oncogenic Ras$^{G12V}$ transformation and in CSCs. (A) NAMEC-Ras and HMLE-Ras cells were injected subcutaneously into both flanks of NOD-SCID mice at limiting dilutions of $5\times10^2$, $5\times10^3$, $2.5\times10^4$ or $5\times10^5$ cells. At $5\times10^2$, $5\times10^3$ and $2.5\times10^4$ cells, HMLE-Ras were completely non-tumor initiating whereas NAMEC-Ras were. At $5\times10^5$ cells, tumors generated by HMLE-Ras were much smaller than NAMEC-Ras. The time-points when tumors were collected are denoted. Western blot indicate comparable levels of Ras overexpression in HMLE-Ras and NAMEC-Ras cells. (B) The expression of selected kinases was maintained at elevated levels in HMLE-Twist-Ras, HMLE-Snail-Ras, HMLE-Slug-Ras and NAMEC-Ras cells relative to HMLE-Ras cells. Values were normalized to β-actin. Data presented as mean±s.e.m. For each kinase, bars from left to right are HMLE-Ras, Twist-Ras, Snail-Ras, Slug-Ras, NAMEC-Ras. (C) Dose response curves of NAMEC-Tom-Ras (CSC-enriched) and HMLE-GFP-Ras (CSC-depleted) cells treated with PKCα inhibitors, paclitaxel or staurosporine over a range of concentrations. Differential sensitivity between both cell types at $LC_{50}$ is indicated. (D) Total PKCα and p-PKCα$^{T497}$ were being expressed in NAMEC-Ras, but not HMLE-Ras, tumor sections. NAMEC-Ras tumors were obtained from $2.5\times10^4$ cells after 15 weeks and HMLE-Ras tumors were obtained from $5\times10^5$ cells after 11 weeks. Tumors of equivalent size (~0.3 g) were compared. Representative sections are shown, n=4. (E) Growth of subcutaneously xenografted NAMEC-Ras cells ($5\times10^4$) in mice treated with daily intraperitoneal administration of agents which began on the same day as the cells were implanted. PKCα Inh (Bisindolylmalmide I, 5 mg/kg/d) or DMSO vehicle were administered continually for 30 days. One group was left untreated. Tumors were collected 10 weeks post-implantation. * denotes significantly different from DMSO-treated or untreated mice, p<0.001.

Cell State-Specific Features are Conserved Upon Oncogenic Transformation and in CSCs The EMT program of immortalized, non-tumorigenic mammary epithelial cells was quite similar to the corresponding programs of their transformed, tumorigenic derivatives. To test whether neoplastic cells that have passed through an EMT program acquire a greater potential to generate CSCs, we transduced NAMECs and HMLE cells with comparable levels of the oncogenic H-$Ras^{G12V}$ (FIG. 3A). As few as 500 NAMEC-Ras cells implanted into NOD-SCID mice were sufficient for tumor-initiation in six out of 10 instances, while up to 25,000 HMLE-Ras cells failed to form tumors (FIG. 3A). Based on a limiting dilution assay, the frequency of CSCs was calculated to be approximately 1/2314 for NAMEC-Ras and 1/463783 for HMLE-Ras cells (FIG. 3A). Thus, within epithelial tissues, stem cells bearing mesenchymal traits rather than bulk epithelial cells tend to give rise to CSCs far more efficiently when transformed. This also was consistent with the notion that the phenotypic state of these cells prior to transformation influenced their behavior following transformation.

To investigate whether PKCα inhibition would also preferentially affect NAMEC-Ras cells (which were enriched for CSCs), we first determined if PKCα remained differentially regulated between NAMEC-Ras and HMLE-Ras cell populations, as it did in the corresponding untransformed precursors of these two cell populations. The levels of PKCα, and other kinases that were examined previously in the corresponding untransformed populations, remained higher in NAMEC-Ras cells compared to the HMLE-Ras cells, as well as for EMT-TF-induced mesenchymal cells transduced with $Ras^{G12V}$ (FIG. 3B). This extended the notion that components of the stem cell program operating in immortalized human MECs continues to operate in the transformants derived from these immortalized cells.

Having determined that NAMEC-Ras cells were enriched for CSCs, we mixed NAMEC-Ras cells labeled with tdTomato (NAMEC-Tom-Ras) and HMLE-Ras cells labeled with GFP (HMLE-GFP-Ras) and re-tested the effects of kinase inhibition as described above. Similar to their immortalized, untransformed counterparts, NAMEC-Tom-Ras cells exhibited a heightened sensitivity of 6.95-7 fold to PKCα inhibition (by both Ro-31-8220 and bisindolylmaleimide I) relative to HMLE-GFP-Ras cells (FIG. 3C). In addition, these NAMEC-Tom-Ras cells were more resistant to paclitaxel (11.3 fold) and staurosporine (32.8 fold) than the corresponding HMLE-GFP-Ras cells used as controls (FIG. 3C). When these cells were implanted into NOD-SCID mice, NAMEC-Ras-derived tumors continued to express PKCα but HMLE-Ras tumors did not (FIG. 3D), suggesting that PKCα inhibition might be useful in vivo for targeting PKCα-expressing tumor cells.

To assess the therapeutic utility of PKCα inhibitors, $5 \times 10^4$ NAMEC-Ras cells were implanted in NOD-SCID mice and treated for 30 days with a daily intraperitoneal dose of either a PKCα inhibitor (Ro-31-8220, 5 mg/kg/d), a DMSO solvent control or an additional control left untreated. These dosages were well-tolerated in mice and had no adverse effects after 30 days of treatment followed by eight weeks of observation. Significant tumor burdens of ~0.68 g each were observed after 15 weeks in all ten control-treated mice, as expected, whereas only four of eight mice treated with PKCα inhibitor formed tumors, all of which were far smaller, ~0.16 g (FIG. 3E). Hence, PKCα inhibition reduced tumor-initiation frequency and tumor growth, indicating that PKCα inhibition had a major effect on the outgrowth of these cells in vivo.

Activation of an EMT Program Induces a Switch from EGFR to PDGFR Signaling

The greater reliance of cancer stem cells on PKCα led us to assess whether cells that have passed through an EMT process mitogenic and trophic signals differently from those that have not. We assess the sources of the upstream signals responsible for activating PKCα. Thus, we assessed whether the expression of certain receptor tyrosine kinases (RTKs) induced by the EMT program were responsible for activating or maintaining signaling in cells that had passed through this program. We assessed whether EFGR activates PKCα in cells that had undergone an EMT. EGFR overexpression and amplification is positively associated with triple-negative, BRCA1-mutant or basal-like breast cancers, which bear clear mesenchymal signatures. However, the mesenchymal NAMECs and EMT-TF-induced mesenchymal cells down-regulated the expression of total and p-$EGFR^{Y1068}$ in contrast to the epithelial HMLE cells, which continued to express abundant levels of these proteins (FIG. 4A). Indeed, treatment of co-mixed NAMEC-Ras-Tom and HMLE-Ras-GFP cells with either of two EGFR inhibitors preferentially selected against HMLE-Ras-GFP cells by 3.4-6.3 fold relative to NAMEC-Ras-Tom cells (FIG. 4B). This indicated that epithelial non-CSC-enriched populations depended upon sustained EGFR signaling more strongly than the mesenchymal/CSC-enriched fractions.

Figure 13:
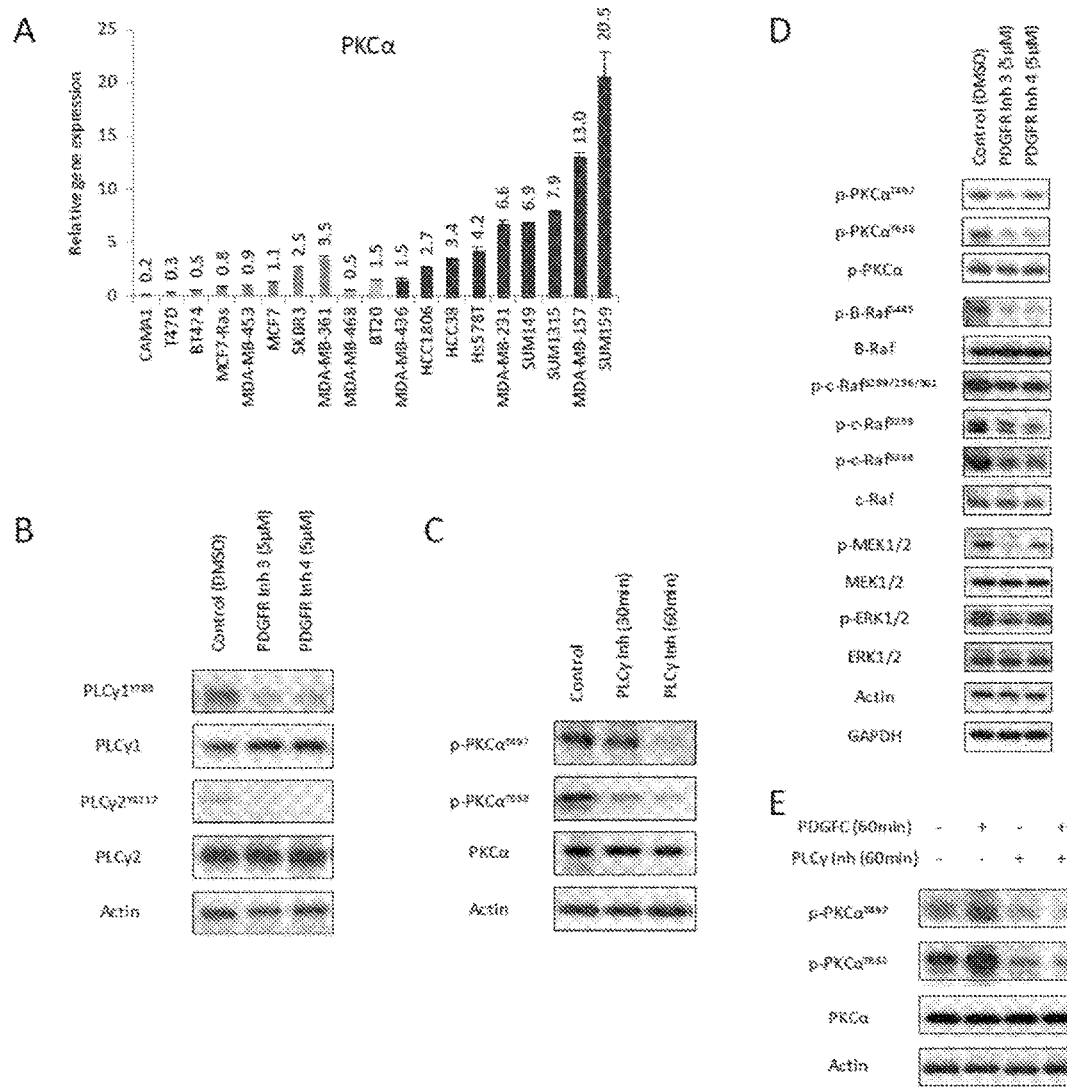
FIG. 13 (A) Relative gene expression of PKCα in a panel of luminal (green), basal A (orange) and basal B (red) breast cancer cell lines normalized to MCF7. Values were normalized to β-actin. Data presented as mean±s.e.m. (B) Treatment of NAMECs with PDGFR Inh 3 (5 μM) reduced p-PLCγ1γ$^{y783}$ and p-PLCγ2$^{Y1217}$ within 30 min. (C) Treatment of NAMECs with a PLCγ inhibitor (U73122) reduced p-PKCα$^{T497}$ and p=PKCα$^{T638}$ within 30 and 60 min. (D) Exposure of NAMECs to PDGFR Inh 3 or PDGFR Inh 4 reduced phosphorylation of PKCα cumulating in the downregulation of B-Raf and C-Raf phosphorylation, and dampening ERK signaling. (E) Exposure of NAMECs that were previously cultured for 24 h in growth factor-depleted media to PDGFC (100 ng/ml) for 60 min increased p-PKCα$^{T497}$ and p-PKCα$^{T638}$. The upregulation of PKCα phosphorylation by PDGFC was blocked by pre-treating the cells with a PLCγ inhibitor (U73122) for 60 min indicating that PDGF signaled to PKCα through PLCγ.

To identify potential RTKs that were associated with the EMT-induced mesenchymal state and might be responsible for the activation of PKCα, we surveyed the expression of several tyrosine kinases in basal-like breast cancer cell lines bearing mesenchymal properties and in luminal-like counterparts bearing more epithelial features. Interestingly, PDGFRα and PDGFRβ (PDGFRα/β), as well as their ligand PDGFC, were preferentially expressed in basal, but not luminal-like cells (FIG. 4C). PKCα was also more highly expressed in basal-like, and not luminal-like, human breast cancer cell lines (FIG. 13A). This is consistent with the notion that basal-like tumors contain cells that behave as if they have undergone at least a partial EMT, explaining their expression of certain mesenchymal markers.

Enhanced PDGFRα and PDGFC expression, with resulting autocrine signaling accompany the EMT program, suggesting their importance in the maintenance of the mesenchymal cell state. We assessed the expression of PDGFR ligands in the mesenchymal products of an EMT and observed that PDGFA, PDGFB and PDGFD were not expressed in both cell states, indicating that only PDGFC could participate autocrine signaling. In both the NAMECs and the TF-induced EMT cells, PDGFC was upregulated during EMT by 6.1-13.7 fold (FIG. 4D); total PDGFR and p-PDGFRα/β were also strongly induced in these cells while being negligible in the parental HMLE cells (FIG. 4E). The culture of NAMECs for 24 h in serum-free, growth factor-depleted media reduced the phosphorylation of PDGFRβ modestly by 1.3-fold relative to NAMECs maintained in complete media whereas either a PDGFR neutralizing antibody or PDGFR inhibitor, when added, led to a 4.3 and 6.8 fold respective reduction in PDGFRβ$^{Y751}$ (FIG. 4F). Conversely, the exposure of these nutrient-starved NAMECs to PDGFC for 30 min, 60 min or 3 h resulted in increased phosphorylation of PDGFRβ (FIG. 4F) while epithelial HMLE cells did not respond to PDGFC stimulation at all (data not shown), thus providing further support for autocrine PDGFR signaling activity following induction of an EMT program.

Protein levels of both phospholipase Cγ1 and 2 (PLCγ1 and PLCγ2), which transduce signals from PDGFRα/β to PKCα, were also elevated in these cells by an average of 4.57 and 2.38-fold, respectively (FIG. 4E). To test whether PLCγ is being activated by PDGFR through phosphorylation, NAMECs were treated with PDGFR inhibitors. Within 30 min, both p-PLCγ1$^{Y783}$ and p-PLCγ2$^{Y1217}$ were downregulated by 3.8-5.7 and 5.4-7.3 fold, respectively, whereas total PLCγ1 and PLCγ2 levels remained unaltered (FIG. 13B).

We subsequently sought to determine whether PKCα activation was directly dependent upon PDGFR-PLCγ. Exposure of NAMECs to a PLCγ inhibitor (U73122) reduced active p-PKCα$^{S497}$ and p-PKCα$^{T638}$ by 1.3 and 3.1-fold respectively within 30 min, and 6.3 and 4.2-fold respectively by 60 min (FIG. 13C); total PKCα level was unchanged (FIG. 13C). The inhibition of PDGFR in NAMECs, similarly, led to a loss of PKCα phosphorylation (p-PKCα$^{S497}$: 2.8 fold, p-PKCα$^{T638}$: 5.9 fold), as illustrated once again by the loss of active p-PKCα$^{S497}$ and p-PKCα$^{T638}$ within 30 min, while total PKCα remained constant (FIG. 13D). Conversely, the treatment of NAMECs that had been previously cultured for 24 h in growth factor-depleted media and then exposed to PDGFC for 60 min markedly increased p-PKCα$^{T638}$ and p-PKCα$^{S497}$ by 5.5 and 4.2-fold respectively (FIG. 13E). However, when these cells were pretreated with the PLCγ inhibitor for 30 min, followed by the addition of PDGFC for 60 min, the phosphorylation of PKCα was efficiently blocked (FIG. 13E), thereby confirming PKCα activity to be downstream of PDGFR signaling and mediated by PLCγ.

We assessed whether inhibition of PDGFR signaling is useful for the selective killing of CSCs relative to non-CSCs. Co-mixed NAMEC-Tom-Ras and HMLE-GFP-Ras cells were treated with two inhibitors specific to PDGFRα/β, but at higher concentrations, could also inhibit c-Kit and VEGFR which were expressed in both cell types. At LC$_{50}$, NAMEC-Tom-Ras cells had 3.2-3.8 fold heightened sensitivity to PDGFR inhibition than HMLE-GFP-Ras cells (FIG. 4G). These results indicated that cell-state transition, along with the acquisition of CSC-like traits, was accompanied by a downregulation of EGFR and concomitant upregulation of PDGFR, highlighting different signaling networks adopted for the maintenance of specific cellular fates (FIG. 4H).

Cell-State Dependent Utilization of c-Fos or FRA1 During EMT

To assess the manner by which PKCα mediates downstream signals crucial for the EMT program, we sought to identify direct substrates of PKCα present in cells that have undergone an EMT by searching for candidates that have been reported in the various cellular systems. Given the numerous potential substrates, we narrowed the field by focusing on candidate proteins that might be upregulated in conjunction with PKCα during activation of an EMT program (FIG. 14). Of these 37 genes we examined, only FRA1 mRNA was upregulated by at least 1.5-fold concomitantly in HMLE-Twist, HMLE-Snail and HMLE-Slug cells based on microarray analyses. It was also the most highly upregulated target of PKCα in all three cell types. We further examined the connection between PKCα and FRA1.

Figure 5:
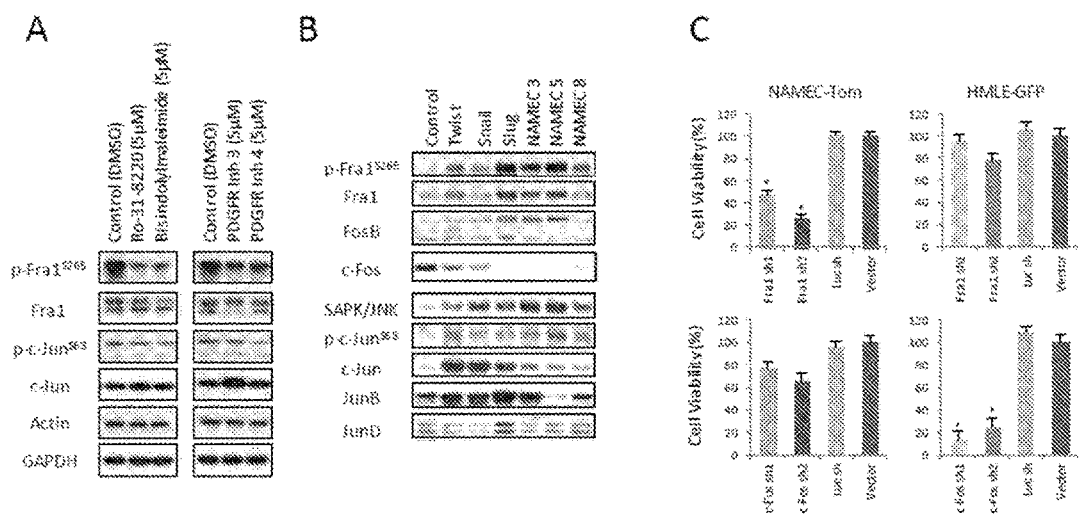
FIG. 5 depicts that PDGFR signaling results in PKCα and ERK1/2 activation that induce FRA1. (A) Inhibition of PKCα (Ro-31-8220 or bisindolylmalmide I) or PDGFRα/β (PDGFR Inh 3 or PDGFR Inh 4) in NAMECs blocked the phosphorylation of FRA1. The inhibitors used in FIG. 5A, F-G were applied to NAMECs for 30 min, after which protein lysates were collected. (B) Protein expression of AP-1 family member subunits. FRA1, p-FRA1$^{S265}$, c-Jun, p-c-Jun$^{S63}$ and JNK were induced in cells that have undergone an EMT while c-Fos was downregulated. (C) Effects of FRA1 or c-Fos knockdown on the viability of NAMEC-Tom and HMLE-GFP cells. NAMEC-Tom or HMLE-GFP cells were infected with shRNAs and then selected for three days with puromycin. 1000 of each cell types were subsequently seeded into wells of a 96-well plate by FACS. At day 6, six wells of each condition were assayed for cell viability. * denotes significantly different from vector control, p<0.005. Data presented as mean±s.e.m; n=6. (D) In mesenchymal NAMECs, c-Jun, JunB and JunD were co-immunoprecipitated with FRA1, and c-Jun was found to be associated with FRA1 but not c-Fos. In epithelial HMLE cells, c-Fos was found to bind JunB and JunD but not c-Jun. Whole cell lysates were used as a positive controls while pull-down with IgG or in absence of an antibody was performed as negative controls. (E) B-Raf, c-Raf and ERK1/2, along with their phospho-proteins were elevated in TF-induced EMT and NAMEC cells. A-Raf and p-A-Raf$^{S199}$ were not expressed (data not shown). H-Ras expression was not upregulated upon EMT. (F) Phospho-proteins for PKCα, B-Raf, c-Raf, MEK1/2 and ERK1/2 were reduced upon PKCα inhibitors treatment which indicated that MAPK/ERK signaling was downregulated. (G) MEK inhibition blocked p-ERK1/2 activation and resulted in reduced p-FRA1. Phospho-c-Jun was not affected.

FRA1 is a member of the Fos family of transcription factors, which is also comprised of c-Fos, FosB and Fra2. Together with the Jun family of transcription factors composed of c-Jun, JunB and JunD, individual members of the Fos and Jun family associate with one another to form heterodimeric activator protein-1 (AP-1) complexes that bind and transcriptionally regulate target gene expression when phosphorylated (Eferl and Wagner, 2003). To demonstrate that FRA1 was downstream of PKCα in cells that have undergone an EMT, NAMECs were treated with two PKCα inhibitors (Ro-31-8220 or bisindolylmaleimide I). Within 30 min of treatment, p-FRA1$^{S265}$ was strongly downregulated 8.3-9.5 fold whereas total FRA1 remained unchanged, indicating that FRA1 phosphorylation was dependent on PKCα activity (FIG. 5A).

Figure 15:
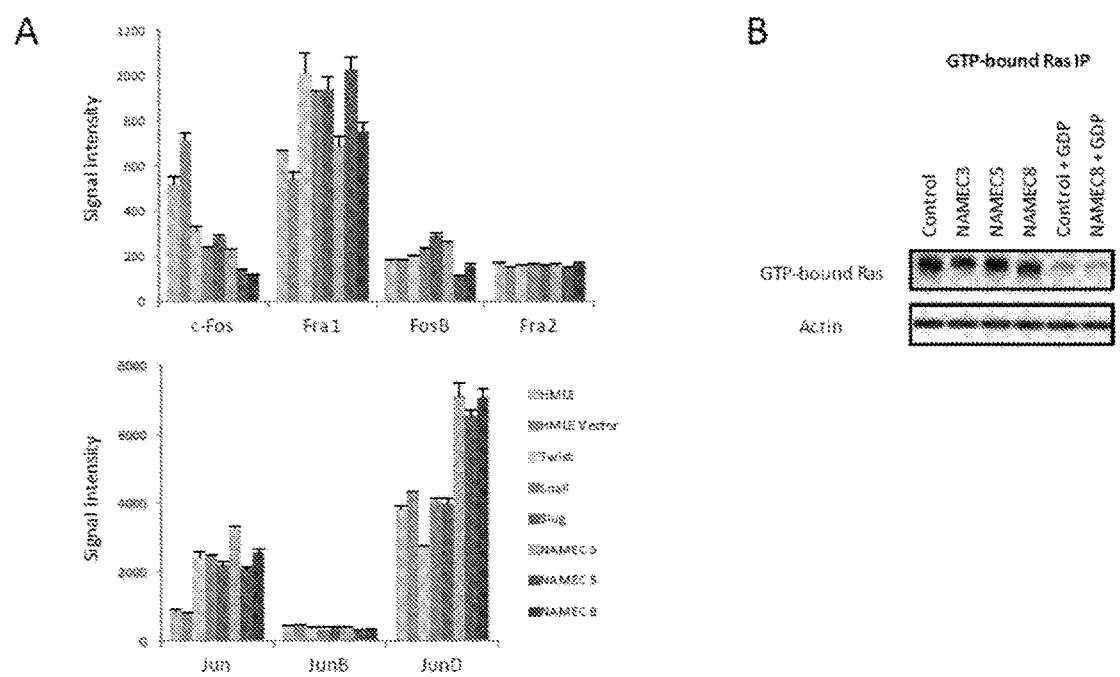
FIG. 15 (A) Relative gene expression of AP-1 proteins in parental epithelial cells (HMLE and HMLE Vector), EMT-TF transduced cells and NAMECs. c-Fos was downregulated in the mesenchymal relative to the epithelial cell state whereas FRA1 was upregulated. Data presented as mean±s.e.m. Bars from left to right are HMLE, HMLE Vector, Twist, Snail, Slug, NAMEC 3, NAMEC 5, NAMEC 8. (B) To compare the amount of active GTP-bound Ras between epithelial and mesenchymal cell states, GTP-bound Ras was immunoprecipitated with Raf-Ras Binding Domain (RBD) beads followed by blotting with a pan-Ras antibody. As a negative control, lysates were treated with GDP which blocked the ability of Ras to bind Raf-RBD beads.

For the formation of an AP-1 dimer complex, we assessed whether c-Jun was a likely binding partner. Total and phospho-c-Jun$^{S63}$, together with the Jun N-terminal kinase (JNK) required for the activation of c-Jun were upregulated in a panel of cells that had undergone an EMT (NAMECs and TF-induced EMT cells) (FIGS. 5B and 15A). Other Jun family members, JunB and JunD, did not show consistent up- or down-regulation following passage through EMT, indicating that their expressions were not cell-state dependent (FIGS. 5B and 15A). Unexpectedly, c-Fos, which has been extensively documented as a partner of c-Jun, was downregulated during passage through an EMT (FIGS. 5B and 15A). Total and phospho-FRA1$^{S265}$, by contrast, were induced (FIGS. 5B and 15A). Thus, we demonstrated that both epithelial and mesenchymal cells assemble AP-1 complexes, but of quite different composition, in that FRA1 replaced c-Fos as the partner of Jun following passage through an EMT.

We assessed the functional significance of the c-Fos-FRA1 switch during cell state transition by testing for their loss of function by RNAi in both HMLE cells and NAMECs. Knockdown of FRA1 reduced NAMEC-Tom cell viability by 53-74% but had lesser impact on HMLE-GFP cells (5-22.5%) (FIG. 5C). In contrast, HMLE-GFP cells were depleted by 75-88% upon c-Fos knockdown while NAMEC-Tom cells were less affected with 23-35% reduction in cell viability, highlighting the cell-state specific dependence on either c-Fos or FRA1 for maintaining cell viability (FIG. 5C).

We further assessed the specific interactions of AP-1 subunits by performing co-immunoprecipitation (co-IP) experiments. In NAMECs, immunoprecipitation of FRA1 showed physical association with c-Jun, JunB and JunD (FIG. 5D). In a reciprocal manner, pull-down of c-Jun detected its interaction with FRA1 but not c-Fos (FIG. 5D). The converse pattern was observed in HMLE cells, in which c-Fos associated with JunB and JunD but not c-Jun, which was largely absent in the epithelial state (FIG. 5D). This confirmed that during execution of the EMT program, there is a switch from the use of c-Fos to FRA1 as the preferred components of AP-1 complexes.

ERK Signaling Augments FRA1 Activation

Apart from FRA1, we assessed additional downstream mediators of PKCα that might also be crucial for supporting the EMT program. The Raf family of proteins (A-Raf, B-Raf and c-Raf), which regulate the ERK signaling cascade, represented another class of potentially important substrates. An examination of proteins involved in this signal transduction pathway revealed increased expression of both total and phosphorylated forms of B-Raf, of c-Raf and of ERK1/2 in NAMECs and in EMT-TF-induced mesenchymal cells relative to HMLE cells (FIG. 5E).

We assessed whether mesenchymal cells contained higher Ras expression or activated Ras. Total Ras and GTP-bound Ras remained comparable among epithelial and mesenchymal cell types (FIGS. 5E and 15B). We assessed whether enhanced ERK signaling in the mesenchymal cell state was primarily mediated through the activated PDGFR and PKCα signaling cascade, rather than through activation via a Ras-Raf pathway. To test this, we exposed NAMECs to PKCα-specific inhibitors for 30 min. This reduced p-B-Raf and p-c-Raf expression, and led to the loss of p-MEK1/2 and p-ERK1/2 (FIG. 5F). Blockage of PDGFR signaling with two inhibitors resulted in the loss of p-PKCα, once again blunting ERK signaling as indicated by decreased p-B-Raf, p-c-Raf, p-MEK1/2 and p-ERK1/2 levels (FIG. 13D). Therefore, the enhanced activity of ERK signaling during EMT was, in part, conferred by signaling through PDGFR and PKCα.

Interestingly, FRA1 is downstream of PKCα and serves as a substrate for p-ERK1/2. We assessed whether the observed increased p-FRA1 activity in the mesenchymal cells could be further augmented by elevated ERK signaling during EMT. Accordingly, inhibition of ERK1/2 phosphorylation with a MEK inhibitor was able to decrease p-FRA1$^{S265}$ levels by 65% but not the levels of total FRA1 or p-c-Jun (FIG. 5G), confirming that ERK1/2 signaling promoted p-FRA1 activity. Thus far, we demonstrated that the PKCα signaling network in cells that have undergone an EMT led to the activation of FRA1 which was downstream of both PKCα and ERK1/2.

FRA1 is a Transcriptional Target of Twist and Snail

Figure 6:
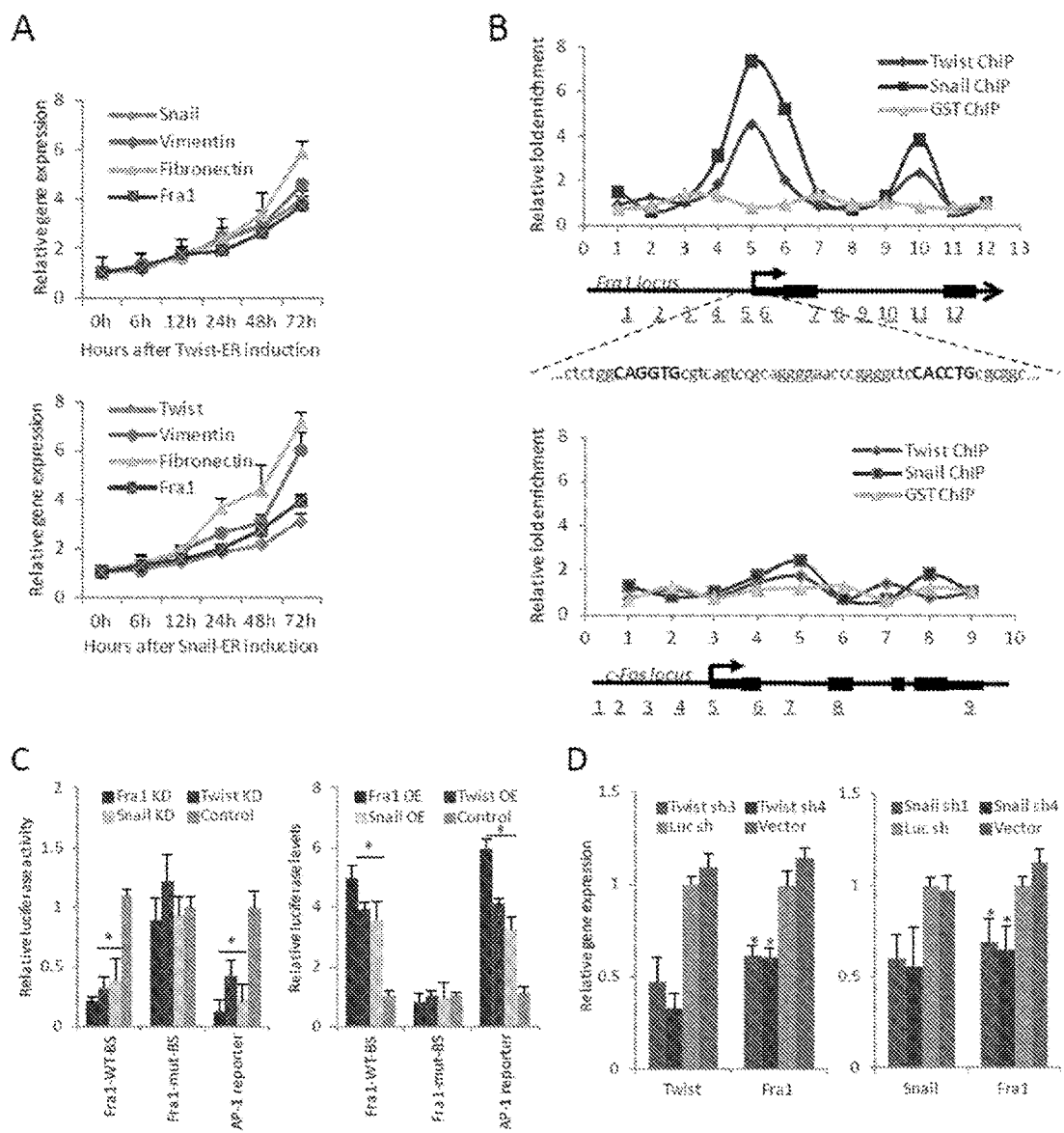
FIG. 6 depicts that FRA1 is a transcriptional target of Twist and Snail. (A) Temporal induction of FRA1 in Twist-ER and Snail-ER cells after the addition of 4-OHT. As controls, Twist, Snail, fibronectin and vimentin were shown to be upregulated upon Twist-ER or Snail-ER induction. Values were normalized to β-actin. Data presented as mean±s.e.m. (B) Twist and Snail occupied the FRA1 promoter in proximity to the transcription start site (7.2 and 4.9 fold, respectively, at probe 5) and within the first intron. E-box motifs found within Twist and Snail-bound sites are denoted. Twist or Snail bound very weakly (1.7 and 2.4 fold, respectively, at probe 5) to the c-Fos genomic locus. Control ChIP was performed with an anti-GST antibody. Binding enrichment was normalized to input DNA and values were plotted relative to probe 12 (FRA1) or probe 9 (c-Fos). Sequence shown is set forth in the sequence listing as SEQ ID NO:141. (C) Effects of Twist and Snail on FRA1-reporter luciferase activity. In NAMEC11 cells bearing a partial EMT, knockdown of FRA1, Twist or Snail resulted in the loss of FRA1 wild-type binding site (FRA1-WT-BS) luciferase activity but had no effect on the FRA1 mutant binding site (FRA1-mut-BS) luciferase activity. The AP-1 luciferase reporter activity, used as a positive control, was also repressed with FRA1, Twist or Snail knockdown. Overexpression of FRA1, Twist or Snail led to the activation of FRA1-WT-BS, but not FRA1-mut-BS activity. The AP-1 reporter was used as a positive control. The firefly luciferase was normalized against SV40-Renilla-luciferase transfection control and the values were compared to control shLuc or vector overexpression treated cells. Cells were co-transfected with firefly luciferase, Renilla luciferase and shRNA or overexpression plasmids, and luciferase activities were analyzed between 36 h and 48 h. * denotes significantly different from Luc shRNA or vector control, p<0.05. Data presented as mean±s.e.m; n=6. Bars from left to right are FRA1 KD, Twist KD, Snail KD, Control. (D) Knockdown of Twist or Snail decreased FRA1 expression in NAMECs. * denotes significantly different from vector control, p<0.05. Values were normalized to β-actin. Data presented as mean±s.e.m. Bars from left to right are Twist sh3, Twist sh4, Luc sh, Vector (left panel), and Snail sh1, Snail sh4, Luc sh, Vector (right panel).

The increased expression of FRA1 in the EMT TFs-induced mesenchymal cells and in NAMECs correlated closely with the abundance of EMT-TFs, indicating they could directly induce FRA1 expression. To assess this further, we first showed with a tamoxifen-inducible system (HMLE-Twist-ER and HMLE-Snail-ER) that induction of Twist or Snail upregulated FRA1 expression by ~1.5 fold within 12 h and reached ~4 fold by three days (FIG. 6A). We next assessed whether this induction was due to the direct binding of Twist or Snail to the FRA1 promoter. Chromatin immunoprecipitation (ChIP) of Twist and Snail, indeed, detected their enrichment at the transcription start site of the FRA1 (7.2 and 4.9 fold respectively) and, in addition, within its first intron (FIG. 6B). These bound regions contained E-box motifs (CANNTG), which Twist and Snail are known to bind (FIG. 6B). In contrast, the promoter c-Fos appeared very weakly enriched for Twist and Snail binding (1.7 and 2.4 fold respectively) (FIG. 6B), thus indicating FRA1, but not c-Fos, might be an important downstream mediator of Twist or Snail-induced EMT.

We utilized a luciferase reporter containing the recognition sequence of promoters that are normally bound by FRA1 (FRA1-WT-BS) as well as a mutant FRA1 binding construct (FRA1-mut-BS), to analyze the activity of FRA1 relative to the expression of EMT-TFs. In NAMECs, knockdown of FRA1 abrogated luciferase activity of the FRA1-WT-BS but not FRA1-mut-BS (FIG. 6C, left panel). Similarly, knockdown of Twist or Snail diminished FRA1-dependent activation of the FRA1-WT-BS reporter by 68% and 61%, respectively (FIG. 6C, left panel). FRA1 expression was also reduced by 35-40% upon either Twist or Snail knockdown in NAMECs (FIG. 6D).

In a reverse experiment, we overexpressed FRA1 in the NAMEC11 cell line, which had undergone only a partial EMT, acquiring mesenchymal markers while continuing to express epithelial ones. The overexpression of FRA1 induced FRA1-WT-BS but not FRA1-mut-BS luciferase activity (FIG. 6C, right panel) Likewise, Twist and Snail overexpression was also able to induce FRA1-WT-BS reporter (FIG. 6C, right panel). The wild-type AP-1 reporter encoding the firefly luciferase under the control of a minimal promoter and tandem repeats of AP-1 response elements was used as a positive control for both RNAi and overexpression studies (FIG. 6C). Altogether, these lines of evidence confirmed that FRA1 levels were transcriptionally regulated by two master EMT-TFs in a direct manner.

Figure 16:
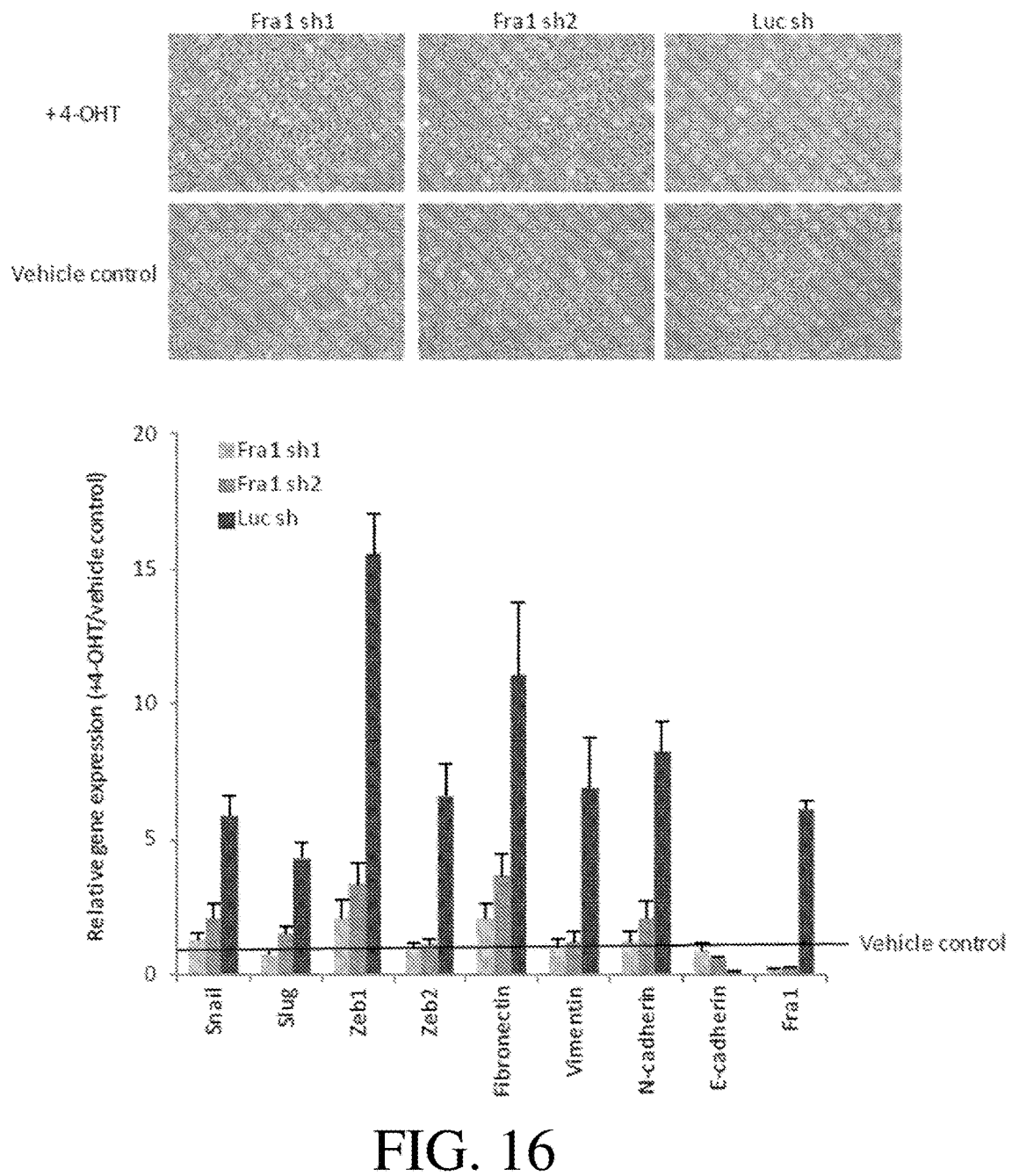
FIG. 16 FRA1 depletion blocks Twist-induced EMT. In control shRNA-treated HMLE-Twist-ER tamoxifen-inducible cells, seven days of 4-OHT exposure resulted in an overt mesenchymal morphology that was accompanied by the upregulation of the EMT-TFs (Snail, Slug, Zeb1 and Zeb2) and EMT markers (fibronectin, vimentin and N-cadherin), as well as repression of E-cadherin expression. FRA1-depleted cells remained epithelial and did not show appreciable increments in mesenchymal cell markers. Values were normalized to β-actin and compared relative to DMSO vehicle-treated control. Data presented as mean±s.e.m. Bars from left to right are FRA1 sh1, FRA1 sh2, Luc sh.

FRA1 is Involved in Tumor-Initiation of Breast Cancer Cells Bearing Mesenchymal Features To assess the role of FRA1 in the EMT program, we utilized cells in which the Twist EMT-TF could be activated in a tamoxifen-dependent fashion. We activated Twist expression, in otherwise-epithelial HMLE-Twist-ER, in the presence or absence of two different shRNAs targeting FRA1 mRNA; we then assessed the subsequent ability of these cells to transit into the mesenchymal state. With control shRNA-treated cells, HMLE-Twist-ER cells lost epithelial morphology and gained mesenchymal traits one week after 4-OH-tamoxifen exposure, as anticipated (FIG. 16). However, FRA1-depleted cells which showed comparable proliferative capabilities as control cells were blocked in their ability to undergo EMT upon Twist induction and retained their epithelial phenotype (FIG. 16). Mesenchymal cell markers such as vimentin, fibronectin and N-cadherin were not induced while E-cadherin expression was retained (FIG. 16). This observation further indicated that FRA1 is a downstream mediator that is important for EMT to proceed.

Figure 7:
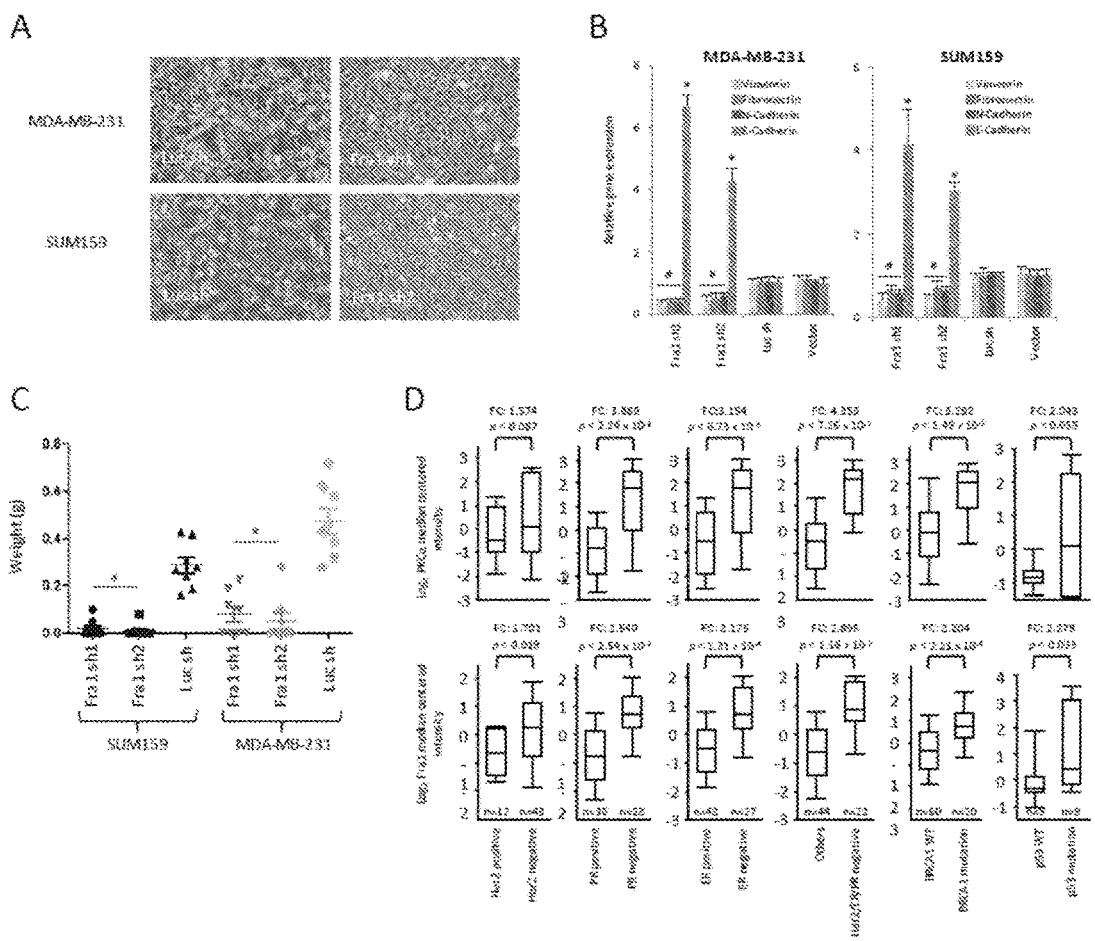
FIG. 7 FRA1 is clinically correlated with basal-like or triple-negative breast tumors and indispensible for tumorigenicity. (A) Knockdown of FRA1 in MDA-MB-231 or SUM159 cells resulted in the formation of cells bearing epithelial features that included cell-cell junctions and sheet-like structures. (B) In these FRA1-depleted cells, the downregulation of vimentin, fibronectin and N-cadherin, accompanied by the upregulation of E-cadherin expression were observed. * denotes significantly different from shLuc, p<0.005; #p<0.05. Data presented as mean±s.e.m. Bars from left to right are Vimentin, Fibronectin, N-Cadherin, E-Cadherin. (C) FRA1 depletion blocked tumor-initiation of MDA-MB-231 and SUM159 cells. 1×10$^6$ cells were implanted subcutaneously into female NOD-SCID mice and tumors were extracted and measured after 4 weeks. * denotes significantly different from shLuc-derived tumors, p<0.0001. (D) Both PKCα and FRA1 were more highly expressed in human primary breast cancer tumors which were Her2$^-$, PR$^-$, ER$^-$ or triple-negative. They were also increased in tumors bearing BRCA1 mutation and in breast cancer cell lines bearing p53 mutation. (E) Tables report the numbers of human breast cancer samples with 'absent/weak', 'moderate', or 'strong' PKCα and FRA1 expression from graded breast tumors. Representative staining intensities shown in images. * denotes significantly different from grade 1, grade 2 or normal specimens, p<0.01. (F) Effects of PKCα inhibitor administration (5 mg/kg/day) on the growth of patient-derived breast tumor xenografts in NOD-SCID mice are shown. Treatment was initiated immediately following implantation and continued for 5 weeks; tumor masses were then determined. The asterisk (*) denotes a significant difference from the vehicle.
Figure 17:
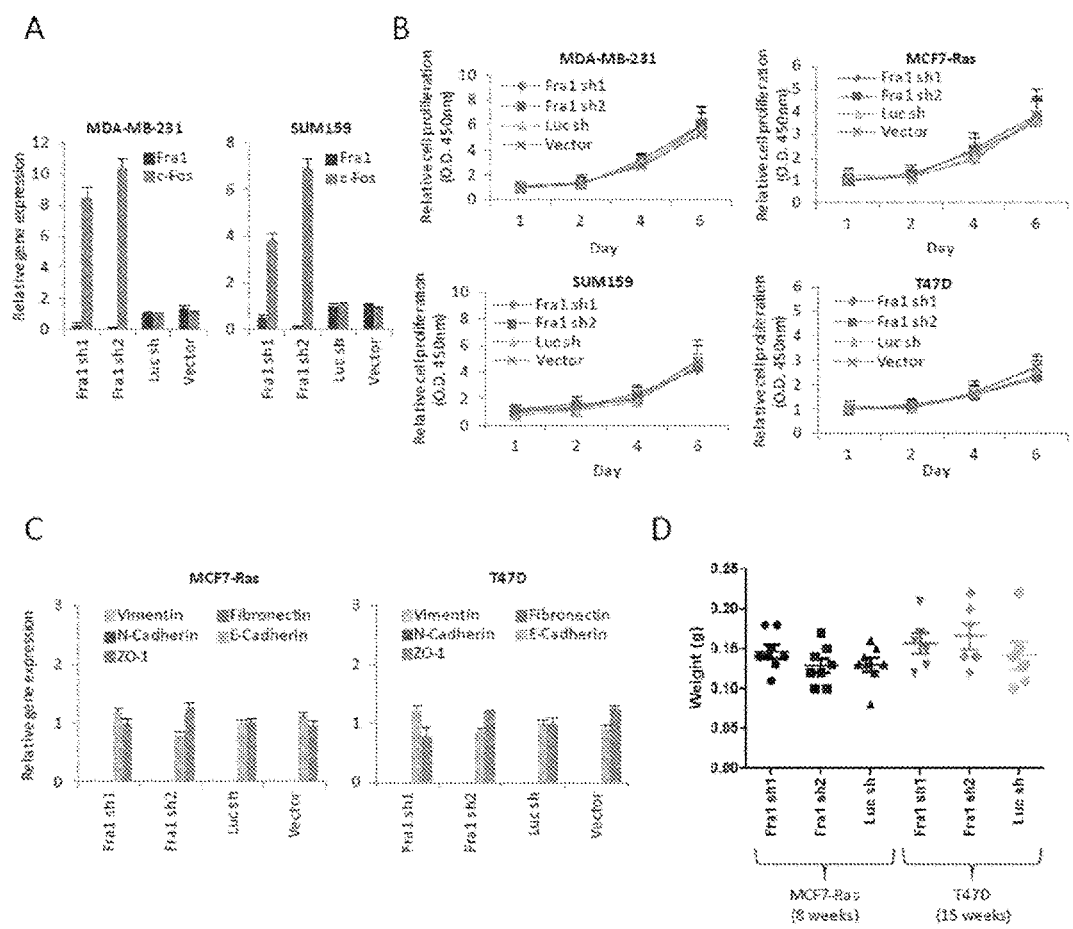
FIG. 17 Effects of FRA1 depletion on the growth kinetics, expression of EMT-associated markers and tumorigenicity of breast cancer cell lines. (A) FRA1 knockdown in MDA-MB-231 and SUM159 cells resulted in the upregulation of c-Fos. Data presented as mean±s.e.m. Left bar is FRA1 expression, right bar is c-Fos expression. (B) FRA1 knockdown did not alter the growth kinetics of MDA-MB-231, SUM159, MCF7-Ras or T47D cells over a 6 day period. Data presented as mean±s.e.m. (C) Expression of EMT-associated markers upon FRA1 knockdown in MCF7-Ras and T47D cells. Vimentin, fibronectin and N-cadherin were not detectable by qPCR. Data presented as mean±s.e.m. Bars from left to right are Vimentin, Fibronectin, N-cadherin (all three were undetectable), E-cadherin, ZO-1. (D) FRA1 knockdown did not affect the tumorigenicity of MCF7-Ras and T47D cells. 1×106 MCF7-Ras or 2×106 T47D cells were xenografted subcutaneously into female NOD-SCID mice and tumor incidence and size were assessed after 8 or 15 weeks.

The role of FRA1 in mediating the EMT of HMLE cells led us to assess whether it might regulate mesenchymal traits in human breast cancer cells. We depleted FRA1 by RNAi in two basal-like breast cancer cell lines, MDA-MB-231 and SUM159, which were Her2$^{neg}$ER$^{neg}$PR$^{neg}$. Interestingly, in both cell types, FRA1 depletion resulted in a differentiation phenotype that resembled a mesenchymal-epithelial transition (MET) in which otherwise mesenchymal-like cancer cells formed epithelial sheets (FIG. 7A). The loss of vimentin, fibronectin and N-cadherin accompanied by the gain of E-cadherin expression were observed (FIG. 7B). Moreover, both MDA-MB-231 and SUM159 that were depleted for FRA1, upregulated c-Fos which we found to be associated with the epithelial phenotype, by 8.5-10.4 and 3.8-6.9 fold respectively (FIG. 17A).

Although FRA1 knockdown did not significantly affect cell proliferation of either MDA-MB-231 or SUM159 cells in vitro (FIG. 17B), the tumorigenic potential of these cancer cells was diminished. Thus, when $0.5 \times 10^6$ SUM159 or MDA-MB-231 cells were xenografted into female NOD-SCID mice, FRA1-depleted cells formed tumors with a frequency of 18.7% and 43.7%, respectively, relative to shRNA controls (FIG. 7C). These tumors were, notably, at least 15.3 and 5.9 times smaller than those of control shRNA-treated SUM159 or MDA-MB-231 cells, respectively. In contrast, the depletion of FRA1 in two luminal-like, hormone receptors-positive breast cancer cell lines, MCF7-Ras and T47D, did not result in phenotypic changes or appreciable differences in the expression of EMT-associated markers (FIG. 17C). FRA1 knockdown in these cells also did not affect their tumor-initiating powers or tumor growth (FIG. 17D), confirming that it was not required for cancer cells bearing epithelial features. Taken together, these observations suggested that FRA1 might be important for maintaining CSCs in basal-like or triple-negative tumors but not in luminal tumors.

FRA1 and PKCα are Clinically Relevant in Aggressive Breast Cancer

Figure 18:
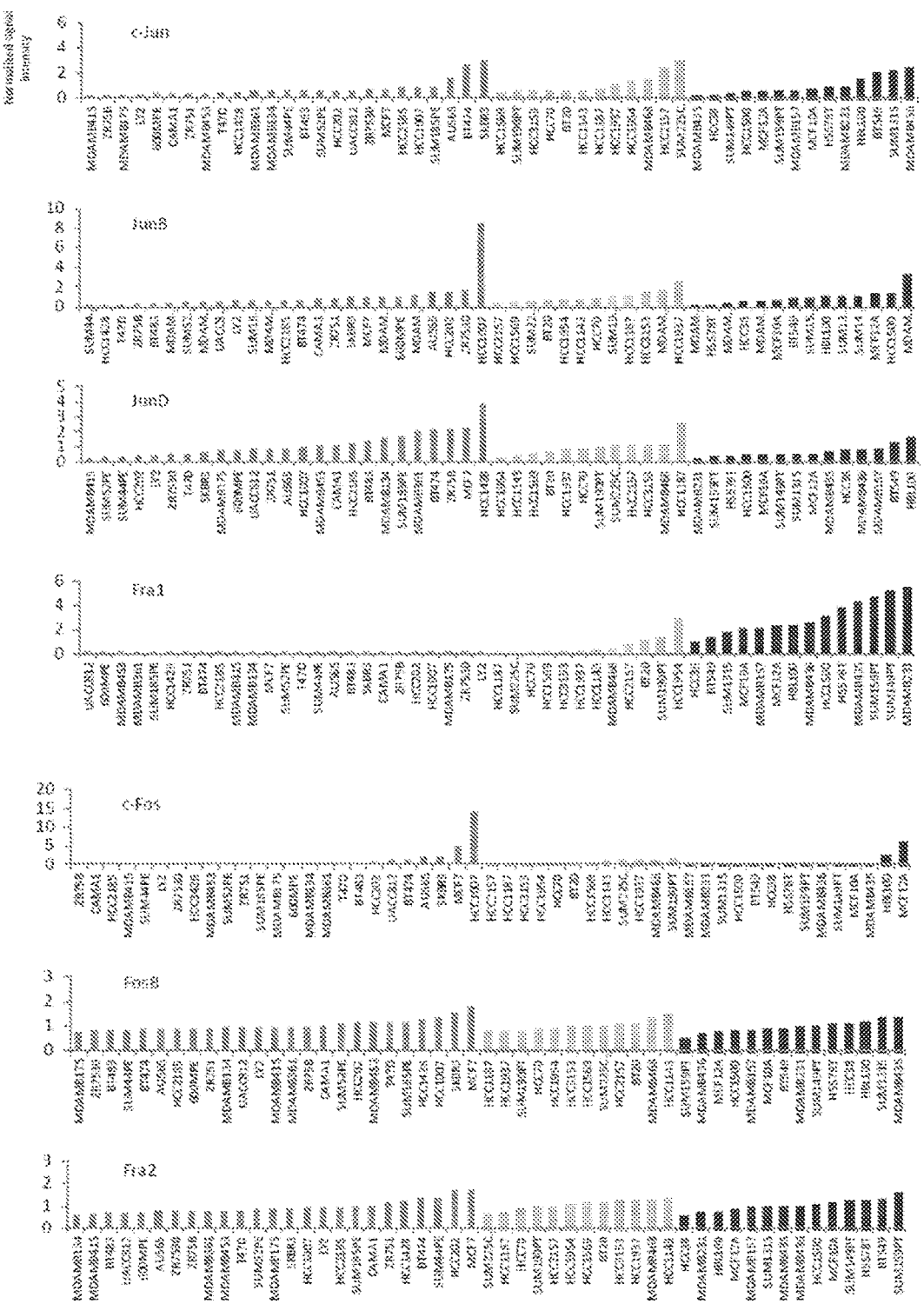
FIG. 18 Microarray gene expression of AP-1 subunits in cancer cell lines (Neve et al., 2009). For each gene, signal intensity was averaged for all cell lines. Individual values were then normalized to the mean intensity and plotted. Cell lines were categorized based on molecular subtypes: luminal (green), basal A (orange) and basal B (red).

The functional significance of FRA1 in mediating cell state transition and maintaining CSCs within the basal-like breast cancer cells led us to wonder whether its expression might be clinically relevant. We assessed whether FRA1 was restricted to the basal-like and triple-negative breast cancer (TNBC) tumors and cell lines, as these bear strong molecular hallmarks of mesenchymal cells and suggest, at least, a partial activation of the EMT program. These subtypes were understood to contain a high representation of CSCs, thereby favoring relapse, metastasis and poor overall survival. We found that FRA1 but not other AP-1 subunits was markedly elevated in all the basal B subtype of breast cancer cell lines surveyed and was reduced or absent in the basal A and luminal subtypes (FIG. 18).

Figure 19:
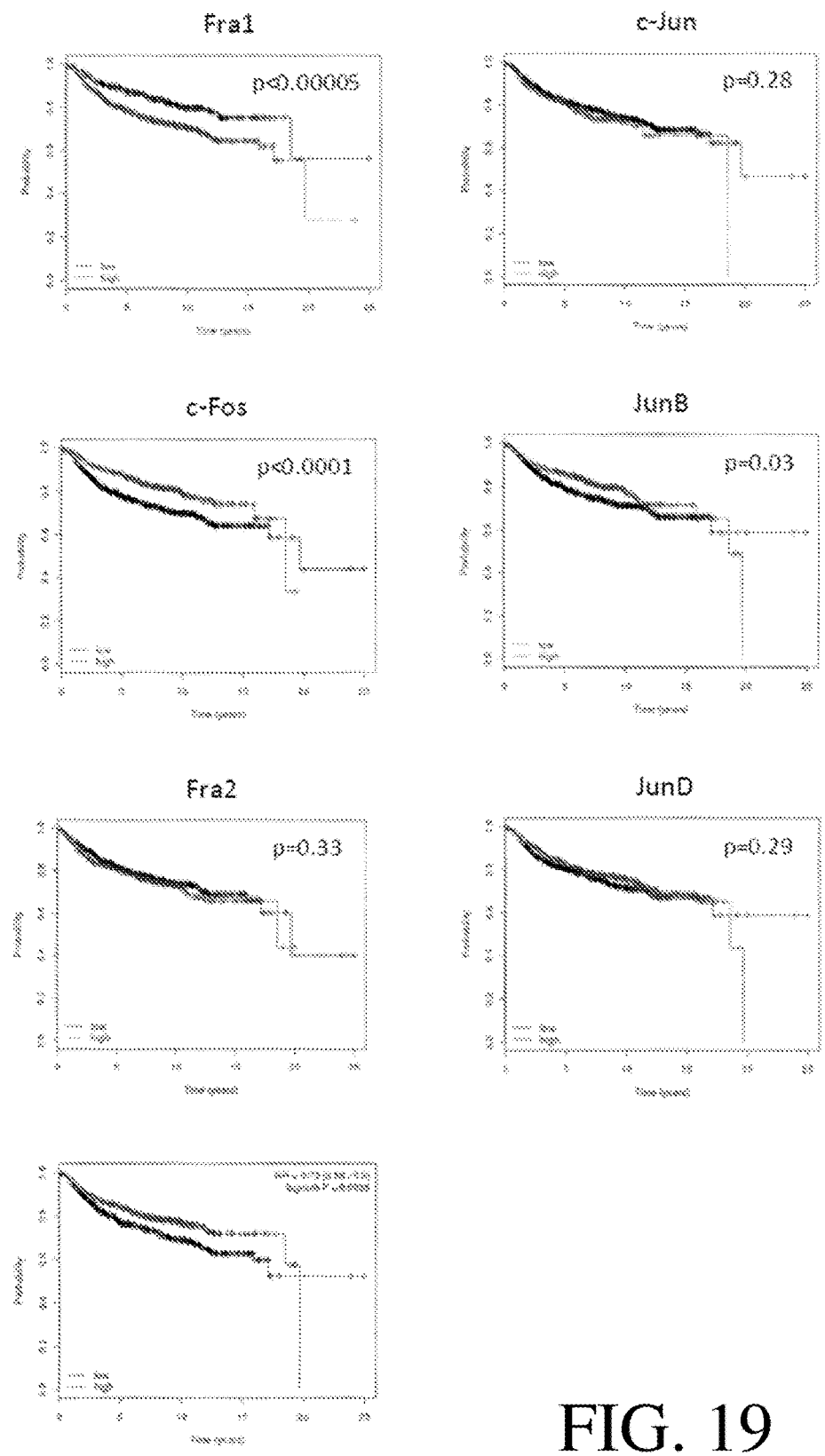
FIG. 19 Association of the AP-1 subunits (FRA1, Fra2, c-Fos, FosB, c-Jun, JunB and JunD) with the distant metastasis-free survival (DMFS) of breast cancer patients (refer to main text for sources of patient datasets). High FRA1 expression (red line; p<0.00005) was significantly correlated with poor prognosis whereas high c-Fos (p<0.0001) or FosB (p<0.005) expression was significantly correlated with more favorable prognosis. Other AP-1 proteins did not have significant prognostic value. n=1354. The datasets used in the survival analyses were GSE2603, GSE17705, GSE21653, GSE16446, GSE17907, GSE19615 and GSE20685, and generated using kmplot.com. High expression is shown as a red (light) line. Low expression is shown as a black (dark) line.
Figure 20:
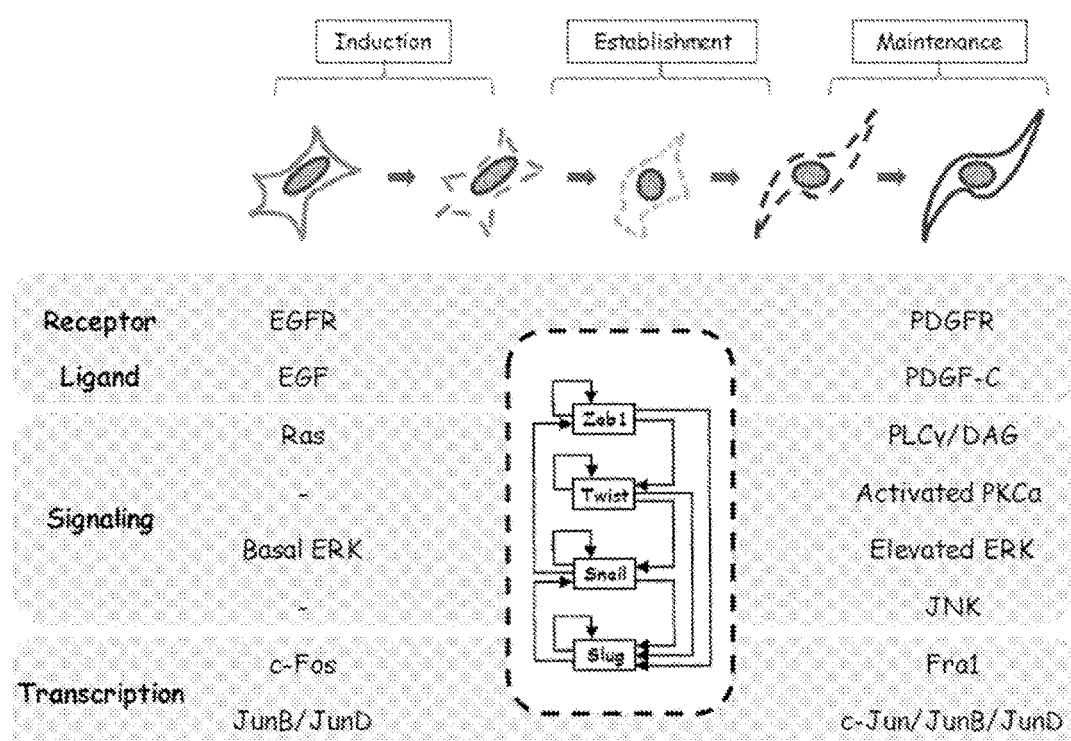
FIG. 20 provides a schematic of factors involved in the EMT program.

In multiple clinical datasets, we observed high FRA1 expression to be clearly and significantly correlated with poor distant metastasis-free survival (DMFS) whereas high c-Fos or FosB expression was associated with better survival prognosis (FIG. 19). The expression levels of other AP-1 subunits also did not predict patient outcome (FIG. 19). Additionally, PKCα and FRA1 gene expressions were significantly associated with Her2$^{neg}$, ER$^{neg}$ or PR$^{neg}$ status, as well as triple-negative tumors (FIG. 7D). Their expression were also elevated in tumors bearing BRCA1 mutations and in breast cancer cell lines containing p53 mutations (FIG. 7D).

To exclude the possibility that FRA1 mRNA expression in bulk tumor cells derived from contamination by infiltrating stromal cells, we examined its protein expression in breast tumor microarrays derived from patients whose tumors were scored for tumor grade. Moderate-to-strong nuclear FRA1 staining was present predominantly in grade 3 tumors (67.9%) that were typically hormone receptors-negative but far less common in grade 1 (17%) and grade 2 (21.1%) tumors, or the normal mammary epithelium (3.8%) (FIG. 7E). A similar trend could be observed with cytoplasmic and membrane-localized PKCα which showed moderate-strong staining in 66.1% of grade 3 tumors (FIG. 7E). Taken together, these results reinforce the notion that FRA1, along with PKCα, are important determinants of aggressive basal-like and TNBCs bearing features of an EMT.

Testing PKCα Inhibition as a Therapeutic Strategy Using Patient-Derived Tumor Samples It was determined that PKCα inhibitors, administered systemically, inhibit the growth of breast cancer cells bearing mesenchymal traits, and that triple-negative breast tumors express elevated levels of PKCα. Thus, we evaluated usefulness of PKCα inhibition as a therapeutic strategy against patient-derived tumor samples. As described herein, we generated three patient-derived breast cancer xenografts from triple-negative tumors (EL12-58, EL12-15, and EL11-26) that had been serially passaged in NOD-SCID mice following their removal from patients. We then transplanted these tumor fragments orthotopically into a fresh set of female NOD-SCID mice and, on the same day, subjected them to either a PKCα inhibitor or vehicle control that was administered intraperitoneally daily for 6 weeks. With all three xenograft lines, tumors that formed in the PKCα-inhibitor-treated mice were consistently smaller (EL12-15: 65.7%, EL11-26: 53.3%, and EL12-58: 39.5%) than the control group (FIG. 7F). Thus, inhibition of PKCα is a useful strategy for targeting triple-negative breast tumors.

Example 2: Assessment of Cellular Plasticity of NAMECs

Figure 24:
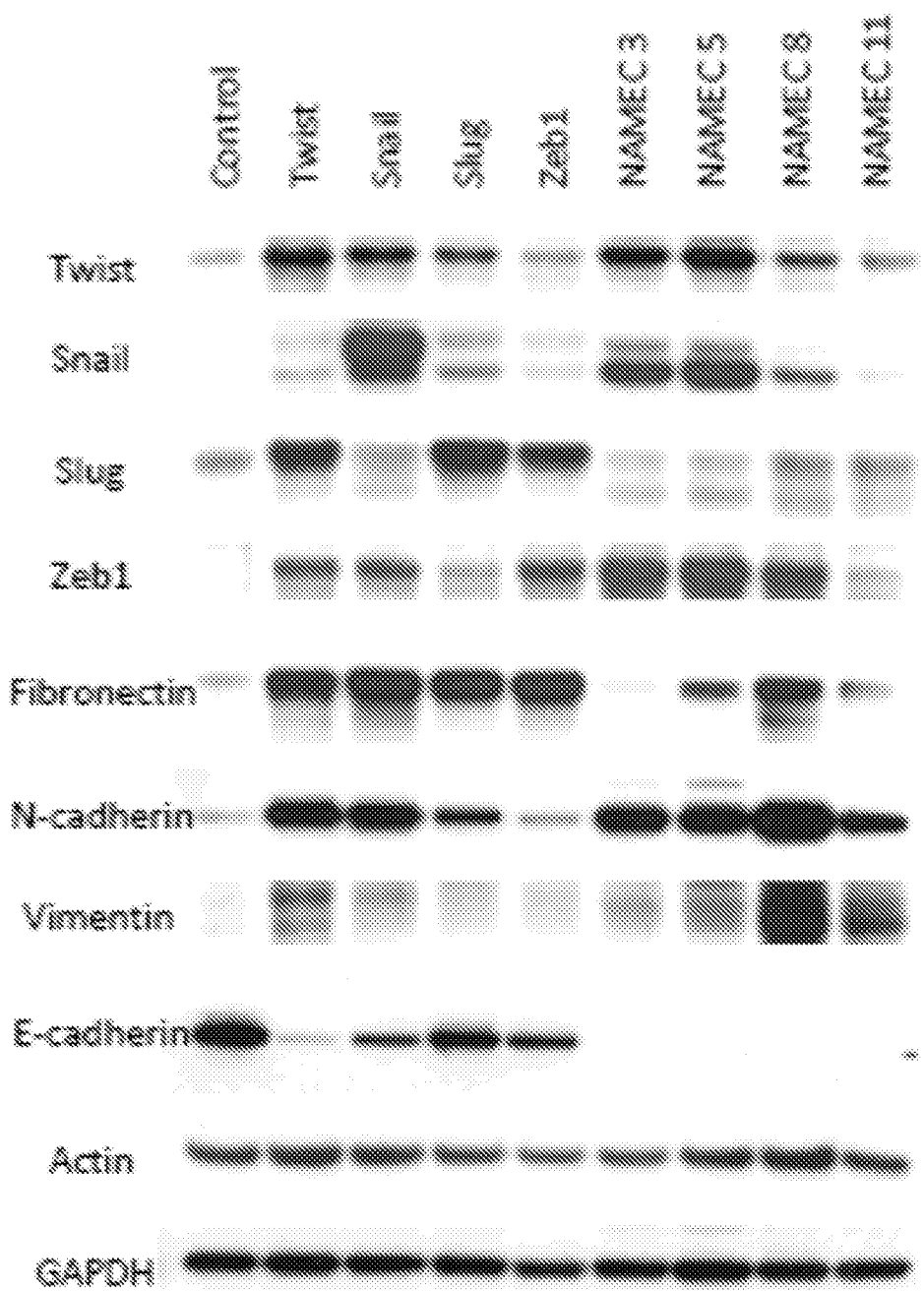
FIG. 24 depicts results of an assessment of cellular plasticity of NAMECs, showing that NAMECs expressed high endogenous levels of the EMT-associated mesenchymal markers (fibronectin, N-cadherin and vimentin) and lost the expression of the epithelial adherens junction protein (E-cadherin).

NAMEC clones were derived from parental HMLE cells. They contained high endogenous expression of the EMT transcription factors (Twist, Snail, Slug and Zeb1) in a manner that is comparable to levels expressed in EMT TF-induced cells (HMLE-Twist, HMLE-Snail or HMLE-Slug). NAMECs also expressed high endogenous levels of the EMT-associated mesenchymal markers (fibronectin, N-cadherin and vimentin) and lost the expression of the epithelial adherens junction protein (E-cadherin) (FIG. 24).

Figure 25:
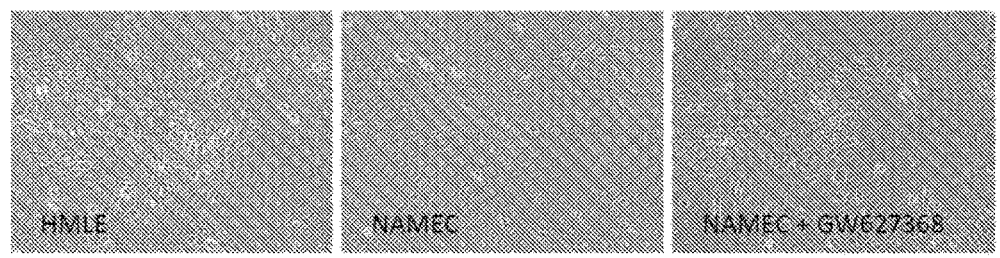
FIG. 25A depicts results of an assessment of cellular plasticity of NAMECs, showing that when treated with an Ep4 receptor antagonist (GW627368) which blocked PGE2 signalling, NAMECs differentiated into an epithelial morphology within three weeks and resembled epithelial HMLE cells.
FIG. 25B shows that NAMECs which were otherwise resistant to non-cell state specific inhibitors such as paclitaxel or staurosporine, became sensitive to these agents when differentiated.
FIG. 25C shows that differentiation in response to PGE2 inhibition was accompanied by the downregulation of p-PKCα and SPHK1/2 proteins.
Figure 25:
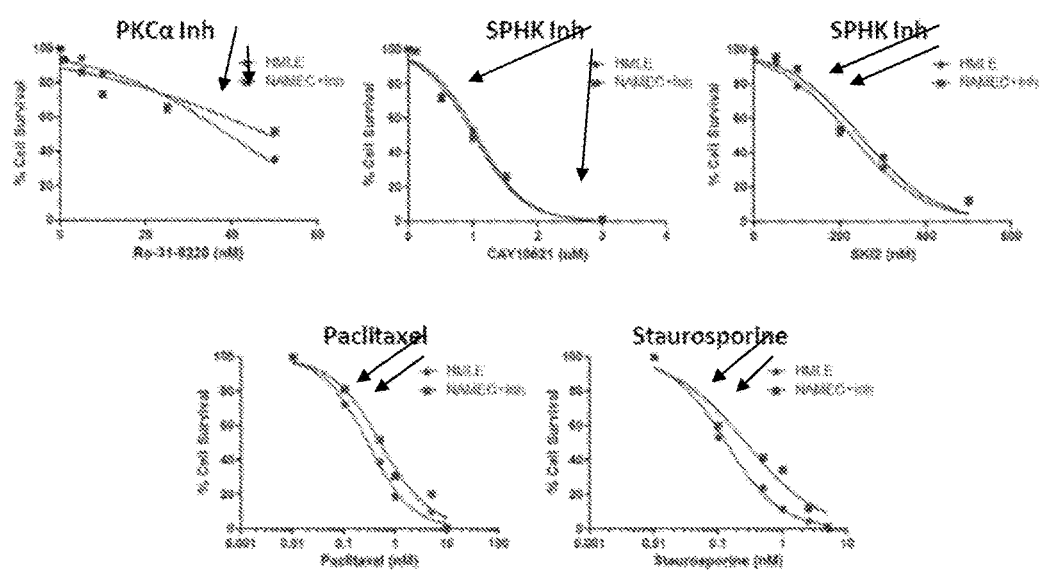

NAMECs are phenotypically plastic and can transit between the epithelial and mesenchymal cell state. The cells relied on autocrinal PGE2 signaling for maintenance of the mesenchymal state. When treated with an Ep4 receptor antagonist (GW627368) which blocked PGE2 signaling, NAMECs differentiated into an epithelial morphology within three weeks and resembled epithelial HMLE cells (FIG. 25A). NAMECs were more sensitive to PKCα or SPHK1/2 inhibitors (Ro-31-8220, CAY10621 or SKI2) relative to parental HMLE cells. However, GW-treated NAMECs lost their sensitivity towards these inhibitors. NAMECs which were otherwise resistant to non-cell state specific inhibitors such as paclitaxel or staurosporine, became sensitive to these agents when differentiated (FIG. 25B). The differentiation in response to PGE2 inhibition was accompanied by the downregulation of p-PKCα and SPHK1/2 proteins (FIG. 25C). These data indicated that CSCs could be induced to differentiate into an epithelial phenotype which could be targeted with chemotherapeutic agents such as paclitaxel used clinically.

Example 3: Identification of SPHK1 and SPHK2 as Therapeutic Targets that are Induced in Cells that have Undergone an Epithelial-Mesenchymal Transition (EMT)

Figure 21:
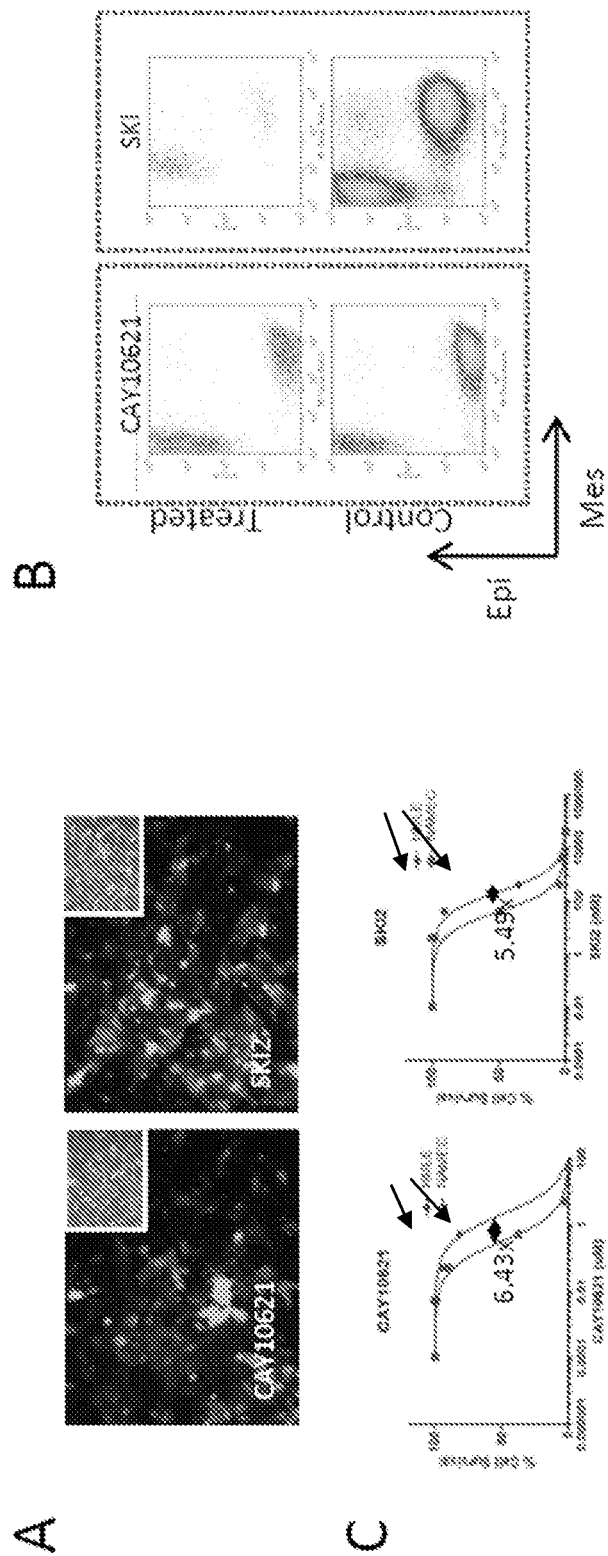
FIG. 21 shows identification of SPHK1 and SPHK2 as therapeutic targets that are induced in cells that have undergone an epithelial-mesenchymal transition (EMT).

Two inhibitors targeting (sphingosine kinase 1 and sphingosine kinase 2) SPHK1/2 showed a 5.5-6.5 fold lower $LC_{50}$ (Lethal Concentration, 50%) in affecting NAMEC-Tom cells (FIGS. 21A, B and C) relative to HMLE-GFP cells. To address whether SPHK1/2 inhibition induced apoptosis, the mixed cell populations described above were treated with inhibitors for three days and assessed with Annexin V, which marks apoptotic cells. Dramatic apoptosis was observed with NAMEC-Tom cells (SPHK inhibitor: 31%), while HMLE-GFP cells remained relatively resistant to these agents (SPHK inhibitor: 2%). (FIG. 21D) By contrast, paclitaxel and staurosporine resulted in HMLE-GFP cell apoptosis, leaving NAMEC-Tom cells less affected (FIG. 21D).

Since the activities of the SPHK1/2 affected the survival of the mesenchymal cells produced by an EMT, we examined their expression in the minority $CD44^{hi}/CD24^{lo}$ stem cell-enriched fraction residing within the HMLE cells. SPHK1 and SPHK2 were upregulated in these $CD44^{hi}/CD24^{lo}$ cells by 6.6 and 5.7 fold, respectively (FIG. 21E). Thus, cells that had undergone an EMT spontaneously, including naturally arising stem cells within bulk parental HLME cells, were similar with respect to these kinases expression (FIG. 21F). Interestingly, SPHK1 were also highly expressed in basal-like, and not luminal-like, human breast cancer cell lines (FIG. 21G). This is consistent with the notion that basal-like tumors contain cells that have undergone at least a partial EMT, explaining their expression of certain mesenchymal markers.

We undertook to deplete SPHK1 or SPHK2 by gene silencing with RNAi. Co-mixed NAMEC-Tom and HMLE-GFP cells were infected with lentiviral vector-expressed shRNAs targeting SPHK1 or SPHK2. At least two shRNAs were used for each kinase. These cells were then re-plated separately based on $Tom^+$ or $GFP^+$ expression at equal numbers by FACS into 96-well plates. Cell proliferation was measured over the course of six days. We found that depletion of either SPHK1 or SPHK2 resulted in the loss of NAMEC viability by 53% and 74%, respectively, whereas HMLE cells were less affected (42% and 35%, respectively) (FIG. 21H). These data indicated a dependence on SPHK1/2 expression in cells that have activated an EMT program.

SPHK1 and SPHK2 are Therapeutic Targets in Breast Cancer Stem Cells (CSCs)

Figure 22:
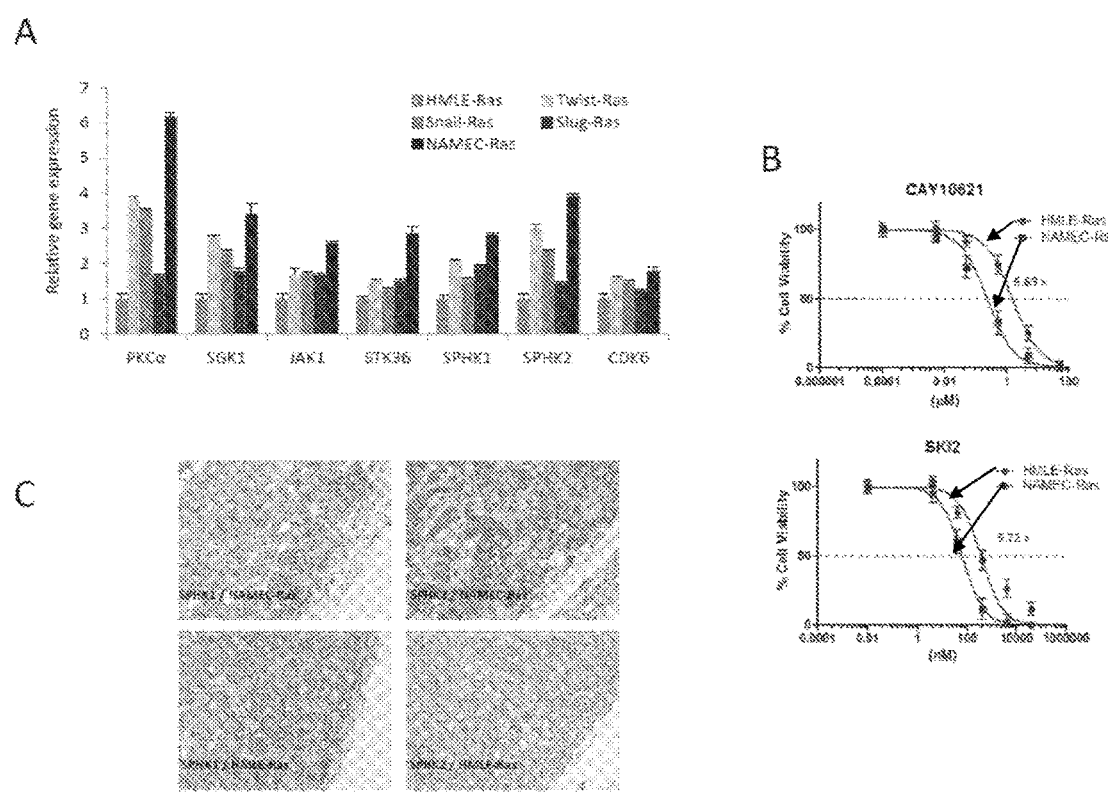
FIG. 22 depicts experimental results indicating that SPHK1 and SPHK2 are therapeutic targets in breast cancer stem cells (CSCs).

To investigate whether SPHK1/2 inhibitors also preferentially targeted NAMEC-Ras cells enriched for CSCs, we determined if SPHK1/2 levels remained differentially regulated between NAMEC-Ras and HMLE-Ras cell populations, as they did in the untransformed precursors of these two cell populations (FIG. 22A). NAMEC-Ras cells continued to express elevated levels of these kinases, like their untransformed precursors, in addition to other selected kinases, when compared with HMLE-Ras cells (FIG. 22A). It appeared that, at this level of analysis, cell state-specific features, including kinase expression, were conserved upon Ras-transformation. The observation also held for TF-induced EMT cells transduced with $Ras^{G12V}$ (FIG. 22A). These results were consistent with the EMT program of immortalized, non-tumorigenic mammary epithelial cells being similar to the corresponding programs of their transformed, tumorigenic derivatives.

Having determined that NAMEC-Ras were enriched for CSCs and represented a useful cell type for assessing the effects of chemical inhibitors relative to HMLE-Ras (CSC-depleted), we co-mixed NAMEC-Ras cells labeled with tdTomato (NAMEC-Tom-Ras) and HMLE-Ras cells labeled with GFP (HMLE-GFP-Ras) and re-tested the effects of kinase inhibition. Similar to their immortalized, untransformed counterparts, NAMEC-Tom-Ras cells exhibited a heightened sensitivity to SPHK1/2 (5.7-6.7 fold) inhibitors relative to HMLE-GFP-Ras cells, and were more resistant to paclitaxel (11.3 fold) and staurosporine (32.8 fold) (FIG. 22B). Consistent with NAMECs and HMLE cells cultured in vitro, NAMEC-Ras-derived xenografted tumors continued to express SPHK1 and SPHK2 whereas these proteins were largely absent in HMLE-Ras tumors (FIG. 22C). These observations lend additional support to the notion that the expression of kinases associated with the EMT program was conserved in a cell-state dependent manner that was not altered during oncogenic transformation.

Synergism of SPHK1/2 and PKCα Inhibitors in Targeting CSCs In Vitro and In Vivo

In both preclinical and clinical situations, redundancies in signalling pathways allow cancer cells to develop resistance to applied chemotherapeutics, highlighting a need for drug treatments to be used in combination. We found that simultaneous inhibition of PKCα and SPHK1/2 yielded a synergistic response that was more selective against NAMEC-Ras. Combining both inhibitors resulted in a >31 fold differential sensitivity for NAMEC-Ras-Tom relative to HMLE-Ras-Tom, whereas PKCα or SPHK1/2 inhibition alone led to a 5.6 and 5.8 fold differential sensitivity, respectively (FIG. 22D). Furthermore, when applied concomitantly, a lower dose of each inhibitor (PKCα inh: 0.88 nM; SPHK1/2 inh: 0.044 µM) was effective in killing NAMEC-Ras-Tom cells by 50% than could be achieved with single application of each (PKCα inh: 6.2 nM; SPHK1/2 inh: 0.15 µM) (FIG. 22D). The application of inhibitors in combination will potentially mitigate non-cell state-dependent cytotoxicity associated with the use of individual compounds at higher concentrations. This synergy also indicates an intersection between the PKCα and SPHK1/2 activity.

In order to assess the therapeutic benefits of PKCα and SPHK1/2 inhibitors, NOD-SCID mice were xenografted with $5 \times 10^4$ NAMEC-Ras cells and treated for 30 days with a daily intraperitoneal dose of either DMSO control, PKCα Inh (5 mg/kg/d), SPHK1/2 Inh (5 mg/kg/d) or PKCα+ SPHK1/2 inhibitors (2.5 mg/kg/d of each). Significant tumor burden of ~0.68 g each was observed after 15 weeks in all ten control-treated mice (FIG. 22E). Four of eight mice treated with PKCα Inh and six of eight mice treated with SPHK1/2 Inh formed tumors but these were far smaller (~0.17 g and ~0.23 g, respectively). Echoing earlier results with cultured cells, the therapeutic benefit of PKCα+ SPHK1/2 inhibitors was the greatest as four of 10 mice formed tumors that weighed ~0.076 g each (FIG. 22E) while tumor masses were undetectable in the remaining six implanted hosts. This indicated that in vivo, as with in vitro, the combined inhibition of both kinases was more effective. These dosages were well-tolerated in mice and had no adverse effects after 30 days of treatment followed by eight weeks of observation.

PKCα or SPHK1/2 inhibition decreased the tumor-initiation frequency and tumor size. We assessed whether these kinase inhibitors would have any effect on the growth of established NAMEC-Ras tumors. We allowed xenografted NAMEC-Ras tumors to reach approximately 0.1 g (assessed by palpation) four weeks after implantation, before administering kinase inhibitors. Tumors from control-treated mice reached ~1.03 g ten weeks after implantation, whereas treatment with either PKCα or SPHK1/2 inhibitor led to a significantly reduced tumor weight of ~0.25 g and ~0.29 g, respectively (FIG. 22F). Joint treatment with PKCα+SPHK1/2 inhibitors treatment resulted in the smallest residual tumor masses of ~0.078 g (FIG. 22G). These results indicated the in vivo therapeutic benefits of combined PKCα and SPHK1/2 inhibition and highlighted their usefulness for targeting CSCs.

Intersection Between SPHK1/2 and PKCα Signaling Networks

Figure 23:
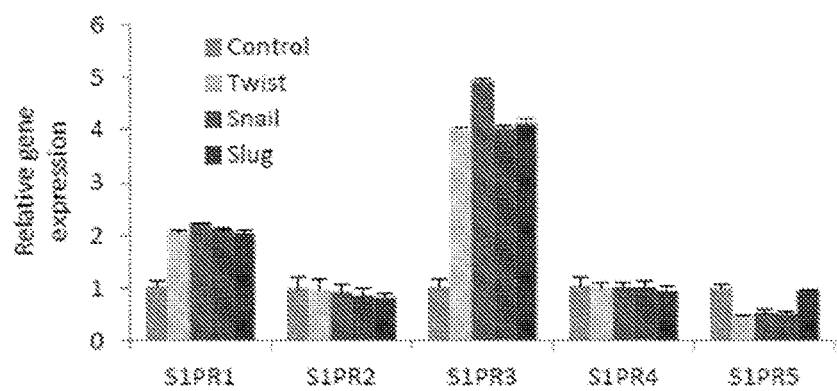
FIG. 23 depicts an intersection between SPHK1/2 and PKCα signalling networks.
Figure 23:
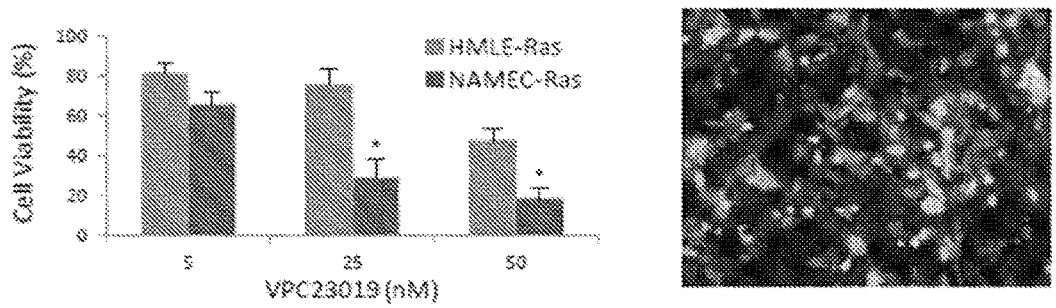

SPHK1/2 was also increased in conjunction with PKCα upon passage through an EMT, and their combined inhibition led to synergistic elimination of mesenchymal cell derivatives. We assessed how the activity of SPHK1/2 was regulated. SPHK1/2 are potential substrates for p-ERK1/2. Sphingosine lipid signalling pathway activation is linked to invasive breast cancer and correlates with poor overall patient survival. Activated SPHK1/2 converts sphingosine to sphingosine-1-phosphate (S1P) which activates its own receptors in an autocrine fashion. We determined that sphingosine-1-phosphate receptors 1 and 3 (S1PR1/3) are upregulated upon EMT by 2.0-2.2 and 4.0-4.9 fold, respectively (FIG. 23A). Treatment with a S1PR1/3 antagonist, VPC23019, selected against NAMEC-Tom-Ras cells relative to HMLE-GFP-Ras cells in a dose-dependent manner (FIG. 23B), indicating the importance of SPHK1/2 signalling during EMT-driven cancer progression. FIG. 23C depicts signalling networks determined to be operating within CSCs in these examples.

TABLE 6

List of kinase-encoding genes that were coordinately overexpressed at least two fold in HMLE-Twist, HMLE-Snail and HMLE-Slug cells relative to the HMLE parental epithelial population.

| Gene Symbol | Entrez Gene ID | Protein Accession | RefSeq ID |
| --- | --- | --- | --- |
| AAK1 | 22848 | NP_055726.3 | NM_014911.3 |
| AAK1 | 22848 | NP_055726.2 | NM_014911.2 |
| AATK | 9625 | NP_001073864.1 | NM_001080395.1 |
| ABL1 | 25 | NP_005148.2 | NM_005157.3 |
| ABL2 | 27 | NP_009298.1 | NM_007314.2 |
| ABL2 | 27 | NP_005149.3 | NM_005158.3 |
| ABL2 | 27 | NP_009298.1 | NM_007314.1 |
| ACVR1 | 90 | NP_001096.1 | NM_001105.2 |
| ACVR1B | 91 | NP_064733.2 | NM_020328.2 |
| ACVR1B | 91 | NP_064732.2 | NM_020327.2 |
| ACVR1B | 91 | NP_004293.1 | NM_004302.3 |
| ACVR2B | 93 | NP_001097.2 | NM_001106.3 |
| ACVRL1 | 94 | NP_000011.1 | NM_000020.1 |
| ADK | 132 | NP_001114.2 | NM_001123.2 |
| ADRBK1 | 156 | NP_001610.1 | NM_001619.2 |
| ADRBK2 | 157 | NP_005151.2 | NM_005160.3 |
| AK2 | 204 | NP_037543.1 | NM_013411.3 |
| AK2 | 204 | NP_001616.1 | NM_001625.2 |
| AK3L1 | 205 | NP_982289.1 | NM_203464.1 |
| AK5 | 26289 | NP_777283.1 | NM_174858.1 |
| AK5 | 26289 | NP_036225.2 | NM_012093.2 |
| AK7 | 122481 | NP_689540.2 | NM_152327.2 |
| AKT1 | 207 | NP_005154.2 | NM_005163.2 |
| AKT2 | 208 | NP_001617.1 | NM_001626.3 |
| AKT3 | 10000 | NP_859029.1 | NM_181690.1 |
| AKT3 | 10000 | NP_005456.1 | NM_005465.3 |
| ALK | 238 | NP_004295.2 | NM_004304.3 |
| AMHR2 | 269 | NP_065434.1 | NM_020547.1 |
| ATM | 472 | NP_612149.1 | NM_138292.3 |
| ATM | 472 | NP_000042.3 | NM_000051.3 |
| ATR | 545 | NP_001175.1 | NM_001184.2 |
| ATR | 545 | XP_001131387.1 | XM_001131387.1 |
| AXL | 558 | NP_068713.2 | NM_021913.2 |
| BCR | 613 | NP_004318.3 | NM_004327.3 |
| BCR | 613 | NP_067585.2 | NM_021574.2 |
| BLK | 640 | NP_001706.2 | NM_001715.2 |
| BMPR1A | 657 | NP_004320.2 | NM_004329.2 |
| BMPR1B | 658 | NP_001194.1 | NM_001203.1 |
| BMPR2 | 659 | NP_001195.2 | NM_001204.5 |
| BMX | 660 | NP_001712.1 | NM_001721.4 |
| BMX | 660 | NP_975010.1 | NM_203281.1 |
| BRD2 | 6046 | NP_005095.1 | NM_005104.2 |
| BRD4 | 23476 | NP_490597.1 | NM_058243.1 |
| BRD4 | 23476 | NP_490597.1 | NM_058243.2 |
| BRDT | 676 | NP_997072.1 | NM_207189.1 |
| BRDT | 676 | NP_001717.2 | NM_001726.2 |
| BTK | 695 | NP_000052.1 | NM_000061.1 |
| BUB1B | 701 | NP_001202.4 | NM_001211.4 |
| CAMK1G | 57172 | NP_065172.1 | NM_020439.2 |
| CAMK2A | 815 | NP_741960.1 | NM_171825.1 |
| CAMK2B | 816 | NP_001211.3 | NM_001220.3 |
| CAMK2D | 817 | NP_001212.2 | NM_001221.2 |

TABLE 6-continued

List of kinase-encoding genes that were coordinately overexpressed at least two fold in HMLE-Twist, HMLE-Snail and HMLE-Slug cells relative to the HMLE parental epithelial population.

| Gene Symbol | Entrez Gene ID | Protein Accession | RefSeq ID |
|---|---|---|---|
| CAMK2D | 817 | NP_742126.1 | NM_172128.1 |
| CAMK2D | 817 | NP_742113.1 | NM_172115.1 |
| CAMK2G | 818 | NP_751912.1 | NM_172172.1 |
| CAMK4 | 814 | NP_001735.1 | NM_001744.3 |
| CAMKK1 | 84254 | NP_115670.1 | NM_032294.2 |
| CAMKK2 | 10645 | NP_705720.1 | NM_153500.1 |
| CAMKK2 | 10645 | NP_757364.1 | NM_172215.1 |
| CARD14 | 79092 | NP_077015.1 | NM_024110.2 |
| CARD14 | 79092 | NP_438170.1 | NM_052819.1 |
| CASK | 8573 | NP_003679.1 | NM_003688.1 |
| CCRK | 23552 | NP_848519.1 | NM_178432.1 |
| CCRK | 23552 | NP_036251.2 | NM_012119.3 |
| CDC2 | 983 | NP_001777.1 | NM_001786.2 |
| CDC2L1 | 984 | NP_277022.1 | NM_033487.1 |
| CDC2L2 | 985 | NP_277073.1 | NM_033531.1 |
| CDC2L5 | 8621 | NP_112557.1 | NM_031267.1 |
| CDC2L5 | 8621 | NP_003709.3 | NM_003718.3 |
| CDC42BPA | 8476 | NP_003598.2 | NM_003607.3 |
| CDC42BPB | 9578 | NP_006026.3 | NM_006035.3 |
| CDK10 | 8558 | NP_003665.2 | NM_003674.2 |
| CDK2 | 1017 | NP_001789.2 | NM_001798.2 |
| CDK3 | 1018 | NP_001249.1 | NM_001258.1 |
| CDK4 | 1019 | NP_000066.1 | NM_000075.2 |
| CDK5 | 1020 | NP_004926.1 | NM_004935.2 |
| CDK6 | 1021 | NP_001250.1 | NM_001259.5 |
| CDK7 | 1022 | NP_001790.1 | NM_001799.2 |
| CDK8 | 1024 | NP_001251.1 | NM_001260.1 |
| CDK9 | 1025 | NP_001252.1 | NM_001261.2 |
| CDKL1 | 8814 | NP_004187.2 | NM_004196.3 |
| CDKL5 | 6792 | NP_003150.1 | NM_003159.2 |
| CERK | 64781 | NP_073603.2 | NM_022766.4 |
| CERK | 64781 | NP_872602.1 | NM_182661.1 |
| CHEK1 | 1111 | NP_001265.1 | NM_001274.3 |
| CHEK2 | 11200 | NP_001005735.1 | NM_001005735.1 |
| CHUK | 1147 | NP_001269.3 | NM_001278.3 |
| CIT | 11113 | NP_009105.1 | NM_007174.1 |
| CKB | 1152 | NP_001814.2 | NM_001823.3 |
| CKM | 1158 | NP_001815.2 | NM_001824.2 |
| CKMT2 | 1160 | NP_001816.2 | NM_001825.2 |
| CLK1 | 1195 | NP_001019817.1 | NM_001024646.1 |
| CLK1 | 1195 | NP_004062.2 | NM_004071.2 |
| CLK2 | 1196 | XP_946485.1 | XM_941392.1 |
| CLK3 | 1198 | NP_001283.1 | NM_001292.1 |
| CLK3 | 1198 | NP_003983.2 | NM_003992.2 |
| CLK4 | 57396 | NP_065717.1 | NM_020666.2 |
| CSNK1A1 | 1452 | NP_001883.4 | NM_001892.4 |
| CSNK1A1 | 1452 | NP_001020276.1 | NM_001025105.1 |
| CSNK1E | 1454 | NP_001885.1 | NM_001894.4 |
| CSNK1G1 | 53944 | NP_071331.2 | NM_022048.3 |
| CSNK1G3 | 1456 | NP_001026982.1 | NM_001031812.2 |
| CSNK1G3 | 1456 | NP_004375.2 | NM_004384.2 |
| CSNK1G3 | 1456 | NP_001038187.1 | NM_001044722.1 |
| CSNK2A1 | 1457 | NP_808227.1 | NM_177559.2 |
| CSNK2A1 | 1457 | NP_001886.1 | NM_001895.3 |
| CSNK2A2 | 1459 | NP_001887.1 | NM_001896.2 |
| DAPK1 | 1612 | NP_004929.2 | NM_004938.2 |
| DAPK2 | 23604 | NP_055141.2 | NM_014326.3 |
| DAPK3 | 1613 | NP_001339.1 | NM_001348.1 |
| DCK | 1633 | NP_000779.1 | NM_000788.1 |
| DDR1 | 780 | NP_054699.2 | NM_013993.2 |
| DDR2 | 4921 | NP_006173.2 | NM_006182.2 |
| DDR2 | 4921 | NP_001014796.1 | NM_001014796.1 |
| DGKA | 1606 | NP_963848.1 | NM_201554.1 |
| DGKA | 1606 | NP_958852.1 | NM_201444.2 |
| DGKA | 1606 | NP_001336.2 | NM_001345.4 |
| DGKA | 1606 | NP_958853.1 | NM_201445.1 |
| DGKB | 1607 | NP_663733.1 | NM_145695.1 |
| DGKB | 1607 | NP_004071.1 | NM_004080.1 |
| DGKD | 8527 | NP_003639.2 | NM_003648.2 |
| DGKD | 8527 | NP_690618.2 | NM_152879.2 |
| DGKE | 8526 | NP_003638.1 | NM_003647.1 |
| DGKG | 1608 | NP_001074214.1 | NM_001080745.1 |
| DGKH | 160851 | NP_821077.1 | NM_178009.2 |
| DGKH | 160851 | NP_690874.2 | NM_152910.3 |

TABLE 6-continued

List of kinase-encoding genes that were coordinately overexpressed at least two fold in HMLE-Twist, HMLE-Snail and HMLE-Slug cells relative to the HMLE parental epithelial population.

| Gene Symbol | Entrez Gene ID | Protein Accession | RefSeq ID |
| --- | --- | --- | --- |
| DGKI | 9162 | NP_004708.1 | NM_004717.2 |
| DGKZ | 8525 | NP_003637.2 | NM_003646.3 |
| DGKZ | 8525 | NP_963290.1 | NM_201532.1 |
| DGUOK | 1716 | NP_550438.1 | NM_080916.1 |
| DLG1 | 1739 | NP_001091894.1 | NM_001098424.1 |
| DLG2 | 1740 | NP_001355.2 | NM_001364.2 |
| DLG2 | 1740 | NP_001355.1 | NM_001364.1 |
| DLG3 | 1741 | NP_066943.2 | NM_021120.2 |
| DLG5 | 9231 | NP_004738.3 | NM_004747.3 |
| DMPK | 1760 | NP_001075032.1 | NM_001081563.1 |
| DTYMK | 1841 | NP_036277.2 | NM_012145.2 |
| DYRK1A | 1859 | NP_569122.1 | NM_130438.1 |
| DYRK1A | 1859 | NP_569121.1 | NM_130437.2 |
| DYRK1A | 1859 | NP_569120.1 | NM_130436.2 |
| DYRK1A | 1859 | NP_567824.1 | NM_101395.2 |
| DYRK1B | 9149 | NP_004705.1 | NM_004714.1 |
| DYRK2 | 8445 | NP_003574.1 | NM_003583.2 |
| DYRK2 | 8445 | NP_006473.2 | NM_006482.2 |
| DYRK3 | 8444 | NP_003573.2 | NM_003582.2 |
| DYRK3 | 8444 | NP_001004023.1 | NM_001004023.1 |
| DYRK4 | 8798 | NP_003836.1 | NM_003845.1 |
| EGFR | 1956 | NP_958439.1 | NM_201282.1 |
| EGFR | 1956 | NP_958441.1 | NM_201284.1 |
| EPHA2 | 1969 | NP_004422.2 | NM_004431.2 |
| EPHA3 | 2042 | NP_005224.2 | NM_005233.3 |
| EPHA3 | 2042 | NP_872585.1 | NM_182644.1 |
| EPHA4 | 2043 | NP_004429.1 | NM_004438.3 |
| EPHA5 | 2044 | NP_004430.3 | NM_004439.4 |
| EPHA7 | 2045 | NP_004431.1 | NM_004440.2 |
| EPHA8 | 2046 | NP_001006944.1 | NM_001006943.1 |
| EPHA8 | 2046 | NP_065387.1 | NM_020526.3 |
| EPHB1 | 2047 | NP_004432.1 | NM_004441.3 |
| EPHB2 | 2048 | NP_059145.2 | NM_017449.3 |
| EPHB2 | 2048 | NP_004433.2 | NM_004442.6 |
| EPHB4 | 2050 | NP_004435.3 | NM_004444.4 |
| EPHB6 | 2051 | NP_004436.1 | NM_004445.2 |
| ERBB2 | 2064 | NP_004439.2 | NM_004448.2 |
| ERBB2 | 2064 | NP_001005862.1 | NM_001005862.1 |
| ERBB3 | 2065 | NP_001005915.1 | NM_001005915.1 |
| ERBB4 | 2066 | NP_005226.1 | NM_005235.1 |
| ERN1 | 2081 | NP_001424.3 | NM_001433.3 |
| ERN2 | 10595 | NP_150296.3 | NM_033266.3 |
| FASTK | 10922 | NP_006703.1 | NM_006712.3 |
| FASTK | 10922 | NP_148936.2 | NM_033015.2 |
| FER | 2241 | NP_005237.2 | NM_005246.2 |
| FES | 2242 | NP_001996.1 | NM_002005.2 |
| FGFR1 | 2260 | NP_075595.1 | NM_023107.2 |
| FGFR1 | 2260 | NP_075594.1 | NM_023106.2 |
| FGFR2 | 2263 | NP_075259.2 | NM_022970.2 |
| FGFR3 | 2261 | NP_000133.1 | NM_000142.2 |
| FGFR4 | 2264 | NP_075252.2 | NM_022963.2 |
| FGFR4 | 2264 | NP_998812.1 | NM_213647.1 |
| FGR | 2268 | NP_001036194.1 | NM_001042729.1 |
| FGR | 2268 | NP_005239.1 | NM_005248.2 |
| FLJ10986 | 55277 | NP_060761.2 | NM_018291.2 |
| FLJ23356 | 84197 | NP_115613.1 | NM_032237.2 |
| FLJ25006 | 124923 | NP_653211.1 | NM_144610.1 |
| FLT1 | 2321 | NP_002010.1 | NM_002019.2 |
| FLT3 | 2322 | NP_004110.2 | NM_004119.2 |
| FLT4 | 2324 | NP_891555.2 | NM_182925.3 |
| FLT4 | 2324 | NP_002011.1 | NM_002020.1 |
| FN3K | 64122 | NP_071441.1 | NM_022158.2 |
| FRAP1 | 2475 | NP_004949.1 | NM_004958.2 |
| FRK | 2444 | NP_002022.1 | NM_002031.2 |
| FYN | 2534 | NP_694592.1 | NM_153047.1 |
| FYN | 2534 | NP_002028.1 | NM_002037.3 |
| FYN | 2534 | NP_694593.1 | NM_153048.1 |
| GALK2 | 2585 | NP_001001556.1 | NM_001001556.1 |
| GALK2 | 2585 | NP_002035.1 | NM_002044.2 |
| GCK | 2645 | NP_277043.1 | NM_033508.1 |
| GK | 2710 | NP_976325.1 | NM_203391.1 |
| GK2 | 2712 | NP_149991.2 | NM_033214.2 |
| GNE | 10020 | NP_005467.1 | NM_005476.3 |
| GSG2 | 83903 | NP_114171.2 | NM_031965.2 |

TABLE 6-continued

List of kinase-encoding genes that were coordinately overexpressed at least two fold in HMLE-Twist, HMLE-Snail and HMLE-Slug cells relative to the HMLE parental epithelial population.

| Gene Symbol | Entrez Gene ID | Protein Accession | RefSeq ID |
| --- | --- | --- | --- |
| GSK3A | 2931 | NP_063937.2 | NM_019884.2 |
| GSK3B | 2932 | NP_002084.2 | NM_002093 .2 |
| GUCY2C | 2984 | NP_004954.1 | NM_004963.1 |
| GUCY2D | 3000 | NP_000171.1 | NM_000180.1 |
| GUCY2F | 2986 | NP_001513.2 | NM_001522.2 |
| GUK1 | 2987 | NP_000849.1 | NM_000858.4 |
| HCK | 3055 | NP_002101.2 | NM_002110.2 |
| HIPK2 | 28996 | NP_073577.2 | NM_022740.2 |
| HIPK3 | 10114 | NP_001041665.1 | NM_001048200.1 |
| HIPK3 | 10114 | NP_005725.3 | NM_005734.3 |
| HK1 | 3098 | NP_277031.1 | NM_033496.1 |
| HK1 | 3098 | NP_000179.1 | NM_000188.1 |
| HK1 | 3098 | NP_277035.1 | NM_033500.1 |
| HK3 | 3101 | NP_002106.1 | NM_002115.1 |
| HUNK | 30811 | NP_055401.1 | NM_014586.1 |
| ICK | 22858 | NP_057597.2 | NM_016513.3 |
| ICK | 22858 | NP_055735.1 | NM_014920.2 |
| IGF1R | 3480 | NP_000866.1 | NM_000875.2 |
| IHPK1 | 9807 | NP_695005.1 | NM_153273.3 |
| IHPK2 | 51447 | NP_001005910.1 | NM_001005910.1 |
| IHPK2 | 51447 | NP_057375.2 | NM_016291.2 |
| IHPK3 | 117283 | NP_473452.2 | NM_054111.3 |
| IKBKB | 3551 | NP_001547.1 | NM_001556.1 |
| IKBKE | 9641 | NP_054721.1 | NM_014002.2 |
| ILK | 3611 | NP_001014794.1 | NM_001014794.1 |
| ILK | 3611 | NP_004508.1 | NM_004517.2 |
| INSRR | 3645 | NP 055030.1 | NM_014215.1 |
| IRAK1 | 3654 | NP_001020414.1 | NM_001025243.1 |
| IRAK2 | 3656 | NP_001561.3 | NM_001570.3 |
| IRAK4 | 51135 | NP_057207.1 | NM_016123.1 |
| ITK | 3702 | NP_005537.3 | NM_005546.3 |
| ITPK1 | 3705 | NP_055031.2 | NM_014216.3 |
| ITPKA | 3706 | NP_002211.1 | NM_002220.1 |
| JAK1 | 3716 | NP_002218.2 | NM_002227.2 |
| JAK2 | 3717 | NP_004963.1 | NM_004972.2 |
| JAK3 | 3718 | NP_000206.2 | NM_000215.2 |
| KDR | 3791 | NP_002244.1 | NM_002253.1 |
| KHK | 3795 | NP_006479.1 | NM_006488.1 |
| KHK | 3795 | NP_000212.1 | NM_000221.2 |
| KIAA0999 | 23387 | NP_079440.2 | NM_025164.3 |
| KIAA1804 | 84451 | NP_115811.1 | NM_032435.1 |
| KIT | 3815 | NP 000213.1 | NM_000222.1 |
| LATS1 | 9113 | NP_004681.1 | NM_004690.2 |
| LATS2 | 26524 | NP_055387.2 | NM_014572.2 |
| LCK | 3932 | NP_001036236.1 | NM_001042771.1 |
| LIMK1 | 3984 | NP_002305.1 | NM_002314.2 |
| LIMK2 | 3985 | NP_005560.1 | NM_005569.3 |
| LOC340156 | 340156 | NP_001012418.1 | NM_001012418.2 |
| LOC91461 | 91461 | NP_612379.1 | NM_138370.1 |
| LTK | 4058 | NP_996844.1 | NM_206961.1 |
| MAK | 4117 | NP_005897.1 | NM_005906.3 |
| MAP2K3 | 5606 | NP_002747.2 | NM_002756.3 |
| MAP2K3 | 5606 | NP_659731.1 | NM_145109.2 |
| MAP2K4 | 6416 | NP_003001.1 | NM_003010.2 |
| MAP2K5 | 5607 | NP_660143.1 | NM_145160.1 |
| MAP2K6 | 5608 | NP_002749.2 | NM_002758.3 |
| MAP3K10 | 4294 | NP_002437.2 | NM_002446.2 |
| MAP3K14 | 9020 | NP_003945.2 | NM_003954.2 |
| MAP3K2 | 10746 | XP_001128799.1 | XM_001128799.1 |
| MAP3K3 | 4215 | NP_976226.1 | NM_203351.1 |
| MAP3K4 | 4216 | NP_005913.2 | NM_005922.2 |
| MAP3K7 | 6885 | NP_663304.1 | NM_145331.1 |
| MAP3K7 | 6885 | NP_663306.1 | NM_145333.1 |
| MAP3K9 | 4293 | NP_149132.2 | NM_033141.2 |
| MAP4K1 | 11184 | NP_001036065.1 | NM_001042600.1 |
| MAP4K3 | 8491 | NP_003609.2 | NM_003618.2 |
| MAP4K4 | 9448 | NP_663720.1 | NM_145687.2 |
| MAP4K5 | 11183 | NP_006566.2 | NM_006575.3 |
| MAP4K5 | 11183 | NP_942089.1 | NM_198794.1 |
| MAPK1 | 5594 | NP_002736.3 | NM_002745.4 |
| MAPK10 | 5602 | NP_620447.1 | NM_138981.1 |
| MAPK10 | 5602 | NP_002744.1 | NM_002753.2 |
| MAPK10 | 5602 | NP_620446.1 | NM_138980.1 |
| MAPK11 | 5600 | NP_002742.3 | NM_002751.5 |

TABLE 6-continued

List of kinase-encoding genes that were coordinately overexpressed at least two fold in HMLE-Twist, HMLE-Snail and HMLE-Slug cells relative to the HMLE parental epithelial population.

| Gene Symbol | Entrez Gene ID | Protein Accession | RefSeq ID |
| --- | --- | --- | --- |
| MAPK14 | 1432 | NP_620582.1 | NM_139013.1 |
| MAPK4 | 5596 | NP_002738.2 | NM_002747.3 |
| MAPK7 | 5598 | NP_620601.1 | NM_139032.1 |
| MAPK7 | 5598 | NP_002740.2 | NM_002749.2 |
| MAPK8 | 5599 | NP_002741.1 | NM_002750.2 |
| MAPK8 | 5599 | NP_620637.1 | NM_139049.1 |
| MAPK9 | 5601 | NP_002743.3 | NM_002752.3 |
| MAPKAPK2 | 9261 | NP_116584.2 | NM_032960.2 |
| MAPKAPK2 | 9261 | NP_004750.1 | NM_004759.3 |
| MAPKAPK5 | 8550 | NP_620777.1 | NM_139078.1 |
| MARK2 | 2011 | NP_001034557.1 | NM_001039468.1 |
| MARK3 | 4140 | NP_002367.4 | NM_002376.4 |
| MARK4 | 57787 | NP_113605.2 | NM_031417.2 |
| MATK | 4145 | NP_002369.2 | NM_002378.3 |
| MATK | 4145 | NP_647611.1 | NM_139354.2 |
| MELK | 9833 | NP_055606.1 | NM_014791.2 |
| MET | 4233 | NP_000236.2 | NM_000245.2 |
| MGC16169 | 93627 | NP_149106.2 | NM_033115.2 |
| MGC42105 | 167359 | NP_699192.1 | NM_153361.2 |
| MKNK1 | 8569 | NP_003675.2 | NM_003684.3 |
| MOS | 4342 | NP_005363.1 | NM_005372.1 |
| MPP1 | 4354 | NP_002427.1 | NM_002436.2 |
| MPP2 | 4355 | NP_005365.3 | NM_005374.3 |
| MPP3 | 4356 |  | NR_003562.1 |
| MPP4 | 58538 | NP_149055.1 | NM_033066.1 |
| MPP5 | 64398 | NP_071919.2 | NM_022474.2 |
| MPP6 | 51678 | NP_057531.2 | NM_016447.2 |
| MST4 | 51765 | NP_001035918.1 | NM_001042453.1 |
| MUSK | 4593 | NP_005583.1 | NM_005592.1 |
| MVK | 4598 | NP_000422.1 | NM_000431.1 |
| MYLK | 4638 | NP_444260.1 | NM_053032.2 |
| MYLK | 4638 | NP_444254.3 | NM_053026.3 |
| MYLK2 | 85366 | NP_149109.1 | NM_033118.2 |
| MYO3A | 53904 | NP_059129.2 | NM_017433.3 |
| MYO3B | 140469 | NP_620482.1 | NM_138995.1 |
| NAGK | 55577 | NP_060037.2 | NM_017567.2 |
| NDUFA10 | 4705 | NP_004535.1 | NM_004544.2 |
| NEK1 | 4750 | NP_036356.1 | NM_012224.1 |
| NEK10 | 152110 | NP_689747.2 | NM_152534.2 |
| NEK10 | 152110 | NP_001026911.1 | NM_001031741.1 |
| NEK11 | 79858 | NP_665917.1 | NM_145910.1 |
| NEK11 | 79858 | NP_079076.2 | NM_024800.3 |
| NEK3 | 4752 | NP_689933.1 | NM_152720.1 |
| NEK3 | 4752 | NP_002489.1 | NM_002498.2 |
| NEK4 | 6787 | NP_003148.2 | NM_003157.3 |
| NEK5 | 341676 | NP_954983.1 | NM_199289.1 |
| NEK6 | 10783 | NP_055212.2 | NM_014397.3 |
| NEK8 | 284086 | NP_835464.1 | NM_178170.2 |
| NEK9 | 91754 | NP_149107.3 | NM_033116.3 |
| NLK | 51701 | NP_057315.3 | NM_016231.4 |
| NME1 | 4830 | NP_000260.1 | NM_000269.2 |
| NME1 | 4830 | NP_937818.1 | NM_198175.1 |
| NME2 | 4831 | NP_001018147.1 | NM_001018137.1 |
| NME2 | 4831 | NP_001018148.1 | NM_001018138.1 |
| NME2 | 4831 | NP_001018149.1 | NM_001018139.1 |
| NME2 | 4831 | NP_002503.1 | NM_002512.2 |
| NME5 | 8382 | NP_003542.1 | NM_003551.2 |
| NME6 | 10201 | NP_005784.1 | NM_005793.3 |
| NME7 | 29922 | NP_037462.1 | NM_013330.3 |
| NME7 | 29922 | NP_932076.1 | NM_197972.1 |
| NPR1 | 4881 | NP_000897.2 | NM_000906.2 |
| NPR2 | 4882 | NP_003986.2 | NM_003995.3 |
| NTRK1 | 4914 | NP_001012331.1 | NM_001012331.1 |
| NTRK1 | 4914 | NP_002520.2 | NM_002529.3 |
| NTRK1 | 4914 | NP_001007793.1 | NM_001007792.1 |
| NTRK2 | 4915 | NP_001018075.1 | NM_001018065.1 |
| NTRK2 | 4915 | NP_001007098.1 | NM_001007097.1 |
| NTRK2 | 4915 | NP_006171.2 | NM_006180.3 |
| NTRK3 | 4916 | NP_002521.2 | NM_002530.2 |
| NTRK3 | 4916 | NP_001007157.1 | NM_001007156.1 |
| OBSCN | 84033 | NP_443075.2 | NM_052843.2 |
| OSR1 | 130497 | NP_660303.1 | NM_145260.2 |
| PAK1 | 5058 | NP_002567.3 | NM_002576.3 |
| PAK2 | 5062 | XP_001126110.1 | XM_001126110.1 |

TABLE 6-continued

List of kinase-encoding genes that were coordinately overexpressed at least two fold in HMLE-Twist, HMLE-Snail and HMLE-Slug cells relative to the HMLE parental epithelial population.

| Gene Symbol | Entrez Gene ID | Protein Accession | RefSeq ID |
| --- | --- | --- | --- |
| PAK2 | 5062 | NP_002568.2 | NM_002577.3 |
| PAK4 | 10298 | NP_001014831.1 | NM_001014831.1 |
| PAK4 | 10298 | NP_005875.1 | NM_005884.3 |
| PAK6 | 56924 | NP_064553.1 | NM_020168.3 |
| PAK7 | 57144 | NP_065074.1 | NM_020341.2 |
| PANK1 | 53354 | NP_612189.2 | NM_138316.2 |
| PANK3 | 79646 | NP_078870.1 | NM_024594.2 |
| PAPSS2 | 9060 | NP_004661.2 | NM_004670.3 |
| PCK1 | 5105 | NP_002582.2 | NM_002591.2 |
| PCK2 | 5106 | NP_001018083.1 | NM_001018073.1 |
| PCK2 | 5106 | NP_004554.2 | NM_004563.2 |
| PCTK1 | 5127 | NP_148978.1 | NM_033018.2 |
| PCTK2 | 5128 | NP_002586.2 | NM_002595.2 |
| PCTK3 | 5129 | NP_997668.1 | NM_212503.1 |
| PCTK3 | 5129 | NP_002587.2 | NM_002596.2 |
| PDGFRA | 5156 | NP_006197.1 | NM_006206.3 |
| PDGFRB | 5159 | NP_002600.1 | NM_002609.3 |
| PDK1 | 5163 | NP_002601.1 | NM_002610.3 |
| PDK2 | 5164 | NP_002602.2 | NM_002611.3 |
| PDK4 | 5166 | NP_002603.1 | NM_002612.3 |
| PDPK1 | 5170 | NP_112558.2 | NM_031268.4 |
| PDPK1 | 5170 | NP_002604.1 | NM_002613.3 |
| PDXK | 8566 | NP_003672.1 | NM_003681.4 |
| PFKFB2 | 5208 | NP_006203.2 | NM_006212.2 |
| PFKFB2 | 5208 | NP_001018063.1 | NM_001018053.1 |
| PFKFB3 | 5209 | NP_004557.1 | NM_004566.2 |
| PFKL | 5211 | NP_001002021.1 | NM_001002021.1 |
| PFTK1 | 5218 | NP_036527.1 | NM_012395.2 |
| PHKA1 | 5255 | NP_002628.1 | NM_002637.2 |
| PHKB | 5257 | NP_000284.1 | NM_000293.1 |
| PHKB | 5257 | NP_001027005.1 | NM_001031835.1 |
| PHKG1 | 5260 | NP_006204.1 | NM_006213.3 |
| PHKG2 | 5261 | NP_000285.1 | NM_000294.1 |
| PI4K2B | 55300 | NP_060793.1 | NM_018323.2 |
| PIK3C2A | 5286 | NP_002636.1 | NM_002645.1 |
| PIK3C2G | 5288 | NP_004561.2 | NM_004570.3 |
| PIK3C3 | 5289 | NP_002638.2 | NM_002647.2 |
| PIK3CA | 5290 | NP_006209.2 | NM_006218.2 |
| PIK3CB | 5291 | NP_006210.1 | NM_006219.1 |
| PIK3CD | 5293 | NP_005017.2 | NM_005026.2 |
| PIK3CG | 5294 | NP_002640.2 | NM_002649.2 |
| PIK3R4 | 30849 | NP_055417.1 | NM_014602.1 |
| PIM1 | 5292 | NP_002639.1 | NM_002648.2 |
| PIM2 | 11040 | NP_006866.2 | NM_006875.2 |
| PINK1 | 65018 | NP_115785.1 | NM_032409.2 |
| PIP5K1A | 8394 | NP_003548.1 | NM_003557.1 |
| PIP5K1B | 8395 | NP_003549.1 | NM_003558.2 |
| PIP5K1C | 23396 | NP_036530.1 | NM_012398.1 |
| PIP5K2A | 5305 | NP_005019.2 | NM_005028.3 |
| PIP5K3 | 200576 | NP_689884.1 | NM_152671.2 |
| PIP5K3 | 200576 | NP_689884.1 | NM_152671.3 |
| PKLR | 5313 | NP_870986.1 | NM_181871.2 |
| PKLR | 5313 | NP_000289.1 | NM_000298.4 |
| PKM2 | 5315 | NP_872271.1 | NM_182471.1 |
| PKM2 | 5315 | NP_002645.3 | NM_002654.3 |
| PKM2 | 5315 | NP_872270.1 | NM_182470.1 |
| PKMYT1 | 9088 | NP_872629.1 | NM_182687.1 |
| PMVK | 10654 | NP_006547.1 | NM_006556.3 |
| PRKAA1 | 5562 | NP_006242.5 | NM_006251.5 |
| PRKAA1 | 5562 | NP_996790.3 | NM_206907.3 |
| PRKACA | 5566 | NP_997401.1 | NM_207518.1 |
| PRKACB | 5567 | NP_891993.1 | NM_182948.2 |
| PRKACB | 5567 | NP_002722.1 | NM_002731.2 |
| PRKACB | 5567 | NP_997461.1 | NM_207578.1 |
| PRKACG | 5568 | NP_002723.2 | NM_002732.2 |
| PRKCA | 5578 | NP_002728.1 | NM_002737.2 |
| PRKCB1 | 5579 | NP_002729.2 | NM_002738.5 |
| PRKCB1 | 5579 | NP_997700.1 | NM_212535.1 |
| PRKCD | 5580 | NP_006245.2 | NM_006254.3 |
| PRKCE | 5581 | NP_005391.1 | NM_005400.2 |
| PRKCG | 5582 | NP_002730.1 | NM_002739.3 |
| PRKCI | 5584 | NP_002731.4 | NM_002740.5 |
| PRKCQ | 5588 | NP_006248.1 | NM_006257.2 |
| PRKCZ | 5590 | NP_001028754.1 | NM_001033582.1 |

TABLE 6-continued

List of kinase-encoding genes that were coordinately overexpressed at least two fold in HMLE-Twist, HMLE-Snail and HMLE-Slug cells relative to the HMLE parental epithelial population.

| Gene Symbol | Entrez Gene ID | Protein Accession | RefSeq ID |
| --- | --- | --- | --- |
| PRKCZ | 5590 | NP_001028753.1 | NM_001033581.1 |
| PRKDC | 5591 | NP_008835.5 | NM_006904.6 |
| PRKG1 | 5592 | NP_006249.1 | NM_006258.1 |
| PRKG2 | 5593 | NP_006250.1 | NM_006259.1 |
| PRKY | 5616 | NP_002751.1 | NM_002760.3 |
| PRPF4B | 8899 | NP_003904.2 | NM_003913.3 |
| PRPF4B | 8899 | NP_789770.1 | NM_176800.1 |
| PRPF4B | 8899 | NP_003904.3 | NM_003913.4 |
| PRPS1 | 5631 | NP_002755.1 | NM_002764.2 |
| PRPS2 | 5634 | NP_001034180.1 | NM_001039091.1 |
| PSKH1 | 5681 | NP_006733.1 | NM_006742.1 |
| PSKH2 | 85481 | NP_149117.1 | NM_033126.1 |
| PTK2 | 5747 | NP_722560.1 | NM_153831.2 |
| PTK2B | 2185 | NP_775268.1 | NM_173176.1 |
| PTK2B | 2185 | NP_775266.1 | NM_173174.1 |
| PTK2B | 2185 | NP_004094.3 | NM_004103.3 |
| RAGE | 5891 | NP_055041.1 | NM_014226.1 |
| RET | 5979 | NP_066124.1 | NM_020975.4 |
| RET | 5979 | NP_065681.1 | NM_020630.4 |
| RIPK1 | 8737 | NP_003795.2 | NM_003804.3 |
| RIPK3 | 11035 | NP_006862.2 | NM_006871.3 |
| ROCK1 | 6093 | NP_005397.1 | NM_005406.2 |
| ROR1 | 4919 | NP_005003.2 | NM_005012.2 |
| ROR2 | 4920 | NP_004551.2 | NM_004560.2 |
| ROS1 | 6098 | NP_002935.2 | NM_002944.2 |
| RPS6KA1 | 6195 | NP_002944.2 | NM_002953.3 |
| RPS6KA2 | 6196 | NP_001006933.1 | NM_001006932.1 |
| RPS6KA2 | 6196 | NP_066958.2 | NM_021135.4 |
| RPS6KA3 | 6197 | NP_004577.1 | NM_004586.2 |
| RPS6KA3 | 6197 | XP_949205.1 | XM_944112.1 |
| RPS6KA4 | 8986 | NP_001006945.1 | NM_001006944.1 |
| RPS6KA5 | 9252 | NP_872198.1 | NM_182398.1 |
| RPS6KA6 | 27330 | NP_055311.1 | NM_014496.2 |
| RPS6KC1 | 26750 | NP_036556.2 | NM_012424.2 |
| RPS6KL1 | 83694 | NP_113652.1 | NM_031464.3 |
| RYK | 6259 | NP_001005861.1 | NM_001005861.2 |
| RYK | 6259 | NP_002949.2 | NM_002958.3 |
| RYK | 6259 | NP_001005861.1 | NM_001005861.1 |
| SGK | 6446 | NP_005618.2 | NM_005627.2 |
| SGK2 | 10110 | NP_057360.2 | NM_016276.3 |
| SMG1 | 23049 | NP_055907.3 | NM_015092.3 |
| SNF1LK | 150094 | NP_775490.2 | NM_173354.3 |
| SPHK1 | 8877 | NP_068807.2 | NM_021972.2 |
| SPHK1 | 8877 | NP_892010.1 | NM_182965.1 |
| SPHK2 | 56848 | NP_064511.2 | NM_020126.3 |
| SRC | 6714 | NP_005408.1 | NM_005417.3 |
| SRC | 6714 | NP_938033.1 | NM_198291.1 |
| SRMS | 6725 | NP_543013.1 | NM_080823.2 |
| SRPK2 | 6733 | NP_872634.1 | NM_182692.1 |
| STK10 | 6793 | NP_005981.3 | NM_005990.3 |
| STK16 | 8576 | NP_001008910.1 | NM_001008910.1 |
| STK16 | 8576 | NP_003682.2 | NM_003691.2 |
| STK17A | 9263 | NP_004751.2 | NM_004760.2 |
| STK17B | 9262 | NP_004217.1 | NM_004226.2 |
| STK24 | 8428 | NP_003567.2 | NM_003576.3 |
| STK31 | 56164 | NP_113602.2 | NM_031414.2 |
| STK31 | 56164 | NP_116562.1 | NM_032944.1 |
| STK33 | 65975 | NP_112168.1 | NM_030906.2 |
| STK35 | 140901 | NP_543026.1 | NM_080836.2 |
| STK36 | 27148 | NP_056505.1 | NM_015690.2 |
| STK38 | 11329 | NP_009202.1 | NM_007271.2 |
| STK38L | 23012 | NP_055815.1 | NM_015000.2 |
| TAF1 | 6872 | NP_620278.1 | NM_138923.1 |
| TAF1L | 138474 | NP_722516.1 | NM_153809.2 |
| TAF9 | 6880 | NP_001015891.1 | NM_001015891.1 |
| TAF9 | 6880 | NP_057367.1 | NM_016283.4 |
| TBK1 | 29110 | NP_037386.1 | NM_013254.2 |
| TEC | 7006 | NP_003206.2 | NM_003215.2 |
| TEK | 7010 | NP_000450.2 | NM_000459.2 |
| TESK1 | 7016 | NP_006276.2 | NM_006285.2 |
| TESK2 | 10420 | NP_009101.2 | NM_007170.2 |
| TEX14 | 56155 | NP_938207.2 | NM_198393.2 |
| TEX14 | 56155 | NP_112562.3 | NM_031272.3 |
| TGFBR1 | 7046 | NP_004603.1 | NM_004612.2 |

TABLE 6-continued

List of kinase-encoding genes that were coordinately overexpressed at least two fold in HMLE-Twist, HMLE-Snail and HMLE-Slug cells relative to the HMLE parental epithelial population.

| Gene Symbol | Entrez Gene ID | Protein Accession | RefSeq ID |
| --- | --- | --- | --- |
| TGFBR2 | 7048 | NP_001020018.1 | NM_001024847.1 |
| TGFBR2 | 7048 | NP_001020018.1 | NM_001024847.2 |
| TJP1 | 7082 | NP_783297.2 | NM_175610.2 |
| TJP1 | 7082 | NP_003248.3 | NM_003257.3 |
| TJP2 | 9414 | NP_963923.1 | NM_201629.1 |
| TJP2 | 9414 | NP_004808.2 | NM_004817.2 |
| TJP3 | 27134 | NP_055243.1 | NM_014428.1 |
| TK1 | 7083 | NP_003249.1 | NM_003258.2 |
| TK2 | 7084 | NP_004605.3 | NM_004614.3 |
| TLK1 | 9874 | NP_036422.3 | NM_012290.3 |
| TLK2 | 11011 | NP_006843.2 | NM_006852.2 |
| TNK1 | 8711 | NP_003976.1 | NM_003985.1 |
| TPK1 | 27010 | NP_001035947.1 | NM_001042482.1 |
| TRIM28 | 10155 | NP_005753.1 | NM_005762.2 |
| TRIM33 | 51592 | NP_148980.2 | NM_033020.2 |
| TRIM33 | 51592 | NP_056990.3 | NM_015906.3 |
| TRIO | 7204 | NP_009049.2 | NM_007118.2 |
| TTBK1 | 84630 | NP_115927.1 | NM_032538.1 |
| TTK | 7272 | NP_003309.2 | NM_003318.3 |
| TTN | 7273 | NP_597676.2 | NM_133432.2 |
| TTN | 7273 | NP_596870.2 | NM_133379.2 |
| TTN | 7273 | NP_596869.3 | NM_133378.3 |
| TTN | 7273 | NP_003310.3 | NM_003319.3 |
| TXK | 7294 | NP_003319.2 | NM_003328.2 |
| TXNDC3 | 51314 | NP_057700.3 | NM_016616.3 |
| TYK2 | 7297 | NP_003322.2 | NM_003331.3 |
| TYRO3 | 7301 | NP_006284.2 | NM_006293.2 |
| UCK1 | 83549 | NP_113620.1 | NM_031432.1 |
| ULK2 | 9706 | NP_055498.2 | NM_014683.2 |
| VRK1 | 7443 | NP_003375.1 | NM_003384.2 |
| VRK2 | 7444 | NP_006287.2 | NM_006296.3 |
| WEE1 | 7465 | NP_003381.1 | NM_003390.2 |
| ZAP70 | 7535 | NP_997402.1 | NM_207519.1 |
| ZAP70 | 7535 | NP_001070.2 | NM_001079.3 |

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only and the invention is described in detail by the claims that follow.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A method of treating a subject having a carcinoma, the method comprising
    (a) detecting FRA1 using an antibody that specifically binds to FRA1 or detecting RNA encoding FRA1 by performing reverse transcription and quantitative PCR, in a sample obtained from the carcinoma and then;
    (b) administering to the subject a therapy effective against non-CSC carcinoma cells; and
    (c) administering to the subject an EGFR inhibitor, a sphingosine kinase pathway inhibitor, and/or a PKC-α/FRA1 pathway inhibitor.

2. The method of claim 1, wherein step (b) comprises administering to the subject a therapy effective against non-CSC carcinoma cells, wherein the therapy comprises radiation therapy, a spindle poison, a DNA replication inhibitor, an alkylating agent, or a platinum-based compound.

3. The method of claim 1, wherein step (a) comprises detecting FRA1 using an antibody that specifically binds to FRA1.

4. The method of claim 1, wherein the PKC-α/FRA1 pathway inhibitor is a Protein Kinase C-alpha (PKC-α) inhibitor, wherein the PKC-α inhibitor targets PKC-α.

5. The method of claim 4, wherein the PKC-α inhibitor is a small interfering nucleic acid comprising a region of complementarity with PKC-α mRNA that inhibits expression of PKC-α protein.

6. The method of claim 5, wherein the small interfering nucleic acid is an antisense oligonucleotide, miRNA, shRNA or siRNA that targets PKC-α mRNA.

7. The method of claim 1, further comprising contacting the carcinoma cells with an inhibitor of PKCη, CLK1, CDK6 or JAK1.

8. The method of claim 1, wherein the PKC-α/FRA1 pathway inhibitor is an inhibitor of PDGFRα or PDGFRβ.

9. The method of claim 8, wherein the inhibitor of PDGFRα or PDGFRβ is imatinib.

10. The method of claim 1, wherein the PKC-α/FRA1 pathway inhibitor is a PDGFR neutralizing antibody or PDGFR inhibitor.

11. The method of claim 1 wherein the PKC-α/FRA1 pathway inhibitor is a FRA1 inhibitor.

12. The method of claim 1, wherein the PKC-α/FRA1 pathway inhibitor is an ERK inhibitor.

13. The method of claim 1, further comprising contacting the carcinoma cells with an EGFR inhibitor.

14. The method of claim 1 further comprising contacting the cells with a sphingosine kinase pathway inhibitor.

15. The method of claim 14, wherein the sphingosine kinase pathway inhibitor is a sphingosine kinase 1 inhibitor or sphingosine kinase 2 inhibitor.

16. The method of claim 14, wherein the sphingosine kinase pathway inhibitor is a sphingosine-1-phosphate receptors 1 and 3 (S1PR1/3) antagonist.

17. The method of claim 1, wherein the carcinoma cells comprise basal-like breast cancer cells.

18. The method of claim 1, wherein the carcinoma cells comprise cells arising from the airway epithelium, pancreas ductal epithelium, intestinal epithelium, prostate epithelium or breast epithelium.

19. The method of claim 1, wherein the carcinoma cells are breast carcinoma cells characterized as Her2neg, ERneg, and PRneg.

20. The method of claim 4, wherein the PKC-α inhibitor inhibits activity and/or expression of PKC-α.

21. The method of claim 16, wherein the sphingosine-1-phosphate receptors 1 and 3 (S1PR1/3) antagonist is VPC23019.

* * * * *

SEQUENCE LISTING

```
<160> NUMBER OF SEQ ID NOS: 141

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1
ggattcctat gtgggcgacg a                                        21

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide
```

-continued

```
<400> SEQUENCE: 2
tggcaaattc catggcaccg                                            20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
cctgcgcaag atcatcccca                                            20

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
cggtattgcc aaccctctgg a                                          21

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
ctgggtgccc tcaagatgca                                            20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
taccgctgct ccattccacg                                            20

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 7
tgttcgagaa cggcagcttc c                                          21

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 8
ttgcaccggt cgacaaagga c                                          21

<210> SEQ ID NO 9
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 9
tgtcggtgac aaagcccctg                                                    20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
acccgcacca acgagaaggt                                                    20

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 11
gagaatggac ctgcaagccc a                                                  21

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
tgcactgagt gtggaaaagc                                                    20

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 13
gtctggagcg tttgggaagg t                                                  21

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
ggacataccc ccgcaaagaa                                                    20

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 15
```
atattagggc gctggtgtgg t                                            21

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
agcgcggaca aggagaacag                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
cgccttcagc atcctccttc                                              20

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 18
tcagggaggg cagtatgttc g                                            21

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 19
tgctgaagac ggtgctgatg a                                            21

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
gccgctcacg ctgaaactgt                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
gggcctgtgc ttgaacctga                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
ggctttcccc ggagactacg                                                    20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
gaggggcaag gtggaacagt                                                    20

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 24
tgccccaaga acgtgacaga t                                                  21

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
ttggcaaccg caccgtctat                                                    20

<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 26
tgactgggac tgggatgaag g                                                  21

<210> SEQ ID NO 27
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 27
gggagcgtac caaaactgtc c                                                  21

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
gtcacgtgca gcccctttg                                                     20

```
<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
tggggcttcg tgtcagatgt                                                 20

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 30
ggcaaaggca cgatgatacc a                                               21

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
gcgatggcac catcacaaca                                                 20

<210> SEQ ID NO 32
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 32
tcttgggcag aatcccacag a                                               21

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
cggctgggca gtggagagta                                                 20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
gggggcacgg atcaatgtaa                                                 20

<210> SEQ ID NO 35
<211> LENGTH: 21
<212> TYPE: DNA
<213> ORGANISM: Artificial Sequence
<220> FEATURE:
<223> OTHER INFORMATION: Synthetic oligonucleotide
```

```
<400> SEQUENCE: 35
aaaagccctc ctctcctcca g                                              21

<210> SEQ ID NO 36
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 36
gaccctgagc tatcggactg g                                              21

<210> SEQ ID NO 37
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 37
tggtgttggg aaagggagt t                                               21

<210> SEQ ID NO 38
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 38
ctgctgcctg gctgatgaga g                                              21

<210> SEQ ID NO 39
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 39
ttctcgtggc cctggtggta t                                              21

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
caccccaacg tggtcaggtt                                                20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
gaatcgccca gtggctgcta                                                20

<210> SEQ ID NO 42
```

```
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 42
gctggggagt caggtcatac g                                              21

<210> SEQ ID NO 43
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 43
tgctgggacc tgcaaactct g                                              21

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
gccaatccga gcctacatcc                                                20

<210> SEQ ID NO 45
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 45
tccagccacc taccaccaca g                                              21

<210> SEQ ID NO 46
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 46
attcccaccg catcctacac c                                              21

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
ggcgctgcat atcgttgttg                                                20

<210> SEQ ID NO 48
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 48
```
atgccaaccc ttctcctcca c         21

<210> SEQ ID NO 49
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 49
ggtggcggca gctactttc t         21

<210> SEQ ID NO 50
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 50
acatggctgg ggtgttgaag g         21

<210> SEQ ID NO 51
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 51
cgccccactt gattttggag g         21

<210> SEQ ID NO 52
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 52
gctgcagctt gccatcttgg a         21

<210> SEQ ID NO 53
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 53
ttgttgtgcc agggtgttc c         21

<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 54
ccggacatgg ccttgtagca         20

<210> SEQ ID NO 55
<211> LENGTH: 21
<212> TYPE: DNA

```
<213> ORGANISM: Artificial Sequence
<220> FEATURE:
<223> OTHER INFORMATION: Synthetic oligonucleotide

<400> SEQUENCE: 55 catggggtc tgaaagcttg g                                          21

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 56
caccttggtg atgaccggca                                           20

<210> SEQ ID NO 57
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 57
tggattccag aaacggaggc c                                         21

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
agggcattgg gatcgtcagc                                           20

<210> SEQ ID NO 59
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 59
attctgctgc tccaggaagc g                                         21

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 60
agtgcaagtg atgcgtccgc                                           20

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 61
tggtgatgct gaaagagacg                                           20
```

<210> SEQ ID NO 62
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 62
gatctggccg tgggttttag c                                              21

<210> SEQ ID NO 63
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 63
ctaactcggc actggggatg t                                              21

<210> SEQ ID NO 64
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 64
tggcaaagct gaaggggta g                                               21

<210> SEQ ID NO 65
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 65
ggcgggagtg agcttgtagg t                                              21

<210> SEQ ID NO 66
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 66
gctgcgccac gtgtagatga                                                20

<210> SEQ ID NO 67
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 67
agaggggcag gatggtagag c                                              21

<210> SEQ ID NO 68
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 68
gttgaccgcc gagttgagga                                             20

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 69
ttggcgtaga gcggcaagac                                             20

<210> SEQ ID NO 70
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 70
tctccgctgc tgctgctact c                                           21

<210> SEQ ID NO 71
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 71
ggactgggcc atggaagaga t                                           21

<210> SEQ ID NO 72
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 72
cttgcaggca ggtcggtgag                                             20

<210> SEQ ID NO 73
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 73
gcctgggttg aagttgctga g                                           21

<210> SEQ ID NO 74
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 74
gggaaggaat ggcgaactga g                                           21

```
<210> SEQ ID NO 75
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 75
gctgaactgc tgtcggaggt c                                              21

<210> SEQ ID NO 76
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 76
ctttgccaac acccatctgg t                                              21

<210> SEQ ID NO 77
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 77
ctcgtgcatc agcccgtctc                                                20

<210> SEQ ID NO 78
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 78
agtggcgggg aggtaggaga                                                20

<210> SEQ ID NO 79
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 79
cccaacgact tccgaccata a                                              21

<210> SEQ ID NO 80
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 80
cggaatgcct cacggatttc t                                              21

<210> SEQ ID NO 81
<211> LENGTH: 21
<212> TYPE: DNA
<213> ORGANISM: Artificial Sequence
<220> FEATURE:
<223> OTHER INFORMATION: Synthetic oligonucleotide
```

```
<400> SEQUENCE: 81
tggcgaagtt ctgcagcact a                                              21

<210> SEQ ID NO 82
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 82
gtagtggagc cggagggaca t                                              21

<210> SEQ ID NO 83
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 83
atcttctctg cccgctctcg                                                20

<210> SEQ ID NO 84
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 84
ttcatctccc cttgcgtgtt g                                              21

<210> SEQ ID NO 85
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 85
acggcttcgg gaataggtga c                                              21

<210> SEQ ID NO 86
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 86
aggagtgcag ctgcgtcaag a                                              21

<210> SEQ ID NO 87
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 87
tggccgtaga agggattgac a                                              21

<210> SEQ ID NO 88
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 88
cttctttcgc cggtggacaa                                              20

<210> SEQ ID NO 89
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 89
aaggccgaag tcagcgagtt t                                            21

<210> SEQ ID NO 90
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 90
ttggcgggga ttggagtaga c                                            21

<210> SEQ ID NO 91
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 91
catggcgggg cttgtagata c                                            21

<210> SEQ ID NO 92
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 92
ggcccacaac ctccacttga                                              20

<210> SEQ ID NO 93
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 93
actggggctc ttcctcctca t                                            21

<210> SEQ ID NO 94
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 94
```
tccagacatc cccgaagaac c                                              21

<210> SEQ ID NO 95
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 95
ccgggcaaat ccaaagtcac                                                20

<210> SEQ ID NO 96
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 96
tgtccccgta gaagccgtag c                                              21

<210> SEQ ID NO 97
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 97
cagaacattc cgctccgaca t                                              21

<210> SEQ ID NO 98
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 98
tgatcacgcc gttgctgttg                                                20

<210> SEQ ID NO 99
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 99
tccacggatc atactgcctc aa                                             22

<210> SEQ ID NO 100
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 100
ccgcctcagc ctccagaaca                                                20

<210> SEQ ID NO 101
<211> LENGTH: 21
<212> TYPE: DNA
<213> ORGANISM: Artificial Sequence

```
<220> FEATURE:
<223> OTHER INFORMATION: Synthetic oligonucleotide

<400> SEQUENCE: 101
cggctgtgac ttggcaacct g                                              21

<210> SEQ ID NO 102
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 102
gtggccctga attaaaactc gt                                             22

<210> SEQ ID NO 103
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 103
tgccaccatt tttgtaaccc tg                                             22

<210> SEQ ID NO 104
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 104
gcgcggcgag gaagttacac                                                20

<210> SEQ ID NO 105
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 105
gccgtgtacc ccgcagagc                                                 19

<210> SEQ ID NO 106
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 106
gcagcgggca gcagagacc                                                 19

<210> SEQ ID NO 107
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 107
cctgcccacc tctgacttct gc                                             22
```

<210> SEQ ID NO 108
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 108
tggagtctgg gctggggtga g                                    21

<210> SEQ ID NO 109
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 109
cgtccgttcc gccgagtca                                       19

<210> SEQ ID NO 110
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 110
cacgcaccac cacacccaac ta                                   22

<210> SEQ ID NO 111
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 111
tggtgcctct cctttgcctt tg                                   22

<210> SEQ ID NO 112
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 112
agcccttaca ccttcacaga ca                                   22

<210> SEQ ID NO 113
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 113
ggcttgtggc caccagactt gt                                   22

<210> SEQ ID NO 114
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 114
tcagcgcccc ctccaagtaa g                                           21

<210> SEQ ID NO 115
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 115
acctccgttt ctgctcccac aa                                          22

<210> SEQ ID NO 116
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 116
tctcgggctg aaccactgcg                                             20

<210> SEQ ID NO 117
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 117
ggttccccgc tccagtccc                                              19

<210> SEQ ID NO 118
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 118
gaaagcgggc acggagacg                                              19

<210> SEQ ID NO 119
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 119
ccctcacccc agcccagact                                             20

<210> SEQ ID NO 120
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 120
cggaggggcg aaggacagac                                             20

<210> SEQ ID NO 121

```
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 121
ggttgggatg gggctcagtg t                                             21

<210> SEQ ID NO 122
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 122
tttaacctcc atgtgcctca gt                                            22

<210> SEQ ID NO 123
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 123
atgctgggga tgggctgtgt                                               20

<210> SEQ ID NO 124
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 124
tagtggggca ggagagggag tc                                            22

<210> SEQ ID NO 125
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 125
cccgagggct ggaggttagg                                               20

<210> SEQ ID NO 126
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 126
cgcgagcagt tcccgtcaat                                               20

<210> SEQ ID NO 127
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 127
```

```
cggcgcctcg tactccaacc                                              20

<210> SEQ ID NO 128
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 128
gcatgggctc gcctgtcaac                                              20

<210> SEQ ID NO 129
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 129
tccggggagg tggcagaaa                                               19

<210> SEQ ID NO 130
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 130
acgtcggctt tccccttctg tt                                           22

<210> SEQ ID NO 131
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 131
tgcattgttg aggtggtctg aa                                           22

<210> SEQ ID NO 132
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 132
ggggatccaa aagtgaaaag g                                            21

<210> SEQ ID NO 133
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 133
gccaggcaac acagaagaag g                                            21

<210> SEQ ID NO 134
<211> LENGTH: 21
<212> TYPE: DNA
```

-continued

<213> ORGANISM: Artificial Sequence
<220> FEATURE:
<223> OTHER INFORMATION: Synthetic oligonucleotide

<400> SEQUENCE: 134
cggcatcgag tacaggaccc c                                              21

<210> SEQ ID NO 135
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 135
ttggcgcgtg tcctaatctc g                                              21

<210> SEQ ID NO 136
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 136
tgctgcagcg ggaggatga                                                 19

<210> SEQ ID NO 137
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 137
agaacgaacc tgcctcccga ag                                             22

<210> SEQ ID NO 138
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 138
tgcgttcccg ttatcccttc ag                                             22

<210> SEQ ID NO 139
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 139
gcgctcggcc tcctgtcat                                                 19

<210> SEQ ID NO 140
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 140
tggaacaata agcaaacaat g                                              21

```
<210> SEQ ID NO 141
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 141
ctctggcagg tgcgtcagtc cgcaggggaa cccggggctc cacctgcgcg gc          52
```